(12) United States Patent
Thompson et al.

(10) Patent No.: US 12,009,088 B2
(45) Date of Patent: Jun. 11, 2024

(54) SYSTEMS AND METHODS FOR MANAGEMENT OF PSYCHIATRIC OR MENTAL CONDITIONS USING DIGITAL OR AUGMENTED REALITY

(71) Applicants: BehaVR, LLC, Elizabethtown, KY (US); Sumitomo Pharma Co., Ltd., Osaka (JP)

(72) Inventors: Aprilia Thompson, Elizabethtown, KY (US); Aneth Canale, Marlborough, MA (US); Todd Grinnell, Marlborough, MA (US); Brandon Hedges, Elizabethtown, KY (US); Georgia Mitsi, Marlborough, MA (US); Morgan Taylor, Elizabethtown, KY (US); Joyce Tsai, Marlborough, MA (US); Sarah Zadd, Elizabethtown, KY (US); Christina Zaluski, Marlborough, MA (US); Eleanor Anderson, Elizabethtown, KY (US)

(73) Assignees: BehaVR, LLC, Elizabethtown, KY (US); Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 17/869,670

(22) Filed: Jul. 20, 2022

(65) Prior Publication Data
US 2023/0056779 A1    Feb. 23, 2023

Related U.S. Application Data

(60) Provisional application No. 63/223,871, filed on Jul. 20, 2021.

(51) Int. Cl.
*G16H 20/70* (2018.01)
*G06F 3/01* (2006.01)
(Continued)

(52) U.S. Cl.
CPC .............. *G16H 20/70* (2018.01); *G06F 3/011* (2013.01); *G06V 20/20* (2022.01); *G16H 40/67* (2018.01)

(58) Field of Classification Search
CPC ........ G16H 20/70; G16H 40/67; G06F 3/011; G06V 20/20; A61B 5/16
See application file for complete search history.

(56) References Cited

U.S. PATENT DOCUMENTS 10,286,179 B2    5/2019   Giap et al.
10,885,719 B1    1/2021   Ravindran et al.
(Continued)

FOREIGN PATENT DOCUMENTS

WO    WO 2021064726 A1 *    4/2021    ............. G16H 20/70
WO    WO 2022164932 A1 *    4/2022    ............. G16H 20/70

OTHER PUBLICATIONS

Hackerearth, "Decision Tree," Accessed via web.archive.org Jul. 9, 2021.
(Continued)

*Primary Examiner* — Ryan R Yang
(74) *Attorney, Agent, or Firm* — Morgan, Lewis & Bockius LLP

(57) ABSTRACT

Systems and methods for preparing a regimen for improving an ability of a subject to manage a psychiatric or mental condition are provided. A method includes presenting a first digital reality scene with interactive digital chart and bin. The bin includes a plurality of nodes. Each node corresponds to a respective category in a plurality of categories and a plurality of proposed experiences associated with the respective category. Each proposed experience is associated with a unique digital reality scene, different than the first digital reality scene, that manifests a challenge represented by the respective category and/or the respective proposed experience. Each node is also associated with at least one respec- (Continued)

tive gate criterion. A method also includes detecting a selection of a node and placing the node on the chart, thus providing access to the corresponding plurality of proposed experiences associated with the respective category.

81 Claims, 57 Drawing Sheets

(51) Int. Cl.
*G06V 20/20* (2022.01)
*G16H 40/67* (2018.01)

(56) References Cited

U.S. PATENT DOCUMENTS

| | | |
|---|---|---|
| 11,101,031 B2 | 8/2021 | Hill et al. |
| 2008/0294013 A1 | 11/2008 | Gobeyn et al. |
| 2010/0010371 A1 | 1/2010 | Zayfert et al. |
| 2010/0223568 A1 | 9/2010 | Quek et al. |
| 2017/0326332 A1 | 11/2017 | Giap et al. |
| 2018/0103867 A1 | 4/2018 | Stephens et al. |
| 2019/0198153 A1 | 6/2019 | Hill et al. |
| 2019/0252080 A1 | 8/2019 | Liu |
| 2019/0385711 A1 | 12/2019 | Shriberg et al. |
| 2020/0023157 A1 | 1/2020 | Lewis et al. |
| 2020/0253527 A1 | 8/2020 | Ellison |
| 2020/0303056 A1* | 9/2020 | Sullivan .................. G06V 20/20 |
| 2020/0330019 A1* | 10/2020 | Brown .................. G16H 10/20 |
| 2020/0402642 A1 | 12/2020 | Hasselberg et al. |
| 2021/0383913 A1 | 12/2021 | Tablan et al. |
| 2022/0008745 A1 | 1/2022 | Kirchner et al. |
| 2022/0223067 A1 | 7/2022 | Franz et al. |
| 2022/0310247 A1 | 9/2022 | Freeman et al. |
| 2023/0005595 A1 | 1/2023 | Garriga Calleja et al. |

OTHER PUBLICATIONS

International Search Report issued in related International Patent Application No. PCT/US2022/051549 dated Mar. 6, 2023.
Written Opinion issued in related International Patent Application No. PCT/US2022/051549 dated Mar. 6, 2023.
International Search Report issued in corresponding International Patent Application No. PCT/US2022/037751 dated Nov. 15, 2022.
Written Opinion issued in corresponding International Patent Application No. PCT/US2022/037751 dated Nov. 15, 2022.

* cited by examiner

400

(402) A method of preparing a regimen for improving an ability of a subject to manage a psychiatric or mental condition exhibited by the subject at a computer system associated with the subject. The computer system includes one or more processors, a display, and a memory coupled to the one or more processors. The memory including one or more programs configured to be executed by the one or more processors.

(404) Obtain, in electronic form, an assessment of the subject, the assessment comprising an identification of each category in the plurality of categories (406) Present, on the display, a first digital reality scene including a respective interactive digital chart and a corresponding interactive digital bin. The respective interactive digital chart consumes a first affordance region. The respective interactive digital chart includes a first area. The corresponding interactive digital bin consumes a second affordance region different than the first affordance region. The corresponding interactive digital bin includes an enumerated plurality of nodes. Each respective node in the enumerated plurality of nodes (i) corresponds to a respective category in a plurality of categories, (ii) is associated with a corresponding plurality of proposed experiences associated with the respective category, wherein each respective proposed experience in the corresponding plurality of proposed experiences is associated with a corresponding unique digital reality scene, different than the first digital reality scene, that manifests a corresponding challenge represented by the respective category and/or the respective proposed experience, and (iii) at least one respective gate criterion in a plurality of gate criteria, wherein each respective category in the plurality of categories is directed to improving an ability of the subject to manage a psychiatric or mental condition of the subject.

(408) Detect a selection of a first node in the enumerated plurality of nodes.

(410) Determine if the selection of the first node satisfies each gate criterion in the at least one respective gate criteria associated with the first node (412) Place the first node at a first location in the first area, thereby providing access to the corresponding plurality of proposed experiences associated with the respective category and improving the ability of the subject to manage the psychiatric or mental condition using the respective interactive digital chart

Which device would you like to run the session on?

Recent Patients　　　Search Patients　　　All Patients

| | | | |
|---|---|---|---|
| User 1 | Session 1<br>1-12-21 13:49:22 | Session 2<br>1-13-21 11:19:00 | Select |
| User 2 | Session 1<br>2-1-21 13:00:00 | Session 2<br>3-1-21 13:00:00 | Select |
| User 4 | Session 1<br>12-12-20 14:00:59 | Session 2<br>1-25-21 07:45:00 | Select |
| User 5 | Session 1<br>12-12-20 14:00:59 | ... | Select |
| User 6 | No Session History | ... | Select |

Next Page

Dashboard
- Overview

Session
- New
- Active
- History

Patient
- New

Required
- ⊙ LSAS Assessment
- ⊙ Introduction to Social Fears
- ⊙ Introduction to Mindfulness Experience 1–Meeting Strangers
- ⊙ Conquering Social Fears Through Building Confidence
- ⊙ Listen to How User 4 Progressed with Therapy
- ⊙ Social Challenge 1 #NPC at the table = 2
- ⊙ Social Challenge 2 #NPC at the table = 3
- ● Social Challenge 3
- ● Social Challenge 4
- ⊙ Mindfulness - Confidence Experience 2–Going to Party
- ⊙ Social Challenge L
- ...

How would you like to configured this session including challenges and/or nodes for User 2?

User 2 -- Next Session

Include all modules in session  | YES | NO |

- ⊙ LSAS Assessment
- ⊙ Introduction to Social Fears
- ⊙ Introduction to Mindfulness
- ⊙ Conquering Social Fears Through Building Confidence
- ⊙ Listen to How User 2 Progressed with Therapy
- ⊙ Social Challenge 1
- ⊙ Social Challenge 2
- ● Social Challenge 3

[Create Session]

Dashboard
- Overview

Session
- New
- Active
- History

Patient
- New

Fig. 9D

1500
| A | Type | Logic function |
|---|---|---|
| 1 |  | $C = A \wedge B$ |
| 2 | 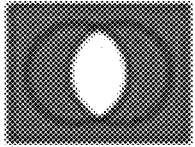 | $C = \sim(A \wedge B)$ |
| 3 | 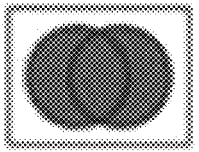 | $C = A \vee B$ |
| 4 | 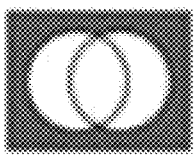 | $C = \sim(A \vee B)$ |
| 5 | 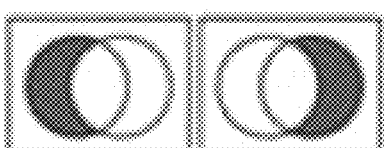 | $C = A \wedge \sim B,\ C = \sim A \wedge B$ |
| 6 | 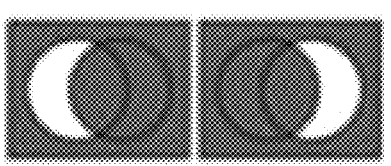 | $C = \sim A \vee B,\ C = A \vee \sim B$ |
| 7 | 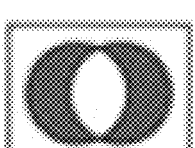 | $C = \sim(A \leftrightarrow B)$ |
| 8 |  | $C = A \leftrightarrow B$ |
Fig. 15

SYSTEMS AND METHODS FOR MANAGEMENT OF PSYCHIATRIC OR MENTAL CONDITIONS USING DIGITAL OR AUGMENTED REALITY

CROSS-REFERENCE TO RELATED APPLICATION

The present Application claims priority to U.S. Provisional Patent Application No. 63/223,871, entitled "Management of Psychiatric or Mental Conditions Using Digital or Augmented Reality," filed Jul. 20, 2021, which is hereby incorporated by reference in its entirety for all purposes.

TECHNICAL FIELD

The present disclosure relates to systems and methods for preparing digital reality or augmented reality based regimens for the management of psychiatric or mental conditions exhibited by subjects.

BACKGROUND

Demand to access mental health care facilities and services that improve the mental health of patients is at an all-time high. However, evidence cannot be found that this increased access to mental health care facilities has also led to decreases in the provenance of mental health issues. Contrarily, mental health problems in patients have increased in recent years. See Mojtabai et al., "Trends in Psychological Distress, Depressive Episodes and Mental-Health Treatment-Seeking in the United States: 2001-2012," Journal of Affective Disorders, 174, pg. 556.

Conventional solutions to improving mental health are laborious and resource intensive for all parties involved. For instance, the conventional solutions often require many time-consuming and expensive, in-person meetings between a clinician and a patient. Moreover, these in-person meetings do not allow a clinician to observe the patient in situations that excite an underlying mental health issue of the patient given the intimate and private nature of in-person meetings with the clinician.

Coinciding with this, interactive computer implemented gaming and services are expanding. However, prior solutions to marry services to improve mental health with computer implemented gaming has been unsatisfactory. One cause of such failure is the requirement that a therapist be present with a patient during a computer implemented gaming session. See Freeman et al., 2017, "Virtual Reality in the Assessment, Understanding, and Treatment of Mental Health Disorders," Psychological Medicine, 47(14), pg. 2393. However, this requirement is burdensome on the temporal, spatial, and financial resources available to both the patient and the medical practitioner.

As such, there is a need for systems and methods for improving the mental health of subjects without overly burdening the subjects or their medical practitioners.

SUMMARY

Given the above background, what is needed in the art are systems and methods for preparing a regimen for improving an ability of a subject to manage a psychiatric or mental condition exhibited by the subject.

The present disclosure provides improved systems and methods for preparing an exposure exercise regimen for improving an ability of a subject to manage a psychiatric or mental condition that is exhibited by the subject. In some such embodiments, the exposure exercise regimen includes one or more education (e.g., psychoeducation) exercises, one or more exposure exercises (e.g., by emotional processing exposure and/or an inhibitory learning exposure), one or more mindfulness exercises, one or more cognitive reframing exercises, or a combination thereof. The exposure exercises are identified by providing an interactive digital exposure therapy that is facilitated by engagement with a digital chart. In some such embodiments, the exposure exercise regimen is prepared for and/or overseen for the subject by a medical practitioner, one or more computational models, or a combination thereof. By having the medical practitioner, the one or more computational models, or the combination thereof prepare and/or oversee the exposure exercise regimen, the systems and methods of the present disclosure improves a quality and efficacy of the exposure exercise regimen and, therefore, the ability of the subject to manage the psychiatric or mental condition exhibited by the subject. Moreover, in some embodiments, the preparation and/or oversight provided by the medical practitioner, the one or more computational models, or the combination thereof is performed prior to presenting the exposure exercise regimen to the subject, which reduces a cognitive and technical burden on the subject.

Accordingly, in one aspect of the present disclosure, a method of preparing a regimen for improving an ability of a subject to manage a psychiatric or mental condition exhibited is provided at a computer system. The system includes processor(s), a display, and a memory coupled to the one or more processors. The memory includes one or more programs configured to be executed by the processor(s).

In some embodiments, the display is a head mounted display.

In some embodiments, the condition is a clinically diagnosed mental disorder or a sub-clinically diagnosed mental disorder.

In some embodiments, the condition includes being stressed in a social setting, fearing a social setting, or being overwhelmed in a social setting.

In some embodiments, the condition is a clinically diagnosed mental disorder. In some such embodiments, the disorder is an anxiety disorder (e.g., a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject). In some such embodiments, the disorder is a mood disorder (e.g., a depression disorder, a bipolar disorder, or a cyclothymic disorder). In some embodiments, the depression disorder is a major depression disorder. In some such embodiments, the disorder is a psychotic disorder (e.g., a schizophrenia disorder, a delusion disorder, or a hallucination disorder). In some such embodiments, the disorder is an eating disorder (e.g., anorexia nervosa, bulimia nervosa, or binge eating disorder). In some such embodiments, the disorder is an impulse control disorder (e.g., a pyromania disorder, a kleptomania disorder, or a compulsive gambling disorder). In some such embodiments, the disorder is a personality disorder, an obsessive-compulsive disorder, or a post-traumatic stress disorder. In some such embodiments, the disorder is an addiction disorder (e.g., an alcohol use disorder or a substance abuse disorder). In some such embodiments, the disorder is a personality disorder (e.g., an antisocial personality disorder, an obsessive-compulsive personality disorder, or a paranoid personality disorder).

In the method, there is presented, on the display, a first digital reality scene including a respective interactive digital chart and a corresponding interactive digital bin. The respective interactive digital chart consumes a first affordance region, with the respective interactive digital chart including a first area. The corresponding interactive digital bin consumes a second affordance region different than the first affordance region. The corresponding interactive digital bin includes an enumerated plurality of nodes.

In some embodiments, the first affordance region is a two-dimensional affordance region in the first digital reality scene. The first area is a respective area bound by the two-dimensional affordance region.

In some embodiments, the first area is circular or polygonal.

In some embodiments, the first affordance region is a three-dimensional affordance region in the first digital reality scene, and the first area is a respective surface area of a three-dimensional object bound by the three-dimensional affordance region. In some such embodiments, the three-dimensional object is a sphere or a polyhedron.

In some embodiments, the first area includes a plurality of tessellated shapes bound by the first area, and the first location is a first shape in the plurality of tessellated shapes. In some such embodiments, the plurality of tessellated shapes includes about 20, 30, 40, 50, 75, 100, 125, 150, 175, 200, 225, 250, 275, 300, 325, or 350 tessellated shapes.

In some embodiments, the first affordance overlaps the second affordance region.

In some embodiments, the respective interactive digital chart further includes a graphical marker configured to visually designate the first location.

In some embodiments, the digital reality scene is a virtual or augmented reality scene.

In some embodiments, the first digital reality scene includes an interactive board. The respective interactive digital chart is placed on a top of the interactive board, where the interactive board is movable, rotatable or tiltable by the subject to facilitate different views of the interactive board.

In some such embodiments, the interactive board includes a rail to allow an avatar of the subject to grab the interactive board and adjust a position of the interactive board.

In some such embodiments, the interactive board further includes a plate surrounded circumferentially by the rail and connected to the rail. The respective interactive digital chart is placed on a top of the plate.

In some such embodiments, the rail has a substantially ring shape. The plate has a substantially circular shape when viewed from top or bottom of the interactive board.

In some such embodiments, when viewed from a side of the interactive board, the plate has a first side that is sloped more than a second side and/or the plate has a substantially boat-bowel shape.

In some such embodiments, a logo is displayed at the bottom of the plate.

In some such embodiments, the plate is rendered white on the display and the rail is rendered on the display such that it appears being made of a metallic material.

In some embodiments, responsive to an avatar hovering a hand over or adjacent to the interactive board for a period of time (e.g., less than 8, 7, 6, 5, 4, or 3 seconds), one or more animated loop arrows and tool tips appear at or adjacent to the interactive board.

In some embodiments, responsive to gripping of the rail by the avatar of the subject or interaction of the avatar of the subject with the interactive board, one or more animated loop arrows and tool tips disappear from the first digital reality scene.

In some embodiments, an activated node or one or more scene-nodes of the activated nodes are tilted at an angle (e.g., between 5 and 15, 15 and 30, 30 and 45, 45 and 60, or between 60 and 90 degrees) with respect to the interactive board.

Continuing with the disclosed method, each respective node in the enumerated plurality of nodes (i) corresponds to a respective category in a plurality of categories, (ii) is associated with a corresponding plurality of proposed experiences associated with the respective category. Each respective proposed experience in the corresponding plurality of proposed experiences is associated with a corresponding unique digital reality scene, different than the first digital reality scene, that manifests a corresponding challenge represented by the respective category and/or the respective proposed experience, and (iii) at least one respective gate criterion in a plurality of gate criteria. Each respective category in the plurality of categories is directed to improving an ability of the subject to manage a psychiatric or mental condition of the subject.

Moreover, in some embodiments, the corresponding challenge is a digital reality exposure therapy.

In some embodiments, an assessment of the subject is obtained in electronic form. The assessment includes an identification of each category in the plurality of categories. In some such embodiments, the assessment includes a Liebowitz Social Anxiety Scale assessment a Clinician Global Impression Severity Scale assessment, a Mini-International Neuropsychiatric Interview assessment, a Subjective Unit of Distress Scale assessment, a Minimally Clinically Important Different assessment, or a Quality-of-Life index assessment.

In some embodiments, the assessment includes determining if the subject is currently consuming a beta blocker pharmaceutical composition and/or a benzodiazepine pharmaceutical composition. Accordingly, in some such embodiments, when the subject is currently consuming a beta blocker pharmaceutical composition and/or a benzodiazepine pharmaceutical composition, the method ceases. Moreover, when the subject is not currently consuming a beta blocker pharmaceutical composition and/or a benzodiazepine pharmaceutical composition, the method proceeds.

In some such embodiments, the assessment is provided by the subject.

In some embodiments, prior to obtaining the assessment, there is obtained, from a remote device associated with a medical practitioner of the subject, a validation of the assessment. In some embodiments, the validation of the assessment includes a first selection by the subject of a set of categories and a second selection by the medical practitioner of a subset of the set of categories. The plurality of categories consists of the subset of categories.

In some embodiments, the validation of the assessment includes determining if the subject satisfies a threshold change in diagnosis status for the psychiatric or mental condition exhibited by the subject. Moreover, in some embodiments, the validation of the assessment includes determining if the subject satisfies a threshold change in subjective distress of the subject caused by the corresponding challenge, a threshold change in cognitive symptoms of the subject, a threshold change in mindfulness state of the subject, or a combination thereof. Furthermore, in some embodiments, the validation of the assessment includes determining if the subject satisfies a threshold quality of life improvement.

In some embodiments, the at least one respective gate criteria includes a ranking gate criterion associated with a hierarchical ranking of each of the nodes.

In some embodiments, the at least one respective gate criteria includes a medical practitioner gate criterion associated with an approval, from the medical practitioner associated with the subject, of the selection of the first node.

In some embodiments, the at least one respective gate criteria includes a subject gate criterion associated with an approval, from the subject, of the first selection.

In some embodiments, the at least one respective gate criteria includes an arrangement gate criterion associated with an order of one or more nodes in the enumerated plurality of nodes. In some embodiments, the enumerated plurality of nodes consists of about 3, 5, 7, 10, 12, 15, or 20 nodes.

In some embodiments, the corresponding unique digital reality scene is a virtual reality scene. Moreover, in some embodiments, the corresponding unique digital reality scene is an augmented reality scene. Furthermore, in some embodiments, the corresponding unique digital reality scene is a panoramic video, a spherical video, or an omnidirectional video.

In some embodiments, the first digital reality scene is a virtual reality scene and the corresponding unique digital reality scene is a panoramic video, a spherical video, or an omnidirectional video.

In some embodiments, the corresponding unique digital reality scene is an augmented reality scene.

In some embodiments, the first digital reality scene is a virtual reality scene and the corresponding unique digital reality scene is an augmented reality scene.

Continuing with the disclosed method, a selection of a first node in the enumerated plurality of nodes is detected.

Continuing with the disclosed method, the first node is placed at a first location in the first area, thereby providing access to the corresponding plurality of proposed experiences associated with the respective category and improving the ability of the subject to manage the psychiatric or mental condition using the respective interactive digital chart.

In some embodiments, responsive to detection of the selection of the first node, the first node is moved from an initial location in the second affordance region to a second location other than the first location.

In some embodiments, a determination is made as to whether the selection of the first node satisfies each gate criterion in the at least one respective gate criteria associated with the first node prior to the placing of the first node.

In some embodiments, the determining if the selection of the first node satisfies each gate criterion is performed by one or more models in a plurality of models.

In some embodiments, the plurality of models includes an unsupervised model and/or a supervised model.

In some embodiments, the plurality of models includes a logistic regression model, a neural network model, a support vector machine model, a Naive Bayes model, a nearest neighbor model, a random forest model, a decision tree model, a boosted trees model, a multinomial logistic regression model, a linear model, a linear regression model, a GradientBoosting model, a mixture model, a hidden Markov model, a Gaussian model, a linear discriminant model, or any combinations thereof.

In some embodiments, the at least one respective gate criterion indicates an order of the first node in the plurality of nodes. Each proposed experience associated with the first node has a gate criterion (e.g., an eye contact, utterance, decibel, pitch, sentiment analysis, medical practitioner scene-approval criterion, or any combination thereof).

In some embodiments, the detecting and placing processes are repeated for successive nodes to select successive nodes for a graph.

In some embodiments, each node in the graph is connected by an edge in a plurality of edges to another node in the graph. Each edge represents a progression within the graph between an initial node and a subsequent node upon successful completion by the subject of the corresponding challenges associated with the respective initial node.

In some embodiments, the progression within the graph is upon successful completion by the subject of the corresponding challenge associated with the respective node.

In some embodiments, the respective category corresponding to the first (initial) node is least challenging for the subject, and the respective category corresponding to the last node is more challenging for subject than the first node.

In some embodiments, the first node is activated to allow the subject to access the respective category corresponding to the first node while the remaining node(s) are locked to prevent access.

In some embodiments, the first node activated allows access to unique mindfulness session(s) and/or cognitive reframing session(s) customized for the respective category of the first node, universal mindfulness session(s) and/or cognitive reframing session(s), or any combination thereof.

In some embodiments, if the at least one respective gate criterion for the second node is satisfied, a second node is activated to allow the subject to access the respective category corresponding to the second node.

In some embodiments, the at least one respective gate criterion indicates one order of the first node in the nodes. Moreover, each proposed experience associated with the first node has a gate criterion (e.g., an eye contact, utterance, decibel, pitch, sentiment analysis, medical practitioner scene-approval criterion, or any combination thereof).

In some embodiments, the activated the second node allows access to unique mindfulness session(s) and/or unique cognitive reframing session(s) customized for respective category of the second node, universal mindfulness session(s) and/or cognitive reframing session(s), or any combination thereof.

In some embodiments, for a node, the corresponding plurality of proposed experiences adjacent to the node are displayed.

Each experience is represented by an experience graphic in a plurality of experience graphics. Each experience graphic in the plurality of experience graphics is connected to the corresponding node by a branch in a plurality of branches.

In some embodiments, there is displayed within the first area, each respective gate criterion associated with each respective node in the subset of nodes.

In some embodiments, there is displayed within the first area, each respective gate criterion associated with each respective node in the graph. A gate criterion associated with a node in the graph specifies a condition to be satisfied prior to advancement to another node. There is displayed within the first area a completion status of each respective gate criterion associated with each node in the graph.

In some embodiments, the processor(s) are used to poll for satisfaction of a gate criterion and update, within the first area, a completion status of the gate criterion associated with a node in the graph when the polling determines that the gate criterion has been satisfied.

In some embodiments, the graph is populated with one or more landmarks/landscapes (e.g., house, a tree, a creek, a pond, a bridge, a hill, a park, etc., or any combination thereof).

In some embodiments, at least one respective gate criterion of each node in the graph is used to determine a placement of each edge.

In some embodiments, a gate criterion associated with one node specifies a condition to be satisfied prior to node advancement. In some such embodiments, a gate criterion of a node is set by a system administrator, the subject, a medical practitioner associated with the subject, or a combination thereof. In some embodiments, a respective gate criteria of a first node in the graph is set by a system administrator or a medical practitioner associated with the subject, and a respective gate criterion of a second node in the graph is set by the subject.

In some embodiments, a respective gate criterion of a node is a length of eye contact with a portion of the corresponding unique digital reality scene associated with a corresponding challenge of a proposed experience in the corresponding plurality of proposed experiences of another node.

In some embodiments, a respective gate criterion of node is an assertiveness, decibel level and/or a pitch of one or more utterances by the subject during a corresponding challenge of a proposed experience of another node.

In some embodiments, a respective gate criterion of node is a number of utterances by the subject during a corresponding challenge of a proposed experience of another node.

In some embodiments, a respective gate criterion of node is a number of words spoken by the subject during a corresponding challenge of a proposed experience of another node.

In some embodiments, a respective gate criterion is a period of time by the subject in the corresponding unique digital reality scene during a corresponding challenge of a proposed experience in the corresponding plurality of proposed experiences of another node in the graph.

In some embodiments, a respective gate criterion is a threshold subjective score for a performance of the subject provided by the subject.

In some embodiments, a respective gate criterion is a threshold number of instances by the subject in the corresponding unique digital reality scene.

In some embodiments, a gate criterion of a first node in the graph is a satisfaction or failure to satisfy a sentiment analysis criterion by the subject during a challenge of a proposed experience in the plurality of proposed experiences of another node in the graph. In some such embodiments, a determination is made as to whether the sentiment analysis criterion is satisfied or not by taking a cosine similarity measure or dot product of one or more utterances of the subject, made during the corresponding challenge, against each statement in a list of statements that are characteristic of a predetermined sentiment. In some such embodiments, the sentiment is amusement, anger, anxiety, awkwardness, boredom, calmness, confusion, craving, disgust, empathetic pain, entrancement, excitement, fear, horror, interest, joy, annoyance, nostalgia, relief, sadness, satisfaction, or surprise.

In some embodiments, a node is added that has not previously been selected in an instance of the detecting responsive to a selection of a node that has been selected in an instance of the detecting in order to add or remove an availability of a category in the plurality of categories to the plurality of nodes.

In some embodiments, a node in the enumerated plurality of nodes is associated with at least one unique mindfulness session customized for the respective category of the respective node.

In some embodiments, the plurality of nodes is associated with at least one universal mindfulness session accessible from each node in the plurality of nodes.

In some embodiments, a respective node in the enumerated plurality of nodes is associated with at least one unique cognitive reframing session customized for the respective category of the respective node.

In some embodiments, each respective node in the enumerated plurality of nodes is associated with at least one unique cognitive reframing session customized for the respective category of the respective node.

In some embodiments, the enumerated plurality of nodes is associated with at least one universal cognitive reframing session that is accessible from each node in the enumerated plurality of nodes.

In some embodiments, for a respective node in the enumerated plurality of nodes, the method further includes displaying the corresponding plurality of proposed experiences. Each proposed experience in the corresponding plurality of proposed experiences is represented by a corresponding experience graphic in a plurality of experience graphics.

In some embodiments, the placing the first node provides access to the corresponding plurality of proposed experiences through a second digital reality scene different than the first digital reality scene and the corresponding unique digital reality scene.

In some embodiments, the second digital reality scene is configured as a portal scene configured to allow the subject to select a respective proposed experience from the corresponding plurality of proposed experiences.

Yet another aspect of the present disclosure is directed to providing a computer system for preparing a regimen for improving an ability of a subject to manage a psychiatric or mental condition exhibited by the subject. The computer system includes one or more processors, a display, and a memory coupled to the one or more processors. The memory includes one or more programs, configured to be executed by the one or more processors, that implement a method. The method includes presenting, on the display, a first digital reality scene including a respective interactive digital chart and a corresponding interactive digital bin, where the respective interactive digital chart consumes a first affordance region, the respective interactive digital chart including a first area and the corresponding interactive digital bin consumes a second affordance region different than the first affordance region, the corresponding interactive digital bin including an enumerated plurality of nodes. Each respective node in the enumerated plurality of nodes (i) corresponds to a respective category in a plurality of categories, (ii) is associated with a corresponding plurality of proposed experiences associated with the respective category, in which each respective proposed experience in the corresponding plurality of proposed experiences is associated with a corresponding unique digital reality scene, different than the first digital reality scene, that manifests a corresponding challenge represented by the respective category and/or the respective proposed experience, and (iii) is associated with at least one respective gate criterion in a plurality of gate criteria. Each respective category in the plurality of categories is directed to improving an ability of the subject to manage a psychiatric or mental condition of the subject. A selection of a first node in the enumerated plurality of nodes is selected and placed at a first location in the first area, thereby providing access to the corresponding plurality of proposed experiences associated with the respective category and improving the ability of the subject to manage the psychiatric or mental condition using the respective interactive digital chart.

Yet another aspect of the present disclosure is directed to providing non-transitory computer readable storage medium storing one or more programs. The one or more programs includes instructions, which when executed by a computer system cause the computers system to perform a method. The method includes presenting, on the display, a first digital reality scene including a respective interactive digital chart and a corresponding interactive digital bin, where the respective interactive digital chart consumes a first affordance region, the respective interactive digital chart including a first area and the corresponding interactive digital bin consumes a second affordance region different than the first affordance region, the corresponding interactive digital bin including an enumerated plurality of nodes. Each respective node in the enumerated plurality of nodes (i) corresponds to a respective category in a plurality of categories, (ii) is associated with a corresponding plurality of proposed experiences associated with the respective category, in which each respective proposed experience in the corresponding plurality of proposed experiences is associated with a corresponding unique digital reality scene, different than the first digital reality scene, that manifests a corresponding challenge represented by the respective category and/or the respective proposed experience, and (iii) is associated with at least one respective gate criterion in a plurality of gate criteria. Each respective category in the plurality of categories is directed to improving an ability of the subject to manage a psychiatric or mental condition of the subject. A selection of a first node in the enumerated plurality of nodes is selected and placed at a first location in the first area, thereby providing access to the corresponding plurality of proposed experiences associated with the respective category and improving the ability of the subject to manage the psychiatric or mental condition using the respective interactive digital chart. The systems and methods of the present disclosure have other features and advantages which will be apparent from or are set forth in more detail in the accompanying drawings, which are incorporated herein, and the following Detailed Description, which together serve to explain certain principles of the present invention.

Yet another aspect of the present disclosure is directed to providing a use of a computer system for improving an ability of a subject to manage a psychiatric or mental condition exhibited by the subject. The computer system includes one or more processors, a display, and a memory coupled to the one or more processors. The memory includes one or more programs, configured to be executed by the one or more processors, that implement a method. The method includes presenting, on the display, a first digital reality scene includes a respective interactive digital chart and a corresponding interactive digital bin, where the respective interactive digital chart consumes a first affordance region, the respective interactive digital chart including a first area and the corresponding interactive digital bin consumes a second affordance region different than the first affordance region, the corresponding interactive digital bin including an enumerated plurality of nodes. Each respective node in the enumerated plurality of nodes (i) corresponds to a respective category in a plurality of categories, (ii) is associated with a corresponding plurality of proposed experiences associated with the respective category, in which each respective proposed experience in the corresponding plurality of proposed experiences is associated with a corresponding unique digital reality scene, different than the first digital reality scene, that manifests a corresponding challenge represented by the respective category and/or the respective proposed experience, and (iii) is associated with at least one respective gate criterion in a plurality of gate criteria. Each respective category in the plurality of categories is directed to improving an ability of the subject to manage a psychiatric or mental condition of the subject. A selection of a first node in the enumerated plurality of nodes is selected and placed at a first location in the first area, thereby providing access to the corresponding plurality of proposed experiences associated with the respective category and improving the ability of the subject to manage the psychiatric or mental condition using the respective interactive digital chart.

BRIEF DESCRIPTION OF THE DRAWINGS

FIG. 4 is a flow chart illustrating exemplary methods for preparing a regimen for improving an ability of a subject to manage a psychiatric or mental condition exhibited by the subject, in accordance with some embodiments of the present disclosure.

FIGS. 7A, 7B, 7C, 7D, 7E, 7F, 7G, 7H, 7I, 7J, 7K, 7L and 7M collectively illustrate user interfaces (e.g., user interfaces 700-1, 700-2, . . . , 700-13) for presenting an exemplary interactive digital chart and an exemplary interactive digital bin, in accordance with some embodiments of the present disclosure.

FIGS. 9A and 9B collectively illustrate user interfaces for presenting a client application that facilitates providing an overview of a progress for improving an ability of the subject to manage a psychiatric or mental condition exhibited by the subject, in accordance with an embodiment of the present disclosure.

FIG. 9D illustrates a user interface for presenting a client application that facilitates controlling a gate criteria for a node of a respective interactive digital chart of a subject, in accordance with an embodiment of the present disclosure.

FIG. 15 illustrates exemplary logical functions that are used implemented in various embodiments of the present disclosure.

Figure 1:
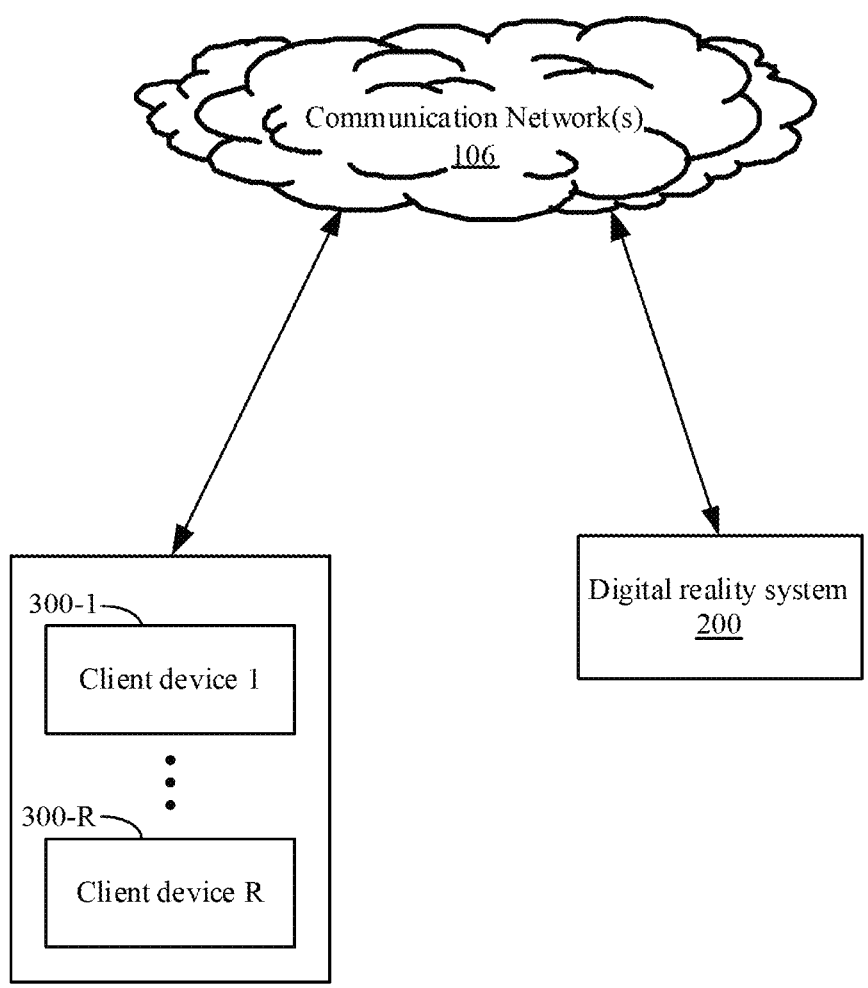
FIG. 1 illustrates a block diagram illustrating an embodiment of a system for displaying a digital reality scene, in accordance with an embodiment of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

The present disclosure provides systems and methods for preparing a regimen for improving an ability of a subject to manage a psychiatric or mental condition. A first digital reality scene including a respective interactive digital chart and a corresponding interactive digital bin is displayed. The respective interactive digital chart consumes a first affordance region, which allows the respective interactive digital chart to be interacted with and/or visualized within the first affordance region. In some embodiments, the corresponding interactive digital bin consumes a second affordance region. Furthermore, the corresponding interactive digital bin includes an enumerated plurality of nodes, which provides for a limited universe of nodes. Each respective node in the enumerated plurality of nodes corresponds to a respective category in a plurality of categories. Moreover, each respective node in the enumerated plurality of nodes is also associated with a corresponding plurality of proposed experiences associated with the respective category. Each respective proposed experience in the corresponding plurality of proposed experiences is associated with a corresponding unique digital reality scene, which is different than the first digital reality scene. This corresponding unique digital reality scene manifests a corresponding challenge represented by the respective category and/or the respective proposed experience. Accordingly, in some embodiments, the corresponding unique digital reality scene and the first digital reality scene are distinct digital reality scenes, which aids in manifesting the corresponding challenge in an efficacious manner for the subject. Each respective node in the enumerated plurality of nodes is further associated with at least one respective gate criterion in a plurality of gate criteria. In some embodiments, the at least one respective gate criterion is configured as response the corresponding challenge is configured to elicit from the subject, such as a positive sentiment analysis criterion by the subject during the corresponding challenge. Accordingly, each respective category in the plurality of categories is directed to improving an ability of the subject to manage a psychiatric or mental condition of the subject. A selection of a first node is detected. For instance, in some embodiments, the first node is selected by the subject within the first digital reality scene. The first node is placed at a first location in the first area to provide access to the corresponding plurality of proposed experiences associated with the respective category and improve the ability of the subject to manage the psychiatric or mental condition.

In some embodiments, an assessment of the subject is obtained. For instance, in some embodiments, the assessment of the subject is obtained in electronic form when the first digital reality scene is presented to the subject. In other embodiments, the assessment is obtained prior to the first digital reality scene being presented to the subject. The assessment includes an identification of each category in the plurality of categories.

In some embodiments, the first node is placed if it is determined that the selection of the first node satisfies each gate criterion in the at least one respective gate criteria associated with the first node prior to the placing of the first node. In some embodiments, this determination if the selection of the first node satisfies each gate criterion is performed by one or more models and/or a medical practitioner associated with the subject.

In some embodiments, the subject is allowed to reorder the plurality of nodes, such as placing the enumerated plurality of nodes in the interactive digital chart based on the levels of the social challenges of the proposed experiences associated with each respective category. For instance, in some embodiments, the subject is guided to place a first node, which corresponds to a category having proposed experiences that the subject considers least challenging, in a first area of the interactive digital chart. After the placement of the first node, the subject is guided to place a second node, which corresponds to a category having proposed experiences that the subject considers least challenging among the remaining node or node(s), in a second area of the interactive digital chart. This process is repeated until all of the plurality of nodes is placed in the interactive digital chart. In some embodiments, the hierarchically arranged nodes collectively form a category progression. In some embodiments, the plurality of nodes is connected to each other by one or more edges, thereby forming a journey map that can be populated with landmarks and/or landscapes and/or can be animated.

In some embodiments, a respective node in the enumerated plurality of nodes is associated with at least one educational or therapeutical session. The at least one educational or therapeutical session can be a unique session that is specifically customized for the respective category of the respective node. The at least one educational or therapeutical session can also be a general session that is configured for multiple categories and accessible from multiple nodes. In some embodiments, the at least one educational or therapeutical session includes a unique mindfulness session customized for the respective category of the respective node, a unique cognitive reframing session customized for the respective category of the respective node, a universal mindfulness session that is accessible from each node in the enumerated plurality of nodes, and a universal cognitive reframing session that is accessible from each node in the enumerated plurality of nodes.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, and components have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For instance, a first digital chart could be termed a second digital chart, and, similarly, a second digital chart could be termed a first digital chart, without departing from the scope of the present disclosure. The first digital chart and the second digital chart are both digital charts, but they are not the same digital chart.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The foregoing description included example systems, methods, techniques, instruction sequences, and computing machine program products that embody illustrative implementations. For purposes of explanation, numerous specific details are set forth in order to provide an understanding of various implementations of the inventive subject matter. It will be evident, however, to those skilled in the art that implementations of the inventive subject matter may be practiced without these specific details. In general, well-known instruction instances, protocols, structures, and techniques have not been shown in detail.

The foregoing description, for purpose of explanation, has been described with reference to specific implementations. However, the illustrative discussions below are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of ±20%, ±10%, ±5%, or ±1% of a given value. Where particular values are described in the application and claims, unless otherwise stated, the term "about" means within an acceptable error range for the particular value. The term "about" can have the meaning as commonly understood by one of ordinary skill in the art. The term "about" can refer to ±10%. The term "about" can refer to ±5%.

As used herein, the term "equally spaced" means that a distance from a first feature to a corresponding second feature is the same for successive pairs of features unless expressly stated otherwise.

As used herein, the term "dynamically" means an ability to update a program while the program is currently running.

Additionally, the terms "client," "patient," "subject," and "user" are used interchangeably herein unless expressly stated otherwise.

Moreover, the terms "avatar" and "player character" are used interchangeably herein unless expressly stated otherwise.

In addition, the terms "therapy" and "treatment" are used interchangeably herein unless expressly stated otherwise.

Moreover, as used herein, the term "parameter" refers to any coefficient or, similarly, any value of an internal or external element (e.g., a weight and/or a hyperparameter) in an algorithm, model, regressor, and/or classifier that can affect (e.g., modify, tailor, and/or adjust) one or more inputs, outputs, and/or functions in the algorithm, model, regressor and/or classifier. For example, in some embodiments, a parameter refers to any coefficient, weight, and/or hyperparameter that can be used to control, modify, tailor, and/or adjust the behavior, learning, and/or performance of an algorithm, model, regressor, and/or classifier. In some instances, a parameter is used to increase or decrease the influence of an input (e.g., a feature) to an algorithm, model, regressor, and/or classifier. As a nonlimiting example, in some embodiments, a parameter is used to increase or decrease the influence of a node (e.g., of a neural network), where the node includes one or more activation functions. Assignment of parameters to specific inputs, outputs, and/or functions is not limited to any one paradigm for a given algorithm, model, regressor, and/or classifier but can be used in any suitable algorithm, model, regressor, and/or classifier architecture for a desired performance. In some embodiments, a parameter has a fixed value. In some embodiments, a value of a parameter is manually and/or automatically adjustable. In some embodiments, a value of a parameter is modified by a validation and/or training process for an algorithm, model, regressor, and/or classifier (e.g., by error minimization and/or backpropagation methods). In some embodiments, an algorithm, model, regressor, and/or classifier of the present disclosure includes a plurality of parameters. In some embodiments, the plurality of parameters is n parameters, where: $n \geq 2$; $n \geq 5$; $n \geq 10$; $n \geq 25$; $n \geq 40$; $n \geq 50$; $n \geq 75$; $n \geq 100$; $n \geq 125$; $n \geq 150$; $n \geq 200$; $n \geq 225$; $n \geq 250$; $n \geq 350$; $n \geq 500$; $n \geq 600$; $n \geq 750$; $n \geq 1,000$; $n \geq 2,000$; $n \geq 4,000$; $n \geq 5,000$; $n \geq 7,500$; $n \geq 10,000$; $n \geq 20,000$; $n \geq 40,000$; $n \geq 75,000$; $n \geq 100,000$; $n \geq 200,000$; $n \geq 500,000$, $n \geq 1 \times 10^6$, $n \geq 5 \times 10^6$, or $n \geq 1 \times 10^7$. In some embodiments, n is between 10,000 and $1 \times 10^7$, between 100,000 and $5 \times 10^6$, or between 500,000 and $1 \times 10^6$. As such, the algorithms, models, regressors, and/or classifiers of the present disclosure cannot be mentally performed. In some embodiments, n is between 10,000 and $1 \times 10^7$, between 100,000 and $5 \times 10^6$, or between 500,000 and $1 \times 10^6$. In some embodiments, the algorithms, models, regressors, and/or classifier of the present disclosure operate in a k-dimensional space, where k is a positive integer of 5 or greater (e.g., 5, 6, 7, 8, 9, 10, etc.). As such, the algorithms, models, regressors, and/or classifiers of the present disclosure cannot be mentally performed.

Furthermore, when a reference number is given an "$i^{th}$" denotation, the reference number refers to a generic component, set, or embodiment. For instance, a digital reality scene termed "digital reality scene i" refers to the $i^{th}$ digital reality scene in a plurality of digital reality scenes (e.g., a digital reality scene 40-i in a plurality of digital reality scenes 40).

In the present disclosure, unless expressly stated otherwise, descriptions of devices and systems will include implementations of one or more computers. For instance, and for purposes of illustration in FIG. 1, a client device 300 is represented as single device that includes all the functionality of the client device 300. However, the present disclosure is not limited thereto. For instance, the functionality of the client device 300 may be spread across any number of networked computers and/or reside on each of several networked computers and/or by hosted on one or more virtual machines and/or containers at a remote location accessible across a communications network (e.g., communications network 106). One of skill in the art will appreciate that a wide array of different computer topologies is possible for the client device 300, and other devices and systems of the preset disclosure, and that all such topologies are within the scope of the present disclosure.

FIG. 1 depicts a block diagram of a distributed client-server system (e.g., distributed client-server system 100) according to some embodiments of the present disclosure. The system 100 facilitates preparing a regimen for improving an ability of a subject to manage a psychiatric or mental condition, such as a clinically diagnosed mental disorder, a sub-clinically diagnosed medical disorder, or a subject that has not been diagnosed by a medical practitioner. The system 100 facilitates obtaining an assessment that includes an identification of a plurality of categories from a subject (e.g., obtained through user interface 800-1 of FIG. 8A, obtained through user interface 800-2 of FIG. 8B, obtained through user interface 800-3 of FIG. 8C, etc.) such as a user of a client device (e.g., client device 300-1 of FIG. 3). Each category in the plurality of categories includes or is associated with a plurality of proposed experiences. Each respective proposed experience in the plurality of proposed experiences represents a corresponding challenge that is associated with improving an ability of the subject to manage a psychiatric or mental condition. Accordingly, a first digital reality scene including a respective interactive digital chart and a corresponding interactive digital bin is displayed. The respective interactive digital chart consumes a first affordance region. The corresponding interactive digital bin consumes a second affordance region and includes an enumerated plurality of nodes. Each respective node corresponds to a respective category in the plurality of categories. Each respective node is also associated with a corresponding plurality of proposed experiences associated with the respective category. Each respective proposed experience is associated with a corresponding unique digital reality scene, different than the first digital reality scene, that manifests the corresponding challenge represented by the respective category and/or the respective proposed experience. Each respective node is further associated with at least one respective gate criteria in a plurality of gate criteria. Each respective category in the plurality of categories is directed to improving an ability of the subject to manage a psychiatric or mental condition of the subject. A selection of a first node is detected. If the selection of the first node satisfies each gate criterion associated with the first node is determined. The first node is placed, (optionally when each gate criterion is satisfied), at a first location in the first area to provide access to the corresponding unique digital reality scene and improve the ability of the subject to manage the psychiatric or mental condition.

Figure 8B:
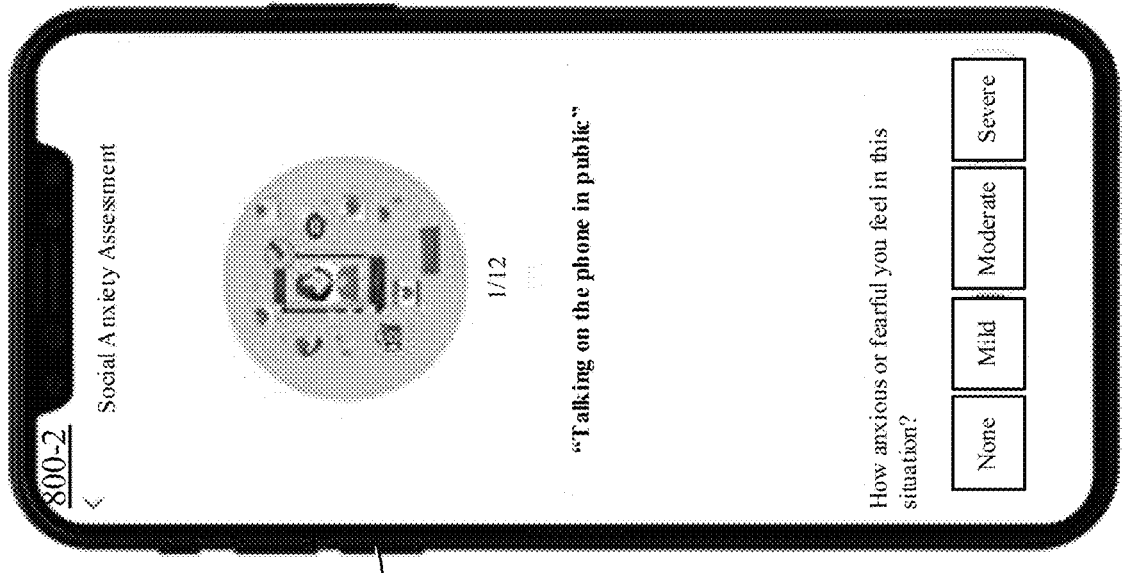
FIGS. 8A, 8B, and 8C collectively illustrate user interfaces for presenting obtaining an assessment of a subject at a client device, in accordance with an embodiment of the present disclosure.
Figure 8A:
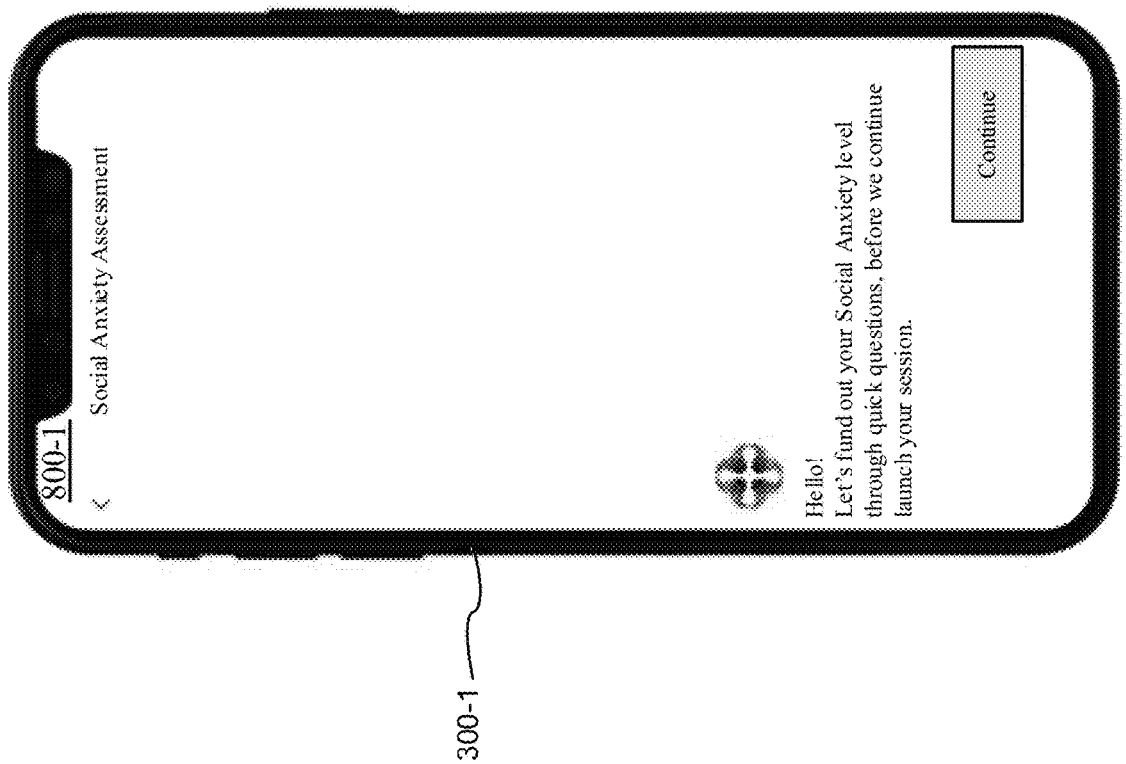
Figures 8C, 8D:
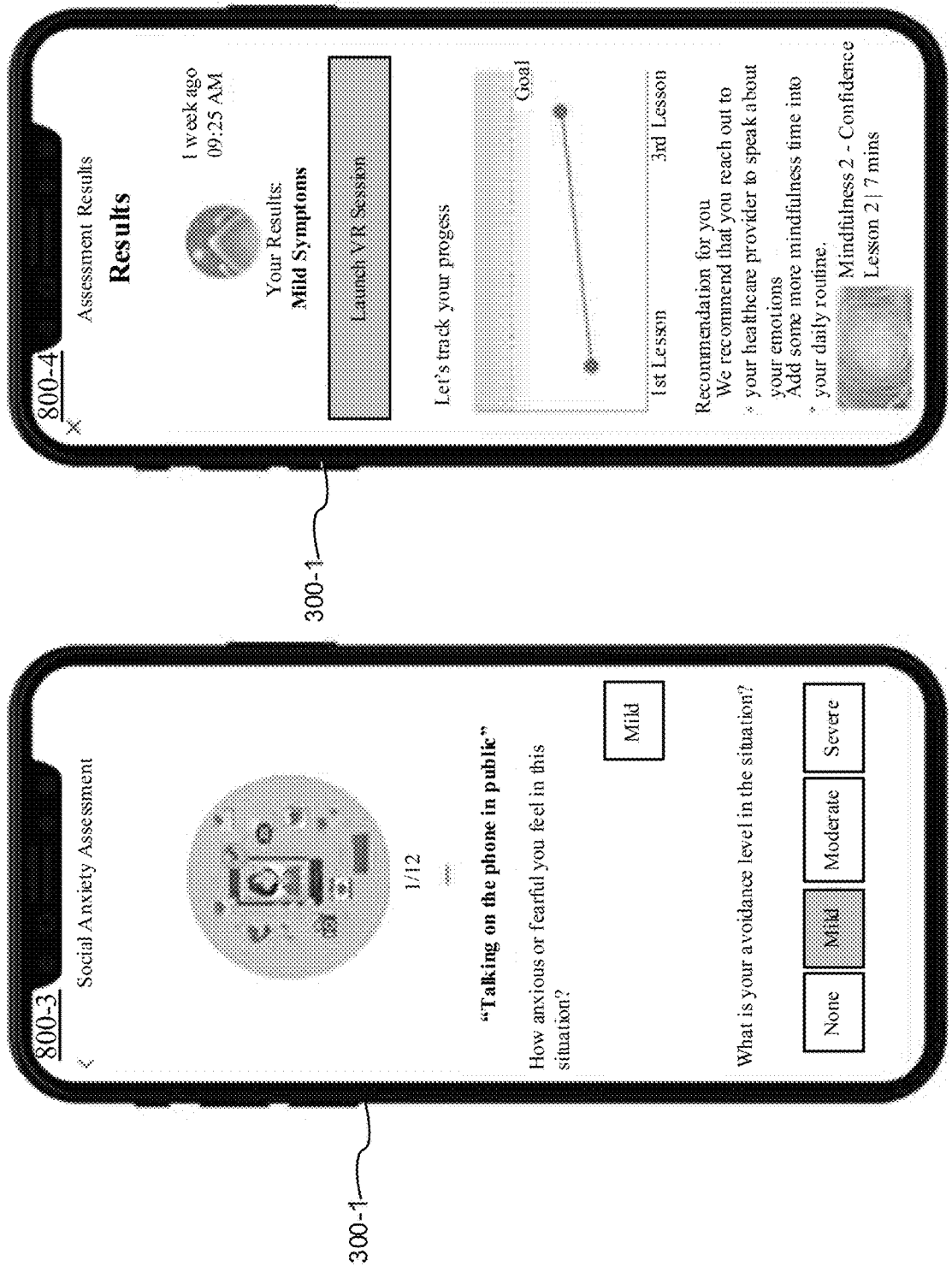
FIG. 8D illustrates a user interface for presenting a client application that facilitates improving an ability of a subject to manage a psychiatric or mental condition exhibited by the subject through a digital reality scene in accordance with an embodiment of the present disclosure.
Figure 9A:
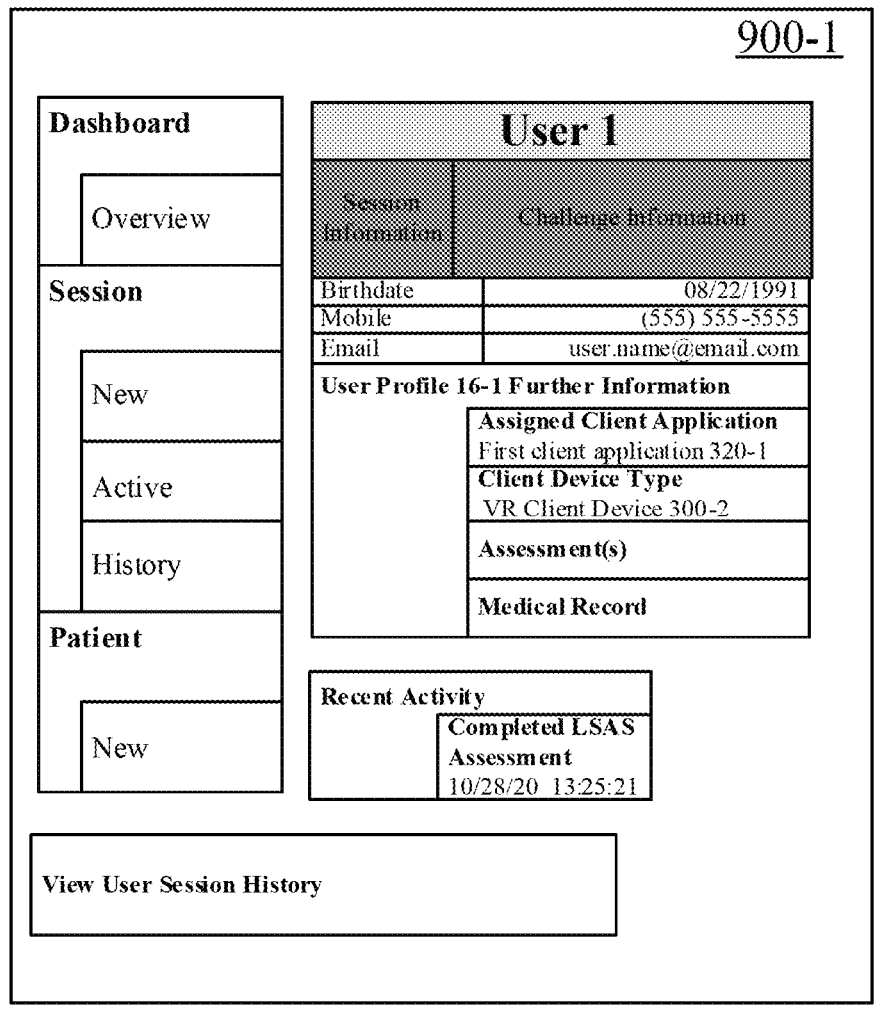

The system 100 facilitates providing a regimen (e.g., first regimen 20-1 of FIG. 2A) for a population of subjects (e.g., client devices 300), in which the population of subjects includes a subject that exhibits a psychiatric or mental condition. In some embodiments, the regimen 20 is prepared at a digital reality system (e.g., digital reality system 200 of FIGS. 2A and 2B) and then the regimen is provided to a subject through a graphical user interface (GUI) (e.g., user interface 374 of FIG. 3) that is displayed through a display of a respective client device 300 (e.g., display 376 of FIG. 3). However, the present disclosure is not limited thereto. For instance, referring briefly to FIG. 9D, in some embodiments, a medical practitioner (e.g., clinician) associated with a subject prepares the regimen 20 at a first client device (e.g., client device 300-1 of FIG. 8D) and the subject performs the regimen at a second client device 300-2. A digital reality scene (e.g., digital reality scene 40 of FIG. 2B), in such a context, broadly means any space (e.g., digital space and/or real-world space) where digital reality content (e.g., an avatar, a digital reality object, etc.) is presented to a user through a display (e.g., display 308 client device 300-1 of FIG. 3). For example, in some embodiments, a digital reality scene 40 includes an avatar creation client application, a video game, a social networking website or forum, a messaging client application, or any other application (e.g., client application 320 of FIG. 3) where a user wants to have a digital representation.

Of course, other topologies of the system 100 are possible. For instance, in some embodiments, any of the illustrated devices and systems can in fact constitute several computer systems that are linked together in a network or be a virtual machine and/or container in a cloud-computing environment. Moreover, rather than relying on a physical communications network 106, the illustrated devices and systems may wirelessly transmit information between each other. As such, the exemplary topology shown in FIG. 1 merely serves to describe the features of an embodiment of the present disclosure in a manner that will be readily understood to one of skill in the art.

Referring to FIG. 1, in some embodiments, a distributed client-server system 100 includes a digital reality system 200 that facilitates providing a digital reality scene 40 for one or more client devices 300 (e.g., a first client device 300-1, a second client device 300-2, . . . , a $R^{th}$ client device 300-R, etc.), hereinafter "client device," each of which is associated with at least one corresponding subject (e.g., a user of a digital reality scene provided by a digital reality system 200 etc.).

In some embodiments, the communication network 106 optionally includes the Internet, one or more local area networks (LANs), one or more wide area networks (WANs), other types of networks, or a combination of such networks.

Examples of communication networks 106 include the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Now that a distributed client-server system 100 has generally been described, an exemplary digital reality system 200 for preparing a regimen for improving an ability of a subject to manage a psychiatric or mental condition that is exhibited by the subject will be described with reference to FIGS. 2A and 2B.

In various embodiments, the digital reality system 200 includes one or more processing units (CPUs) 202, a network or other communications interface 204, and memory 212.

Memory 212 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. Memory 212 may optionally include one or more storage devices remotely located from the CPU(s) 202. Memory 212, or alternatively the non-volatile memory device(s) within memory 212, includes a non-transitory computer readable storage medium. Access to memory 212 by other components of the digital reality system 200, such as the CPU(s) 202, is, optionally, controlled by a controller. In some embodiments, memory 212 can include mass storage that is remotely located with respect to the CPU(s) 202. In other words, some data stored in memory 212 may in fact be hosted on devices that are external to the digital reality system 200, but that can be electronically accessed by the digital reality system 200 over an Internet, intranet, or other form of network 106 or electronic cable using communication interface 204.

Figure 2A:
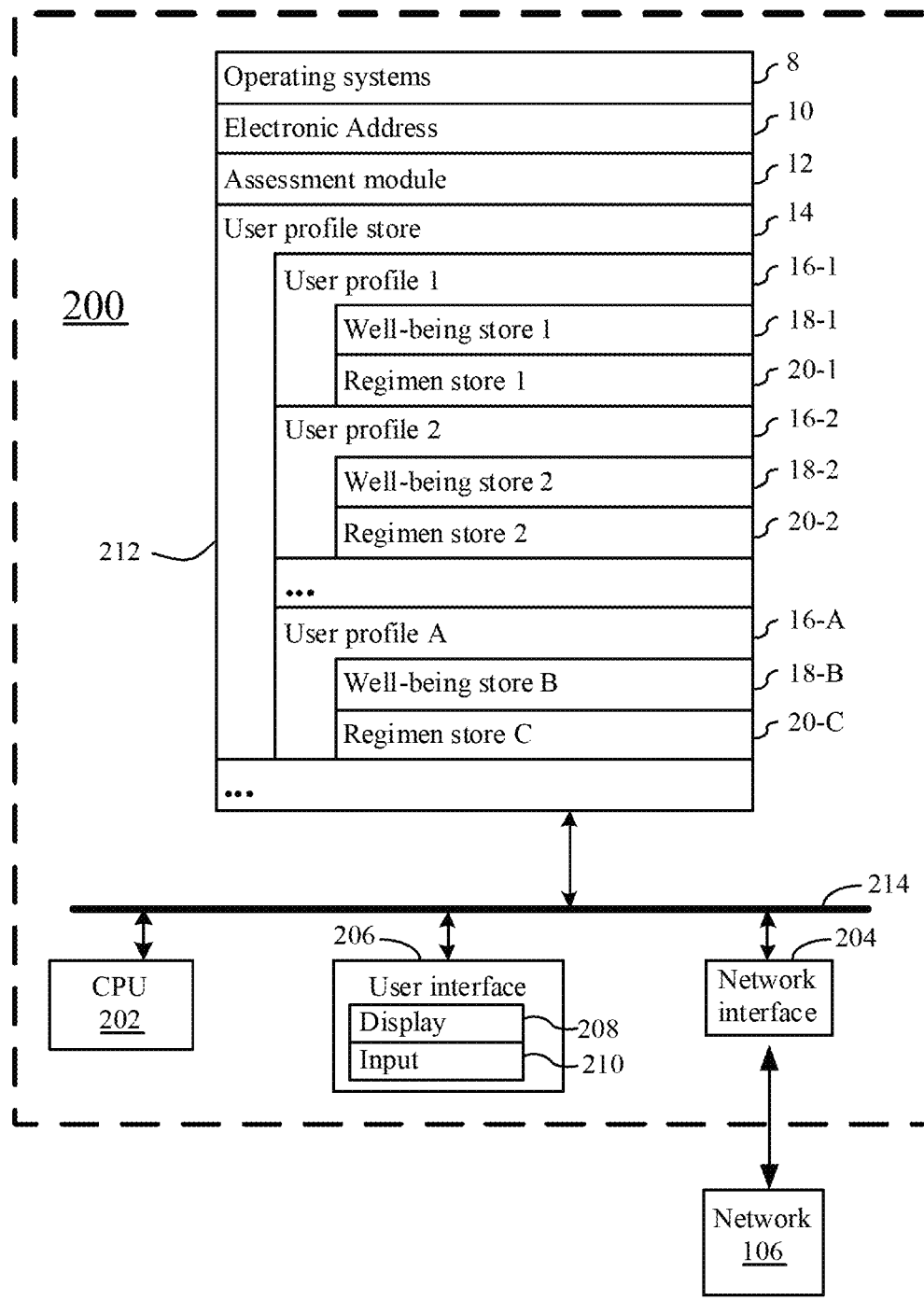
FIGS. 2A and 2B collectively illustrate a digital reality host system for facilitating a digital reality experience, in accordance with an embodiment of the present disclosure.
Figure 2B:
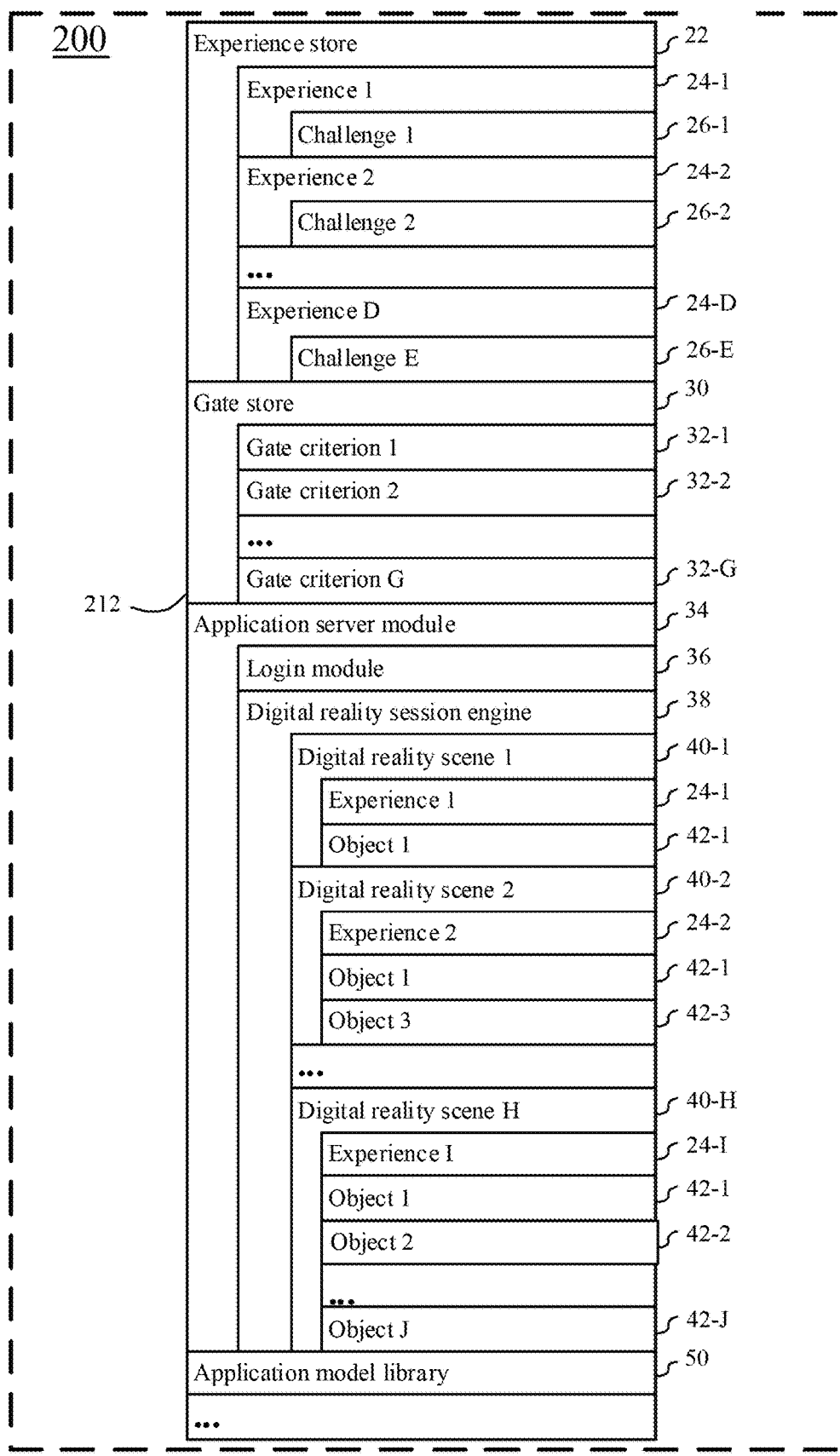

In some embodiments, the memory 212 of the digital reality system 200 for preparing a regimen for improving an ability of a subject to manage a psychiatric or mental condition exhibited by the subject stores:

an operating system 8 (e.g., ANDROID, iOS, DARWIN, RTXC, LINUX, UNIX, OS X, WINDOWS, or an embedded operating system such as VxWorks) that includes procedures for handling various basic system services;

an electronic address 10 associated with the digital reality system 200 that identifies the digital reality system 200;

an optional assessment module 12 for obtaining an assessment of a subject that, for instance, provides an identification of a plurality of proposed experiences through the assessment;

a user profile store 14 for retaining information associated with a population of users (e.g., user of client devices 300 of FIG. 1), including a user profile 16 for each user in the population of users (e.g., user 1, user 2, . . . , user 6 of FIG. 9B), the user profile 16 including a corresponding well-being store 18 and a regimen store 20 associated with a subject of the user profile 16;

an experience store 22 including a plurality of experiences (e.g., first experience 24-1, second experience 24-2, . . . experience 24-I of FIG. 2B), each experience 24 including a corresponding challenge 26;

a gate store 30 including a plurality of gate criteria (e.g., first gate criterion 32-1, second gate criterion 32-2, . . . , gate criterion G 32-G of FIG. 2B), each gate criterion 32 representing a condition, for instance, for user engagement;

an application server module 34 that facilitates providing a plurality of digital reality scenes 40 to a population of client devices 300, the application server module 34 including a login module 36 for accesses a digital reality scene 40 and a digital reality session engine 38 that facilitates providing a plurality of digital reality scenes (e.g., first digital reality scene 40-1, second digital reality scene 40-2, . . . , digital reality scene H 40-H of FIG. 2B) for a population of users (e.g., client devices 300); and an application model library 50 that retains one or more models for providing an evaluation of a characteristic of a respective input, such as providing a first evaluation of whether completion of a corresponding challenge 26 satisfies one or more corresponding gate criteria 32.

An electronic address 10 is associated with the digital reality system 200. The electronic address 10 is utilized to at least uniquely identify the digital reality system 200 from other devices and components of the distributed system 100 (e.g., uniquely identify digital reality system 200 from second client device 300-2 and third client device 300-3 of FIG. 9C). For instance, in some embodiments, the electronic address 10 is utilized to receive a request from a client device 300 to participate in a respective digital reality scene via login module 36 of an application server module 34.

In some embodiments, an assessment module 12 facilitates obtaining an assessment from a subject (e.g., initial assessment of FIG. 6B, block 404 of FIG. 4, social anxiety assessment of FIGS. 8A through 9C, etc.), such as a user of a respective client device 300 or a medical practitioner associated with the user. In some embodiments, the assessment module 12 includes one or more assessments that is communicated to the respective client device 300 (e.g., via communications network 106 of FIG. 1). In some embodiments, the assessment model includes 3 or more assessments, 5 or more assessments, 8 or more assessments, 12 or more assessments, 15 or more assessments, 20 or more assessments, 30 or more assessments, 45 or more assessments, or 75 or more assessments. Moreover, in some embodiments, the assessment module 12 stores a standardized assessment that is provided to each subject. The standardized assessment provides a uniform assessment to each subject. By utilizing a standardized assessment, the assessments obtained from multiple users can be normalized in order to optimize identification a plurality of proposed experiences (e.g., experiences 24 of experience store 22 of FIG. 2B) between different users. However, the present disclosure is not limited thereto.

In some embodiments, the assessment includes a plurality of prompts that is answered by a subject. Through the answers to the plurality of prompts provided by the subject, an identification of a plurality of proposed experiences is obtained from the subject. For instance, referring briefly to FIG. 8B, an assessment for a social anxiety psychiatric or medical condition includes a prompt asking a user of a first client 300-1 "How anxious or fearful [the subject feels" in this situation?" Here, the user is provided with a selection of four predetermined answers (e.g., none, mild, moderate, or severe), and a user selection of a first answer from the group consisting of the four predetermined answers forms the basis for the identification of the plurality of proposed experiences 24.

In some embodiments, the assessment module 12 includes one or more authorization criteria that is associated with approving an assessment obtained from a subject. For instance, in some embodiments, the assessment is provided to a first subject of a first client device 300, in which the first subject exhibits a psychiatric or mental condition. In such embodiments, obtaining the assessment from the first subject is conditioned on satisfying a first authorization criterion. This first authorization criterion is associated with the first subject obtaining an authorization of the assessment from a medical practitioner associated with the subject. By way of example, in some embodiments, the first authorization criterion requires that the medical practitioner validate a subject aspect of the assessment, such as a truthfulness of the assessment. In some embodiments, by adding a level of human authorization, the digital reality system 200 ensures that a subject that exhibits a psychiatric or mental condition improves an ability of the subject to manage the psychiatric or mental condition when utilizing the systems and methods of the present disclosure by providing honest answers to the assessment. In this way, in some embodiments, the assessment module 12 prevents the subject from gamify the assessment, which would provide a regiment that might not improve an ability of the subject to manage the psychiatric or mental condition.

In some embodiments, a user profile store 14 retains a plurality of user profiles 16. In some embodiments, the plurality of user profiles includes at least 50 user profiles, at least 100 user profiles, at least 500 user profiles, at least 2,000 user profiles, at least 5,000 user profiles, at least 10,000 user profiles, at least 25,000 user profiles, at least 50,000 user profiles, at least 100,000 user profiles, at least 500,000 user profiles, or at least 1 million user profiles. Each respective user profile 16 is associated with a corresponding user of the digital reality system 200, such as a user of a client device 300 that exhibits a psychiatric or mental condition and/or a medical practitioner associated with the user. For instance, in some embodiments, a respective user first customizes their profile (e.g., first user profile 16-1) at a client device 300 by making a selection of a plurality of user login information, such as a password, an address (e.g., E-mail address of FIG. 9A, physical address, etc.), a personal name (e.g., a personal name, a user name, etc.), and the like. In some embodiments, the user profile uniquely identifies the respective user in a digital reality scene 40. In this way, each user profile 16 allows the digital reality system 200 to retain login information, privacy information (e.g., which psychiatric or mental condition is exhibited by a corresponding subject associated with a respective user profile 16) and other preferences, and/or biographical data. In some embodiments, a login name associated with a respective user is the same as the username displayed for the user. In other embodiments, a login name associated with a respective user is different from the username displayed for the user (e.g., displayed usernames with a digital reality scene 40 are different from associated user logins). In some embodiments, the user profile 16 includes some or all of a corresponding medical record of the subject associated with the user profile 16. In some embodiments, the digital reality system 200 stores a plurality of avatar information, including a plurality of traits for each avatar user, and/or a contact list of contacts within a digital reality scene 40 (e.g., recent patients listing of FIG. 9B).

Additionally, each user profile 16 includes a well-being store (e.g., first user profile 16-1 includes first well-being store 18-1, second user profile 16-2 includes second well-being store 18-2, . . . , user profile A 16-A includes well-being store B 18-B, etc.). The well-being store 18 retains a plurality of health information associated with the subject, such as an indication of a clinical diagnosis for a psychiatric or mental condition, a plurality of insurance information associated with an insurance provider of a corresponding subject, an electronic medical record (e.g., the corresponding medical record of the subject associated with the user profile), and the like. In some embodiments, the well-being store 18 includes a status of a treatment administered to a subject, such as a result of a previous treatment for the psychiatric or mental condition, a result of a previous regimen 20 provided to the subject, and the like. For instance, in some embodiments, the well-being store 18 includes one or more previous assessments obtained from the subject as the result of the previous treatment for the psychiatric or mental condition, which helps provide additional data points (e.g., endpoints) to quantify effects of improving the ability of the subject to manage the psychiatric or mental condition when utilizing the systems and methods of the present disclosure.

In some embodiments, the well-being store 18 includes a plurality of biometric data elements that is associated with the respective user. For instance, in some embodiments, a client device 300 obtains a set of biometric data elements when presenting a digital reality scene on a display 308 of the client device, and a plurality of biometric data elements from the set of biometric data elements is retained by the well-being store 18. As a non-limiting example, in some embodiments, the plurality of biometric data elements retained by the well-being store 18 includes a heart rate of the subject (e.g., a baseline heart rate, one or more heart rate zones of the subject, etc.). In some embodiments, the plurality of biometric data elements retained by the well-being store 18 includes a blood pressure of the subject (e.g., a baseline systolic blood pressure, a threshold diastolic blood pressure, etc.). Furthermore, in some embodiments, the plurality of biometric data elements includes a plurality of spatiotemporal data elements, which describe a spatial and temporal aspect of the user when engaging with a digital reality scene. Non-limiting examples of the plurality of spatiotemporal data elements includes an area of a portion of an eye of the user, a change in a position of the eye of the subject when addressing the corresponding challenge 26, a count of occurrences of the eye of the user at a predetermined reference position, and the like. In some embodiments, the plurality of biometric data elements includes electroencephalographic (EEG) data elements, galvanic skin response (GSR) data elements, facial electromyography (fEMG) data elements, electrocardiogram (EKG) data elements, video facial action unit (FAU) data elements, brain machine interface (BMI) data elements, video pulse detection (VPD) data elements, functional magnetic resonance imaging (fMRI) data elements, functional near-infrared (fNIR) data elements, or a combination thereof. However, the present disclosure is not limited thereto.

Moreover, in some embodiments, the well-being store 18 includes one or more annotations. In some embodiments, each annotation is associated with the corresponding subject participating in a digital reality scene 40 and/or one or more assessments obtained from the subject. For instance, in some embodiments, the one or more assessments obtained from the subject that is stored by the well-being store 18 includes a first assessment for obtaining the identification of the plurality proposed experiences (e.g., block 404 of FIG. 4) and/or a second assessment based on a proposed experience 24 conducted by the user (e.g., assessment of user interface 1000-C FIG. 10C). In some embodiments, the one or more annotations include a first annotation provided by the medical practitioner associated with the subject. For instance, in some embodiments, the medical practitioner associated with the subject provides the first annotation when the subject is engaging with a respective digital reality scene. In some embodiments, the one or more annotations includes a second annotation provided by the subject.

Figure 6A:
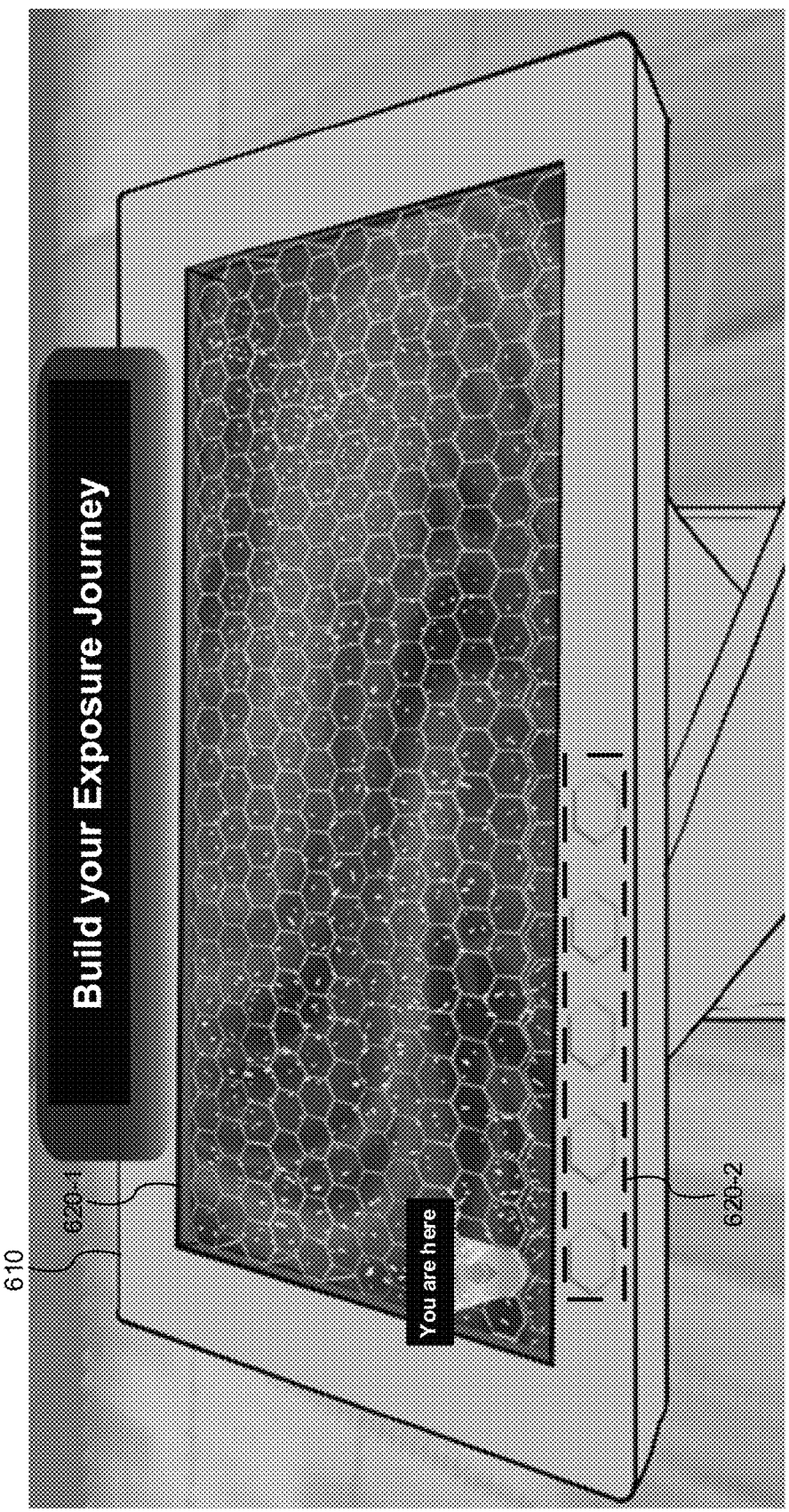
FIGS. 6A, 6B, 6C, 6D, 6E, 6F, 6G, and 6H collectively illustrate user interfaces for presenting an exemplary interactive digital chart and an exemplary interactive digital bin, in accordance with an embodiment of the present disclosure.

Furthermore, in some embodiments, each user profile includes a regimen store (e.g., first user profile 16-1 includes first regimen store 20-1, second user profile 16-2 includes second regimen store 20-2, . . . , user profile A 16-A includes regimen store C 20-C, etc.) that retains information associated with a plurality sessions of a corresponding user engaging with the digital reality system in order to track various parameters associated with improving an ability of a subject to manage a psychiatric or mental condition exhibited by the subject. In some embodiments, the various parameters associated with improving an ability of a subject to manage a psychiatric or mental condition exhibited by the subject that are retained by the regimen store 20 include a status of a respective interactive digital chart associated with the subject (e.g., interactive digital chart 610 of FIG. 6A), such as a location of one or more nodes (e.g., first node 630-1, second node 630-2, . . . , fifth node 630-5 of FIG. 6F), a location of an avatar in a digital reality scene 40, and the like. In some embodiments, the various parameters associated with improving an ability of a subject to manage a psychiatric or mental condition exhibited by the subject that are retained by the regimen store 20 include a status of a corresponding interactive digital bin (e.g., interactive digital bin 625 of FIG. 6B), such as an availability of a respective node 630 for placement within the respective interactive digital chart 610 or a determination if one or more gate criteria (e.g., gate criteria 32 of FIG. 2B) is satisfied. However, the present disclosure is not limited thereto. By retaining a well-being store 18 and a regimen store 20 with each user profile 16, the digital reality system 200 can allow each subject associated with a user profile to engage with the digital reality system 200 when and where the subject desires without losing progress for improving an ability of a subject to manage a psychiatric or mental condition exhibited by the subject.

An experience store 22 includes a plurality of experiences 24 (e.g., first experience 24-1, second experience 24-2, . . . , experience 24-D of FIG. 2B). Each experience 24 includes a digital reality task in the form of a challenge (e.g., first challenge 26-1, second challenge 26-2, . . . , challenge E 26-2 of FIG. 2B) that is designed to improve an ability of a subject to manage a psychiatric or mental condition exhibited by the subject. In some embodiments, the plurality of experiences includes 3 or more experiences, 5 or more experiences, 7 or more experiences, 10 or more experiences, 18 or more experiences, 25 or more experiences, 35 or more experiences, 50 or more experiences, 75 or more experiences, 125 or more experiences, or 300 or more experiences. Accordingly, in some embodiments, each proposed experience 24 is a social challenge 26, which challenges the subject to perform a digital reality task in a social setting within a digital reality scene 40. By way of example, some categories of the experiences 24 include those directed to general performance of the subject, such as a first experience 24-1 that is a first challenge 26-1 that tasks the subject to give a presentation to an audience in a digital reality scene 40 or tell a story to a group in the digital reality scene 40. In some embodiments, the categories of the experiences 24 include those directed to being assertive, such as a second experience 24-2 that is a second challenge 26-2 tasking the subject to walk up to a person in a digital reality scene 40 or reminding the person of a task you assigned the person in the digital reality scene 40. In some embodiments, the categories of the experiences 24 include those directed to interactions with persons, such as a third experience 24-3 that is a third challenge 26-3, such as tasking a subject to look at someone in the eyes in a digital reality scene 40. However, the present disclosure is not limited thereto.

In some embodiments, each respective challenge 26 is associated with a specific setting, such as a specific digital reality scene 40. For instance, consider a first experience 24-1 is a first challenge 26-1 that tasks a subject to walk up to a person in a first digital reality scene 40-1 that presents a crowded, public setting, and a second experience 24-2 is a second challenge 26-2 that tasks the subject to walk up to the person in a second digital reality scene 40-2 that presents a quiet, private setting. Accordingly, both of the first experience 24-1 and the second experience 24-2 are associated with being assertive yet accomplish the goal of improving an ability of a subject to manage a psychiatric or mental condition exhibited by the subject through the difference in challenge 26. In this way, in some embodiments, a corresponding proposed experience 24 provides a broad categorization of content in a digital reality scene that is designed to improve an ability of a subject to manage a psychiatric or mental condition exhibited by the subject and a challenge provides a granular implementation of a corresponding proposed experience.

Moreover, in some embodiments, each experience 24 of the experience store 22 is provided by the digital reality system 200 without an association to a respective digital reality scene 40, which allows the digital reality system 200 to design and configure the respective digital reality scene based on a proposed experience 24.

Furthermore, a gate store 30 facilitates retaining a plurality of gate criteria (e.g., first gate criterion 32-1, second gate criterion 32-2, . . . , gate criterion G 32-G). Each respective gate criterion 32 is defined by a node 630 of a respective interactive digital chart 610. In some embodiments, the node 630 defines a single gate criterion 32, such that a one-to-one relationship exists between the nodes 630 of the respective interactive digital chart 610 and the gate criteria 32. However, the present disclosure is not limited thereto. In alternative embodiments, the node 630 defines a plurality of gate criteria 32, such that a one-to-many relationship exists between the nodes 630 of the respective interactive digital chart 610 and the gate criteria 32. In some embodiments, the respective gate criterion 32 is a condition precedent for executing the node 630 or a condition that must be achieved in order to deem the node 630 complete. When a node 630 is deemed complete (e.g., each gate criterion 32 associated with the node is satisfied, block 410 of FIG. 4) then an edge of a graph (e.g., edge 635 of graph 640 of FIG. 6G) is formed between the node 630 that is deemed complete and a proceeding node 630 (e.g., a first node 630-1 selected by a user, block 408 of FIG. 4). A non-limiting example of a condition precedent is a requirement that a second node 630-2 be successfully completed before the user is allowed to invoke a first node 630-1. Another non-limiting example of a condition that must be achieved in order to deem a third node 630-3 complete is a minimum eye contact duration by a subject during the proposed experience 24 of the node 630. However, the present disclosure is not limited thereto. For instance, in some embodiments, the condition precedent is a requirement for the subject to complete a task within a respective digital reality scene 40, such as satisfying a first task of a baseline biometric threshold criterion when exposed to an experience in the digital reality scene 40 and/or a second task of completing the corresponding challenge at an intermediate graded difficulty. Accordingly, in some such embodiments, the subject gradually confronts each category, from least to most feared, and engages with each challenge until the ability of the subject to manage the psychiatric or mental condition using the interactive digital chart improves (e.g., anxiety exhibited by the subject decreases).

In addition, the digital reality system 200 includes an application server module 34 that facilitates providing access to a digital reality scene 40 for a user of a client device 300. The application server module 34 sends each respective client device 300 data elements associated with a digital reality scene 40 when there is a request for such data elements by the respective client device 300, such as when the user logs into a client application 320 at the client device 300 (e.g., "Launch VR Session" of FIG. 8D). For instance, a login module 36 of the application server 34 can verify the information provided by the user of the client device 300 against the information stored in a user profile 16 to ensure the correct user is requesting access to a digital reality scene 40. Accordingly, a population of users employ the client devices 300 to access the application server module 34 at the digital reality system 200 and to interact with a digital reality scene 40 that is hosted by the digital reality system 200 (e.g., digital reality scene 40-1 of FIG. 5A, digital reality scene 40 of user interface 500-3 of FIG. 5C, etc.).

In some embodiments, the application server module 34 also facilitates allowing the user of the client device 300 to configure a digital reality scene 40 in accordance with a determination that the user is a medical practitioner. For instance, referring briefly to FIG. 9D, a user interface 900-4 presented through a display 308 of a client device allows the user to configure a number of non-player characters (NPCs) associated with a first social challenge 26-1 and a second social challenge 26-2.

Each respective digital reality scene 40 defines a digital domain for use by a population of users. Specifically, in some embodiments, a respective digital reality scene 40 includes a plurality of objects (e.g., first object 42-1, second object 42-2, . . . , object J 42-J of digital reality scene H 40-H of FIG. 2B) that populates the respective digital reality scene 40. In some embodiments, the plurality of objects 42 includes a plurality of player character objects 42 (e.g., avatars, such as hand 602-1 of FIG. 6D) that represent and/or is controlled by the user, a plurality of NPC objects 42 that represent NPC in the respective digitality scene that the user cannot directly control, and a plurality of scene objects 42 (e.g., objects that are not player character objects 42 or NPC objects 42, such as bodies of water in a digital reality scene 40, buildings, and furniture in the digital reality scene 40, etc.). As used herein, a digital reality scene refers to any space (e.g., digital space and/or real-world space) where digital reality content (e.g., an avatar, a digital reality object, etc.) is presented to a user through a display (e.g., display 308 client device 300-1 of FIG. 3).

By way of example, in some embodiments, a digital reality scene 40-1 includes a first object 42-1 that is a stone pathway, a second object 42-2 that is a mailbox, a third object 42-3 that is a wooden sign, and/or other objects.

Figure 5A:
FIG. 5A illustrates an exemplary digital reality scene for cognitive reframing training or session, in accordance with an embodiment of the present disclosure.

As another non-limiting example, FIG. 5A illustrates a digital reality scene 40-1 that includes a first object 42-1, a second object 42-2, a third object 42-3 and/or other objects. In some embodiments, the digital reality scene illustrated in FIG. 5A or the like is used for cognitive reframing training or session, and/or other educational or therapeutic sessions.

Figure 5B:
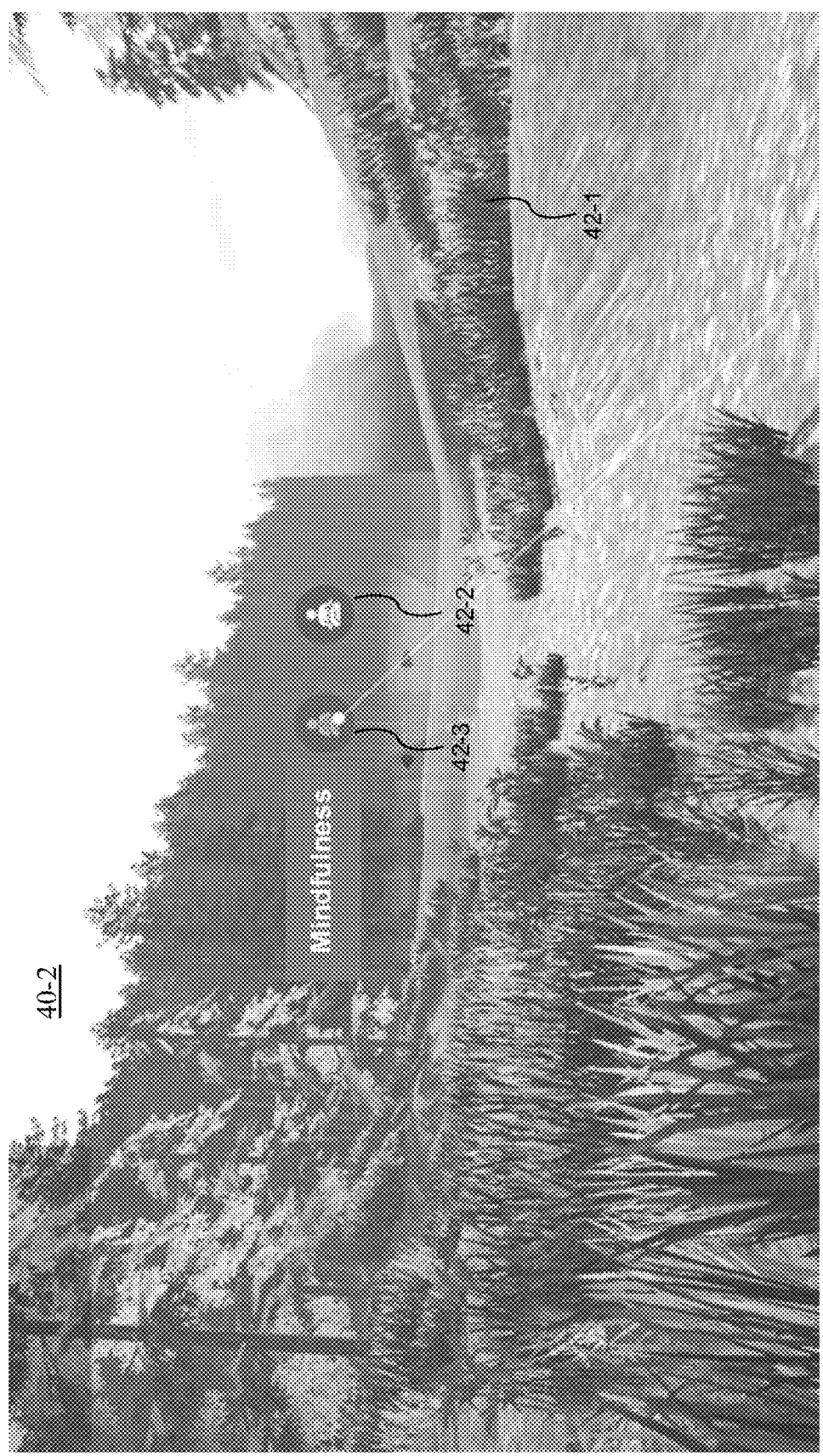
FIG. 5B illustrates an exemplary digital reality scene for mindfulness training or session, in accordance with an embodiment of the present disclosure.

As still another non-limiting example, FIG. 5B illustrates a digital reality scene 40-2 that includes a first object 42-1, a second object 42-2, a third object 42-3 and/or other objects. In some embodiments, the digital reality scene 40 illustrated in FIG. 5B or the like is used for mindfulness training or session, and/or other educational or therapeutic sessions.

Figure 5C:
FIG. 5C illustrates an exemplary digital reality scene for presenting an interactive digital chart and corresponding interactive digital bin, in accordance with an embodiment of the present disclosure.

As yet another non-limiting example, FIG. 5C illustrates a digital reality scene 40-3 presented by a user interface 500-3. In some embodiments, the digital reality scene illustrated in FIG. 5C or the like is used for exposure therapy (e.g., for presenting an interactive digital chart and corresponding interactive digital bin) and/or other educational or therapeutical sessions. For instance, in some embodiments, the digital reality scene illustrated in FIG. 5C includes a first object 42-1 that is a chair, a second object 42-2 that is a respective interactive digital chart 610, a third object 42-3 that is a plant, a fourth object 42-4 that is a trajectory between a first position of a user and a second position of the second object 42-2, and a fifth object 42-5 that is a doorway (e.g., doorway that facilitates access to another digital reality scene such as digital reality scene 40-1 illustrated in FIG. 5A or the digital reality scene 40-2 illustrated in FIG. 5B).

Figure 10A:
FIG. 10A illustrates an exemplary digital reality scene for social challenge training or session, in accordance with an embodiment of the present disclosure.
Figure 10B:
FIG. 10B illustrates an exemplary digital reality scene for social challenge training or session, in accordance with an embodiment of the present disclosure.
Figure 10C:
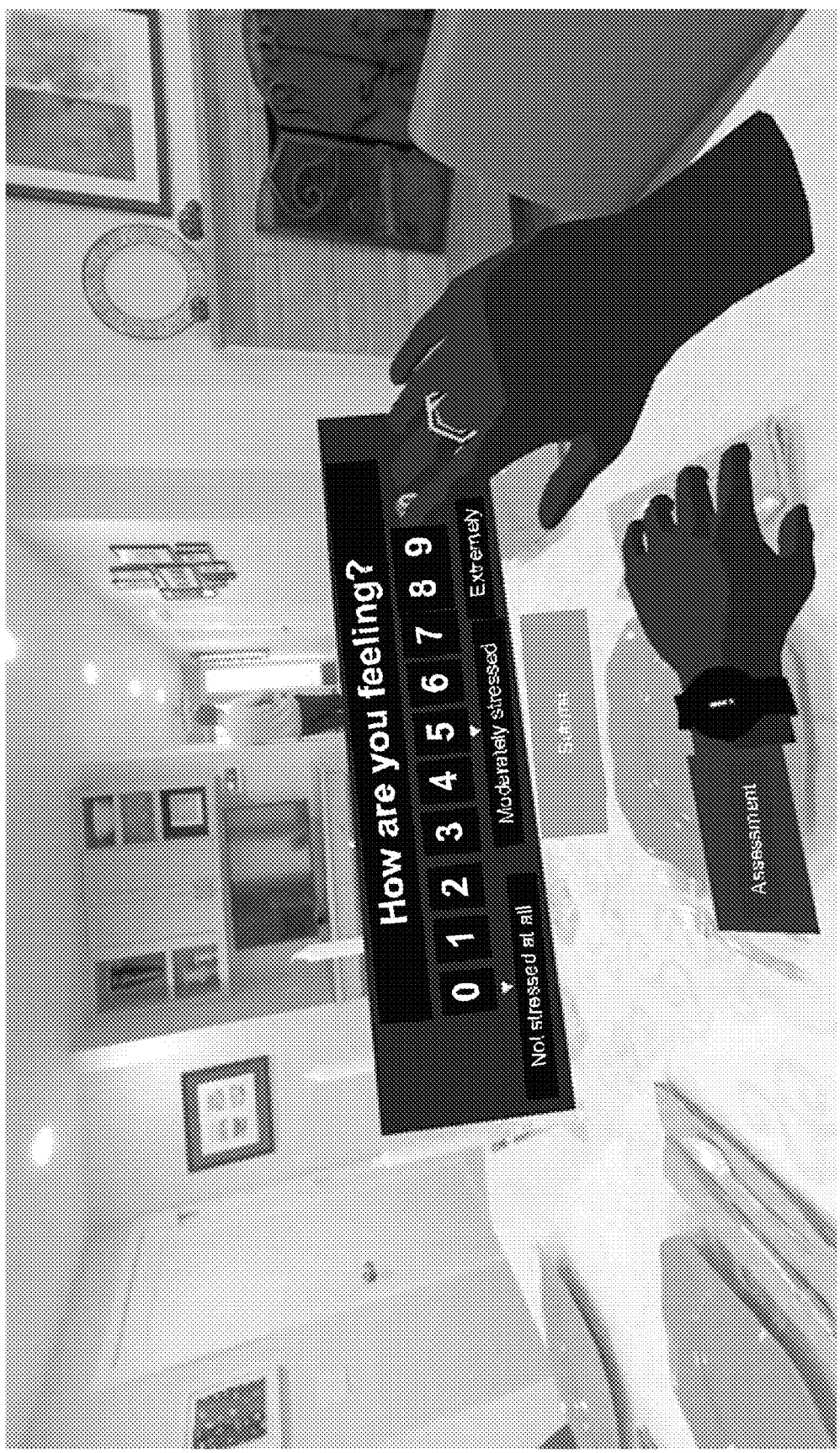
FIG. 10C illustrates a user interface for presenting an assessment of a digital reality scene, in accordance with an embodiment of the present disclosure.

As further non-limiting examples, FIGS. 10A and 10B illustrate digital reality scenes that include human character object(s). In some embodiments, the digital reality scenes illustrated in FIGS. 10A, 10B or the like are used for social challenge training or therapeutic session.

However, the present disclosure is not limited thereto. For instance, in some embodiments, the object 42 is that is consumable by a user in the digital reality scene 40, such a video or text. Collectively, the plurality of objects 42 enables a user of a client device 300 to actively engage with the digital reality scene 40, such as one or more users that are online and interacting in the digital reality scene 40 and form the respective digital reality scene 40.

Each respective object 42 includes a plurality of attributes that describe not only how a respective object 42 interacts with a digital reality scene 40, such as with other objects 42 in the digital reality scene 40, but also how the respective object 42 interacts with other users in the digital reality scene 40. In some embodiments, attributes of an object 42 that can be modified or varied include a mass of the object 42, a volume of the object 42, a coefficient of friction of the object 42, a state of matter of the object 42, a rigidity of a body of the object 42, a position of the object 42, a health value of the object 42 (e.g., hit points of the object 42, energy points of the object, etc.), joints of the object 42, and the like. As a non-limiting example, consider a first attribute that describes a response to a collision with a respective object 42 (e.g., a hardness of the object 42, an adhesiveness of the object 42, etc.).

In some embodiments, the attributes associated with a respective object 42 are the same for each user in a digital reality scene 40. For example, if a respective object 42 has an attribute that makes the respective object 42 interactive with users, each user in the digital reality scene 40 can interact with the respective object 42. On the other hand, if the respective object 42 has an attribute that makes the respective object 42 interactive for a select group of users, such as those subjects that have an indication in a user profile 16 of exhibiting a psychiatric or mental condition, only the users in the select group of users can interact with the respective object 42. For example, in some embodiments, an administrator user of a digital reality scene 40 restricts interaction with a specific object 42 for all users except for the administer user or one or more particular users, such as those exhibiting a psychiatric or mental condition.

In some embodiments, the digital reality system 200 includes an application model library 50 that stores one or more models (e.g., classifiers, regressors, etc.). In some embodiments, the model library stores two more models, three or more models, four or more models, ten or more models, 50 or more models, or 100 or more models.

In some embodiments, each model in the one or more models includes one or more logical operation (e.g., logical functions of FIG. 15). In some embodiments, referring briefly to chart 1500 of FIG. 15, the one or more logical operation is based on some Boolean operation. For instance, in some embodiments, a first logical operation describes an "AND" Boolean operation that requires both elements of the first logical operation to be satisfied for a respective threshold to be deemed satisfied. A second logical operation describes an "OR" Boolean operation that requires any one element of the second logical operation to be satisfied for a respective threshold to be deemed satisfied. Moreover, a third logical operation describes an "EXCLUSIVE OR (XOR)" Boolean operation that requires any one element of the third logical operation to be satisfied and no other element satisfied for a respective threshold to be deemed satisfied. A fourth logical operation describes a singular "NOT" Boolean operation that requires absence of an element of the fourth logical operation to be satisfied for a respective threshold to be deemed satisfied. A fifth logical operation describes a plural "NOT" Boolean operation that requires both absence of a first element and presence of a second element of the fifth logical operation to be satisfied for a respective threshold to be deemed satisfied. In some embodiments, a logical operation of a respective model includes a combination of one or more of the above described logical operations. For instance, in some embodiments, a respective logical operation includes one or more AND, OR, XOR, or NOT operations within the respective logical operation (e.g., an operation including an AND operation and a NOT operation, etc.). However, the present disclosure is not limited thereto.

In some embodiments, the model is implemented as an artificial intelligence engine. For instance, in some embodiments, the model includes one or more gradient boosting models, one or more random forest models, one or more neural networks (NN), one or more regression models, one or more Naïve Bayes models, one or more machine learning algorithms (MLA), or a combination thereof. In some embodiments, an MLA or a NN is trained from a training data set (e.g., a first training data set including the user profile store 14, the experience store 22, the gate store 30, the application server module 34, or a combination thereof) that includes one or more features identified from a data set. By way of example, in some embodiments, the training data set includes data associated with a first user profile 16-1 and data associated with user tendencies in when confronted with an experience 24 in a digital reality scene 40. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using a priori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as minimum cut, harmonic function, manifold regularization, etc.), heuristic approaches, or support vector machines. In some embodiments, the supervision of a respective model is performed by a medical practitioner associated with a user of a client device 300 that utilizes the systems and methods of the present disclosure.

NNs include conditional random fields, convolutional neural networks, attention based neural networks, deep learning, long short term memory networks, or other neural models.

While MLA and neural networks identify distinct approaches to machine learning, the terms may be used interchangeably herein. Thus, a mention of MLA may include a corresponding NN or a mention of NN may include a corresponding MLA unless explicitly stated otherwise. In some embodiments, the training of a respective model includes providing one or more optimized datasets, labeling these features as they occur (e.g., in user profile 16 records), and training the MLA to predict or classify based on new inputs, such as based on data captured when a user is interacting with a digital reality scene 40 including meta data of the digital reality scene 40 and/or biometric data associated with the user. Artificial NNs are efficient computing models which have shown their strengths in solving hard problems in artificial intelligence. For instance, artificial NNs have also been shown to be universal approximators, that is, they can represent a wide variety of functions when given appropriate parameters.

Accordingly, in some embodiments, a first model is a neural network classification model, a second model is a Naïve Bayes classification model, and the like. Furthermore, in some embodiments, the model includes decision tree algorithm, a neural network algorithm, a support vector machine (SVM) algorithm, and the like. Moreover, in some embodiments, the model used in the (e.g., method 400 of FIG. 4, method 1300 of FIGS. 413A through 4F 13M, etc.) described herein is a logistic regression algorithm, a neural network algorithm, a convolutional neural network algorithm, a support vector machine (SVM) algorithm, a Naive Bayes algorithm, a nearest neighbor algorithm, a boosted trees algorithm, a random forest algorithm, a decision tree algorithm, a clustering algorithm, or a combination thereof.

One of skill in the art will readily appreciate other models that are applicable to the systems and methods of the present disclosure. In some embodiments, the systems and methods of the present disclosure utilize more than one model to provide an evaluation (e.g., arrive at an evaluation given one or more inputs) with an increased accuracy. For instance, in some embodiments, each respective model arrives at a corresponding evaluation when provided a respective data set. Accordingly, each respective model can independently arrive and a result and then the result of each respective model is collectively verified through a comparison or amalgamation of the models. From this, a cumulative result is provided by the models. However, the present disclosure is not limited thereto.

In some embodiments, a respective model is tasked with performing a corresponding activity (e.g., step within method 400 of FIG. 4, step within method 1300 of FIGS. 13A through 13M, etc.). As a non-limiting example, in some embodiments, the task performed by the respective model includes diagnosing a mental disorder, generating a manifestation of a corresponding challenging in the form of an experience 24 associated with a digital reality scene 40, identifying each category in a plurality of categories of an assessment obtained from a subject (e.g., block 1368 of FIG. 13F), conducting a validation of the assessment obtained from the subject, conducting a further validation of another validation by a medical practitioner of the assessment obtained from the subject, generating a respective gate criteria (e.g., generate gate criterion G stored in gate store 30 of FIG. 2B), generating a hierarchical ranking of each node in an enumerated plurality of nodes, approving a placement of a first node at a first location on an interactive digital chart (e.g., block 1392 of FIG. 13H), determining if a selection of the first node satisfies each gate criterion in at least one respective gate criteria that is associated with the first node prior to the placing of the first node (e.g., block 1396 of FIG. 13H), connecting each node in a graph by an edge, activating a respective node (e.g., block 1406 of FIG. 13I, block 1410 of FIG. 13I, etc.), generating a sentiment analysis criterion, determining if the sentiment analysis criterion is satisfied, or a combination thereof. For instance, in some embodiments, a first model is tasked with generating a plurality of gate criterion 32 that is associated with an experience 24 and that a user must satisfied in order to advance past a first node associated with the experience 24. However, the present disclosure is not limited thereto. By way of example, in some embodiments, a second model is tasked with generating a respective challenge 26 for a user and/or determining if the respective challenge 26 is deemed complete by the user. In some embodiments, each respective model of the present disclosure makes use of 10 or more parameters, 100 or more parameters, 1000 or more parameters, 10,000 or more parameters, or 100,000 or more parameters. In some embodiments, each respective model of the present disclosure cannot be mentally performed.

Each of the above identified modules and applications correspond to a set of executable instructions for performing one or more functions described above and the methods described in the present disclosure (e.g., the computer-implemented methods and other information processing methods described herein; method 400 of FIG. 4; method 1300 of FIG. 13A through 13M; etc.). These modules (e.g., sets of instructions) need not be implemented as separate software programs, procedures or modules, and thus various subsets of these modules are, optionally, combined or otherwise re-arranged in various embodiments of the present disclosure. In some embodiments, the memory 212 optionally stores a subset of the modules and data structures identified above. Furthermore, in some embodiments, the memory 212 stores additional modules and data structures not described above.

It should be appreciated that the digital reality system 200 of FIGS. 2A and 2B is only one example of a digital reality system 200, and that the digital reality system 200 optionally has more or fewer components than shown, optionally combines two or more components, or optionally has a different configuration or arrangement of the components. The various components shown in FIGS. 2A and 2B are implemented in hardware, software, firmware, or a combination thereof, including one or more signal processing and/or application specific integrated circuits.

Figure 3:
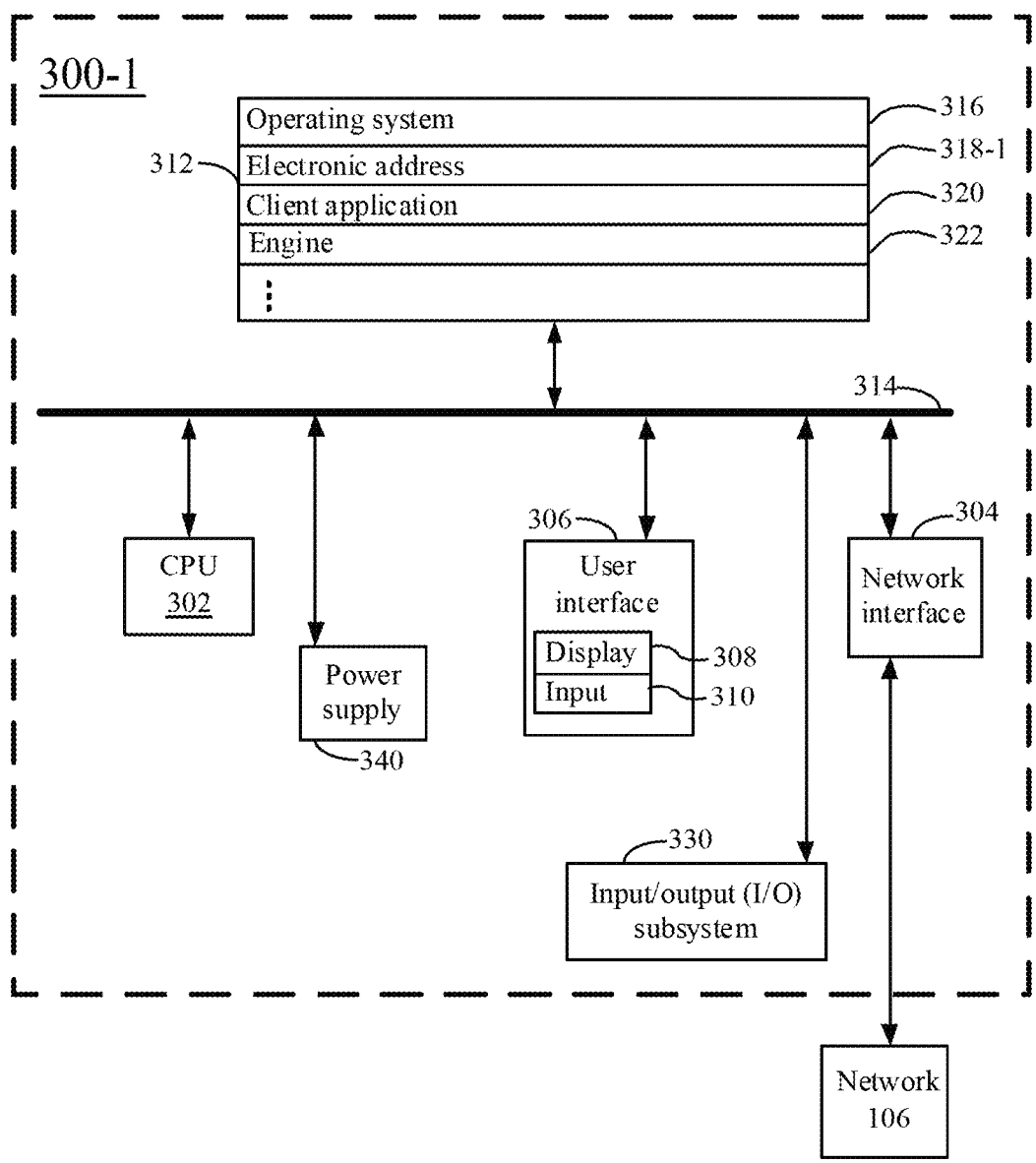
FIG. 3 illustrates a client device for displaying a digital reality scene, in accordance with an embodiment of the present disclosure.

Referring to FIG. 3, an exemplary client device 300 is provided (e.g., first client device 300-1). A client device 300 includes one or more processing units (CPUs) 302, one or more network or other communication interfaces 304, memory 312 (e.g., random access memory and/or non-volatile memory) optionally accessed by one or more controllers, and one or more communication busses 314 interconnecting the aforementioned components.

In some embodiments, a client device 300 includes a mobile device, such as a mobile phone, a tablet, a laptop computer, a wearable device such as a smart watch, and the like. In such embodiments, a respective digital reality scene 40 that is accessible through the client device 300 includes an augmented reality scene. In some embodiments, the respective digital reality scene accessible through the client device 300 includes a mixed reality scene. However, the present disclosure is not limited thereto. For instance, in some embodiments, the client device 300 is a desktop computer or other similar devices that accepts one or more wearable devices (e.g., wearable display). In some embodiments, the client device 300 is a standalone device that is dedicated to providing a digital reality scene 40 of the systems and methods of the present disclosure. Further, in some embodiments, each client device 300 enables a respective subject to provide information related to the respective subject (e.g., subject preferences, subject feedback, etc.).

In addition, the client device 300 includes a user interface 306. The user interface 306 typically includes a display device 308 for presenting media, such as a digital reality scene 40, and receiving instructions from the subject operating the client device 300. In some embodiments, the display device 308 is optionally integrated within the client device 300 (e.g., housed in the same chassis as the CPU 302 and memory 312), such as a smart (e.g., smart phone) device. In some embodiments, the client device 300 includes one or more input device(s) 310, which allow the subject to interact with the client device 300. In some embodiments, input devices 310 include a keyboard, a mouse, and/or other input mechanisms. Alternatively, or in addition, in some embodiments, the display device 308 includes a touch-sensitive surface, e.g., where display 308 is a touch-sensitive display or client device 300 includes a touch pad.

In some embodiments, the client device 300 includes an input/output (I/O) subsystem 330 for interfacing with one or more peripheral devices with the client device 300. For instance, in some embodiments, audio is presented through an external device (e.g., speakers, headphones, etc.) that receives audio information from the client device 300 and/or a remote device (e.g., digital reality system 200), and presents audio data based on this audio information. In some embodiments, the input/output (I/O) subsystem 330 also includes, or interfaces with, an audio output device, such as speakers or an audio output for connecting with speakers, earphones, or headphones. In some embodiments, the input/output (I/O) subsystem 330 also includes voice recognition capabilities (e.g., to supplement or replace an input device 310).

In some embodiments, the client device 300 also includes one or more sensors (e.g., an accelerometer, a magnetometer, a proximity sensor, a gyroscope, etc.), an image capture device (e.g., a camera device or an image capture module and related components), a location module (e.g., a Global Positioning System (GPS) receiver or other navigation or geolocation system module/device and related components), or a combination thereof, and the like. In some embodiments, the one or more sensors includes one or more biometric sensors, such as a first sensor that is positioned on a body of a subject in order to generate at least one physiological signal. However, the present disclosure is not limited thereto.

As described above, the client device 300 includes a user interface 306. The user interface 306 typically includes a display device 308, which is optionally integrated within the client device 300 (e.g., housed in the same chassis as the CPU and memory, such as with a smart phone or an all-in-one desktop computer client device 300). In some embodiments, the client device 300 includes a plurality of input device(s) 310, such as a keyboard, a mouse, and/or other input buttons (e.g., one or more sliders, one or more joysticks, one or more radio buttons, etc.). Alternatively, or in addition, in some embodiments, the display device 308 includes a touch-sensitive surface, e.g., where display 308 is a touch-sensitive display 308 or a respective client device 300 includes a touch pad. Furthermore, in some embodiments, the client device 300 includes a heads-up display (HUD) device, e.g., where display 308 is head-mounted on the user such as a virtual reality headset that facilitates presenting a virtual reality scene 40 (e.g., digital reality scene 40 presented via user interface 1000-1 of FIG. 10A), an augmented reality headset that facilitates presenting an augmented reality scene 40 (e.g., digital reality scene 40 presented via user interface 1000-2 of FIG. 10B), or a mixed reality headset that facilitates presenting a mixed reality scene 40. In such embodiments, the client device 300 includes the input device(s) 310 such as a haptic feedback device. Accordingly, the HUD client device 300 provides the functionality of a virtual reality client device 300 with synchronized haptic and audio feedback, an augmented reality client device 300 with synchronized haptic and audio feedback, a mixed reality client device 300 with synchronized haptic and audio feedback, or a combination thereof.

Additionally, in some embodiments, the client device 300 includes, or is a component part of a digital reality kit for presenting a digital reality scene 40. Additional details and information regarding a digital reality kit can be found at U.S. Patent Application Publication no.: 2020/0121050 A1, entitled "Virtual Reality Kit," filed Oct. 18, 2019, which is hereby incorporated by reference in its entirety.

In some embodiments, the client device 300 includes a one or more readily available (e.g., off the shelf) components such a Pico Neo 3 pro (Pico Interactive Inc., San Francisco, Calif.), Oculus Quest 2 (Oculus VR, Irvine, Calif.), Snapchat Spectacles 3 (Snap Inc., Santa Monica, Calif.), Google Cardboard (Google LLC, Mountain View, Calif.), HTC VIVE Pro 2 (HTC Corporation, Taoyuan City, Taiwan), or the like. One of skill in the art will appreciate that the present disclosure is not limited thereto.

In some embodiments, the client device 300 presents media to a user through the display 308. Examples of media presented by the display 308 include one or more images, a video, audio (e.g., waveforms of an audio sample), or a combination thereof. In typical embodiments, the one or more images, the video, the audio, or the combination thereof is presented by the display through a digital reality scene 40. In some embodiments, the audio is presented through an external device (e.g., speakers, headphones, etc.) that receives audio information from the client device 300, the digital reality system 200, or both, and presents audio data based on this audio information. In some embodiments, the user interface 306 also includes an audio output device, such as speakers or an audio output for connecting with speakers, earphones, or headphones. In some embodiments, the user interface 306 also includes an audio input device (e.g., a microphone), and optional voice recognition capabilities (e.g., to supplement or replace the keyboard). Optionally, the client device 300 includes an audio input device 310 (e.g., a microphone) to capture audio (e.g., speech from a user). In some embodiments, the audio input device 310 is a single omni-directional microphone.

In some embodiments, the client device 300 also includes one or more of: one or more sensors (e.g., accelerometer, magnetometer, proximity sensor, gyroscope); an image capture device (e.g., a camera device or module and related components); and/or a location module (e.g., a Global Positioning System (GPS) receiver or other navigation or geolocation device and related components). In some embodiments, the sensors include one or more hardware devices that detect spatial and motion information about the client device 300. Spatial and motion information can include information about a position of the client device 300, an orientation of the client device 300, a velocity of the client device 300, a rotation of the client device 300, an acceleration of the client device 300, or a combination thereof. For instance, in some embodiments, the sensors include one or more inertial measurement units (IMUs) that detect rotation of the user's head while the user is utilizing (e.g., wearing) the client device 300. This rotation information can then be used (e.g., by client application 320 of FIG. 3 and/or digital reality session engine 38 of FIG. 2B) to adjust the images displayed on the display 308 of the client device 300. In some embodiments, each IMU includes one or more gyroscopes, one or more accelerometers, and/or one or more magnetometers that collect the spatial and motion information. In some embodiments, the sensors include one or more cameras positioned on the client device 300.

Memory 312 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. Memory 312 may optionally include one or more storage devices remotely located from the CPU(s) 302. Memory 312, or alternatively the non-volatile memory device(s) within memory 312, includes a non-transitory computer readable storage medium. Access to memory 312 by other components of the client device 300, such as the CPU(s) 302 and the I/O subsystem 330, is, optionally, controlled by a controller. In some embodiments, memory 312 can include mass storage that is remotely located with respect to the CPU 302. In other words, some data stored in memory 312 may in fact be hosted on devices that are external to the client device 300, but that can be electronically accessed by the client device 300 over an Internet, intranet, or other form of network 106 or electronic cable using communication interface 304.

In some embodiments, the memory 312 of the client device 300 stores:
- an operating system 316 that includes procedures for handling various basic system services;
- an electronic address 318 associated with the client device 300 that identifies the client device 300 within a distributed system 100;
- a client application 320 for generating content for display through a graphical user interface presented on the display 308 the client device 300; and
- an engine 322 that allows a client application 320 to operate in conjunction with the client device 300.

An electronic address 318 is associated with the client device 300, which is utilized to at least uniquely identify the client device 300 from other devices and components of the distributed system 100. In some embodiments, the electronic address 318 associated with the client device 300 is used to determine a source of an assessment provided by the client device 300 (e.g., receiving an assessment from the digital reality system 200 and communicating one or more responses based on the assessment).

Figure 7A:
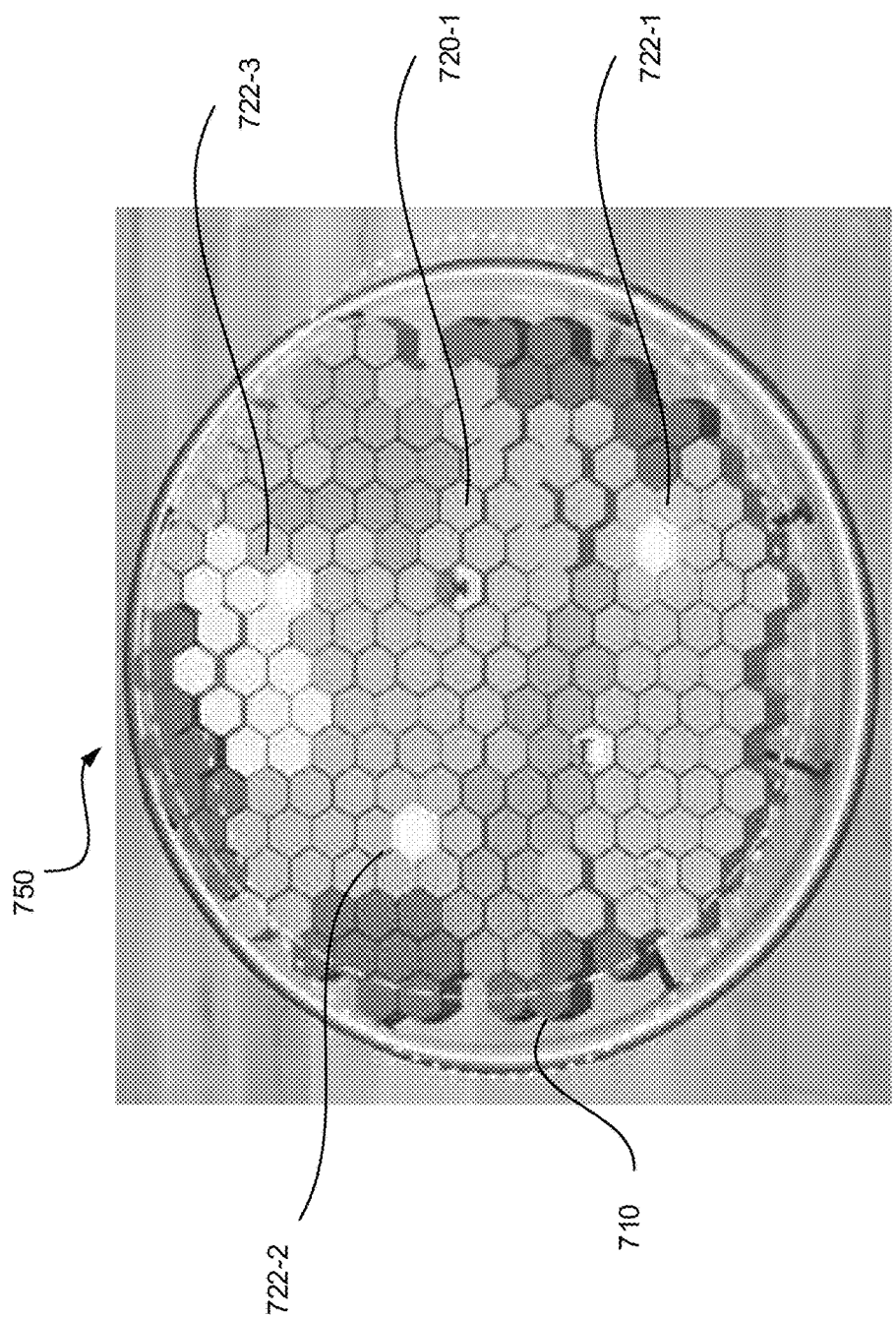
Figure 7B:
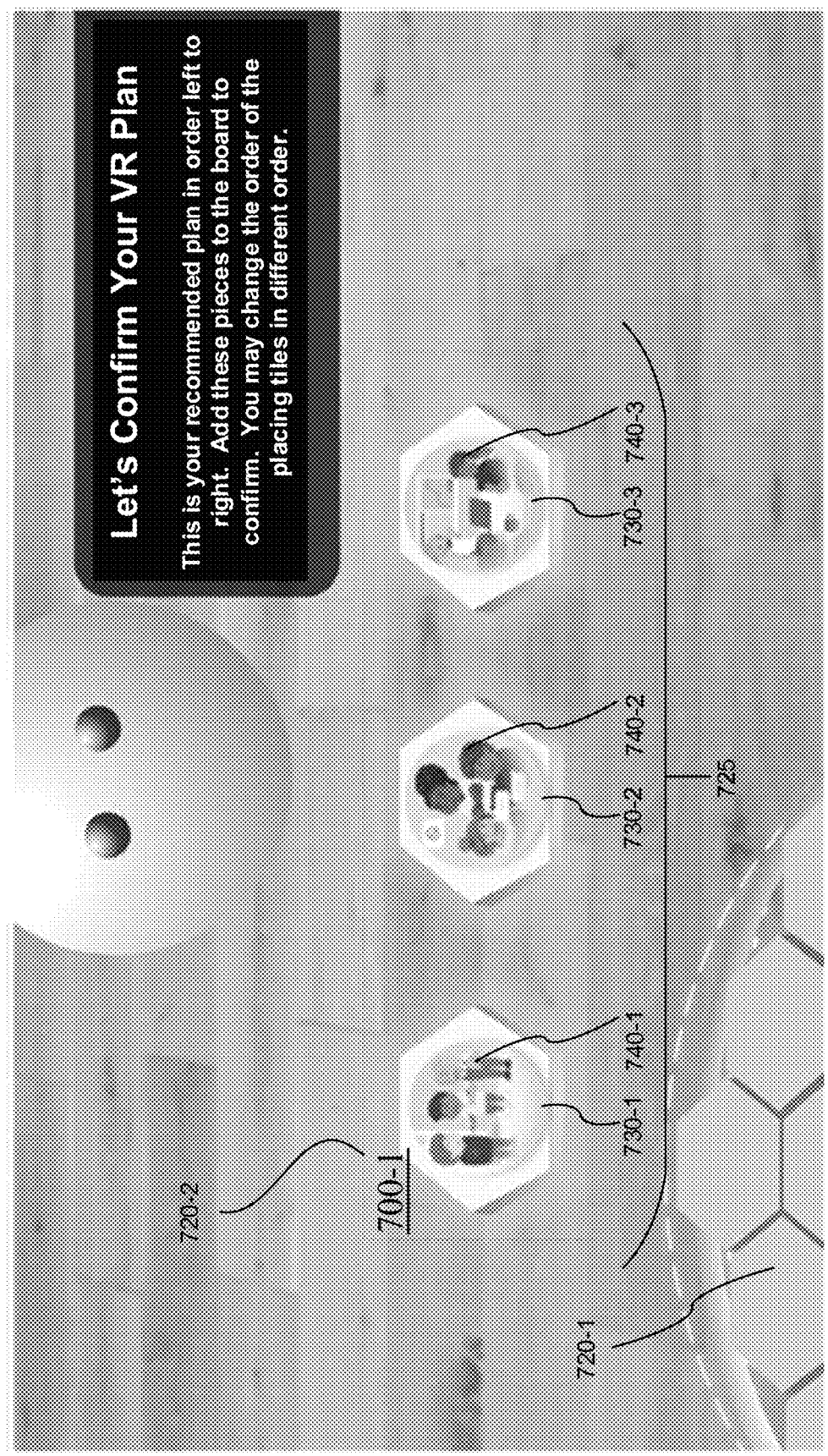
Figure 7C:
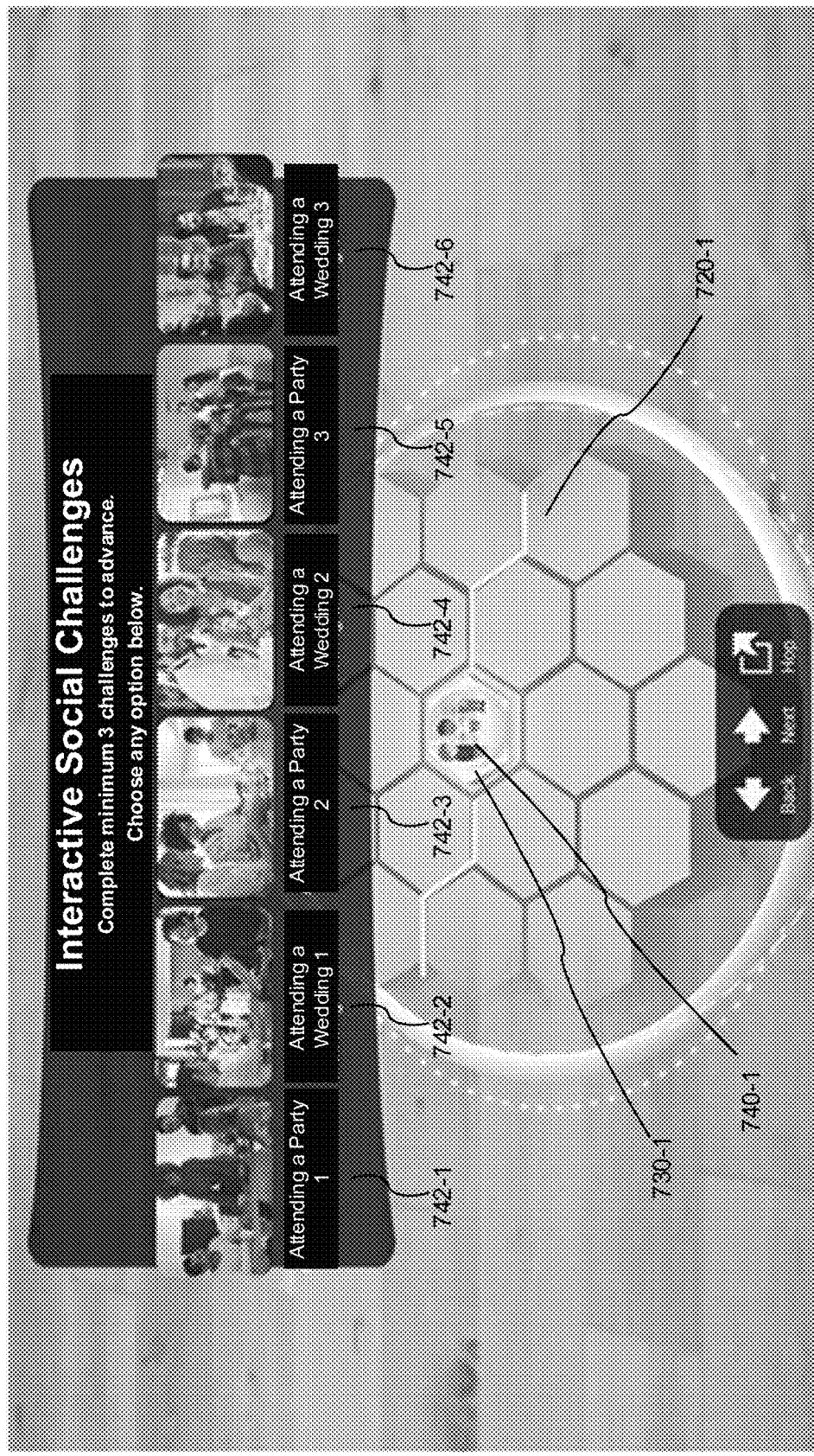
Figure 7D:
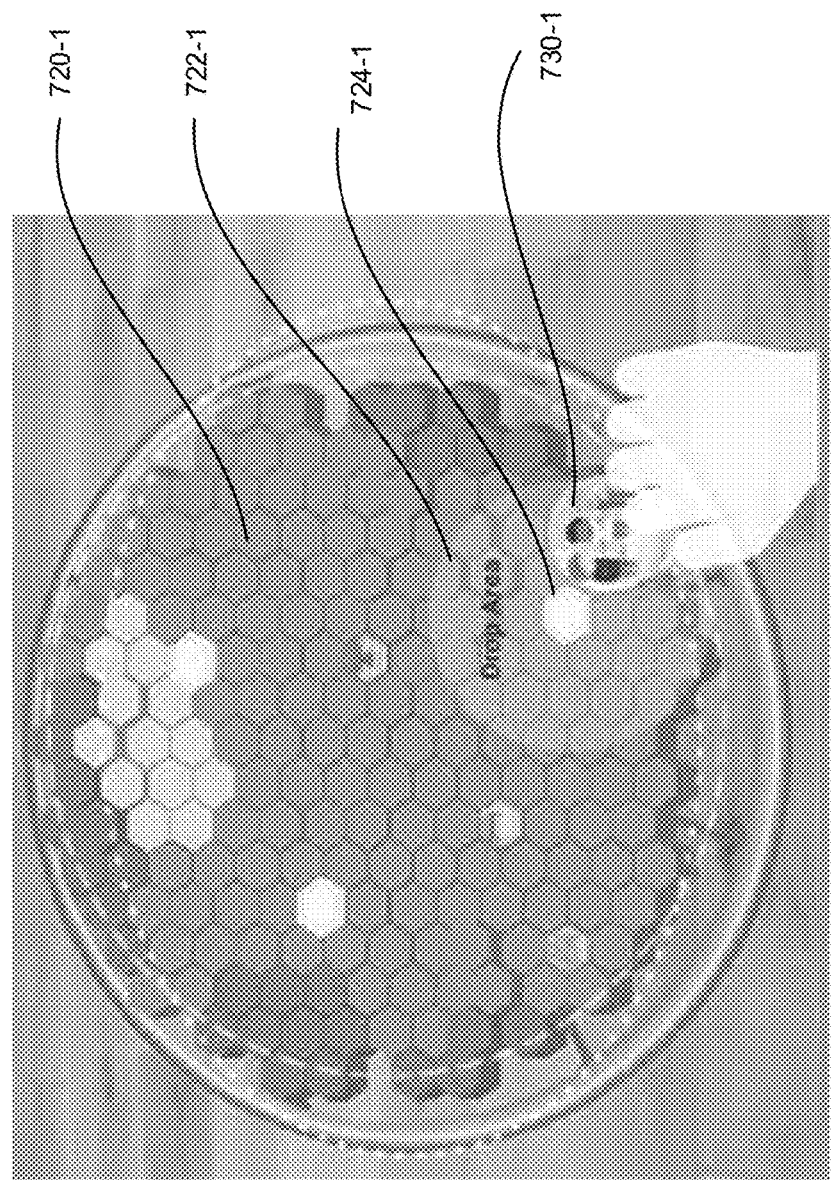
Figure 7E:
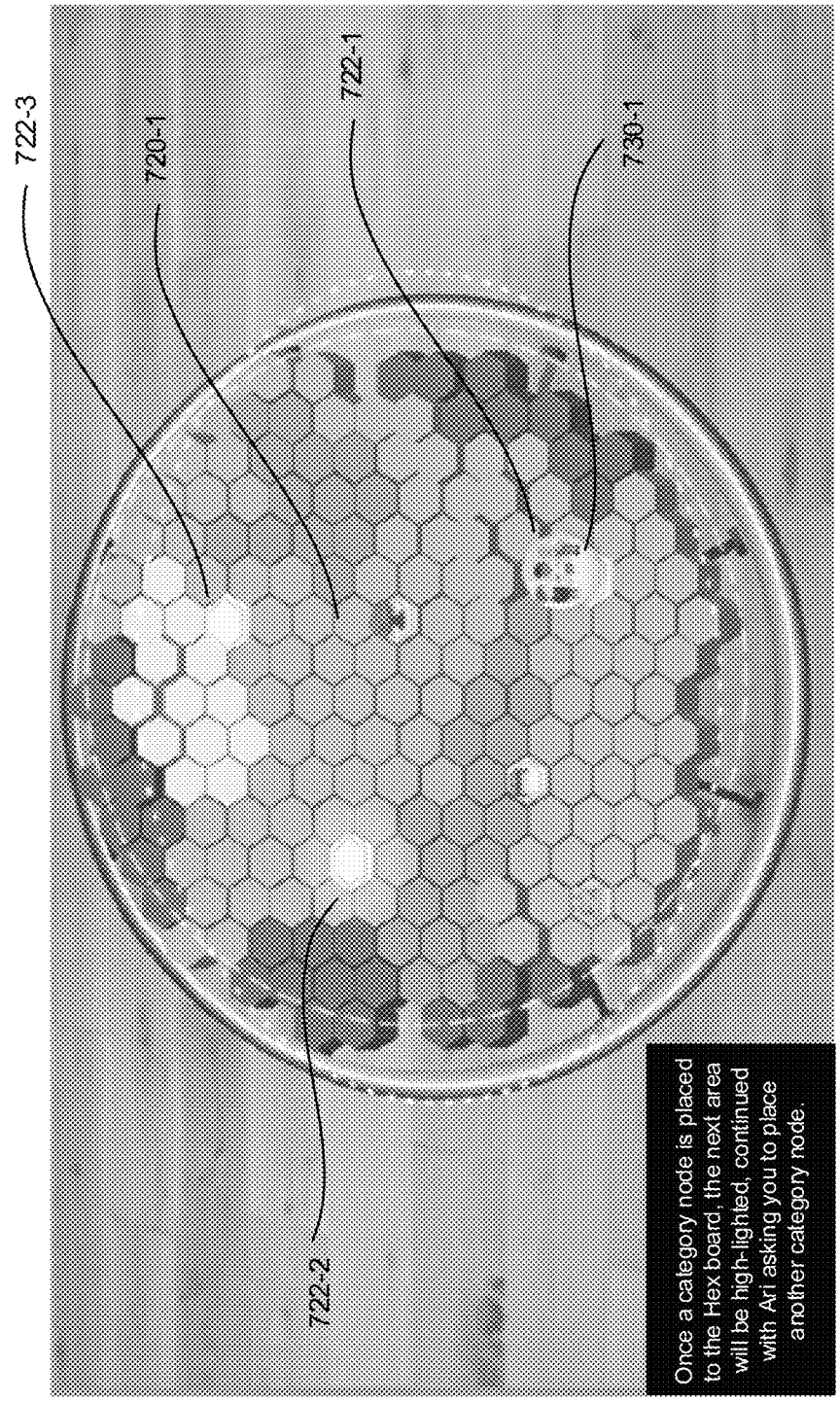
Figure 7F:
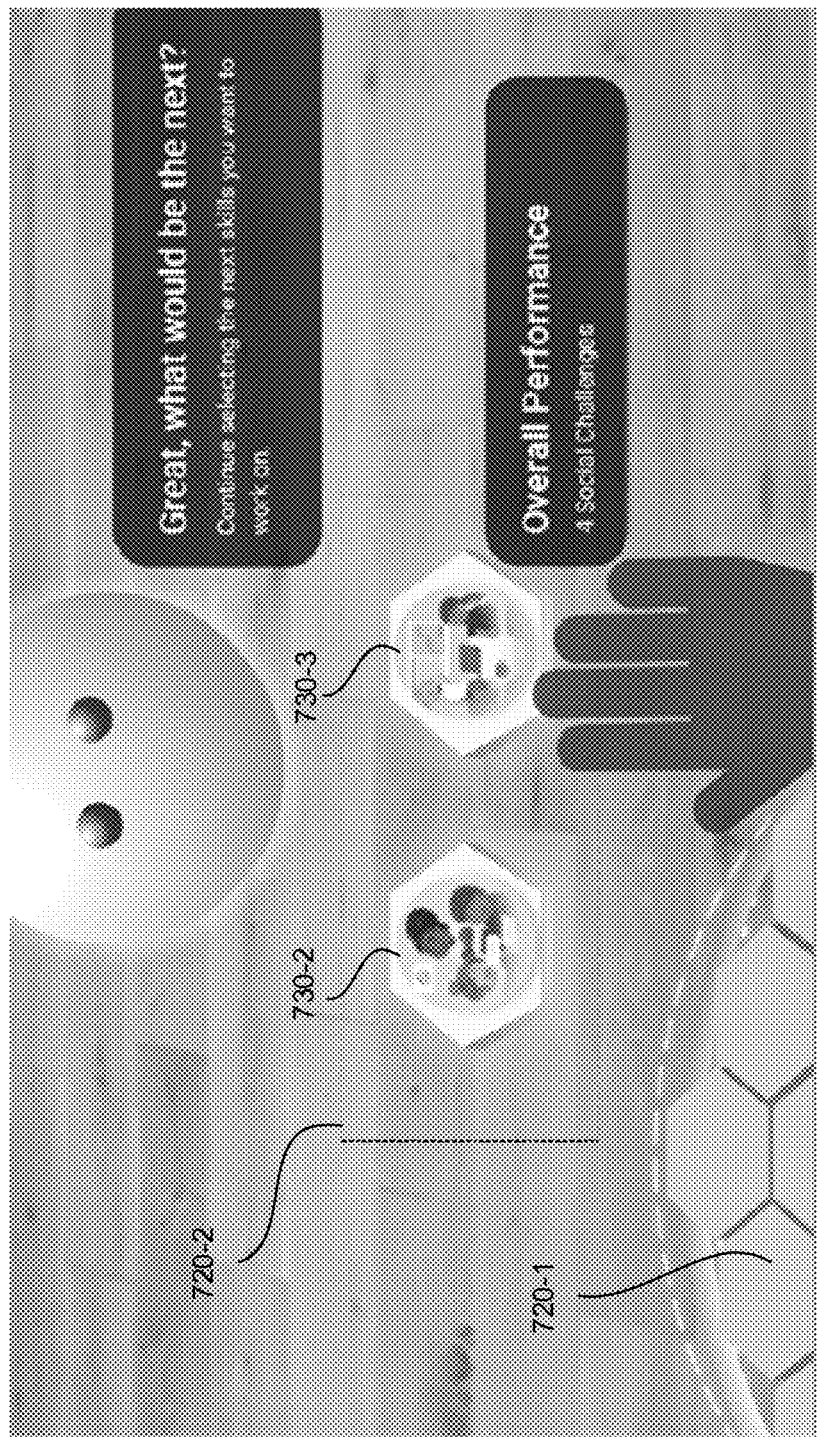
Figure 7G:
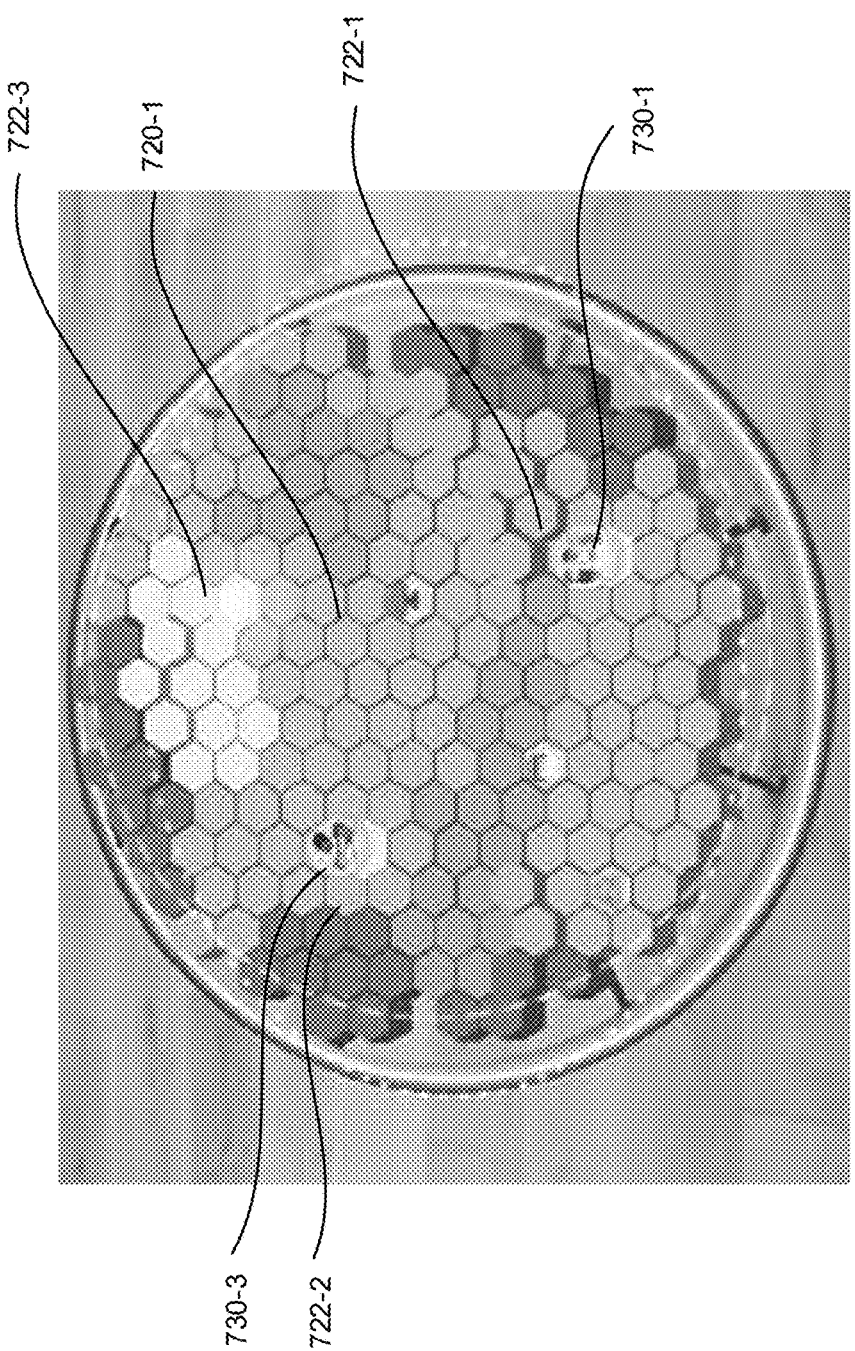
Figure 7H:
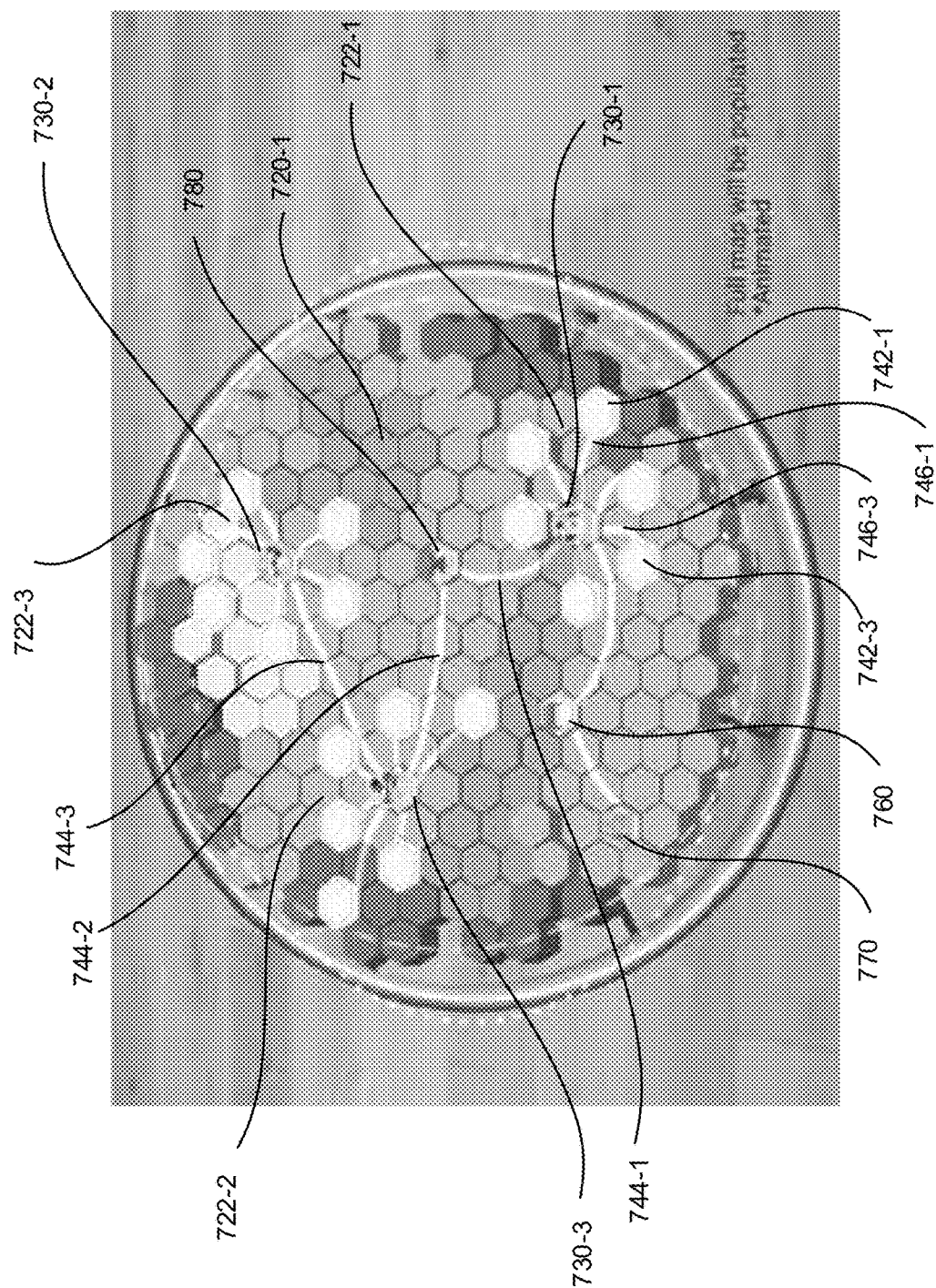
Figure 71:
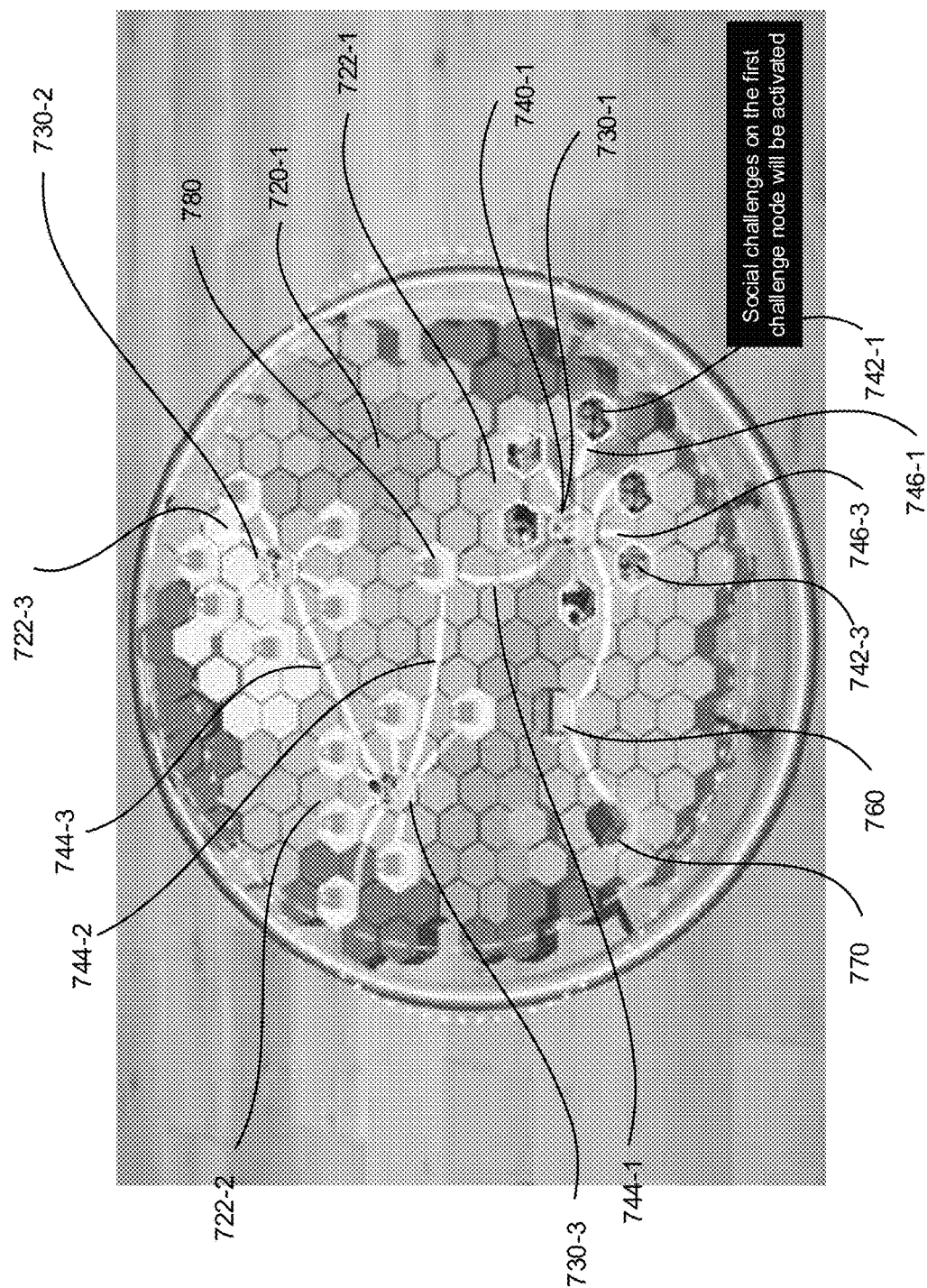
Figure 7J:
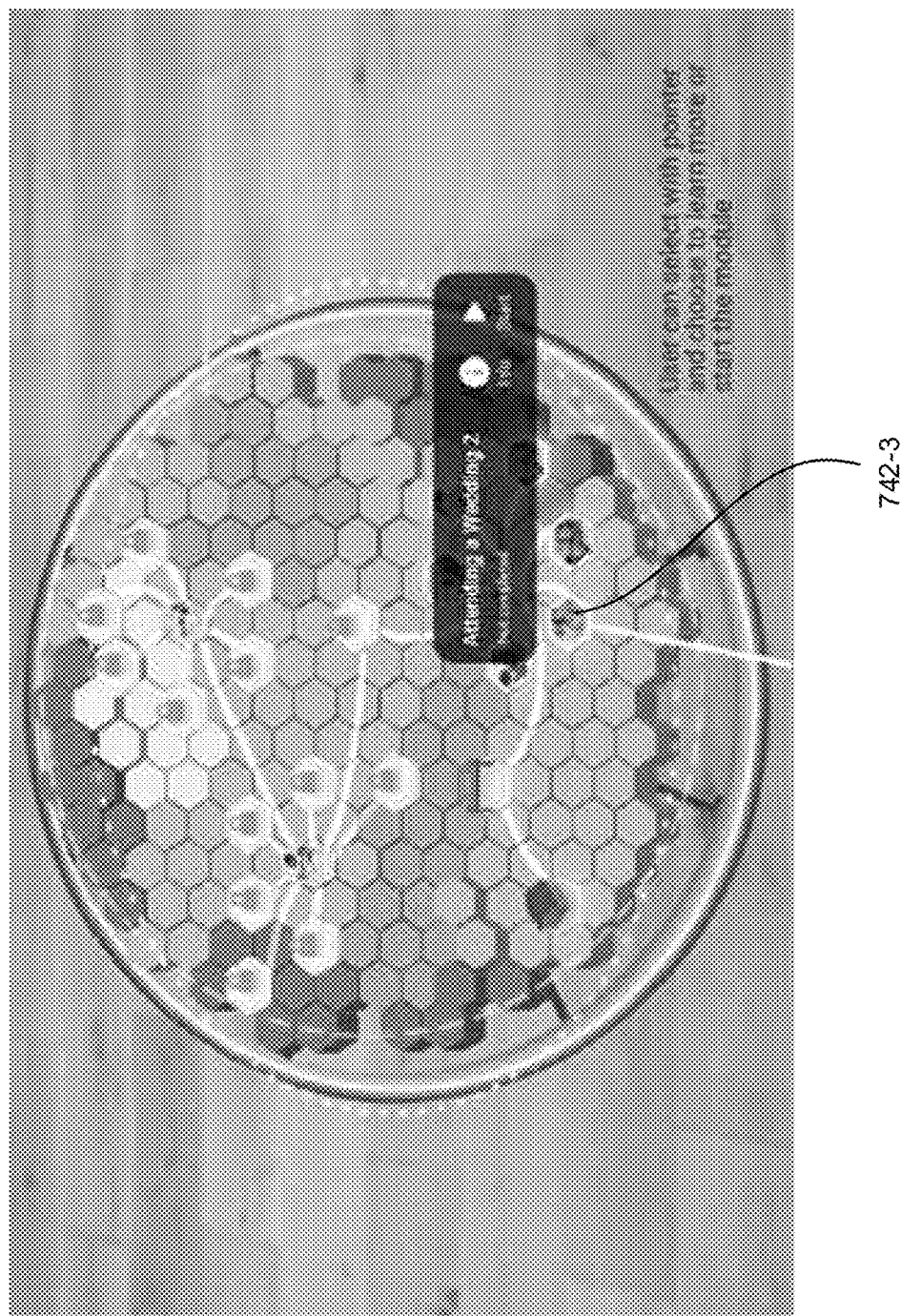
Figure 7K:
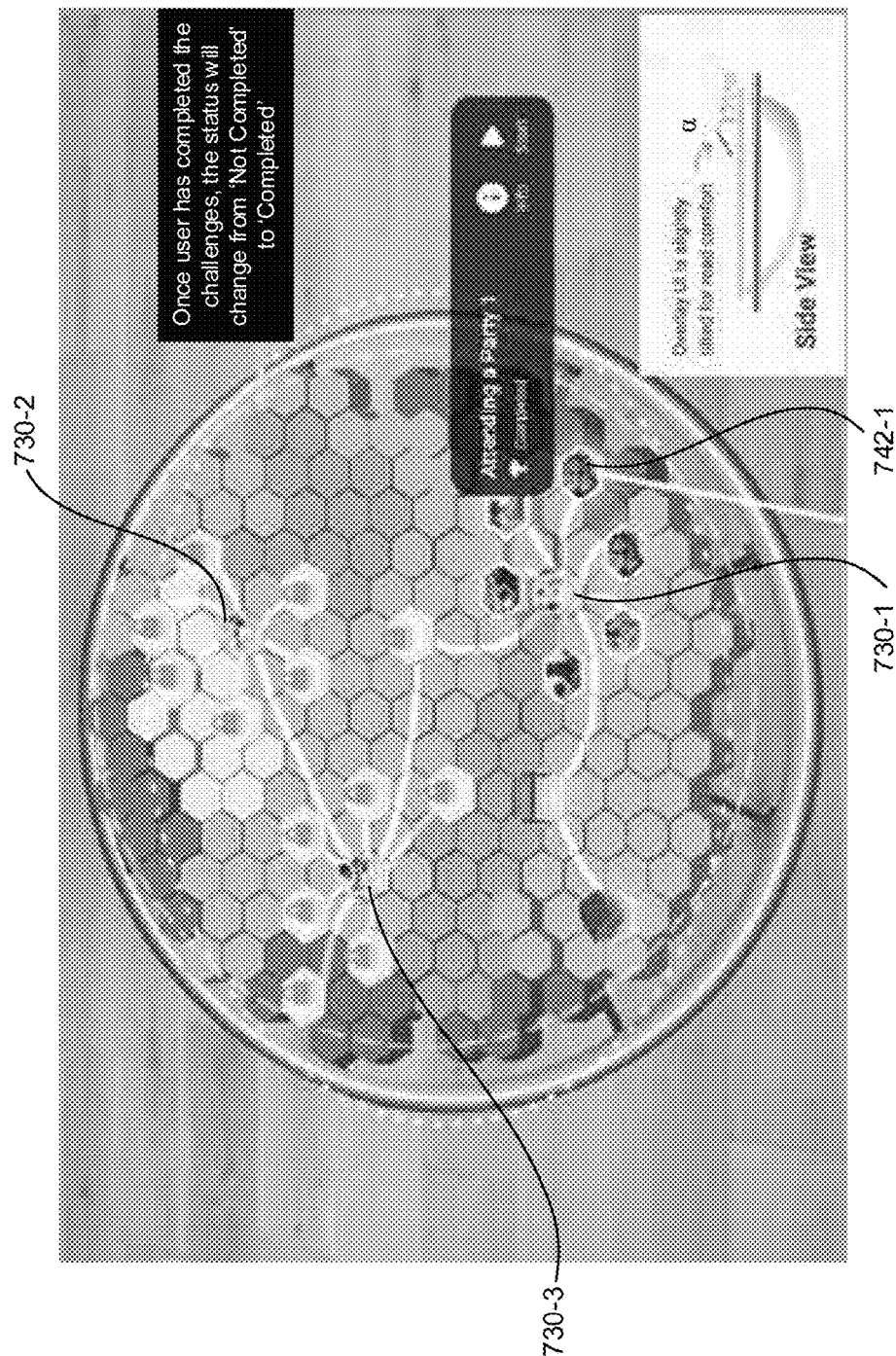
Figure 9C:
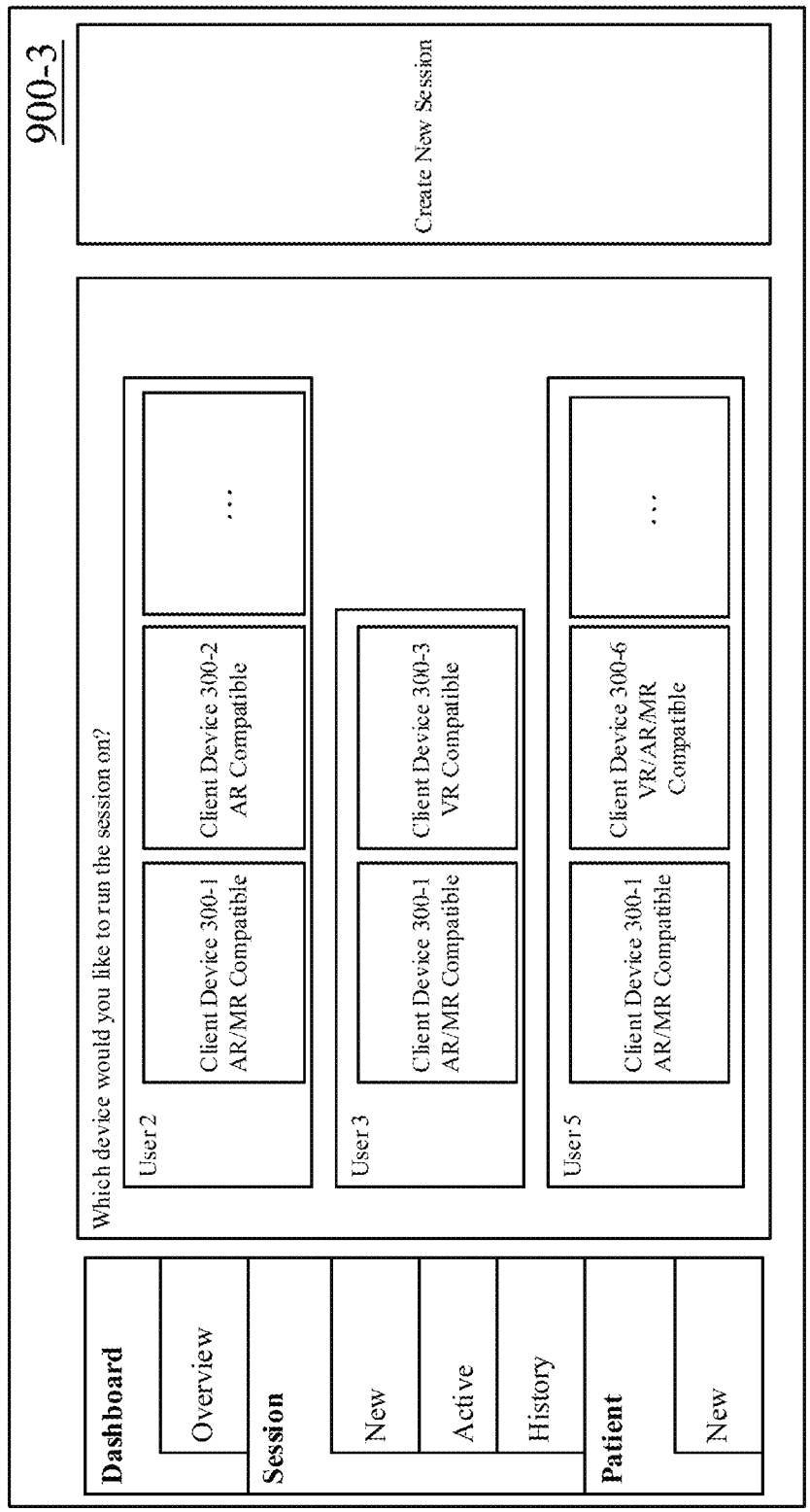
FIG. 9C illustrates a user interface for presenting a client application that facilitates controlling a digital reality scene for a population of client devices, in accordance with an embodiment of the present disclosure.

In some embodiments, each client application 320 is a group of instructions that, when executed by a processor, generates content for presentation to the user, such as a virtual reality scene 40, an augmented reality scene 40, a mixed reality scene 40. In some embodiments, a client application 320 generates content in response to inputs received from the user through movement of the client device 300, such as the inputs 310 of the client device. Here, the client application 320 includes a gaming application, a conferencing application, a video playback application, or a combination thereof. For instance, in some embodiments, the client application 320 facilitates providing one or more sessions of a first digital reality scene, such as the digital reality scene 40-3 illustrated in FIG. 5C. The first digital reality scene includes, or allows the user to access, a respective interactive digital chart and a corresponding interactive digital bin, such as the interactive digital chart 610 and the interactive digital bin 625 illustrated in FIG. 6A-6I, or the interactive digital chart 710 and bin 725 illustrated in FIG. 7A-7M. The respective interactive digital chart and corresponding interactive digital bin allow the user to participate in the first digital reality scene. Referring briefly to FIGS. 8A through 8C, in some embodiments, the client application 320 is utilized to obtain an assessment from a subject that includes an identification of a plurality of proposed experiences 24. Referring to FIGS. 9C and 9D, in some embodiments, the client application 320 is utilized to configure one or more gate criteria 32 associated with a node that is coupled to a proposed experience 24, and, optionally, configure the proposed experience within a digital reality scene 40, such as a number of player characters and/or a number of non-player characters that can participate in the digital reality scene 40 at during a given session.

In some embodiments, an engine 322 is a software module that allows a client application 320 to operate in conjunction with the client device 300. In some embodiments, the engine 322 receives information from the sensors on the client device 300 and provides the information to a client application 320. Based on the received information, the engine 322 determines media content to provide to the client device 300 for presentation to the user through the display 308 or the one or more audio devices, and/or a type of haptic feedback. For example, if the engine 322 receives information from the sensors of the client device 300 indicating that the user has looked to the left, the engine 322 generates content for the display 308 that mirrors the user's movement in a digital reality scene 40. As another example, if the user hits a wall (e.g., in a digital reality scene 40), the engine 322 generates control signals for a haptic-feedback mechanism of the client device 300 to generate a vibration, and, optionally, audio that corresponds to the user action (e.g., sound of a human first striking a wooden wall, or sound of a human first hitting a Plexiglas wall, which would be different from the sound generated for the wooden wall). As yet another non-limiting example, in some embodiments, the engine 322 receives information from one or more sensors in electronic communication with the client device 300, in which the one or more sensors obtain biometric data from a user of the client device 300 such as an instantaneous heart rate of the user captured over a period of time. In such embodiments, the engine 322 generates content for the display 308 that is responsive to the biometric data from the user, such as changing a color of a first object 42-1 in a digital reality scene 40 from a first color of orange to a second color of violet in order to reflect a lowering of the instantaneous heart rate of the user. However, the present disclosure is not limited thereto.

Similarly, in some embodiments, the engine 322 receives information from the sensors of the client device 300 and provides the information from the sensors to a client application 320. Accordingly, in some embodiments, the application 320 uses the information to perform an action within a digital reality scene of the application 320. In this way, if the engine 322 receives information from the sensors that the user has raised his or her hand, a simulated hand in the digital reality scene 40 lifts to a corresponding height. For example, referring briefly to FIGS. 6C and 6D, information is received describing that a user of a client device 300 has closed his or her hands from an open position (e.g., to an object 42-1 in a virtual reality scene 40, such as a node 630). Accordingly, a simulated hand 602-1 associated with a hand of the user is closed from an open position illustrated in FIG. 6C to a closed position illustrated in FIG. 6D. However, the present disclosure is not limited thereto.

In some embodiments, the engine 322 generates control signals for the haptic-feedback mechanism, which cause a haptic-feedback mechanism to create one or more haptic ques. As described supra, the information received by the engine 322 can also include information from the client device 300. For example, in some embodiments, one or more cameras (e.g., inputs 310, I/O subsystem 330 of FIG. 3) disposed on the client device 300 captures movements of the client device 300, and the client application 320 can use this additional information to perform the action within a digital reality scene 40 of the client application 320.

In some embodiments, the engine 322 provides feedback to the user that the action was performed. In some embodiments, the provided feedback is visually provided through the display 308 of the client device 300, provided in an auditory manner through the one or more audio devices of the client device 300 (e.g., I/O subsystem 330), and/or provided in a haptic manner via one or more of the haptic-feedback mechanisms of the client device 300.

Additional details and information regarding utilizing an engine (e.g., digital reality session engine 38 of FIG. 2B, engine 322 of FIG. 3) can be found at U.S. Patent Application Publication no.: 2018/0254097 A1, entitled "Dynamic Multi-Sensory Simulation System for Effecting Behavior Change," filed Mar. 5, 2018; U.S. Patent Application Publication no.: 2020/0022632 A1, entitled "Digital Content Processing and Generation for a Virtual Environment," filed Jul. 16, 2019; and U.S. Patent Application Publication no.: 2020/0023157 A1, entitled "Dynamic Digital Content Delivery in a Virtual Environment," filed Jul. 16, 2019; each of which is hereby incorporated by reference in its entirety.

Each of the above identified modules and applications correspond to a set of executable instructions for performing one or more functions described above and the methods described in the present disclosure (e.g., the computer-implemented methods and other information processing methods described herein, method 400 of FIG. 4, etc.). These modules (e.g., sets of instructions) need not be implemented as separate software programs, procedures or modules, and thus various subsets of these modules are, optionally, combined or otherwise re-arranged in various embodiments of the present disclosure. In some embodiments, the memory 312 optionally stores a subset of the modules and data structures identified above. Furthermore, in some embodiments, the memory 312 stores additional modules and data structures not described above.

It should be appreciated that the client device 300 of FIG. 3 is only one example of a client device 300, and that the client device 300 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Now that a general topology of the distributed system 100 has been described in accordance with various embodiments of the present disclosures, details regarding some processes in accordance with FIG. 4 will be described. FIG. 4 illustrates a flow chart of methods (e.g., method 400) for of preparing a regimen (e.g., first regimen 20-1 of first user profile 16-1 of FIG. 2A) for improving an ability of a subject to manage a psychiatric or mental condition exhibited by the subject, in accordance with embodiments of the present disclosure. Specifically, an exemplary method 400 for preparing a regimen 20 for improving an ability of a subject to manage a psychiatric or mental condition exhibited by the subject through a respective interactive digital chart (e.g., respective interactive digital chart 610 of FIG. 6E) is provided, in accordance with some embodiments of the present disclosure. In the flow charts, the preferred parts of the methods are shown in solid line boxes, whereas optional variants of the methods, or optional equipment used by the methods, are shown in dashed line boxes. As such, FIG. 4 illustrate methods for preparing a regimen for improving an ability of a subject to manage a psychiatric or mental condition exhibited by the subject.

Various modules in the memory 212 of the digital reality system 200, the memory 312 of a client device 300, or both perform certain processes of the methods described in FIGS. 4 and 13, unless expressly stated otherwise. Furthermore, it will be appreciated that the processes in FIGS. 4 and 13 can be encoded in a single module or any combination of modules.

Block 402. Referring to block 402 of FIG. 4, a method 400 of preparing a regimen 20 for improving an ability of a subject to manage a psychiatric or mental condition exhibited by the subject is provided. The method 400 is conducted at a computer system (e.g., distributed system 100 of FIG. 1, digital reality system 200 of FIGS. 2A and 2B, client device 300-1 of FIG. 3, client device 300-1 of FIG. 8D, client device 1100 of FIG. 11, etc.) associated with the subject. The computer system 100 includes one or more processors (e.g., CPU 202 of FIG. 2A, CPU 302 of FIG. 3), a display (e.g., display 308 of FIG. 3), and a memory (e.g., memory 212 of FIGS. 2A and 2B, memory 312 of FIG. 3) that is coupled to the one or more processors 302. The memory 312 includes one or more programs (e.g., assessment module 12 of FIG. 2A, experience store 22 of FIG. 2B, gate store 30 of FIG. 2B, application server module 34 of FIG. 2B, client application 320 of FIG. 3, engine 322 of FIG. 3, etc.) that is configured to be executed by the one or more processors 302. In other words, the method 400 cannot be mentally performed because the computational complexity addressed by the method requires use of the computer system.

Figure 11:
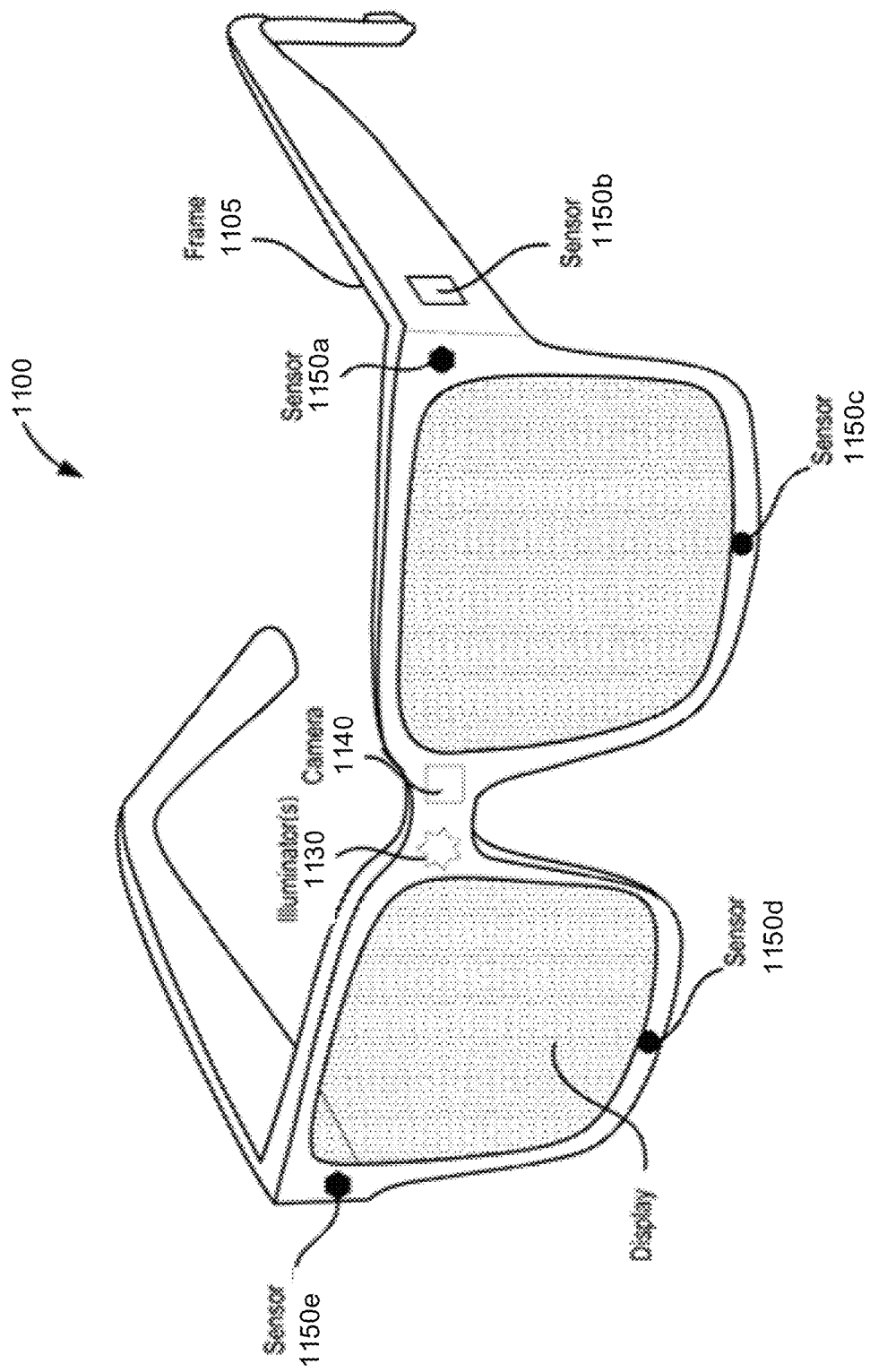
FIG. 11 illustrates an exemplary display in accordance with an embodiment of the present disclosure.

In some embodiments, the display 308 is a wearable display, such as a smart watch, head mounted display or a smart garment client device (e.g., display 1100 of FIG. 11). One such non-limiting example of a wearable display 308 includes a near-eye display or a head mounted display. In other embodiments, the display 308 is a smart mobile device display (e.g., a smart phone), such as client device 300-1 of FIG. 8A. In some embodiments, display 308 is a head-mounted display (HMD) connected to host computer system 300, a standalone HMD, a mobile device or computing system, or any other hardware platform capable of providing artificial reality content to one or more viewers. FIG. 11 is a perspective view of an example of a near-eye display 1100 in the form of a pair of glasses for implementing some of the examples of displays 308 disclosed herein. In some embodiments, the near-eye display 1100 is configured to operate as a virtual reality display, an augmented reality display, and/or a mixed reality display. In some embodiments, the near-eye display 1100 includes a frame 1105 and a display 1110. In some embodiments, the display 1110 is configured to present content to a user. In some embodiments, the display 1100 includes display electronics and/or display optics. For example, in some embodiments, the display 1100 includes an LCD display panel, an LED display panel, or an optical display panel (e.g., a waveguide display assembly). In some embodiments, the near-eye display 1100 further includes various sensors 1150a, 1150b, 1150c, 1150d, and 1150e on or within frame 1105. In some embodiments, the various sensors 1150a-1150e include one or more depth sensors, motion sensors, position sensors, inertial sensors, or ambient light sensors. In some embodiments, the various sensors 1150a-1150e include one or more image sensors configured to generate image data representing different fields of views in different directions. In some embodiments, the various sensors 1150a-1150e are used as input devices to control or influence the displayed content of near-eye display 1100, and/or to provide an interactive VR/AR/MR experience to a user of near-eye display 1100. In some embodiments, the various sensors 1150a-1150e also are used for stereoscopic imaging.

In some embodiments, the near-eye display 1100 further includes one or more illuminators 1130 to project light into the physical environment. In some embodiments, the projected light is associated with different frequency bands (e.g., visible light, infra-red light, ultra-violet light, etc.) and, in such embodiments, serves various purposes. For example, in some embodiments, the illuminator(s) 1130 project light in a dark environment (or in an environment with low intensity of infra-red light, ultra-violet light, etc.) to assist sensors 1150a-1150e in capturing images of different objects within the dark environment. In some embodiments, the illuminator(s) 1130 are used to project certain light pattern onto the objects within the environment. In some embodiments, the illuminator(s) 1130 are used as locators.

In some embodiments, the near-eye display 1100 includes a high-resolution camera 1140. In some embodiments, the camera 1140 captures images of the physical environment in the field of view. In some embodiments, the captured images are processed, for example, by a virtual reality engine (e.g., engine 322 of FIG. 3) to add one or more virtual objects 42 to the captured images or modify physical objects in the captured images. In some embodiments, the processed images are displayed to the user by display 1100 for the AR or MR applications (e.g., client application 320 of FIG. 3) provided by the present disclosure.

Figure 12:
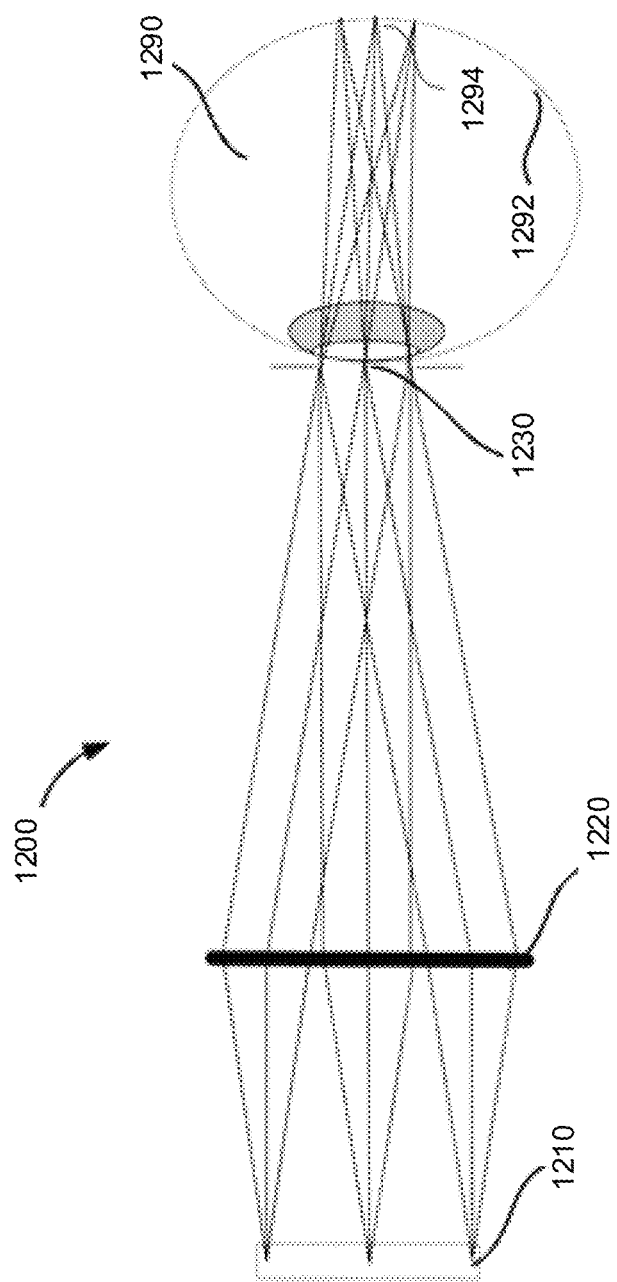
FIG. 12 is a simplified diagram illustrating an example of an optical system for a display in accordance with an embodiment of the present disclosure.

FIG. 12 is a simplified diagram illustrating an example of an optical system 1200 for a near-eye display 1100. In some embodiments, the optical system 1200 includes an image source 1210 and projector optics 1220. In the example shown in FIG. 12, image source 1210 is in front of projector optics 1220. In various embodiments, the image source 1210 is located outside of the field of view of user's eye 1290. For example, in some embodiments, one or more reflectors or directional couplers is used to deflect light from an image source that is outside of the field of view of user's eye 1290 to make the image source appear to be at the location of image source 1210 shown in FIG. 12. In some embodiments, light from an area (e.g., a pixel or a light emitting device) on image source 1210 is collimated and directed to an exit pupil 1230 by projector optics 1220. Thus, in some embodiments, objects at different spatial locations on image source 1210 appear to be objects far away from user's eye 1290 in different viewing angles (FOVs). In some embodiments, the collimated light from different viewing angles then be focused by the lens of user's eye 1290 onto different locations on retina 1292 of user's eye 1290. For example, in some embodiments, at least some portions of the light are focused on a fovea 1294 on retina 1292. In some embodiments, collimated light rays from an area on image source 1210 and incident on user's eye 1290 from a same direction is focused onto a same location on retina 1292. As such, in such embodiments, a single image of image source 1210 is formed on retina 1292.

In some embodiments, the user experience of using a digital reality system 200 depends on several characteristics of the optical system, including field of view (FOV), image quality (e.g., angular resolution), size of the eyebox (to accommodate for eye and head movements), and brightness of the light (or contrast) within the eyebox. Field of view describes the angular range of the image as seen by the user, usually measured in degrees as observed by one eye (for a monocular HMD) or both eyes (for either biocular or binocular HMDs). To create a fully immersive visual environment, a large FOV is desirable in some embodiments because a large FOV (e.g., greater than about 60 degrees) provides a sense of "being in" an image, rather than merely viewing the image. Smaller fields of view may also preclude some important visual information. For example, a head mounted display system with a small FOV may use a gesture interface, but the users may not see their hands in the small FOV to be sure that they are using the correct motions. On the other hand, wider fields of view may require larger displays or optical systems, which may influence the size, weight, cost, and comfort of using the HMD.

In some embodiments, resolution refers to the angular size of a displayed pixel or image element appearing to a user, or the ability for the user to view and correctly interpret an object as imaged by a pixel and/or other pixels. The resolution of a HMD may be specified as the number of pixels on the image source for a given FOV value, from which an angular resolution may be determined by dividing the FOV in one direction by the number of pixels in the same direction on the image source For example, for a horizontal FOV of 40 degrees and 1080 pixels in the horizontal direction on the image source, the corresponding angular resolution may be about 2.2 arc-minutes, compared with the one-arc-minute resolution associated with Snellen 20/20 human visual acuity.

Accordingly, by requiring use of the display the method 400 cannot be mentally performed because the computational complexity addressed by the method requires use of the computer system. Moreover, by using the display to present media to the subject, the method improves the ability of the subject to manage the psychiatric or mental condition exhibited by the subject in comparison with in vivo treatment methods since the display allows the method to control stimuli presented to the subject.

In some embodiments, the psychiatric or mental condition exhibited by the subject is a clinically diagnosed mental disorder, such that a medical practitioner associated with the subject has verified the diagnosis of the psychiatric or mental condition. In some embodiments, the psychiatric or mental condition is a sub-clinically diagnosed mental disorder, which differs from the clinically diagnosed mental disorder in that the sub-clinically diagnosed mental cannot be quantified or is overly burdensome to quantify. Additional details and information regarding sub-clinically diagnosed mental disorders and clinically diagnosed mental disorders can be found at Thomas et al., 2006, "Comprehensive Handbook of Personality and Psychopathology, Personality and Everyday Functioning," John Wiley & Sons, 1, print;

Andrasik et al., 2005, "Comprehensive Handbook of Personality and Psychopathology, Adult Psychopathology," John Wiley and Sons, 2, print, each of which is hereby incorporated by reference in its entirety. In other embodiments, the psychiatric mental condition has not been diagnosed by a medical practitioner (e.g., self-diagnosed by a user of a client device 300), such as a desire to improve the general well-being of the user. Non-limiting examples of a psychiatric or mental condition exhibited by a subject include separation anxiety disorder, selective mutism, specific phobia, social anxiety disorder (i.e., social phobia), panic disorder, agoraphobia, generalized anxiety disorder, induced anxiety disorder (e.g., substance-induced anxiety disorder, medication-induced anxiety disorder, etc.), or anxiety disorder due to another medical condition (e.g., other than the psychiatric or mental condition). As another non-limiting example, in some embodiments, a model of an application model library 50 is utilized, either alone or supervised by the medical practitioner, to determine a diagnosis of a mental disorder, such as an improvement or reduction in an ability of a subject to manage the mental disorder. One of skill in the art of the present disclosure will appreciate that other specified psychiatric or mental conditions or unspecified psychiatric or mental conditions are within the domain of the present disclosure.

Turning to more specific aspects of the psychiatric or mental condition exhibited by the subject, in some embodiments, the psychiatric or mental condition exhibited by the subject includes one or more responses to a social setting, such as a first response of being stressed in a social setting, a second response of fearing the social setting, a third response of being overwhelmed in the social setting, or a combination thereof.

For instance, in some embodiments, the psychiatric or mental condition exhibited by the subject is triggered by a differential neurochemical disturbance. Moreover, in some embodiments, the psychiatric or mental condition exhibited by the subject is triggered by a differential neuropsychological disturbance. Additionally, in some embodiments, the psychiatric or mental condition exhibited by the subject is triggered by a differential pharmacologic disturbance. Additional details and information regarding triggering the psychiatric or mental condition exhibited by the subject can be found at Theil et al., 1999, High Versus Low Reactivity to a Novel Environment: Behavioral, Pharmacological and Neurochemical Assessments," Neuroscience, 93(1), pg. 243, which is hereby incorporated by reference in its entirety.

In some embodiments, a clinically diagnosed mental disorder is a psychiatric or mental condition that has been diagnosed in a clinical setting (e.g., recorded in a medical record associated with a subject, such as a well-being store 18 of a user profile 16), such as by evaluating (e.g., by the medical practitioner and/or one or more models of the application model library 50) one or more biomarkers of the subject such as one or more neuroimaging biomarkers, one or more gastrointestinal biomarkers, one or more immunology biomarkers, one or more neurotrophic biomarkers, one or more neurotransmitter biomarkers, one or more hormone biomarkers, one or more oxidative stress biomarkers, or a combination thereof. In some embodiments, the diagnosis in the clinical setting includes a diagnosis of an onset of the psychiatric or mental condition, or a recurrence of the psychiatric or mental condition. For instance, in some embodiments, the method 400 improves the ability of the subject to manage the psychiatric or mental condition exhibited by the subject by providing a modification to the psychiatric or mental condition (e.g., disorder modification), such as a refresher treatment and/or a booster treatment that requires evaluation of the subject on a recurring basis (e.g., revaluated every three months). However, the present disclosure is not limited thereto. In some embodiments, the clinically diagnosed mental disorder is an anxiety disorder. Accordingly, the anxiety disorder includes a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject.

In some embodiments, the clinically diagnosed mental disorder is a mood disorder. In such embodiments, the mood disorder exhibited by the subject includes a depression disorder, a bipolar disorder, or a cyclothymic disorder. For instance, in some embodiments, the mood disorder is a borderline personality disorder (BPD), a bipolar I disorder (BI-I), a bipolar II disorder (BP-II), a bipolar III disorder (e.g., pharmacologic hypomania), or the like. As another non-limiting example, in some embodiments, the mood disorder exhibited by the subject includes a major depressive disorder. Additional details and information regarding psychiatric or mental conditions including mood disorders can be found Perugi et al., 2011, "Are Atypical Depression, Borderline Personality Disorder and Bipolar II Disorder Overlapping Manifestations of a Common Cyclothymic Diathesis?," World Psychiatry, 10(1)), pg. 45; Kennis et al., 2020, "Prospective Biomarkers of Major Depressive Disorder: A Systematic Review and Meta-analysis," Molecular Psychiatry, 25, pg. 321; Zuckerman et al., 2018, "Recognition and Treatment of Cognitive Dysfunction in Major Depressive Disorder," Frontiers in Psychiatry, 9, pg. 955, each of which is hereby incorporated by reference in its entirety.

In some embodiments, the clinically diagnosed mental disorder is a psychotic disorder. In such embodiments, the psychotic disorder exhibited by the subject includes a schizophrenia disorder, a delusion disorder, or a hallucination disorder. For instance, in some embodiments, the psychotic disorder includes one or more criterion exhibited by the subject of disorganized speech and/or disorganized or catatonic behavior. In some embodiments, these one or more criterion is evaluated by a model of the digital reality system 200 in order to determine if the subject is exhibiting disorganized speech and/or disorganized or catatonic behavior when engaging with a digital reality scene 40.

In some embodiments, the clinically diagnosed mental disorder is an eating disorder. In such embodiments, the eating disorder exhibited by the subject includes anorexia nervosa, bulimia nervosa, or binge eating disorder.

In some embodiments, the clinically diagnosed mental disorder is an impulse control disorder. In such embodiments, the impulse control disorder exhibited by the subject includes a pyromania disorder, a kleptomania disorder, or a compulsive gambling disorder.

In some embodiments, the clinically diagnosed mental disorder is an addiction disorder. In such embodiments, the addiction disorder includes an alcohol use disorder or a substance abuse disorder. Additional details and information regarding alcohol use disorder can be found at Miller et al., 2001, "How effective is alcoholism treatment in the United States?," Journal of studies on alcohol, 62(2), pg. 211.

In some embodiments, the clinically diagnosed mental disorder is a personality disorder. In such embodiments, an antisocial personality disorder, an obsessive-compulsive personality disorder, or a paranoid personality disorder.

In some embodiments, the clinically diagnosed mental disorder is an obsessive-compulsive disorder. In some embodiments, the clinically diagnosed mental disorder is a post-traumatic stress disorder.

Additional details and information regarding psychiatric or mental conditions exhibited by a subject can be found at American Psychiatric Association, 2013, "Diagnostic and Statistical Manual of Mental Disorders (DSM-5)," American Psychiatric Pub., print, which is hereby incorporated by reference in its entirety.

Block 404. Referring to block 404, the method 400 includes obtaining an assessment (e.g., from assessment module 12 of FIG. 2A) of the subject in electronic form. In some embodiments, the assessment of the subject includes a plurality of responses by the subject to a corresponding plurality of prompts configured to elect a response from the subject.

In some embodiments, the obtaining the assessment of the subject is additional or optional. For instance, in some embodiments, the method 400 obtains an assessment of the subject prior to presenting a first digital reality scene 40-1 illustrated in block 406. In some other embodiments, the method 400 obtains an assessment of the subject after presenting the first digital reality scene illustrated in block 406 or other processes. In still some other embodiments, the method 400 does not obtain an assessment of the subject either before or after presenting the first digital reality scene. In some embodiments, the assessment of the subject is obtained from a client device 300 that is remote from a digital reality system 200.

For instance, referring to FIGS. 8A through 8C, a social anxiety assessment (e.g., assessment of assessment module 12 of FIG. 2A) is obtained from a user of a first client device 300 through a user interface 700 of presented through a display 308 of the first client device 300. In some embodiments, the assessment of the subject is obtained solely by the subject. However, the present disclosure is not limited thereto. In alternative embodiments, the assessment of the subject is obtained by a medical practitioner associated with subject or a pairing of both the subject and the medical practitioner associated with subject. For instance, in some embodiments, the medical practitioner obtains the assessment of the subject in a clinical setting, such as in a conference (e.g., in person conference, video and/or audio conference, etc.). By allowing the subject to participate in obtaining the assessment, the subject is free to provide honest, subjective responses without exposing the subject to a chance of exhibiting a psychiatric or mental condition of the subject when responding to the assessment in a social setting (e.g., with a medical practitioner).

In this way, in some embodiments, prior to obtaining the subject assessment, a validation of the assessment is obtained. In some embodiments, the validation of the assessment includes a first selection by the subject of a plurality of proposed experiences 24 and a second selection by the medical practitioner and/or a model, in which the second selection includes of a subset of the plurality of proposed experiences 24. By way of a first example, a subject selects 12 proposed experiences from a panel of 30 different proposed experiences. Of these 12 proposed experiences, the medical practitioner selects 5 proposed experiences. By way of a second example, a subject selects 14 proposed experiences from a panel of 23 different proposed experiences. The medical practitioner selects 3 of the 14 proposed experiences but also picks four additional proposed experiences from the panel of 23 different proposed experiences that the subject did not pick. In this way, the medical practitioner curates the plurality of proposed experiences 24 in order to optimize the regimen 20 for the subject. As a non-limiting third example, consider a subject selections 5 proposed experiences from a panel of 1,000 proposed experiences, the medical practitioner selects 3 of the 5 proposed experiences, and a model selects one of the 3 proposed experiences, such that the one of the 3 proposed experiences is validated by both medical practitioner and the model. In some embodiments, this curating removes a proposed experience from the plurality of experiences and/or adds a new proposed experience to the plurality of experiences. In some embodiments, the plurality of proposed experiences is 2 proposed experiences, 3 proposed experiences, 4 proposed experiences, 5 proposed experiences, 6 proposed experiences, 7 proposed experiences, 8 proposed experiences, 9 proposed experiences, 10 proposed experiences, 11 proposed experiences, 12 proposed experiences, 13 proposed experiences, 14 proposed experiences, 15 proposed experiences, 16 proposed experiences, 17 proposed experiences, 18 proposed experiences, 19 proposed experiences, 20 proposed experiences, 21 proposed experiences, 22 proposed experiences, 23 proposed experiences, 24 proposed experiences, 25 proposed experiences, or about 30 proposed experiences (e.g., 27 proposed experiences). In some embodiments, the plurality of proposed experiences is between 2 and 100 proposed experiences, between 3 and 80 proposed experiences, between 4 and 70 proposed experiences, between 5 and 60 proposed experiences, between 6 and 50 proposed experiences, or between 7 and 40 proposed experiences. In some embodiments, the plurality of proposed experiences includes 100 or more, 200 or more, 300 or more, or 400 or more proposed experiences. In some embodiments, the subject selects 2, 3, 4, 5, 6, 7, 8, 9, 10, 11, 12, 13, 14, 15, 16, 17, 18, 19, or 20 proposed experiences. In some embodiments, a number of proposed experiences in the plurality of proposed experiences is defined by the medical practitioner. In some embodiments, the medical practitioner selects all of the proposed experiences that the subject selected and no additional proposed experiences. In some embodiments, the medical practitioner selects some of the proposed experiences that the subject selected and no additional proposed experiences. In some embodiments, the medical practitioner selects some of the proposed experiences that the subject selected and some additional proposed experiences from the plurality of proposed experiences. Moreover, in some embodiments, the model selects all of the proposed experiences that the subject selected and no additional proposed experiences. In some embodiments, the model selects some of the proposed experiences that the subject selected and no additional proposed experiences. In some embodiments, the model selects some of the proposed experiences that the subject selected and some additional proposed experiences from the plurality of proposed experiences. Furthermore, in some embodiments, the model selects all of the proposed experiences that the medical practitioner selected and no additional proposed experiences. In some embodiments, the model selects some of the proposed experiences that the medical practitioner and no additional proposed experiences. In some embodiments, the model selects some of the proposed experiences that the medical practitioner selected and some additional proposed experiences from the plurality of proposed experiences.

In some embodiments, the assessment is a subject feasibility assessment, which is configured to determine if the subject is deemed acceptable for use with the systems and methods of the present disclosure. For instance, in some embodiments, the subject feasibility assessment is utilized to determine: if the subject has previous experience with digital reality scenes; if the subject has enjoyed using digital reality scenes; if the participants perceive the content as useful, helpful or effective for managing the psychiatric or mental condition exhibited by the subject; acceptability for the subject with a proposed frequency, duration, intensity or combination thereof of the regimen; comfort of a remote device and/or adverse effects experienced by the subject when exposed to digital reality scenes, and the like.

As a non-limiting example, in some embodiments, the assessment includes one or more prompts including: whether the subject has received treatment from a therapist, a psychologist, a psychiatrist, or a medical practitioner; whether the subject has ever practiced exposure therapy with a medical practitioner; whether the subject has ever practiced meditation or mindfulness; whether the subject has ever practiced cognitive-behavioral therapy or cognitive restructuring with a medical practitioner; what are some recent/current social situations in the life of the subject that were difficult; would the subject prefer to receive medication for managing stress, anxiety, fear, or a combination thereof; a subject preference for a higher level of guidance or clinician support/involvement; were the challenges progressively harder because of the sequence they chose to order; or a combination thereof.

In some embodiments, the assessment is a standardized assessment, which allows for normalization when identifying the plurality of proposed experiences 24 due to a lack of variance in the standard assessment. Moreover, in some embodiments, the standardized assessment allows for the method 400 to obtain information of a change (e.g., variance) in scores (e.g., responses) obtained from the subject over a period of time, such as determining if a meaningful or clinically significance difference (e.g., a change in 5 points in the LSAS assessment score, a change in 10 points in the LSAS assessment score, etc.) is satisfied by the subject. In some embodiments, the standardized assessment is unique to a particular psychiatric or mental condition, such as social anxiety assessment of FIGS. 8A through 8C. For instance, in some embodiments, the standard assessment includes about twelve prompts for a subject to answer. In alternative embodiments, the standard assessment includes about twenty-four prompts. In still alternative embodiments, the standard assessment includes 3, 4, 5, 6, 7, 8, 9, 10, 11, 12, 13, 14, 15, 16, 17, 18, 19, 20, 21, 22, 23, 24, 25, 26, 27, 28, 29, or between 30 and 200 prompts. A non-limiting example of such a standard assessment includes the Liebowitz Social Anxiety Scale (LSAS) assessment (e.g., a LSAS-self reported (LSAS-SR) assessment). In some embodiments, the LSAS assessment is administered by a medical practitioner associated with a subject (e.g., a LSAS-clinician reported (LSAS-CR) assessment), such as through a digital reality scene 40 that includes a first subject user and a second medical practitioner user. In alternative embodiments, the LSAS assessment is self-administered by the subject, such as through a web browser or a digital reality scene 40 (e.g., user interface 800-1 of FIGS. 8A, user interface 800-2 of FIG. 8B, user interface 800-3 of FIG. 8C, etc.). Additional details and information regarding an LSAS assessment is found at Rytwinski et al., 2009, "Screening for Social Anxiety Disorder with the Self-Report Version of the Liebowitz Social Anxiety Scale," Depression and Anxiety, 26(1), pg. 34, which is hereby incorporated by reference in its entirety.

As yet another non-limiting example, in some embodiments, the standard assessment includes a quality-of-life index assessment that seek to measure objective indicators of the quality of life of the subject. Additional details and information regarding the quality-of-life assessment can be found at Atkinson et al., 1997, "Characterizing Quality of Life Among Patients with Chronic Mental Illness: A Critical Examination of the Self-Report Methodology," American Journal of Psychiatry, 154(1), pg. 99, which is hereby incorporated by reference in its entirety.

As yet another non-limiting example, in some embodiments, the standard assessment includes a clinical global impression (CGI) scale assessment. The CGI scale assessment is configured to evaluate a severity and/or changes in an ability of the subject to manage the psychiatric or mental condition. Additional details and information regarding CGI scale assessments can be found at Pérez et al., 2007, "The Clinical Global Impression Scale for Borderline Personality Disorder Patients (CHI-BPD): A Scale Sensible to Detect Changes," Actas Españolas de Psiquiatria, 35(4), pg. 229, which is hereby incorporated by reference in its entirety. In some embodiments, the CGI scale assessment is utilized in order to determine a characteristic (e.g., label) associated with the subject, such as mapping the assessment obtained from the subject with an n-ary (e.g., 2-ary) operation. In some embodiments, the CGI scale assessment is utilized to determine a threshold confidence score for improving the ability of the subject to manage the psychiatric or mental condition exhibited by the subject.

Furthermore, as yet another non-limiting example, in some embodiments, the standard assessment includes a patient generated index (PGI), which provides a patient rated format, as opposed to a clinician rated format of the CGI scale assessment. Additional details and information regarding the PGI assessment can be found at Faith et al., 2007, "Twelve Years-Experience with the Patient Generated Index (PGI) of Quality of Life: A Graded Structured Review," Quality of Life Research, 16(4), pg. 705, which is hereby incorporated by reference in its entirety.

As yet another non-limiting example, in some embodiments, the standard assessment includes establishing a minimally clinically important difference (MCID). In some embodiments, the MCID is based on an initial assessment of the subject and must be satisfied by the subject in order to improve. Additional details and information regarding MCID assessments can be found at Kaplan, R., 2005, "The Minimally Clinically Important Difference in Generic Utility-based Measures," COPD: Journal of Chronic Obstructive Pulmonary Disease, 2(1), pg. 91, which is hereby incorporated by reference in its entirety.

In some embodiments, the assessment includes a Fear of Negative Evaluation (e.g., brief form (FNE-B), standard form, etc.) (FNE) assessment; a Personal Report of Confidence as a Speaker (PRCS) assessment; a Social Interaction Anxiety Scale (SIAS) assessment; a Social Phobia Scale (SPS) assessment; a Behavioural Assessment Task (BAT) assessment; a state communication apprehension (SCA) assessment; a trait communication apprehension (TCA) assessment; a Rathus Assertiveness Schedule (RAS) assessment; a Questionnaire on Social Contexts Inducing Anxiety (SCIA) assessment; an Appraisal of Social Concerns for consequences (ASC-C) assessment; an Appraisal of Social Concerns for probability (ASC-P) assessment; an Self-Statements During Public Speaking (SSPS) assessment; a completed post-treatment assessment; or a combination thereof. Additional details and information regarding one or more assessments can be found at Chesham et al., 2018, "Meta-analysis of the Efficacy of Virtual Reality Exposure Therapy for Social Anxiety," Behavior Change, 35(3), pg. 152, which is hereby incorporated by reference in its entirety for all purposes.

Furthermore, in some embodiments, the assessment includes determining if the subject is currently consuming a beta blocker pharmaceutical composition and/or a benzodiazepine pharmaceutical composition. For instance, in embodiments, the assessment determines if the subject is currently consuming acebutolol, atenolol, bisoprolol, metoprolol, nadolol, nebivolol, propranolol, or a combination thereof. In some embodiments, when the subject is currently consuming a beta blocker pharmaceutical composition and/or a benzodiazepine pharmaceutical composition, the method ceases the placing of a respective node. In some embodiments, when the subject is not currently consuming a beta blocker pharmaceutical composition and/or a benzodiazepine pharmaceutical composition, the method proceeds with the placing of a respective node. However, the present disclosure is not limited thereto.

In some embodiments, the assessment of the subject identifies a plurality of categories, each category including or associated with a plurality proposed experiences (e.g., experiences 24 of FIG. 2B). In some embodiments, the plurality of categories is 2, 3, 4, 5, or more than 5 categories. In some embodiments, the plurality of proposed experiences associated with a category in the plurality of categories is 2, 3, 4, 5, 6, 7, 8, 9, 10, 11, 12, 13, 14, 15, or more proposed experiences. In some embodiments, the assessment of the subject identifies the plurality of categories from a predetermined set of categories. In some embodiments, the plurality of identified categories is a selection of a subset of categories from the predetermined set of categories. Each category includes or is associated with a plurality (2, 3, 4, 5, 6, 7, 8, 9, 10, 11, 12, 13, 14, 15, or more) of proposed experiences 24 (e.g., stored by the experience store 22 of the digital reality system 200 of FIG. 2B). For instance, in some embodiments, the selection is a first user selection of a plurality (e.g., 2, 3, 4, 5, etc.) of categories. In some embodiments, the selection is a second curated medical practitioner selection based on the first user selection. By way of example, consider a first user of a first client device 300-1 that exhibits a social anxiety disorder and a second user of a second client device 300-2 that exhibits an addiction disorder. If the first user and the second user are both provided the same standardized assessment (e.g., the LSAS self-administered assessment), the method 400 can obtain a different identification of a plurality of categories with different proposed experiences 24 for the first user in comparison to the second user based on the difference in psychiatric or mental condition exhibited by the first user in comparison to the second user. As such, each respective user identifies a different plurality of categories with different proposed experiences 24 based on the psychiatric or mental condition exhibited by the subject. In some embodiments, the plurality of categories identified by the user is unique to the user.

For each category in the plurality of categories identified by a user, each respective proposed experience 24 in the plurality of proposed experiences 24 represents a corresponding challenge (e.g., first experience 24-1 represents challenge 26-1, experience 24-D represents challenge E 26-E, etc.) that is designed to improve the ability of the subject to manage their psychiatric or mental condition. In some embodiments, the corresponding challenge is a digital reality exposure therapy, such as a virtual reality exposure therapy (VRET). In some embodiments, the virtual reality exposure therapy is configured to reduce anxiety by implementing an emotional processing model and/or an inhibitory learning model. Both the emotional processing model and the inhibitory learning model postulate that exposure to the challenge allows the subject to learn corrective information about a feared stimulus. Moreover, in some embodiments, the emotional processing model specifically is configured to present fear stimuli in order to activate a fear structure. Accordingly, when corrective information is incompatible with this fear structure of the subject, a portion of this fear structure is replaced with a new, non-fear structure by the subject. Furthermore, in some embodiments, the inhibitory learning model is configured to enable the subject to tolerate, rather than replace, the fear, such that new learning can inhibit old fear expressions. Additional details and information regarding the emotional processing model and the inhibitory learning model can be found at Chesham et al., 2018; Foa et al., 1986, "Emotional processing of fear: exposure to corrective information," Psychological bulletin, 99(1), pg. 20; Craske et al., 2008, "Optimizing inhibitory learning during exposure therapy," Behaviour research and therapy, 46(1), pg. 5, each of which is hereby incorporated by reference in its entirety for all purposes. However, the present disclosure is not limited thereto. For instance, in some embodiments, the corresponding challenge is configured to include cognitive reframing (e.g., cognitive restructure), social skills training, relaxation training (e.g., meditation and/or mindfulness training/sessions), or a combination thereof.

As such, each proposed experience 24 is a digital reality task in the form of a challenge (e.g., challenge 26-E of FIG. 2B) that improves the ability of the subject to manage their psychiatric or mental condition. For instance, in some embodiments, one or more challenges is set in a corresponding proposed experience 24 that is known to cause a respective subject to exhibit a psychiatric or mental condition (e.g., a first subject with a social anxiety disorder condition), such as a corresponding unique digital reality scene that presents a social setting (e.g., one or more non-player characters and/or one or more player characters) that is configured to induce stress in the subject including in a school cafeteria, a classroom, a job interview, a romantic date at a park, traveling at an airport, a house party, or the like. However, the present disclosure is not limited thereto. In some embodiments, a category in the plurality of categories includes or is associated with one or more experiences 24 directed to social interaction and/or one or more experiences 24 directed to performance in front of others. For instance, in some embodiments, when the subject exhibits a social anxiety condition, a respective gate criterion is a performance criteria associated with performing a challenge for public speaking or performance situations. In some embodiments, a category in the plurality of categories includes or is associated with one or more experiences 24 directed to interaction anxiety (e.g., specific challenges 26 for meeting strangers), public speaking (e.g., specific challenges 26 for giving a report to a small group), observation fear (e.g., specific challenges 26 for writing while being observed), ingestion anxiety (e.g., specific challenges 26 for eating and/or drinking), or any combination thereof. As a nonlimiting example, consider an interaction anxiety of meeting strangers. A nonlimiting example of a category configured for the interaction anxiety of meeting strangers includes a first proposed experience 24-1 of a corresponding first challenge 26-1 of looking at a unknown bartender in the eyes when grabbing a drink off the bar, a second proposed experience 24-2 of a corresponding second challenge 26-2 of introducing yourself to a player character in a digital reality scene 40 (e.g., another avatar) and say something about yourself, and a third proposed experience 24-3 of a corresponding third challenge 26-3 of attending an augmented digital reality scene 40 or a mixed digital reality scene 40. In other embodiments, a category in the plurality of categories includes one or more experiences 24 directed to interaction anxiety (e.g., meeting strangers), nonverbal performance anxiety (e.g., taking a test), ingestion anxiety, public performance anxiety, assertiveness anxiety (e.g., resisting a high-pressure salesperson), or any combination thereof. In some embodiments, a category in the plurality of categories includes one or more experiences 24 directed to interacting with strangers (e.g., talking to face to face with someone you do not know very well, such as another non-player character or NPC in a digital reality scene), general performance (e.g., speaking up in a meeting, giving a prepared oral talk to a group, etc.), assertiveness (e.g., expressing disagreement or disapproval to someone you do not know very well), or any combination thereof. Additional details and information regarding types of categories and/or proposed experiences is disclosed in Heimberg et al., 1999, Psychometric Properties of the Leibowitz Social Anxiety Scale," Psychological Medicine, 29(1), pg. 199; Safren et al., 1999, "Factor Structure of Social Fears: The Liebowitz Social Anxiety Scale," Journal of Anxiety Disorders, 13(3), pg. 253; Baker et al., 2002, "The Liebowitz Social Anxiety Scale as a Self-Report Instrument: A preliminary Psychometric Analysis," Behavior Research and Therapy, 40(6), pg. 701, each of which is hereby incorporated by reference in its entirety. By using these aforementioned different limited types of proposed experiences (e.g., interactive, performance, and/or assertiveness), the subject can follow and track progress of the regimen 20 more easily. Moreover, in some embodiments, the different types of proposed experiences are configured for a respective psychiatric or mental condition. For instance, in some embodiments, an addiction disorder condition requires use of a first experience whereas a social anxiety disorder requires use of a second experience different from the first experience. However, the present disclosure is not limited thereto.

More specifically, in some embodiments, the corresponding challenge 26 of a proposed experience 24 includes: a first challenge 26-1 of using a telephone in public; a second challenge 26-2 of participating in small group activity; a third challenge 26-3 of eating in public; a fourth challenge 26-4 of drinking with others; a fifth challenge 26-6 of talking to someone in authority; a sixth challenge 26-6 of acting, performing, or speaking in front of an audience; a seventh challenge 26-7 of going to a party; an eight challenge 26-8 of working while being observed; a ninth challenge 26-9 of writing while being observed; a tenth challenge 26-10 of calling someone you do not know very well; an eleventh challenge 26-11 of talking face to face with someone you do not know very well; a twelfth challenge 26-12 of meeting strangers urinating in a public bathroom; a thirteenth challenge 26-13 of entering a room when others are already seating; a fourteenth challenge 26-14 of being the center of attention; a sixteenth challenge 26-16 of speaking up at a meeting; a seventeenth challenge 16-17 of taking a test of your ability, skill, or knowledge; an eighteenth challenge 26-18 of expressing disagreement or disapproval to someone you do not know very well; a ninetieth challenge 26-19 of looking someone who you do not know every well straight in the eyes (e.g., maintain eye contact); a twentieth challenge 26-20 of giving a prepared oral talk to a group; a twenty-first challenge 26-21 of trying to make someone's acquaintance for the purpose of a romantic and/or sexual relationship; a twenty-second challenge 26-22 of returning goods to a store for a refund; a twenty-third challenge 26-23 of giving a party; a twenty-fourth challenge 26-24 of resisting a high pressure sales person; or any sub-combination (e.g., any 2, 3, 4, 5, 6, 7, 8, 9, 10, 11, 12, 13, 14, 15, 16, 17, 18, 19, 20, 21, or 22 of the forgoing challenges) thereof.

Figure 6B:
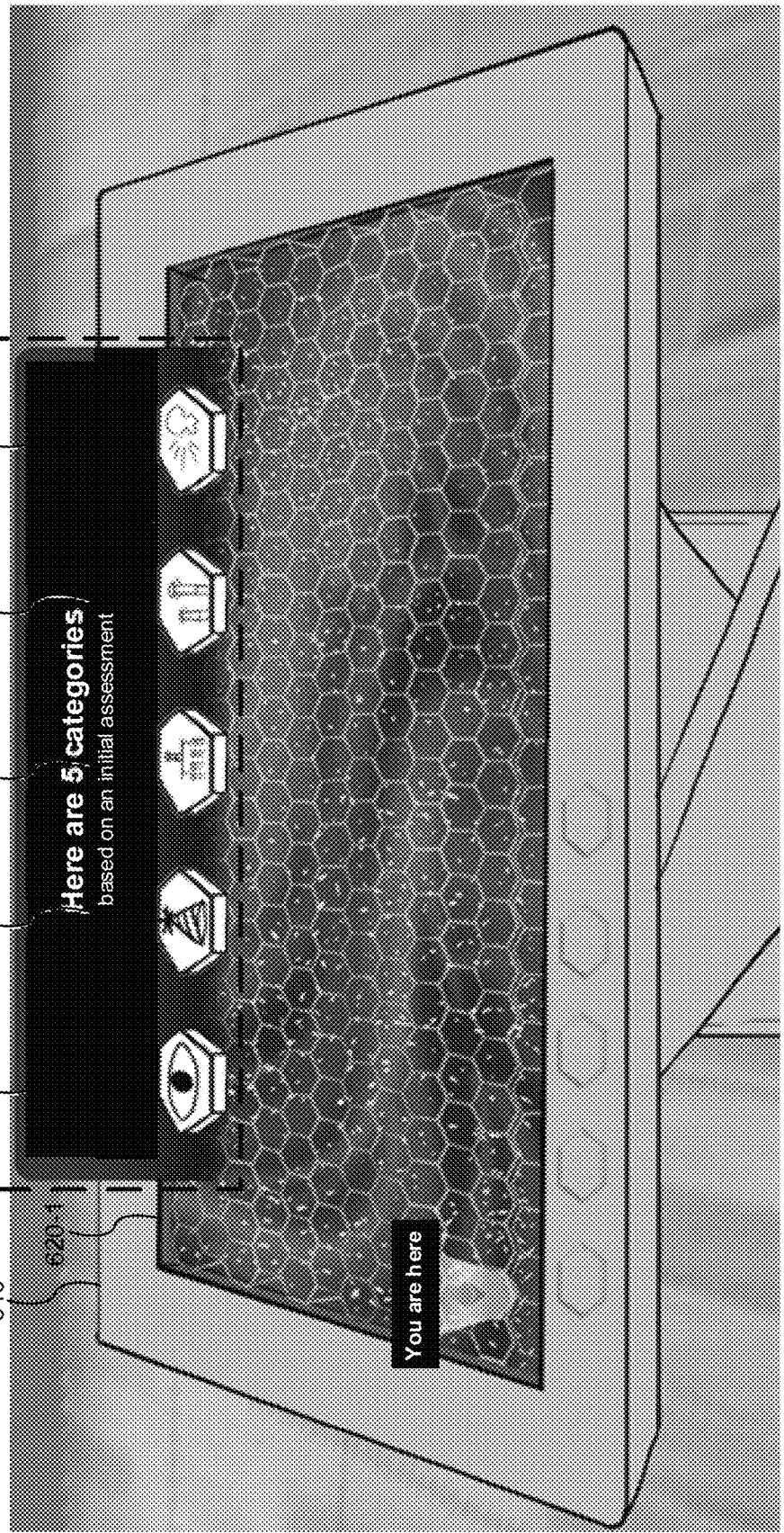
Figure 6C:
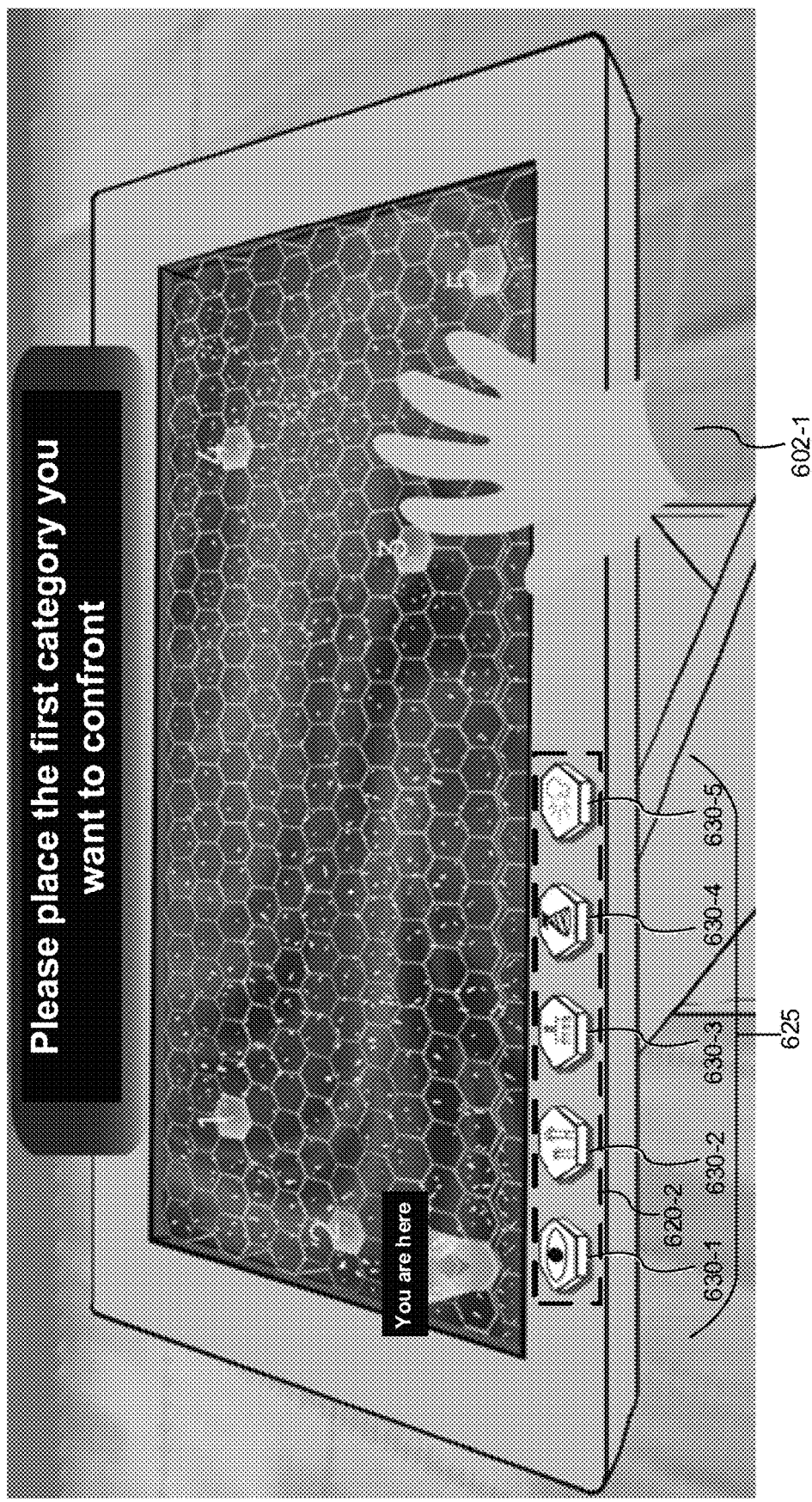

In some embodiments, the plurality of categories identified by a user includes two, three, four, five, or more than five categories. By way of example, FIGS. 6B and 6C illustrates five categories corresponding to the five nodes 630 of FIG. 6B or 6C). In some embodiments, a category in the plurality of categories includes or is associated with 2, 3, 4, 5, 6, 7, 8, 9, 10, 11, 12, 13, 14, 15 or more than 15 proposed experiences. By way of example, referring briefly to FIG. 6B, a category (e.g., the category corresponding to node 630-1, node 630-2, node 630-3, node 630-4, or node 630-5) identified by a user of a user interface 600-2 includes a first experience 24-1 that is a first challenge 26-1 to maintain eye contact, a second experience 24-2 that is a second challenge 26-2 to go to a party, a third experience 24-3 that is a third challenge 26-3 to participate in a small group, a fourth experience 24-4 that is a fourth challenge 26-4 to meet one or more strangers, and a fifth experience 24-5 that is a fifth challenge 26-6 to perform in front of other subjects (e.g., other user player characters in a digital reality scene 40 and/or a non-player character (NPC) in the digital reality scene 40).

Referring briefly to FIGS. 8A through 8C, an assessment associated with a social anxiety psychiatric or mental condition is presented on a display of a client device (e.g., display 308 of client device 300-1 of FIG. 3). The assessment includes a plurality of prompts (e.g., 2, 3, 4, 5, 6, 7, 8, 9, 10, or more than 10) that are answered by a user of the client device 300. In some embodiments, the user of the client device 300 is a subject that exhibits the social anxiety psychiatric or mental condition and/or a medical practitioner associated with the subject.

In the example of FIGS. 8A-8D, a first prompt of the assessment is provided to the user that determines how anxious or fearful the subject feels in in a particular situation, such as talking on the phone in public. In some embodiments, the particular situation is a challenge (e.g., challenge 26 of FIG. 2B) that is represented by a proposed experience. In the example of FIGS. 8A-8D, the user has selected "Mild" in response to the prompt. In this instance, since the response is mild, as opposed to moderate or severe, the proposed experience associated with the first prompt (e.g., talking on the phone in public) is excluded from an identification of a plurality of proposed experiences. This process of obtaining the assessment continues until the plurality of proposed experiences is identified, such as when the assessment is deemed complete.

Block 406. Referring to block 406, the method 400 includes presenting a first digital reality scene, such as the digital reality scene 40-3 illustrated in FIG. 5C or the like, on the display (e.g., display 308 of FIG. 3). A virtual reality scene 40 is a digital reality scene 40 that facilitates a fully digital immersion, which allows for one or more digital objects (e.g., objects 42 of FIG. 2B) within a digital space (e.g., three-dimensional digital space). For instance, in some embodiments, the digital reality scene 40 presented on the display 308 is a virtual reality scene 40, such as a multiscale virtual reality environment (MSVE). In alternative embodiments, the digital reality scene 40 presented on the display 308 is an augmented reality scene 40. An augmented reality scene 40 is a digital reality scene 40 that facilitates user immersion by presenting an augmentation of the real world using digital objects 42. In other embodiments, the digital reality scene 40 presented on the display 308 is a mixed reality scene 40. A mixed reality scene 40 is a digital reality scene 40 that facilitates user immersion by providing spatial mapping and data contextualization in real-time, which allows for one or more digital objects 42 within a digital space that is correlated to a user space (e.g., a field of view of the user or client device 300). Furthermore, in some embodiments, the digital reality scene 40 is a panoramic video, a spherical video, or an omnidirectional video. As a non-limiting example, in some such embodiments, the panoramic video, the spherical video, or the omnidirectional video provides greater than or equal to 180° view within the digital reality scene 40. Additional details and information regarding a type of digital reality scene 40 can be found at Parveau et al., 2018, 3iVClass: A New Classification Method for Virtual, Augmented and Mixed Realities," Procedia Computer Science, 141, pg. 263; Xu, et al., 2020, "State-of-the-art in 360 Video/image Processing: Perception, Assessment and Compression," IEEE Journal of Selected Topics in Signal Processing, 14(1), pg. 5, each of which is hereby incorporated by reference in its entirety. Accordingly, by presenting the first digital reality scene, which requires use of a computer system, the method 400 cannot be mentally performed.

In some embodiments, the first digital reality scene is a first type of digital reality scene, and the corresponding unique digital reality scene is second type of digital reality scene different than the first type of digital reality scene. For instance, in some embodiments, the first digital reality scene is a virtual reality scene, and the corresponding unique digital reality scene is a panoramic video, a spherical video, or an omnidirectional video. As another non-limiting example, in some embodiments, the first digital reality scene is the virtual reality scene, and the corresponding unique digital reality scene is an augmented reality scene. However, the present disclosure is not limited thereto. By using different types of digital reality scenes, the subject is digitally transported to various scenes through the regimen, which increases an efficacy having the subject satisfy the manifestation of the corresponding challenge.

Accordingly, in some embodiments, the first digital reality scene is statically displayed on display 308, such that a user interacting with the first digital reality scene is restricted from modifying a field of view of the first digital reality scene. In this way, a view of the first digital reality scene is fixed. Moreover, in such embodiments, while the view of the first digital reality scene is fixed, a position one or more objects 42 (e.g., interactive digital chart 610, interactive digital bin 625, etc.), such as a tilt of a respective object 42, a height of the respective object 42, a pitch of the respective object 42, a roll of the respective object 42, a yaw of the respective object, and the like. However, the present disclosure is not limited thereto. For instance, in alternative embodiments, the first digital reality scene provides three-degrees of freedom for a user controlling an avatar in the first digital reality scene, such as three rotational degrees of freedom or three translational degrees of freedom, or six degrees of freedom for controlling the avatar.

In this way, each such avatar is a two-dimensional or three-dimensional model rendered in a digital reality scene 40. In some embodiments, each respective digital reality scene 40 includes one or more predetermined avatars that is associated with a corresponding experience 40. For instance, in some such embodiments, the user is restricted to selecting an avatar from the one or more predetermined avatars associated with the digital reality scene 40, which provides a consistent theme within the digital reality scene. As a non-limiting example, a cosmic theme is associated with a first digital reality scene 40-1 that is rendered on a client device 300 by way of a client application 320 and/or engine 322 of the client device 400. To maintain conformity with this cosmic theme, users interacting with the cosmic themed first digital reality scene 40-1 are restricted to selecting similarly themed avatar, such as an astral theme avatar or an alien theme avatar. In some embodiments, a user is provided an opportunity to customize an avatar prior to interacting with a digital reality scene 40. In some embodiments, the user modifies one or more traits associated with a respective avatar, such as a gender of the respective avatar, a color of a feature of the respective avatar, a voice of the respective avatar, a visibility of the respective avatar (e.g., publicly visible, private, etc.) and the like. Accordingly, in some embodiments, a capacity, or degree of, customization is restricted such that users do not stray from a theme of a digital reality scene 40. Moreover, in some embodiments, restricting a capacity of customization provided to each user maintains a level of anonymity for the users since each avatar has similar, or the same, visual characteristics in the digital reality scene 40, which provides confidence to the user that the user can privately engage with the digital reality scene 40 without providing personally identifiably information.

The first digital reality scene includes a respective interactive digital chart, such as the interactive digital chart 610 illustrated in FIGS. 6A-6H. In some embodiments, the respective interactive digital chart 610 is an object 42 within the first digital reality scene that allows a user to chart a graph (e.g., graph 640 of FIG. 6G) of a regimen for improving the ability of the subject to manage the psychiatric or mental condition. By utilizing a respective interactive digital chart, such as the interactive digital chart 610, the user retains at least partial control of their progression through the regimen 20. Moreover, in some embodiments, the user can progress forward through the graph 640 or reiterate a previous challenge 26 of a node 630 that has been deemed complete. That is, even though a challenge has been deemed complete, the user can redo the challenge as many times as they would like to build self-confidence, etc. Moreover, as an interactive digital chart in a digital reality scene 40, the interactive digital chart presents an engaging and ornamental digital mechanism that graphically illustrates progression through a regimen 20 for improving an ability of the subject to manage their psychiatric or medical condition.

Figure 6D:
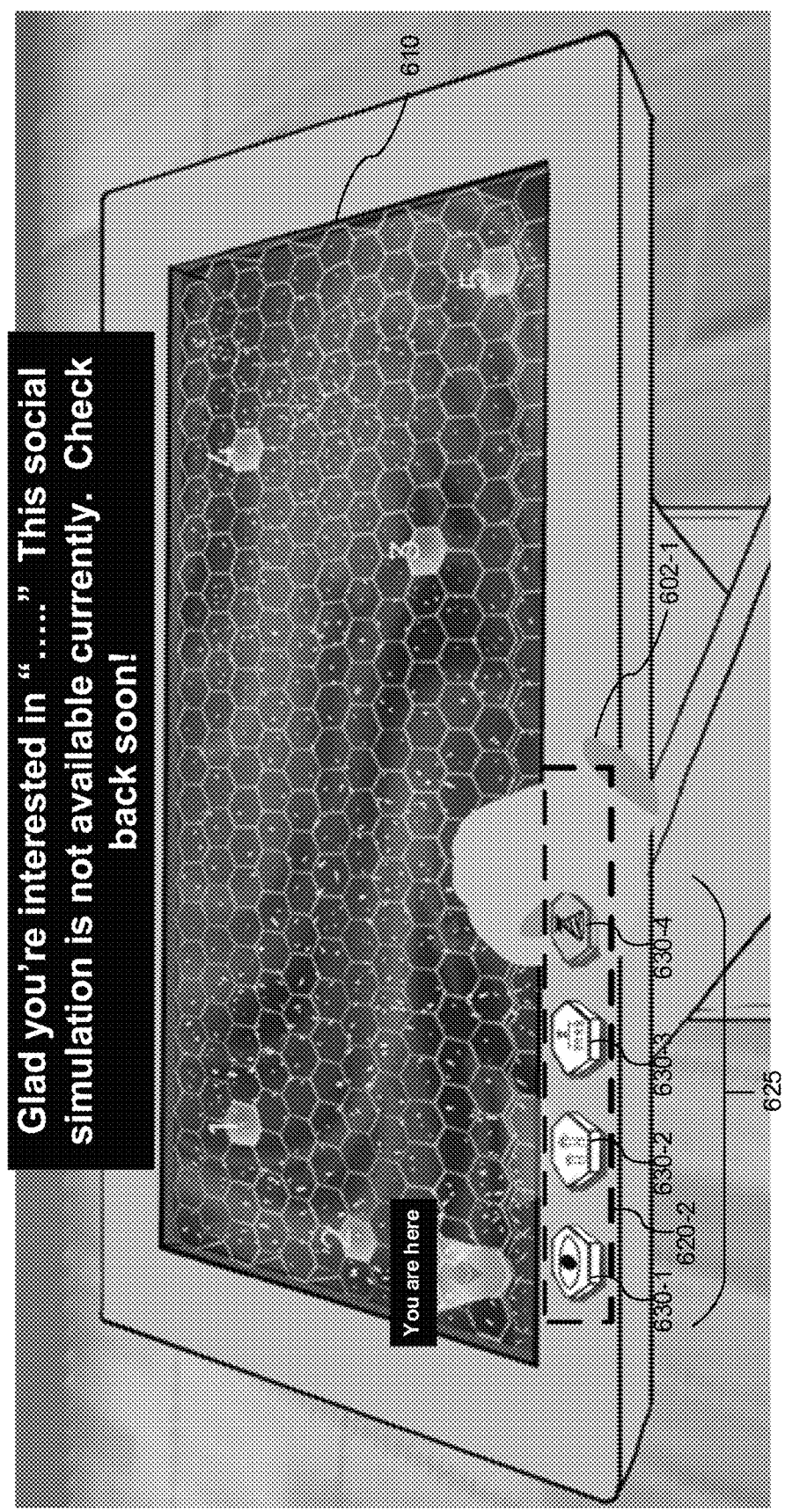
Figure 6E:
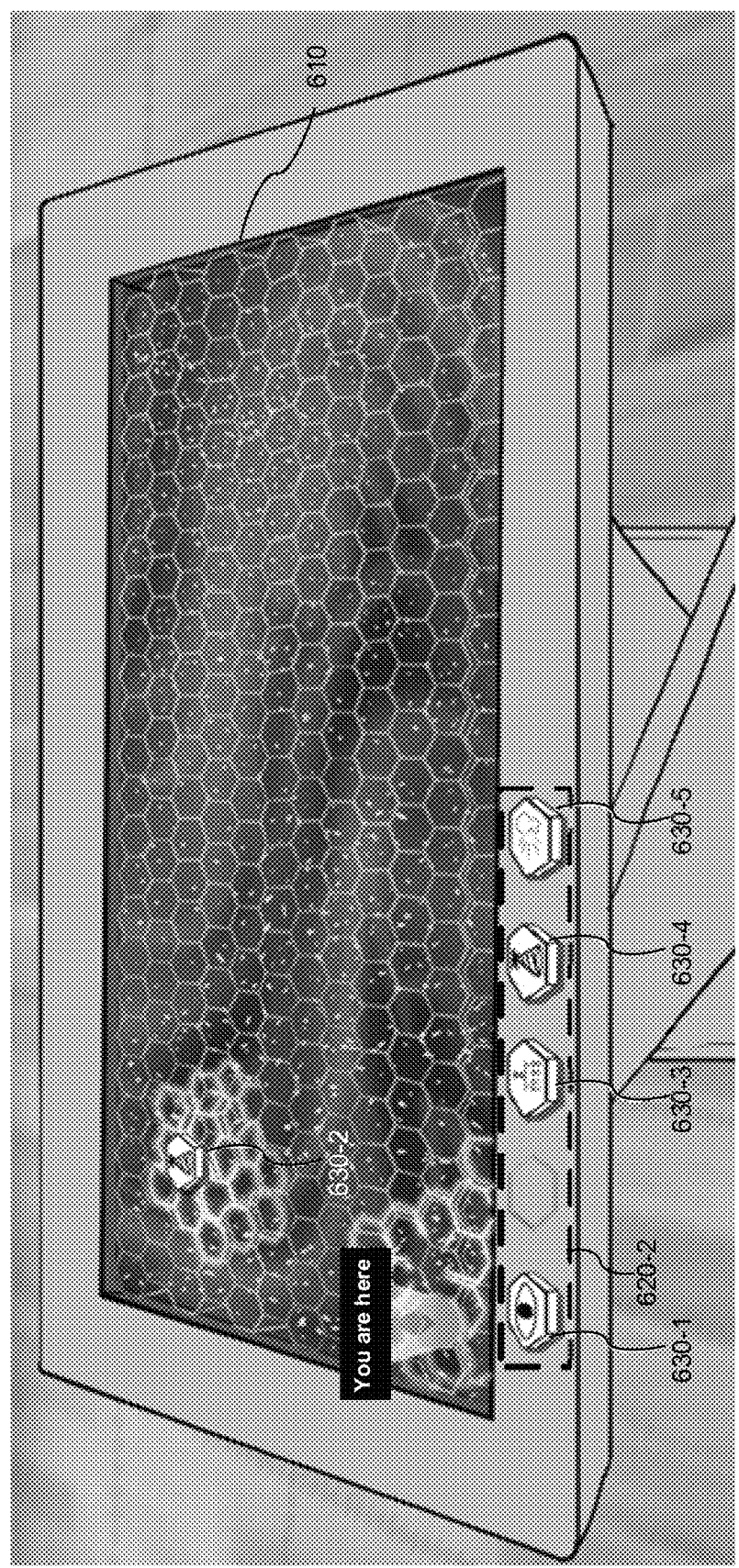
Figure 6F:
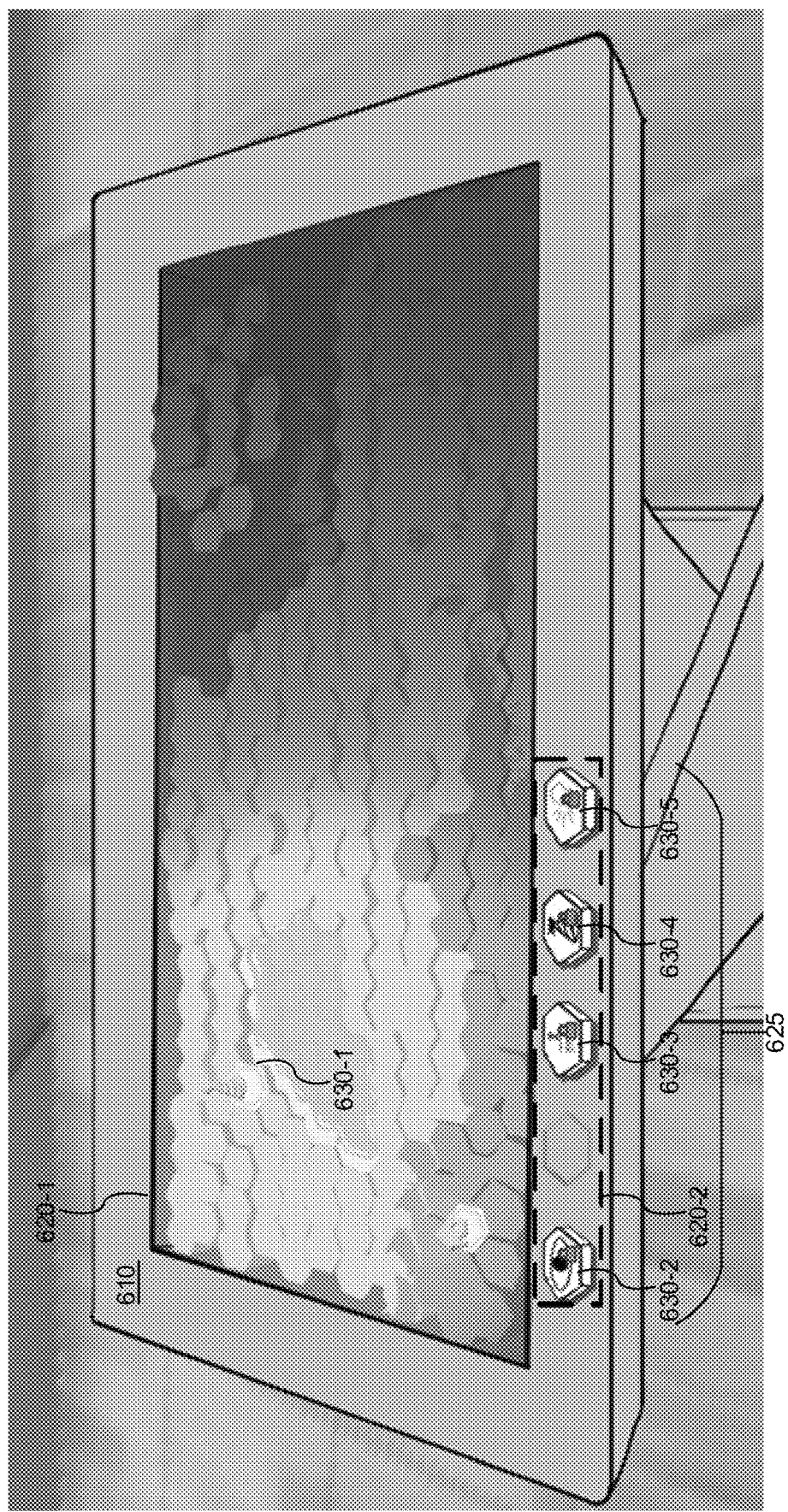
Figure 6G:
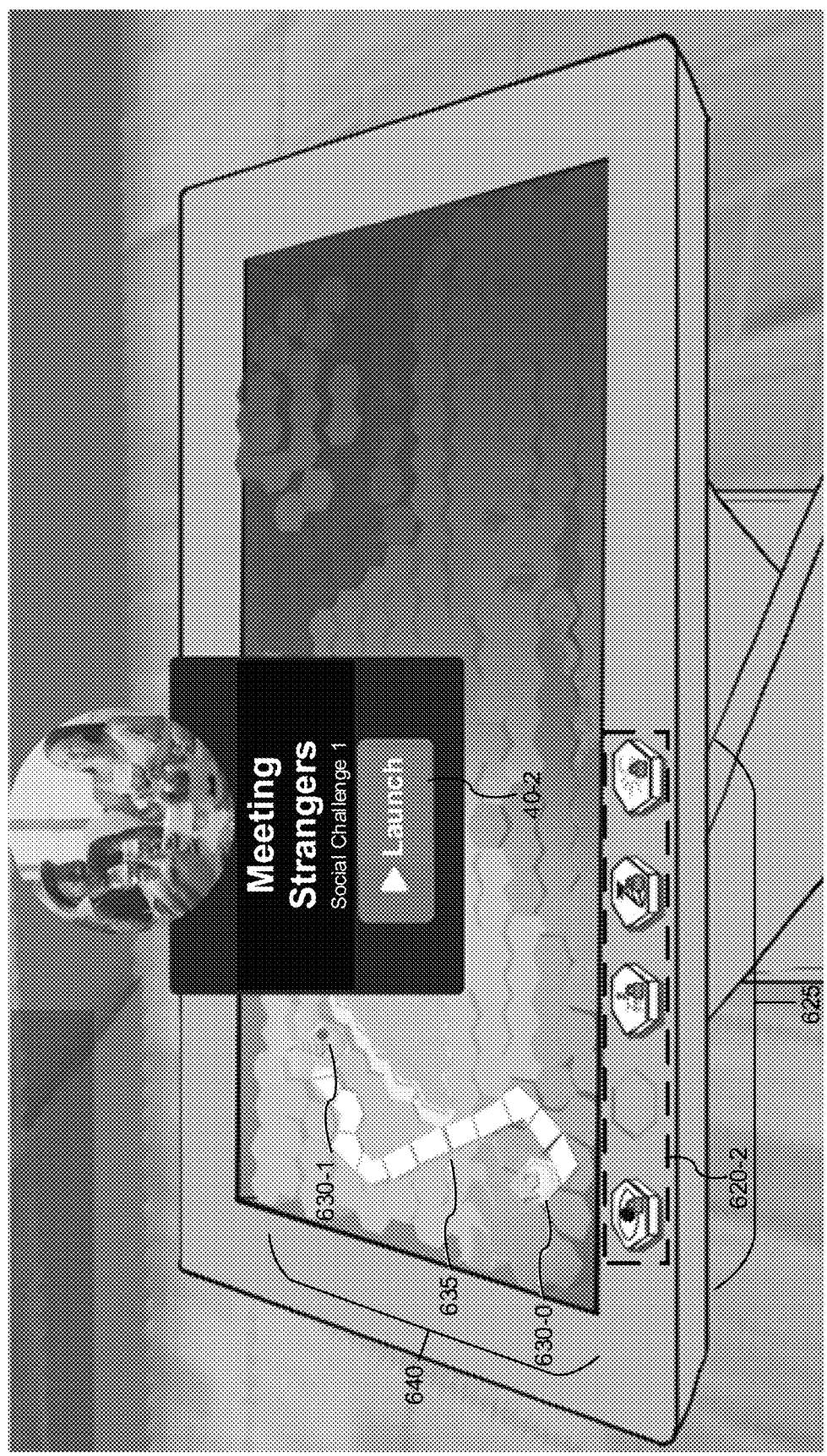
Figure 6H:
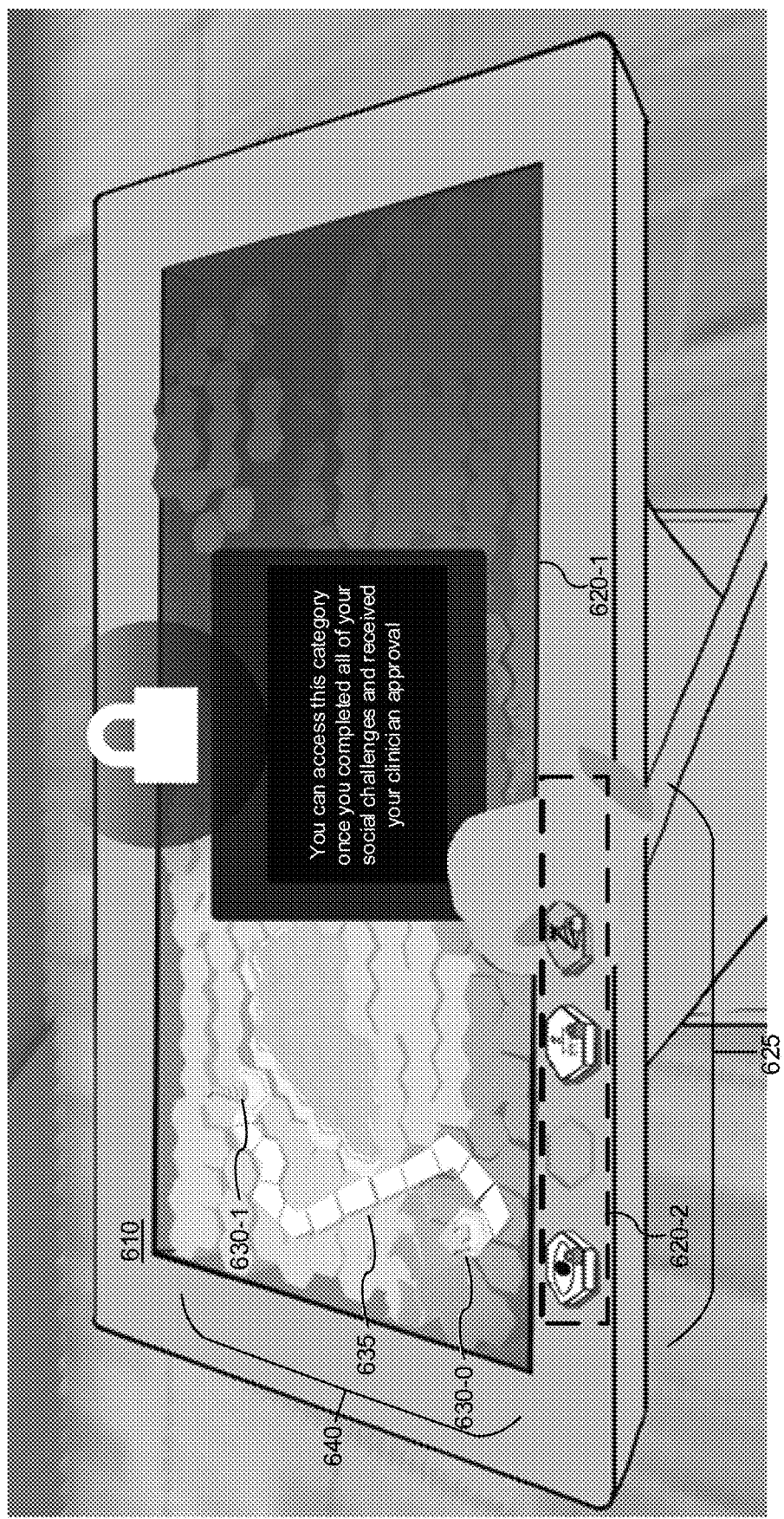

Additionally, the first digital reality scene includes a corresponding interactive digital bin (e.g., interactive digital bin 625 of second affordance region 620-2 of FIG. 6B, interactive digital bin 625 of second affordance region 620-2 of FIG. 6F, interactive digital bin 625 of second affordance region 620-2 of FIG. 6G, interactive digital bin 625 of second affordance region 620-2 of FIG. 6H, interactive digital bin 625 of second affordance region 620-2 of FIG. 6I, etc.). In some embodiments, the corresponding interactive digital bin 625 is a menu of the proposed experiences 24 that are available for selection by a user engaging with the first digital reality scene. For instance, in some embodiments, the menu of the proposed experiences 24 includes a proposed experience 24 for one or more fears (e.g., social anxieties) that is determined by an assessment obtained from the subject (e.g., block 404 of FIG. 4). Accordingly, the corresponding interactive digital bin 625 provides a graphical representation of the plurality of proposed experiences 24 that is identified from the assessment obtained from the subject based on the associated with the enumerated plurality of nodes 630. Moreover, in some embodiments, the corresponding interactive digital bin provides a graphical presentation of a hierarchy of proposed experiences 24 that were identified when obtaining the assessment of the subject (e.g., block 404 of FIG. 4).

The respective interactive digital chart 610 consumes (occupies) a first affordance region of a user interface (e.g., first affordance region 620-1 of user interface 600-4 of FIG. 6D). Moreover, the respective interactive digital chart 610 includes (encompasses) a first area. In this way, the respective interactive digital chart 610 is typically visible to a user within the first digital reality scene, which allows the user to contemplate placement of a respective node 630 at a location within the first area prior to selecting (e.g., block 408 of FIG. 4) the respective node 630, and then place the respective node 630 at the location. Accordingly, the first area of the first affordance region 620-1 is a portion of a respective interactive digital chart that illustrates the nodes 630 and edges (e.g., edge 635 of FIG. 6G, edge 635 of FIG. 6H) of a graph (e.g., graph 640 of FIG. 6G, graph 640 of FIG. 6H, etc.) and thus provides a graphical representation of progress through the regimen 20 for improving the ability of the subject to manage their psychiatric or mental condition. In some embodiments, the first area is constant, such as a fixed plane. In other embodiments, the first area dynamically reconfigures its size or shape based on a variety of parameters defined by a user of the digital reality scene 40, such as a number of nodes 630 placed by a user.

Furthermore, the corresponding interactive digital bin 625 consumes (occupies) a second affordance region 620-2 that is different than the first affordance region 620-1 of the respective interactive digital chart 610. For instance, referring briefly to FIG. 6F, a user interface 600-6 presents a virtual reality scene 40 that includes a respective interactive digital chart 610 and a corresponding interactive digital bin 625. Here, the respective interactive digital chart 610 consumes a first affordance region 620-1 and includes a substantially rectangular first area with a plurality of tessellated shapes, whereas the corresponding interactive digital bin 625 consumes a second affordance region 620-2 that that includes a substantially rectangular second area adjacent to the first affordance region 620-1. However, the present disclosure is not limited thereto. For instance, referring briefly to FIG. 6B, in some embodiments, the first affordance region 620-1 consumed by the respective interactive graphical digital chart 610 overlaps the second affordance region 620-2 consumed by the corresponding interactive digital bin 625. In some embodiments, the first affordance region 620-1 and the second affordance region 620-2 are concurrently presented on the display 308, such that both the first affordance region 620-1 and the second affordance region 620-2 are visible to a user. In other embodiments, the first affordance region 620-1 and the second affordance region 620-2 are presented separately, such that the first affordance region 620-1 and the second affordance region 620-2 are not displayed concurrently. For instance, in some embodiments, display of first affordance region 620-1 and second affordance region 620 is mutually exclusive.

In this way, in some embodiments, the first area of the first affordance region 620-1 includes a plurality of tessellated shapes that is bound by the first area. By way of example, referring briefly to FIG. 6I, a respective interactive digital chary 610 consumes a first affordance region 620-1 that is a substantially rectangular area, which includes a plurality of tessellated shapes in the form hexagons. The plurality of tessellated shapes provides a visualization of the first area.

Moreover, in some embodiments, each tessellated shape in the plurality of tessellated shapes is associated with a unique location in the first area that is available for placement of a respective node 630. Here, an initial node 630-0 is at a tessellated shape and a first node 630-1 is at a second tessellated shape connected by an edge 635. In some embodiments, the plurality of tessellated shapes bounded by the first area of the first affordance region 620-1 includes about 20 tessellated shapes (e.g., 19 tessellated shapes, 22 tessellated shapes, etc.), about 30 tessellated shapes, about 40 tessellated shapes (e.g., 42 tessellated shapes), about 50 tessellated shapes, about 75 tessellated shapes, about 100 tessellated shapes, about 125 tessellated shapes, about 150 tessellated shapes, about 175 tessellated shapes, about 200 tessellated shapes, about 225 tessellated shapes, about 250 tessellated shapes, about 275 tessellated shapes, about 300 tessellated shapes, about 325 tessellated shapes, or about 350 tessellated shapes (e.g., 368 tessellated shapes). In some embodiments, the plurality of tessellated shapes bounded by the first area of the first affordance region 620-1 includes between 20 and 1000 tessellated shapes. However, the present disclosure is not limited thereto. In some embodiments, the plurality of tessellated shapes includes at least 30 tessellated shapes, at least 40 tessellated shapes (e.g., 44 tessellated shapes), at least 50 tessellated shapes, at least 75 tessellated shapes, at least 100 tessellated shapes, at least 125 tessellated shapes, at least 150 tessellated shapes, at least 175 tessellated shapes, at least 200 tessellated shapes, at least 225 tessellated shapes, at least 250 tessellated shapes, at least 275 tessellated shapes, at least 300 tessellated shapes, at least 325 tessellated shapes, or at least 350 tessellated shapes (e.g., 368 tessellated shapes). In some embodiments, the plurality of tessellated shapes includes no more than 30 tessellated shapes, no more than 40 tessellated shapes (e.g., 32 tessellated shapes), no more than 50 tessellated shapes, no more than 75 tessellated shapes, no more than 100 tessellated shapes, no more than 125 tessellated shapes, no more than 150 tessellated shapes, no more than 175 tessellated shapes, no more than 200 tessellated shapes, no more than 225 tessellated shapes, no more than 250 tessellated shapes, no more than 275 tessellated shapes, no more than 300 tessellated shapes, no more than 325 tessellated shapes, or no more than 350 tessellated shapes (e.g., 328 tessellated shapes). In some embodiments, the plurality of tessellated shapes and the enumerated plurality of nodes have a one-to-one relationship such that each respective node in the enumerated plurality of nodes has a corresponding tessellated shape in the plurality of tessellated shapes. In some embodiments, the plurality of tessellated shapes and the enumerated plurality of nodes have a many to one relationship such that each respective node in the enumerated plurality of nodes has at least one corresponding tessellated shape in the plurality of tessellated shapes.

In some embodiments, the first affordance region 620-1 consumed by the respective graphical interactive digital chart 610 is a two-dimensional affordance region 620 in the first digital reality scene 40-1. In this way, the first area of the first affordance region 620-1 is a respective area that is bounded by the two-dimensional first affordance region 620-1. For instance, in some embodiments, the first area is circularly bounded by a circular first affordance region, such as a projection of a globe, or polygonal bounded by a polygona first affordance region, such as substantially rectangular first area of FIG. 6A. However, the present disclosure is not limited thereto. By way of example, in alternative embodiments, the first affordance region 620-1 consumed by the respective interactive digital chart 610 is a three-dimensional affordance region in the first digital reality scene. Accordingly, the first area is a respective surface area of a three-dimensional object (e.g., object 42 of FIG. 2B) that is bound by the three-dimensional affordance region. Accordingly, in such embodiments, the three-dimensional affordance region is two-dimensional in nature but depicts a three dimensional "perspective view" of the affordance region. In this way, in some embodiments, the three-dimensional object is a sphere (e.g., a globe) or a polyhedron (e.g., object 42-2 of FIG. 5C).

The corresponding interactive digital bin 625 includes an enumerated plurality of nodes (e.g., first node 630-1, second node 630-2, . . . , fifth node 630-5 of FIG. 6C). Each respective node 630 in the enumerated plurality of nodes 630 corresponds to a respective proposed experience 24 in the plurality of proposed experiences 24 identified by the subject through the assessment (e.g., block 404 of FIG. 4). In this way, in some embodiments, the enumerated plurality of nodes 630 and the plurality of proposed experiences 24 identified by a subject through an assessment have a one to one relationship (e.g., the plurality of proposed experiences 24 includes five proposed experiences 24 and the enumerated plurality of nodes 630 includes five nodes 630). However, the present disclosure is not limited thereto. In some embodiments, the enumerated plurality of nodes 630 includes of about 3 nodes 630, about 5 nodes 630, about 7 nodes 630, about 10 nodes 630, about 12 nodes 630, about 15 nodes 630, about 20 nodes 630, or between 3 and 50 nodes 630. In some embodiments, the enumerated plurality of nodes 630 includes at least 3 nodes, at least 5 nodes, at least 10 nodes, at least 15 nodes, at least 20 nodes, at least 25 nodes, at least 30 nodes, at least 35 nodes, at least 40 nodes, at least 50 nodes, or at least 100 nodes.

Additionally, in some embodiments, each respective node 630 in the enumerated plurality of nodes 630 is associated with a corresponding unique digital reality scene 40 that is different than the first digital reality scene. This corresponding unique digital reality scene 40 that is associated with a respective node 630 manifests the corresponding challenge 26 that is represented by the respective proposed experience 24. Furthermore, each respective node 630 is associated with at least one respective gate criteria in a plurality of gate criteria (e.g., gate criteria 32 of gate store 30 of FIG. 2B). In this way, each node 630 in the enumerated plurality of nodes 630 is a proposed experience 24 that has been coupled to a specific corresponding unique digital reality scene 40 and one or more gate criteria 32. Accordingly, the specific corresponding unique digital reality scene 40 of the node 630 is designed to mimic the challenge 26 (e.g., type of fear) of the proposed experience 24 the node 630 is designed to address.

In some embodiments, the corresponding unique digital reality scene 40 associated with a respective node 630 is a virtual reality scene 40. In some embodiments, the corresponding unique digital reality scene 40 associated with a respective node 630 is an augmented reality scene 40. In some embodiments, the corresponding unique digital reality scene 40 associated with a respective node 630 is a mixed reality scene 40. Moreover, in some embodiments, the corresponding unique digital reality scene 40 associated with a respective node 630 is a panoramic video, a spherical video, or an omnidirectional video (e.g., a 360° video). In this way, the corresponding unique digital reality scene 40 associated with the respective node 630 and the first digital reality scene 40-1 of the respective interactive digital chart 610 are the same type of digital reality (e.g., both virtual reality scenes 40, both augmented reality scenes 40, both mixed reality scenes 40, etc.) or a different type of digital reality scene (e.g., a first virtual reality scene 40-1 and a corresponding second augmented reality scene 40-2). Each gate criterion 32 is defined by a node 630. In this way, the gate criterion 32 can be a condition precedent for executing the node 630 or a condition that must be achieved in order to deem the node 630 complete. An example of a condition precedent is a requirement that some other node 630 be successfully completed before the user is allowed to invoke a given node 630. An example of a condition that must be achieved in order to deem a node 630 complete, is a minimum eye contact duration during the proposed experience 24 of the node 630.

In some embodiments, the at least one respective gate criteria 32 associated with a respective node 630 includes a ranking gate criterion 32. The ranking gate criterion 32 is associated with a hierarchical ranking of each node 630 in the enumerated plurality of nodes 630, such as a subjective rating from highest to lowest (e.g., user-provided rating of "mild," "moderate," "severe," or "no reaction") and/or an objective rating from highest to lowest (e.g., a ranking from most effective to least effective as determined by a digital reality system 200 or a medical practitioner associated with the subject). From this, the ranking gate criterion 32 conditions placement of the respective node 630 based on an initial or terminal position of a respective node 630 in the hierarchical ranking of each node 630 in the enumerated plurality of nodes 630.

In some embodiments, the at least one respective gate criteria 32 associated with a respective node 630 includes a medical practitioner gate criterion 32. The medical practitioner gate criterion 32 is associated with an approval of the selection by the user of the first node 630-1 from the medical practitioner associated with the subject. In this way, the medical practitioner associated with the subject can provide oversight to improving the psychiatric or mental condition exhibited by the subject by either approving or denying access to the category and proposed experiences that are associated with the node. For instance, the medical practitioner can deny accesses to a node corresponding to a particular category and particular proposed experience to a particular user until the medical practitioner believes the user is "ready" for the particular category and proposed experience.

In some embodiments, the at least one respective gate criteria 32 associated with a respective node 630 includes a user gate criterion 32. The user gate criterion 32 associated with an approval, from the subject, of the first selection of the first node 630-1, such as re-confirmation of selection of the first node 630-1.

In some embodiments, the at least one respective gate criteria 32 is generated by a remote administrator associated with the digital reality system that is a user other than the medical practitioner or the user. In some embodiments, the at least one gate criteria 32 is generated by the remote administrator or the model and then further modified by the medical practitioner associated with the subject. In some embodiments, the at least one gate criteria 32 is generated by the remote administrator or the medical practitioner and then further modified by the model. For instance, in some embodiments, the model further modifies the at least one gate criteria 32 that is generated by the user and/or the medical practitioner based an evaluation of one or more parameters associated with the user, such a number of challenges 26 completed by the user. In some embodiments, the model modifies the at least one gate criteria based on one or more results of the model that indicates a classification, a clustering, or other identification of parameters of the user that indicate that changing a respective gate criterion in the at least one gate criteria improves the likelihood of engagement and/or a better clinical outcome when using the systems and methods of the present disclosure.

In some embodiments, the at least one respective gate criteria 32 associated with a respective node 630 includes an arrangement gate criterion 62. The arrangement gate criterion 32 is associated with an order of one or more nodes 630 in the enumerated plurality of nodes 630, such as an order of one or more nodes 630 in a sequence of nodes 630 that form a story or common narrative thread. For instance, consider a set of three nodes, A, B and C that form a story or a common narrative thread. To realize the story or common narrative thread in the correct order of A, B, and then C, a first arrangement gate criterion is imposed on B that requires A to be completed before B is initiated, and a second arrangement gate criterion is imposed on C that requires both A and B to be completed before C is initiated.

In some embodiments, the at least one respective gate criteria 32 of each respective node 630 in the graph 640 is used to determine the placement of each edge 635 in the plurality of edges 635 of the graph 640. For instance, in some embodiments, the at least one respective gate criteria 32 determines the placement of each edge 635 in accordance with the determination of the nearest neighbor to a corresponding node 630 in the enumerated plurality of nodes 630. In other words, an edge 635 is drawn from one corresponding node 630 to the node that is closest to the corresponding node 630. In alternative embodiments, the determination of the placement of each edge 635 of the graph 640 is based on a minimum and/or maximum displacement between adjacent nodes 630 when placed in the first area of the first affordance region 620-1 of the respective interactive digital chart 610.

In some embodiments, a gate criterion 32 associated with one node 630 in the graph 640 specifies a condition that is to be satisfied by the subject prior to advancement to another node 630 in the graph 640. As a non-limiting example, referring briefly to FIG. 6E, a user has provided a selection of a fourth node 630-4 included in the corresponding interactive digital bin 625. However, this selection of the fourth node 630-4 fails to satisfy a condition of a gate criterion associated with the fourth node 630-4 that enables the "Going to Party," challenge 26 available to the subject, and therefore cannot be placed in the first area of the respective digital interactive digital chart 610.

In some embodiments, a gate criterion 32 of a node 630 in the graph 640 is set by a system administrator (e.g., administrator of a digital reality system 200 of FIGS. 2A and 2B). For instance, in some embodiments, the system administrator configures a gate criterion of a node 630 to be conditioned on receipt of payment from a subject (e.g., for access to the digital reality system 200, for access to a specific digital reality scene 40, and the like). However, the present disclosure is not limited thereto as one of skill in the art of the present disclosure will appreciate that other respective gate criteria set by a system administrator are within the scope of the present disclosure. Furthermore, in some embodiments, a gate criterion 32 of a node 6230 in the graph 640 is set by the subject (e.g., first user of a first client device 300-1). In some embodiments, the gate criterion 32 of the node 6320 in the graph 640 is set by a health care worker, such as a medical practitioner, associated with the subject (e.g., second user of a second client device 300-2, via client application 320 presented through user interface 900-4 of FIG. 9D, etc.). In some embodiments, a gate criterion 32 of a first node 630-1 in the graph 640 is set by the system administrator or the medical practitioner associated with the subject while a respective gate criterion 32 of a second node 630-2 in the graph 640 (that shares an edge with first node 630-1) is set by the subject.

In some embodiments, a gate criterion is set (e.g., configured) by one or more models and/or the medical practitioner. For instance, in some embodiments, the gate criterion is a difficult level or setting of a challenge that the subject is required to complete the corresponding challenge (e.g., a highest difficultly level, an intermediate difficulty level, etc.). As a non-limiting example, in some embodiments, after playing a first challenge at a first difficulty setting and not satisfying a first gate criterion associated with the first challenge, a first model and/or the medical practitioner configures the first gate criterion to an easier difficulty in order to ensure the subject is able to accomplish satisfy the first challenge. In some embodiments, the first model and/or the medical practitioner configures the first gate criterion based on a win rate for the subject at a particular category and/or challenge (e.g., a lower win rate for the subject at the first challenge indicates a lower level of difficulty is needed for the subject). However, the present disclosure is not limited thereto.

The one or more models and/or the medical practitioner use a data set from a corresponding user profile associated with the subject to determine an expected behavior of the subject, such as an expected response to a stimuli within a digital reality scene. As a non-limiting example, if it is known that the subject has attempted a particular challenge a certain number of times and yet has continued interacting with various digital reality scenes, the one or more models predict that the subject is able to satisfy a level of difficulty when manifesting a corresponding challenge. In some embodiments, the data set from the user profile data is with a historical data set associated with a plurality of subjects, in order to assess how the subject is expected to behave.

In some embodiments, a gate criterion 32 of a node 630 in the graph 640 is a required minimum length (e.g., a duration of a period of time) of eye contact with a designated portion of the corresponding unique digital reality scene 40 that is associated with the corresponding challenge 26 of the node 630, such as with the face of a NPC in the corresponding unique digital reality scene 40. In some such embodiments, the user cannot progress out of the node bearing this gate criterion (e.g., node 630-1) until the user has established the eye contact with the designated portion of the corresponding unique digital reality scene 40 for the required minimum length (e.g., at least 3 seconds, at least 5 seconds, at least 10 second, at least 30 seconds, etc.).

In some embodiments, a gate criterion 32 of a node 630 in the graph 640 is an assertiveness of the subject during each corresponding challenge 26 in a predetermined number of the corresponding challenges of the category associated with the node 630. The predetermined number of the corresponding challenges is generally more than 2, more than 3, more than 4, or more than 5 corresponding challenges of the node 630. In an exemplary embodiment, the predetermined number of the corresponding challenges is one half of corresponding challenges of the node 630. In another exemplary embodiment, the predetermined number of the corresponding challenges is the total number of corresponding challenges of the node 630. In some embodiments, the gate criterion 32 of the node 630 is a decibel level and/or a pitch of one or more utterances by the subject during each corresponding challenge 26 in a predetermined number of the corresponding challenges of the category associated with the node 630. Furthermore, in some embodiments, a gate criterion 32 of a node 630 in the graph 640 is a number of utterances by the subject during each corresponding challenge 26 in a predetermined number of the corresponding challenges of the category associated with the node. Additionally, in some embodiments, a respective gate criterion 32 of a node 630 in the graph 640 is a number of words spoken by the subject during each corresponding challenge 26 in a predetermined number of the corresponding challenges of the category associated with the node 630. In some embodiments, a gate criterion 32 of a node 630 in the graph 640 is any combination of an assertiveness of the subject, a decibel level and/or a pitch of one or more utterances by the subject, a number of utterances by the subject, a number of words spoken by the subject, and a satisfaction or failure to satisfy a sentiment analysis criterion by the subject.

In some embodiments, a respective gate criterion is a period of time by the subject in the corresponding unique digital reality scene during a corresponding challenge of a proposed experience in the corresponding plurality of proposed experiences of another node in the graph. For instance, in some embodiments, the period of time is a threshold amount of time the subject must play a proposed experience, such as about 1 hour, about 5 hours, about 10 hours, about 15 hours, about 25 hours, about 50 hours, about 75 hours, about 100 hours, or about 120 hours. However, the present disclosure is not limited thereto. For instance, in some embodiments, the period of time is a length of time played by the subject, a frequency of instances by the subject, or the like In some embodiments, a respective gate criterion 32 is a threshold subjective score for a performance of the subject provided by the subject. For instance, in some embodiments, before staring, during, or after completing a corresponding challenge 26 of a proposed experience 24, the subject is presented with an assessment configured to obtain a subjective score (e.g., a subjective unit of distress score) by the subject. Accordingly, in some such embodiments, by requiring the subject to select one or more subjective units of distress scores via the assessment, a medical practitioner and/or one or more models is allowed to track one or more physiological markers and/or biometrics characteristics associated with the subject, such as one or more stress levels of the subject based on the challenges as the subject progresses (e.g., progresses from a first node to a second node, progresses from a first challenge of a third node to a second challenge of the third node, etc.). Additional details and information regarding the use of the subjective score of the subject is found at Demetillo et al., 2021, "Subjective level of distress and psychological well-being of selected SDCA students: Basis for guidance and counseling intervention," SDCA Asia-Pacific Multidisciplinary Research Journal, (3), pg. 62, which is hereby incorporated by reference in its entirety.

In some embodiments, a respective gate criterion is a threshold number of instances by the subject in the corresponding unique digital reality scene. In some embodiments, each instance is an attempt by the subject (e.g., a successful or unsuccessful attempt) to complete a challenge. In some embodiments, an instance by the subject in the corresponding unique digital reality scene is when the subject initiates, or starts, the unique corresponding digital reality scene associated with the corresponding challenge. For instance, in some embodiments, the threshold number of instances by the subject in the corresponding unique digital reality scene is 3 or more instances, 5 or more instances, 7 or more instances, 10 or more instances, 12 or more instances, 15 or more instances, 20 or more instances, 25 or more instances, 30 or more instances, 50 or more instances, 70 or more instances, 100 ore more instances, or 200 or more instances. In this way, the subject is required to interact with the corresponding unique digital reality scene at least by the threshold number of instances (e.g., at least 20 times) in order to progress to another node (e.g., a third node deemed more challenging by the subject in comparison to a second node). For instance, in some embodiments, this required interaction allows the subject to be administered inhibitory learning exposure treatment or therapy by the method 400 in order to improve the ability of the subject to manage a social anxiety disorder exhibited by the subject. Accordingly, in some such embodiments, the higher the number of instances the user is required to satisfy, the higher an engagement level is provided by the subject. However, the present disclosure is not limited thereto. In some embodiments, the respective gate criterion is a threshold number of instances by the subject in a corresponding challenge. In some embodiments, the instance by the subject in the corresponding unique digital reality scene is when the subject is deemed to have completed the unique corresponding digital reality scene associated with the corresponding challenge.

In some embodiments, a gate criterion 32 of a node 630 in the graph 640 is a satisfaction or failure to satisfy a sentiment analysis criterion by the subject during each corresponding challenge 26 in a predetermined number of the corresponding challenges of the category associated with the node 630. Accordingly, in some embodiments, the method 400 further includes determining whether the sentiment analysis criterion is satisfied or not satisfied. In some embodiments, this determination is made by using a distance metric, such as a cosine similarity measure or dot product of one or more utterances of the subject made during each corresponding challenge 26 in the predetermined number of the corresponding challenges of the category associated with the node 630 against each statement in a list of statements that are deemed to be characteristic of a predetermined sentiment. In some exemplary embodiments, the determination is based on those described in Duda et al., 1973, "Pattern Classification and Scene Analysis," Wiley, Print., and/or that described in Salton et al., 1983, "Introduction to Modern Information Retrieval," McGraw-Hill Book Co., Print, each of which is hereby incorporated by reference in their entirety. For instance, consider $X^p=[X_1^p, \ldots, X_n^p]$ and $X^q=[X_1^q, \ldots, X_n^q]$ to be two vectors representing, respectively, the utterances made by the subject and statement in a list of statements that are deemed to be characteristic of a predetermined sentiment. The similarity measure may be determined using the following formula:

$$d(X^p, X^q) = 1 - \frac{\sum_{i=1}^{n} X_i^p X_i^q}{\sqrt{\sum_{i=1}^{n} X_i^{p^2} \cdot \sum_{i=1}^{n} X_i^{q^2}}}$$

Table 1 below shows various other types of measures for distance and further describes the nomenclature of the above-identified formula.

TABLE 1

Exemplary distance metrics for the distance based classification model 208. Consider $X^p = [X_1^p, \ldots, X_n^p]$ and $X^q = [X_1^q, \ldots, X_n^q]$ to be two pattern vectors (be two vectors representing, respectively, the utterances made by the subject and statement in a list of statements). Also consider $max_i$ and $min_i$ to be the maximum value and the minimum value of an $i^{th}$ attribute of the patterns in a data set (e.g., a text string), respectively. The distance between $X^p$ and $X^q$ is defined as follows for each distance metric:

| Type | Distance Metric |
|---|---|
| Euclidean | $d(X^p, X^q) = \sqrt{\sum_{i=1}^{n}(X_i^p - X_i^q)^2}$ |
| Manhattan | $d(X^p, X^q) = \sum_{i=1}^{n}\lvert X_i^p - X_i^q\rvert$ |
| Maximum Value | $d(X^p, X^q) = \mathrm{argmax}_i \lvert X_i^p - X_i^q\rvert$ |
| Normalized Euclidean | $d(X^p, X^q) = \sqrt{\frac{1}{n}\sum_{i=1}^{n}\left(\frac{X_i^p - X_i^q}{max_i - min_i}\right)^2}$ |
| Normalized Manhattan | $d(X^p, X^q) = \frac{1}{n}\sum_{i=1}^{n}\frac{\lvert X_i^p - X_i^q\rvert}{max_i - min_i}$ |
| Normalized Maximum Value | $d(X^p, X^q) = \mathrm{argmax}_i \frac{\lvert X_i^p - X_i^q\rvert}{max_i - min_i}$ |
| Dice Coefficient | $d(X^p, X^q) = 1 - \frac{2\sum_{i=1}^{n}X_i^p X_i^q}{\sum_{i=1}^{n}X_i^{p2} + \sum_{i=1}^{n}X_i^{q2}}$ |
| Cosine coefficient | $d(X^p, X^q) = 1 - \frac{\sum_{i=1}^{n}X_i^p X_i^q}{\sqrt{\sum_{i=1}^{n}X_i^{p2} \cdot \sum_{i=1}^{n}X_i^{q2}}}$ |
| Jaccard coefficient | $d(X^p, X^q) = 1 - \frac{\sum_{i=1}^{n}X_i^p X_i^q}{\sum_{i=1}^{n}X_i^{p2} + \sum_{i=1}^{n}X_i^{q2} - \sum_{i=1}^{n}X_i^p X_i^q}$ |

Additional details and information regarding the distance based classification model 208 can be learned from Yang et al., 1999, "DistAI: An Inter-pattern Distance-based Constructive Learning Algorithm," Intelligent Data Analysis, 3(1), pg. 55.

In some embodiments, the predetermined sentiment is amusement, anger, anxiety, awkwardness, boredom, calmness, confusion, craving, disgust, empathetic pain, entrancement, excitement, fear, horror, interest, joy, annoyance, nostalgia, relief, sadness, satisfaction, or surprise. One of skill in the art will appreciate that other sentiments are within the domain of the systems and methods of the present disclosure.

In some embodiments, the method 400 further includes displaying (e.g., via display 308 of client device 300-1 of FIG. 3) within the first area each respective gate criterion 62 that is associated with each respective node 630 in the subset of nodes 630. In doing so, the user of the client device 300 is provided with a visual indication of each respective gate criterion that the user must satisfy to complete the regimen 20.

In some embodiments, the method 400 further includes displaying (e.g., via display 308 of client device 300-1 of FIG. 3) within the first area of the first affordance region 620-1 each respective gate criterion 32 that is associated with each respective node 630 in the graph 640. Moreover, the method 400 further includes displaying within the first area of the first affordance region 620-1 a completion status of each respective gate criterion 32 associated with each respective node 630 in the graph 640.

In some embodiments, the method 400 further includes using the one or more processors (e.g., CPU 202 of digital reality system 200 of FIG. 2A, CPU 302 of client device 300-1 of FIG. 3) to poll for satisfaction of a respective gate criterion 32. Additionally, in some embodiments, the method 400 includes updating, within the first area of the first affordance region 620-1, a completion status of a respective gate criterion 32 associated with a respective node 630 in the graph 640 when the polling determines that the respective gate criterion 32 is satisfied.

Block 408. Referring to block 408, the method 400 further includes detecting a selection of a node 630 in the enumerated plurality of nodes 630. In some embodiments, selection of the node 630 is detected by sensing input provided by a user of the client device through an input 310, such as a keyboard, a mouse, a joystick, and the like. In other embodiments, selection of the node 630 is detected by a peripheral device in communication with the client device 300 via an I/O subsystem (e.g., I/O subsystem 330 of FIG. 3), such as a microphone of the IO subsystem 330.

In some embodiments, the method 400 includes adding or removing a node 630 in the enumerated plurality of nodes 630 that has not been selected by the user in an instance of the detecting a selection of a node. In some embodiments, this adding or removing the node 630 is responsive to a selection of a node 630 that has been selected in an instance of the detecting the selection of the first node 630-1. Accordingly, this adding or removing of a node 630 that has not been selected allows the method 400 to add or remove an availability of the category and the plurality of proposed experiences 24 associated with the node to the enumerated plurality of nodes 630. For instance, referring briefly to FIGS. 6E and 6F, a user selects a fourth node 630-4 that is associated with a category. However, the fourth node 630-4 is not available for placement on the interactive digital chart 610 based on a failure of the user to satisfy a corresponding gate criterion 32 associated with the fourth node 630-4. Accordingly, at FIG. 6E, the user selection of the fourth node 630-4 is bypassed for the addition of a second node 630-2 that has not been selected by the user. Here, the user satisfies the corresponding gate criterion 32 associated with the second node 630-2, to allow placement of the second node 630-2 on the respective interactive digital chart 610.

Block 410. Referring to block 410, the method 400 further includes determining (e.g., via CPU 202 of digital reality system 200 of FIG. 2A and/or CPU 302 client device 300-1 of FIG. 3) if the selection of the first node 630-1 satisfies each gate criterion 32 in the at least one respective gate criteria 32 that is associated with the first node 630-1.

In some embodiments, this determining is conducted without human intervention (e.g., by digital reality system 200), such as by one or more models (e.g., using two models, three models, 5 models, 10 models, etc.). Accordingly, in some such embodiments, the determining if the selection of the first node 630-1 satisfies each gate criterion 32 in the at least one respective gate criteria 32 that is associated with the first node 630-1 is a computational problem that has a computational complexity that requires use of a computer system and, therefore, cannot be mentally performed.

In some embodiments, this determination if the selection of the first node 630-1 satisfies each gate criterion 32 in the at least one respective gate criteria 32 that is associated with the first node 630-1 is conducted by a medical practitioner associated with the subject or a client device 300 associated with the medical practitioner. For instance, in some embodiments, the selection of the first node 630-1 is communicated (e.g., via communications network 106) to the client device 300 associated with the medical practitioner, which allows the medical practitioner to approve or deny the selection at the client device 300. In some embodiments, prior to the selection of the first node, the medical practitioner provides prior approval or denial for one or more selections by the subject.

In some embodiments, the determining if the selection of the first node satisfies each gate criterion is performed by one or more models in a plurality of models. For instance, in some embodiments, the one or more models includes one model, two or more models, three or more models, four or more models, five or more models, seven or more models, or ten or more models (e.g., 12 models), which collectively determine if the selection of the first node satisfies each gate criterion, such as whether or not the subject is responsive to stress and/or stimuli associated with a first challenge.

In some embodiments, a model is an unsupervised learning algorithm. One example of an unsupervised learning algorithm is cluster analysis.

In some embodiments, a model is supervised machine learning. Non-limiting examples of supervised learning algorithms include, but are not limited to, logistic regression, neural networks, support vector machines, Naive Bayes algorithms, nearest neighbor algorithms, random forest algorithms, decision tree algorithms, boosted trees algorithms, multinomial logistic regression algorithms, linear models, linear regression, GradientBoosting, mixture models, hidden Markov models, Gaussian NB algorithms, linear discriminant analysis, or any combinations thereof. In some embodiments, a model is a multinomial classifier algorithm. In some embodiments, a model is a 2-stage stochastic gradient descent (SGD) model. In some embodiments, a model is a deep neural network (e.g., a deep-and-wide sample-level classifier).

Neural networks. In some embodiments, the model is a neural network (e.g., a convolutional neural network and/or a residual neural network). Neural network algorithms, also known as artificial neural networks (ANNs), include convolutional and/or residual neural network algorithms (deep learning algorithms). Neural networks can be machine learning algorithms that may be trained to map an input data set to an output data set, where the neural network comprises an interconnected group of nodes organized into multiple layers of nodes. For example, the neural network architecture may comprise at least an input layer, one or more hidden layers, and an output layer. The neural network may comprise any total number of layers, and any number of hidden layers, where the hidden layers function as trainable feature extractors that allow mapping of a set of input data to an output value or set of output values. As used herein, a deep learning algorithm (DNN) can be a neural network comprising a plurality of hidden layers, e.g., two or more hidden layers. Each layer of the neural network can comprise a number of nodes (or "neurons"). A node can receive input that comes either directly from the input data or the output of nodes in previous layers, and perform a specific operation, e.g., a summation operation. In some embodiments, a connection from an input to a node is associated with a parameter (e.g., a weight and/or weighting factor). In some embodiments, the node may sum up the products of all pairs of inputs, $x_i$, and their associated parameters. In some embodiments, the weighted sum is offset with a bias, b. In some embodiments, the output of a node or neuron may be gated using a threshold or activation function, f, which may be a linear or non-linear function. The activation function may be, for example, a rectified linear unit (ReLU) activation function, a Leaky ReLU activation function, or other function such as a saturating hyperbolic tangent, identity, binary step, logistic, arcTan, softsign, parametric rectified linear unit, exponential linear unit, softPlus, bent identity, softExponential, Sinusoid, Sine, Gaussian, or sigmoid function, or any combination thereof.

The weighting factors, bias values, and threshold values, or other computational parameters of the neural network, may be "taught" or "learned" in a training phase using one or more sets of training data. For example, the parameters may be trained using the input data from a training data set and a gradient descent or backward propagation method so that the output value(s) that the ANN computes are consistent with the examples included in the training data set. The parameters may be obtained from a back propagation neural network training process.

Any of a variety of neural networks may be suitable for use in performing the methods disclosed herein. Examples can include, but are not limited to, feedforward neural networks, radial basis function networks, recurrent neural networks, residual neural networks, convolutional neural networks, residual convolutional neural networks, and the like, or any combination thereof. In some embodiments, the machine learning makes use of a pre-trained and/or transfer-learned ANN or deep learning architecture. Convolutional and/or residual neural networks can be used for preparing a regimen for improving an ability of a subject to manage a psychiatric or mental condition in accordance with the present disclosure.

For instance, a deep neural network model comprises an input layer, a plurality of individually parameterized (e.g., weighted) convolutional layers, and an output scorer. The parameters (e.g., weights) of each of the convolutional layers as well as the input layer contribute to the plurality of parameters (e.g., weights) associated with the deep neural network model. In some embodiments, at least 100 parameters, at least 1000 parameters, at least 2000 parameters or at least 5000 parameters are associated with the deep neural network model. As such, deep neural network models require a computer to be used because they cannot be mentally solved. In other words, given an input to the model, the model output needs to be determined using a computer rather than mentally in such embodiments. See, for example, Krizhevsky et al., 2012, "Imagenet classification with deep convolutional neural networks," in *Advances in Neural Information Processing Systems* 2, Pereira, Burges, Bottou, Weinberger, eds., pp. 1097-1105, Curran Associates, Inc.; Zeiler, 2012 "ADADELTA: an adaptive learning rate method," CoRR, vol. abs/1212.5701; and Rumelhart et al., 1988, "Neurocomputing: Foundations of research," ch. Learning Representations by Back-propagating Errors, pp. 696-699, Cambridge, Mass., USA: MIT Press, each of which is hereby incorporated by reference.

Neural network algorithms, including convolutional neural network algorithms, suitable for use as models are disclosed in, for example, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference. Additional example neural networks suitable for use as models are disclosed in Duda et al., 2001, *Pattern Classification*, Second Edition, John Wiley & Sons, Inc., New York; and Hastie et al., 2001, *The Elements of Statistical Learning*, Springer-Verlag, New York, each of which is hereby incorporated by reference in its entirety. Additional example neural networks suitable for use as models are also described in Draghici, 2003, *Data Analysis Tools for DNA Microarrays*, Chapman & Hall/CRC; and Mount, 2001, *Bioinformatics: sequence and genome analysis*, Cold Spring Harbor Laboratory Press, Cold Spring Harbor, N.Y., each of which is hereby incorporated by reference in its entirety.

Support vector machines. In some embodiments, the model is a support vector machine (SVM). SVM algorithms suitable for use as models are described in, for example, Cristianini and Shawe-Taylor, 2000, "An Introduction to Support Vector Machines," Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety. When used for classification, SVMs separate a given set of binary labeled data with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space can correspond to a non-linear decision boundary in the input space. In some embodiments, the plurality of parameters (e.g., weights) associated with the SVM define the hyper-plane. In some embodiments, the hyper-plane is defined by at least 10, at least 20, at least 50, or at least 100 parameters and the SVM model requires a computer to calculate because it cannot be mentally solved.

Naïve Bayes algorithms. In some embodiments, the model is a Naive Bayes algorithm. Naïve Bayes classifiers suitable for use as models are disclosed, for example, in Ng et al., 2002, "On discriminative vs. generative classifiers: A comparison of logistic regression and naive Bayes," Advances in Neural Information Processing Systems, 14, which is hereby incorporated by reference. A Naive Bayes classifier is any classifier in a family of "probabilistic classifiers" based on applying Bayes' theorem with strong (naïve) independence assumptions between the features. In some embodiments, they are coupled with Kernel density estimation. See, for example, Hastie et al., 2001, *The elements of statistical learning: data mining, inference, and prediction*, eds. Tibshirani and Friedman, Springer, New York, which is hereby incorporated by reference.

Nearest neighbor algorithms. In some embodiments, a model is a nearest neighbor algorithm. Nearest neighbor models can be memory-based and include no model to be fit. For nearest neighbors, given a query point $x_0$ (a first data set), the k training points $x_{(r)}$, r, . . . , k (e.g., training dataset(s)) closest in distance to $x_0$ are identified and then the point $x_0$ is classified using the k nearest neighbors. In some embodiments, the distance to these neighbors is a function of the values of a discriminating set. In some embodiments, Euclidean distance in feature space is used to determine distance as $d_{(i)} = \|x_{(i)} - x_{(o)}\|$. Typically, when the nearest neighbor algorithm is used, the value data used to compute the linear discriminant is standardized to have mean zero and variance 1. The nearest neighbor rule can be refined to address issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, The Elements of Statistical Learning, Springer, New York, each of which is hereby incorporated by reference.

A k-nearest neighbor model is a non-parametric machine learning method in which the input consists of the k closest training examples in feature space. The output is a class membership. An object is classified by a plurality vote of its neighbors, with the object being assigned to the class most common among its k nearest neighbors (k is a positive integer, typically small). If k=1, then the object is simply assigned to the class of that single nearest neighbor. See, Duda et al., 2001, *Pattern Classification*, Second Edition, John Wiley & Sons, which is hereby incorporated by reference. In some embodiments, the number of distance calculations needed to solve the k-nearest neighbor model is such that a computer is used to solve the model for a given input because it cannot be mentally performed.

Random forest, decision tree, and boosted tree algorithms. In some embodiments, the model is a decision tree. Decision trees suitable for use as models are described generally by Duda, 2001, Pattern Classification, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can be used is a classification and regression tree (CART). Other specific decision tree algorithms include, but are not limited to, ID3, C4.5, MART, and Random Forests. CART, ID3, and C4.5 are described in Duda, 2001, Pattern Classification, John Wiley & Sons, Inc., New York, pp. 396-408 and pp. 411-412, which is hereby incorporated by reference. CART, MART, and C4.5 are described in Hastie et al., 2001, The Elements of Statistical Learning, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety. In some embodiments, the decision tree model includes at least 10, at least 20, at least 50, or at least 100 parameters (e.g., weights and/or decisions) and requires a computer to calculate because it cannot be mentally solved.

Regression. In some embodiments, the model uses a regression algorithm. A regression algorithm can be any type of regression. For example, in some embodiments, the regression algorithm is logistic regression. In some embodiments, the regression algorithm is logistic regression with lasso, L2 or elastic net regularization. In some embodiments, those extracted features that have a corresponding regression coefficient that fails to satisfy a threshold value are pruned (removed from) consideration. In some embodiments, a generalization of the logistic regression model that handles multicategory responses is used as the model. Logistic regression algorithms are disclosed in Agresti, An Introduction to Categorical Data Analysis, 1996, Chapter 5, pp. 103-144, John Wiley & Son, New York, which is hereby incorporated by reference. In some embodiments, the model makes use of a regression model disclosed in Hastie et al., 2001, *The Elements of Statistical Learning*, Springer-Verlag, New York. In some embodiments, the logistic regression model includes at least 10, at least 20, at least 50, at least 100, or at least 1000 parameters (e.g., weights) and requires a computer to calculate because it cannot be mentally solved.

Linear discriminant analysis algorithms. Linear discriminant analysis (LDA), normal discriminant analysis (NDA), or discriminant function analysis can be a generalization of Fisher's linear discriminant, a method used in statistics, pattern recognition, and machine learning to find a linear combination of features that characterizes or separates two or more classes of objects or events. The resulting combination can be used as the model (e.g., a linear classifier) in some embodiments of the present disclosure.

Mixture model and Hidden Markov model. In some embodiments, the model is a mixture model, such as that described in McLachlan et al., Bioinformatics 18(3):413-422, 2002. In some embodiments, in particular, those embodiments including a temporal component, the model is a hidden Markov model such as described by Schliep et al., 2003, Bioinformatics 19(1):i255-i263.

Clustering. In some embodiments, the model is an unsupervised clustering model. In some embodiments, the model is a supervised clustering model. Clustering algorithms suitable for use as models are described, for example, at pages 211-256 of Duda and Hart, Pattern Classification and Scene Analysis, 1973, John Wiley & Sons, Inc., New York, (hereinafter "Duda 1973") which is hereby incorporated by reference in its entirety. The clustering problem can be described as one of finding natural groupings in a dataset. To identify natural groupings, two issues can be addressed. First, a way to measure similarity (or dissimilarity) between two samples can be determined. This metric (e.g., similarity measure) can be used to ensure that the samples in one cluster are more like one another than they are to samples in other clusters. Second, a mechanism for partitioning the data into clusters using the similarity measure can be determined. One way to begin a clustering investigation can be to define a distance function and to compute the matrix of distances between all pairs of samples in a training dataset. If distance is a good measure of similarity, then the distance between reference entities in the same cluster can be significantly less than the distance between the reference entities in different clusters. However, clustering may not use a distance metric. For example, a nonmetric similarity function s(x, x') can be used to compare two vectors x and x'. s(x, x') can be a symmetric function whose value is large when x and x' are somehow "similar." Once a method for measuring "similarity" or "dissimilarity" between points in a dataset has been selected, clustering can use a criterion function that measures the clustering quality of any partition of the data. Partitions of the data set that extremize the criterion function can be used to cluster the data. Particular exemplary clustering techniques that can be used in the present disclosure can include, but are not limited to, hierarchical clustering (agglomerative clustering using a nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering. In some embodiments, the clustering comprises unsupervised clustering (e.g., with no preconceived number of clusters and/or no predetermination of cluster assignments).

Ensembles of models and boosting. In some embodiments, an ensemble (two or more) of models is used. In some embodiments, a boosting technique such as AdaBoost is used in conjunction with many other types of learning algorithms to improve the performance of the model. In this approach, the output of any of the models disclosed herein, or their equivalents, is combined into a weighted sum that represents the final output of the boosted model. In some embodiments, the plurality of outputs from the models is combined using any measure of central tendency known in the art, including but not limited to a mean, median, mode, a weighted mean, weighted median, weighted mode, etc. In some embodiments, the plurality of outputs is combined using a voting method. In some embodiments, a respective model in the ensemble of models is weighted or unweighted.

In some embodiments, the term "classification" refers to any number(s) or other characters(s) that are associated with a particular property of a sample. For example, a "+" symbol (or the word "positive") can signify that a sample is classified as having a desired outcome or characteristic, whereas a "−" symbol (or the word "negative") can signify that a sample is classified as having an undesired outcome or characteristic. In another example, the term "classification" refers to a respective outcome or characteristic (e.g., high risk, medium risk, low risk). In some embodiments, the classification is binary (e.g., positive or negative) or has more levels of classification (e.g., a scale from 1 to 10 or 0 to 1). In some embodiments, the terms "cutoff" and "threshold" refer to predetermined numbers used in an operation. In one example, a cutoff value refers to a value above which results are excluded. In some embodiments, a threshold value is a value above or below which a particular classification applies. Either of these terms can be used in either of these contexts.

Block 412. Referring to block 412, in some embodiments, the method 400 includes placing a node 630 at a first location in the first area of the first affordance region 620-1 when each gate criterion 32 in the at least one respective gate criteria 32 associated with the node 630 is satisfied (e.g., at a first location in the first area). From this, the method 400 provides access to the category and the plurality of proposed experiences associated with the node (each experience associated with a corresponding unique digital reality scene 40) while improving the ability of the subject to manage the psychiatric or mental condition using the respective interactive digital chart 610.

Figure 14A:
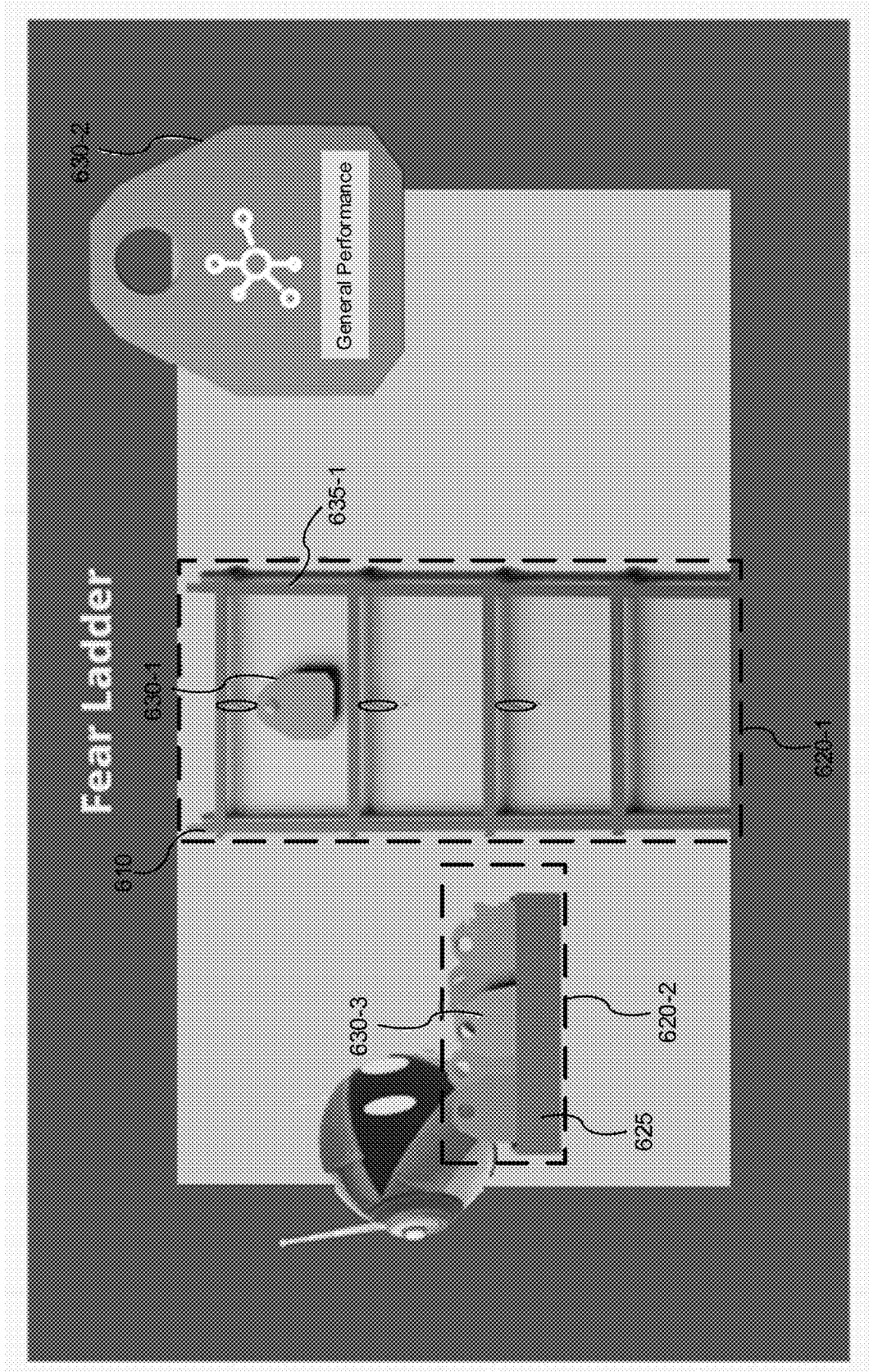
FIG. 14A illustrates a user interface for presenting a digital reality scene including an interactive digital chart and a corresponding interactive digital bin in order to allow a subject to place a respective node associated with the corresponding interactive digital bin at a location in an area of the interactive digital chart.
Figure 14B:
FIG. 14B illustrates a user interface for presenting a digital reality scene that provides access for a subject to a corresponding plurality of proposed experiences.

Referring to FIG. 14B, in some embodiments, the placing the first node by the subject (e.g., placing node 630-2 on the digital interactive chart 610 of FIG. 14A) provides access to the corresponding plurality of proposed experiences, in which the access is provided through a second digital reality scene. In some embodiments, the second digital reality scene is different than the first digital reality scene and the corresponding unique digital reality scene associated with a proposed experience in the corresponding plurality of proposed experiences. From this, the subject is allowed to access the corresponding plurality of proposed experiences through the second digital reality scene that is separate and different from the first digital reality scene where the subject is allowed to select one or more nodes (e.g., forming a hierarchy of categories based on an order of selection of the one or more nodes by the subject, block 408 of FIG. 4). For instance, in some embodiments, after placing the first node, the subject is transitioned from the first digital reality scene to the second digital reality scene in order to select a proposed experience from the corresponding plurality of proposed experiences associated with the first node. As a non-limiting example, referring to FIG. 14A, a first digital reality scene is presented through a first user interface 1400-1, in which the first digital reality scene depicts a chromatic background and an interactive digital chart 610. Referring to FIG. 14B, after selecting at least the first node, the subject is transitioned to a second digital reality scene that is presented through a second user interface 1400-2, in which the second digital reality scene depicts an interior of a house with a portal object in the house (e.g., a portal scene) utilized for selecting a proposed experience. In some embodiments, the second digital reality scene is configured as a portal scene configured to allow the subject to select a respective proposed experience from the corresponding plurality of proposed experiences. For instance, in some embodiments, the portal scene includes a link represented by a portal, a wormhole, or a rip in an ether that connects two digital reality scenes (e.g., the second digital reality scene and a corresponding unique digital reality scene associated with a proposed experience). Accordingly, in some embodiments, the portal scene allows the subject to select the respective proposed experience in order to be virtually transported to the corresponding unique digital reality scene associated with a proposed experience (e.g., transported to digital scene of FIG. 10A). However, the present disclosure is not limited thereto. In some embodiments, the portal scene includes either a two-dimensional or three-dimensional object, with at least one display surface of the two-dimensional or three-dimensional object having a preview (e.g., a thumbnail) of the proposed experience. In some cases, the portal is virtually selected by the subject by clicking or touching of the portal (e.g., via input 310 of FIG. 3). In further cases, the portal is virtually selected by the subject by a specific hand gesture (e.g., knocking, pulling, pushing, turning, etc.).

In some embodiments, the method 400 further includes repeating the detecting the selection of the first node 630-1 (e.g., block 408 of FIG. 4), determining if the selection of the first node 630-1 satisfies each gate criterion 32 (e.g., block 410 of FIG. 4), and placing the first node 630-1 (e.g., block 412 of FIG. 4) one or more times (e.g., once, two times, three times, four times, five times, seven times, ten times, fifteen times, twenty times, etc.) for successive nodes 630 in the enumerated plurality of nodes 630. From this, the method 400 selects a subset of nodes 630 in the enumerated plurality of nodes 630 for inclusion in a graph 640 within the respective interactive virtual digital chart 610 that satisfies each gate criteria 32 associated with a corresponding node 630 in the subset of nodes 630.

Each respective node 630 in the graph 640 is connected by an edge 635 in a plurality of edges 635 to at least one other node 630 in the graph 640. In some embodiments, the coupling of a first node and a second node by an edge imposed a gate on one of the two nodes that requires at least a predetermined number of the challenges of the category associated with the first node to be successfully completed before the second node can be initiated. That is, each edge has a source node and a destination node. The edge has the effect of imposing a gate criterion on the destination node that requires at least successful completion of a predetermined number of the challenges of the category associated with the source node before the destination node can be initiated. By the same token, the coupling of a source node and a destination node of an edge means that once a user has completed the predetermined number of the challenges of the category associated with the source node and all of the precedent conditions of the destination node, the user can initiate the destination node as well as the category and the challenges associated with the destination node. By contrast consider a pair of nodes that are not directly connected by an edge. Because they are not directly connected by an edge, completion of the predetermined number of challenges of the category associated with one of the nodes in the pair does not qualify the user to progress to the other of the nodes in the pair.

Figure 14C:
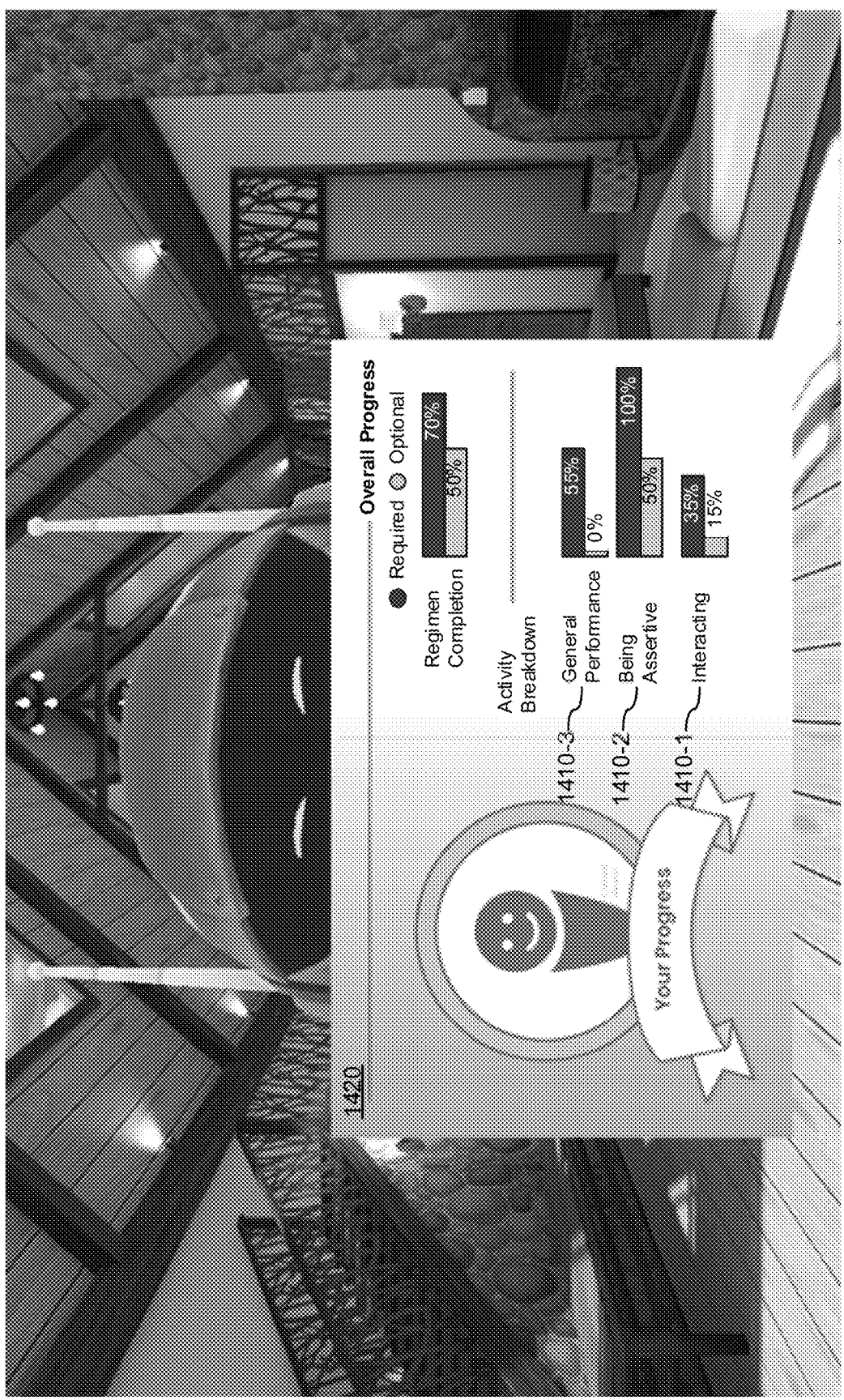
FIG. 14C illustrates a user interface for presenting a digital reality scene that provides a chart depicting a status of a plurality of gate criteria associated with each respective node in an enumerated plurality of nodes.

As such, each respective edge 635 in the plurality of edges 635 represents a progression within the graph 640 between a respective initial node 630 and a respective subsequent node 630 in the graph 640. In some embodiments, the progression is displayed (e.g., an edge is rendered in the digital reality scene) upon successful completion by the subject of a predetermined number of the corresponding challenges 26 of the category associated with the respective initial node 630. For instance, referring to FIG. 14C, a user interface 1400-3 is configured to present a chart showing a completion status by the subject for the corresponding challenges 26 of a first category 1410-1 (e.g., a 35% completion status for required challenges of the first category and a 15% completion status for optional challenges of the first category), a second category 1410-2 (e.g., a 100% completion status for required challenges of the second category and a 50% completion status for optional challenges of the second category), and a third category 1410-3 (e.g., a 55% completion status for required challenges of the third category and a 0% completion status for optional challenges of the third category). In some embodiments, a threshold completion status for a respective category is 100% of the required challenges, about 95% of the required challenges, about 90% of the required challenges, about 85% of the required challenges, about 75% of the required challenges, or about 50% of the required challenges. However, the present disclosure is not limited thereto. Furthermore, the graph 640 includes a final node 630 other than the first node 630-1. In some embodiments, arrival and/or completion of the final node 630 indicates completion of the regimen 20 for improving an ability of the subject to manage the psychiatric or mental condition exhibited by the subject.

Referring now to FIGS. 13A-13M, there is depicted a flowchart illustrating an exemplary method 1300 in accordance with some embodiments of the present disclosure. In the flowchart, the preferred parts of the method are shown in solid line boxes, whereas additional, optional, or alterative parts of the method are shown in dashed line boxes. The method prepares a regimen for improving an ability of a subject to manage a psychiatric or mental condition exhibited by the subject. It generally includes a presenting process, a detecting process, and a placing process, such as the presenting process exemplified by at least block 1328, detecting process exemplified by at least block 1390, and placing process exemplified at block 1392. The presenting, detecting, and placing processes allow the subject to place a node, associated with a category with proposed experiences of social challenges, on an interactive digital chart. In some embodiments, the method 1300 also repeats the detecting and placing processes as exemplified by at least block 1400, thereby allowing the subject to place multiple nodes, each associated with a respective category with corresponding proposed experiences of social challenges, on the interactive digital chart. In some embodiments, the plurality of nodes is placed on the interactive digital chart in an order that satisfies certain criteria. In some embodiments, the method 1300 further includes one or more additional, optional and/or alternative processes, such as the obtaining process as exemplified by at least block 1370, activating process as exemplified by at least block 1406, and/or displaying process as exemplified by at least block 1414.

It should be noted that, in some embodiments, the processes illustrated in the Figures are not necessarily in order. For instance, in some embodiments, the obtaining process is performed prior to the presenting process or during the presenting process. The activating process can be performed prior to the repeating process (e.g., after the first node has been placed on the interactive digital chart), during the repeating process (e.g., after the first or second node has been placed on the interactive digital chart), or subsequent to the repeating process (e.g., after all of the plurality of nodes have been placed on the interactive digital chart). Similarly, the displaying process can be performed prior to, during or subsequent to the repeating process.

It should also be noted that the method can include the additional, optional and/or alternative processes exemplified in the flowchart in any meaningful and useful combinations. For instance, in some embodiments, the method includes both the activating process and the displaying process. In some other embodiments, the method includes the activating process but not the displaying process. In some further embodiments, the method includes the displaying process but not the activating process.

Block 1302. Referring to block 1302 of FIG. 13A, in various embodiments, the method 1300 is provided at a computer system (e.g., system 100 of FIG. 1, digital reality system 200 of FIG. 2, client device 300-1 of FIG. 3, etc.) associated with the subject. The computer system includes one or more processors (e.g., CPU 202 of FIG. 2A, CPU 302 of FIG. 3, etc.), a display (e.g., display 1100 of FIG. 11), and a memory (e.g., member 212 of FIG. 2A, memory 312 of FIG. 3, etc.) coupled to the one or more processors. The memory includes one or more programs configured to be executed by the one or more processors.

Block 1304. Referring to block 1304, in some embodiments, the display is any suitable display, such as a head mounted display (HUD), a near-eye display 1100 illustrated in FIG. 11 or the like. As described supra, by utilizing the HUD display, the user is provided with an immersive, sensory experience.

Blocks 1306-1326. Referring to blocks 1306 through block 1326 of FIG. 3B, in some embodiments, the psychiatric or mental condition is a clinically diagnosed mental disorder or a sub-clinically diagnosed mental disorder. Examples of a psychiatric or mental condition include, but are not limited to, those being stressed in a social setting, fearing a social setting, or being overwhelmed in a social setting. For instance, in some embodiments, the clinically diagnosed mental disorder is an anxiety disorder such as a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject. In some embodiments, the clinically diagnosed mental disorder is a mood disorder such as a depression disorder, a bipolar disorder, or a cyclothymic disorder. For instance, in some embodiments, the depression disorder is a major depression disorder. In some embodiments, the clinically diagnosed mental disorder is a psychotic disorder such as a schizophrenia disorder, a delusion disorder, or a hallucination disorder. In some embodiments, the clinically diagnosed mental disorder is an eating disorder such as anorexia nervosa, bulimia nervosa, or binge eating disorder. In some embodiments, the clinically diagnosed mental disorder is an impulse control disorder such as a pyromania disorder, a kleptomania disorder, or a compulsive gambling disorder. In some embodiments, the clinically diagnosed mental disorder includes, but is not limited to, a personality disorder, an obsessive-compulsive disorder, or a post-traumatic stress disorder. In some embodiments, the clinically diagnosed mental disorder is an addiction disorder such as an alcohol use disorder or a substance abuse disorder. In some embodiments, the clinically diagnosed mental disorder is a personality disorder such as an antisocial personality disorder, an obsessive-compulsive personality disorder, or a paranoid personality disorder.

Block 1328. Referring to block 1328, the method 1300 includes presenting, on the display, a first digital reality scene (e.g., first digital reality scene 40-1 of FIG. 10B). The first digital reality scene includes a respective interactive digital chart. For instance, in some embodiments, the first digital reality scene includes an interactive digital chart 710 illustrated in FIG. 7A. The respective interactive digital chart consumes (occupies) a first affordance region such as the first affordance region 720-1. The interactive digital chart or the first affordance region includes a plurality of areas. As a non-limiting example, FIG. 7A illustrates a first area 722-1, a second area 722-2, and a third area 722-3.

The first digital reality scene also includes a corresponding interactive digital bin. For instance, in some embodiments, the first digital reality scene includes a corresponding interactive digital bin 725 illustrated in FIG. 7B. The corresponding interactive digital bin consumes (occupies) a second affordance region such as the second affordance region 720-2. The second affordance region is different than the first affordance region 720-1. The corresponding interactive digital bin includes an enumerated plurality of nodes, or initially an enumerated plurality of nodes is presented in the corresponding interactive digital bin. Any suitable number of nodes can be initially presented in the corresponding interactive digital bin. For instance, the enumerated plurality of nodes can be of about 3 nodes, about 5 nodes, about 7 nodes, about 10 nodes, about 12 nodes, about 15 nodes, or about 20 nodes. As a non-limiting example, FIG. 7B illustrates three nodes, i.e., node 730-1, node 730-2, and node 730-3.

Block 1330-1332. Referring to block 1330 and block 1332 of FIG. 13C, in some embodiments, the first affordance regions and/or the second affordance region is a two-dimensional or a three-dimensional region in the first digital reality scene. In some embodiments, also, the first and second affordance regions can have regular or irregular shapes. Similarly, an area (e.g., the first, second and third area in the first affordance region) can be a two-dimensional or three-dimensional area and can have a regular or irregular shape. By way of example, FIGS. 7A and 7B illustrate a generally two-dimensional first affordance region in the first digital reality scene, and the first area being bound by the generally two-dimensional affordance region. This is by way of example and is non-limiting. The first and second affordance regions and the area can have other shapes.

Blocks 1334-1336. Referring to block 1334 and block 1336, for instance, in some embodiments, the first affordance region is a three-dimensional affordance region in the first digital reality scene, and the first area is a respective surface area of a three-dimensional object (e.g., object 42 of FIG. 2B) bound by the three-dimensional affordance region. In some embodiment, the three-dimensional region is a sphere or a polyhedron object. For instance, in some embodiments, the interactive digital chart has an appearance of a globe by way of the spherical three-dimensional region in the digital scene. However, the present disclosure is not limited thereto. For instance, in some embodiments, the first area is circular or polygonal. By way of example, referring briefly to FIG. 7B, in some embodiments, the circular first area gives a map appearance for the interactive digital chart.

Block 1338. Referring to block 1340, in some exemplary embodiments, an area (e.g., the first, second and third area in the first affordance region) includes a plurality of tessellated shapes. For instance, in some embodiments, the first area 714-1 includes a plurality of tessellated shapes such as tiles illustrated in FIG. 7A.

Block 1340. Referring to block 1340, in some embodiments, the plurality of tessellated shapes includes about 20 tessellated shapes, about 30 tessellated shapes, about 40 tessellated shapes, about 50 tessellated shapes, about 75 tessellated shapes, about 100 tessellated shapes, about 125 tessellated shapes, about 150 tessellated shapes, about 175 tessellated shapes, about 200 tessellated shapes, about 225 tessellated shapes, about 250 tessellated shapes, about 275 tessellated shapes, about 300 tessellated shapes, about 325 tessellated shapes, or about 350 tessellated shapes. In some embodiments, the plurality of tessellated shapes is the same, or substantially the same, as block 406 of FIG. 4.

Block 1342. Referring to block 1342, it should be noted that the first and second affordance regions can be presented in the first digital reality scene at any suitable locations with respect to each other. For instance, the first affordance region can overlap with the second affordance region, or vice versa. The first and second affordance regions can also be spaced apart from each other. By way of example, FIG. 7B illustrates the first and second affordance regions being spaced apart from each other.

Block 1344. Referring to block 1344, it should be noted that the respective interactive digital chart or the corresponding interactive digital bin can include other additional, optional, or alternative features. For instance, in some embodiments, the respective interactive digital chart includes a graphical marker disclosed elsewhere herein and configured to visually designate a location (e.g., the first location) in the first affordance region. In some embodiments, the graphical marker is configured by the medical practitioner associated with the subject, with allows the medical practitioner to bring special attention to one or more elements to the interactive digital chart by way of the graphical marker. However, the present disclosure is not limited thereto.

Block 1346. Referring to block 1346, in some embodiments, the first digital reality scene is any suitable digital reality scene. For instance, the first digital reality scene can be a virtual reality scene, an augmented reality scene, or a mixed reality scene as disclosed herein. In some embodiments, the first digital reality scene is, or is substantially similar to, the digital reality scene 40-3 illustrated in FIG. 5C or the like.

Block 1348. Referring to block 1348, in some embodiments, the first digital reality scene (e.g., the digital reality scene 40-3 illustrated in FIG. 5C or the like) includes an interactive board. The interactive board can be a two-dimensional or three-dimensional object in the first digital reality scene and can have a regular or irregular shape. The interactive board can also be static or movable in the first digital reality scene.

Figure 7L:
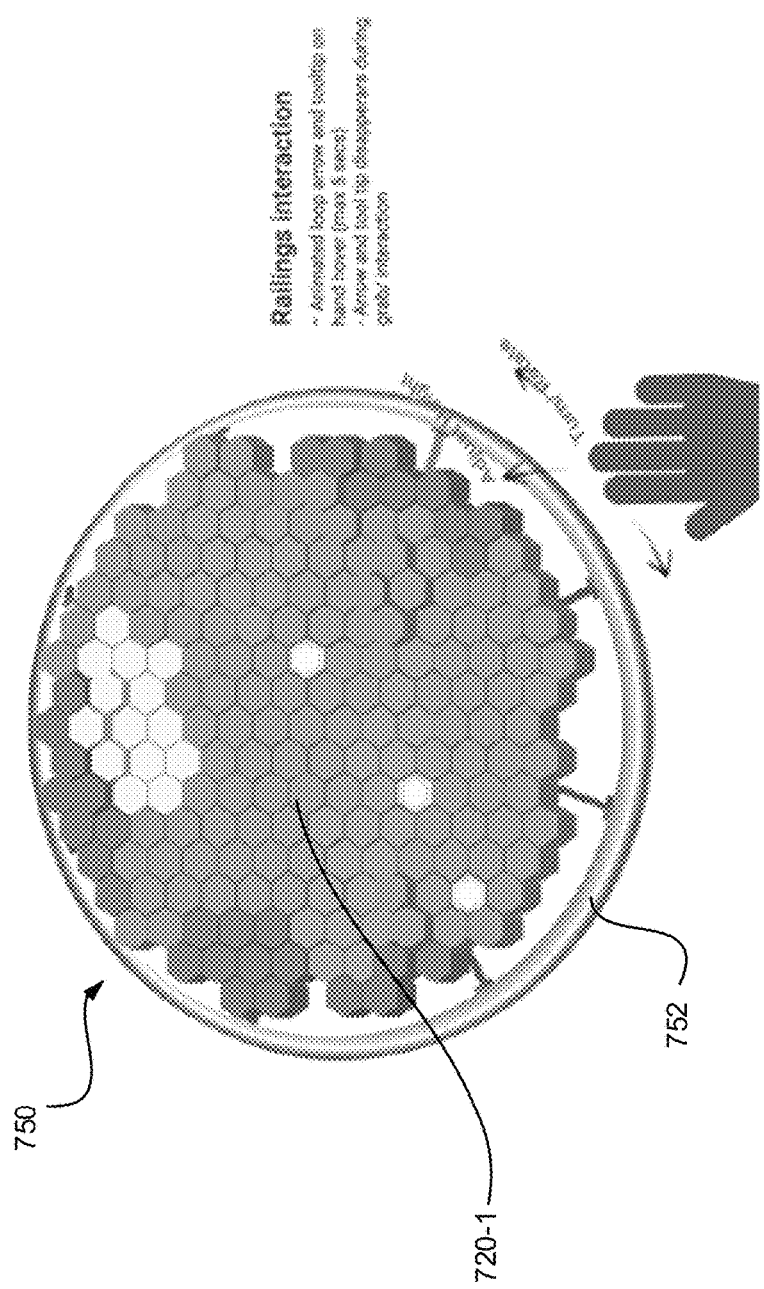
Figure 7M:
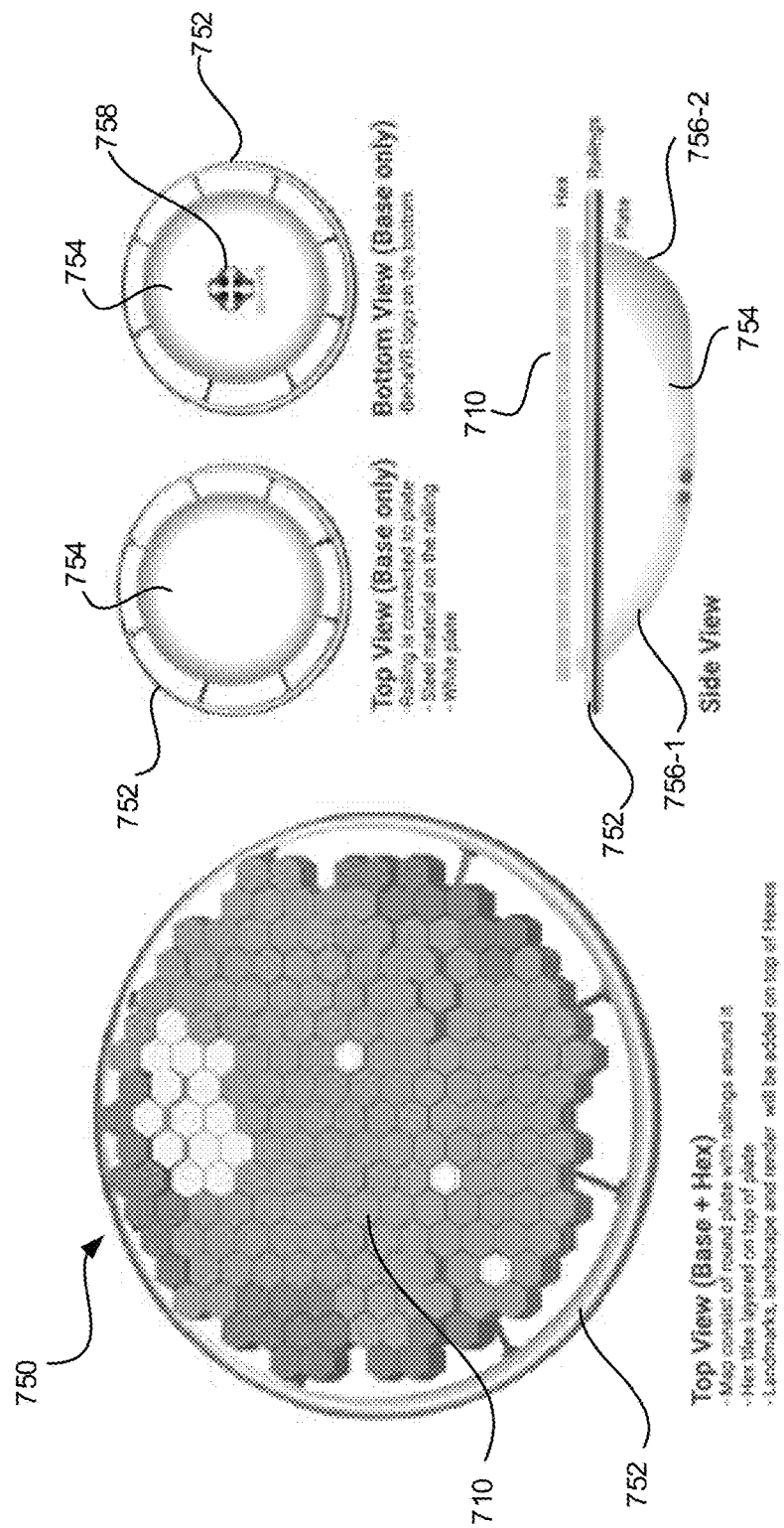

For instance, in some embodiments, the first digital reality scene includes an interactive board 750 illustrated in FIGS. 7A, 7L and 7M. The respective interactive digital chart 710 is placed on a top of the interactive board or is a component of the interactive board disposed at the top of the interactive board. The interactive board 750 is movable, rotatable or tiltable in the first digital reality scene, as illustrated by the dashed lines in FIG. 7A. That is, the subject can move, rotate, or tilt the interactive board in the first digital reality scene to facilitate different views of the interactive board.

Block 1350. Referring to block 1350, in some embodiments, the interactive board includes a rail, such as the rail 752, to allow an avatar of the subject to grab the interactive board and adjust the position of the interactive board. By allowing the subject to grab the interactive board and adjust the position of the interactive board the subject is further enabled to adjust the position of the interactive digital chart by way of the interactive board. In this way, in some embodiments, viewing the interactive digital chart from a first position is advantageous for improving the ability of the subject to manage the psychiatric or mental condition using the respective interactive digital chart modify an initial position of the interactive digital chart to the first position, since a perception of progression within the interactive digital chart can change when changing the position of the interactive board by way of the rail.

Block 1352. Referring to block 1352, in some embodiments, the interactive board 750 includes a plate, such as the plate 754, with the respective interactive digital chart 610 directly or indirectly placed on the top of the plate. In some embodiments, the plate includes each surface, or face, of the interactive board other than a surface, or face of the interactive digital chart. In some embodiments, the plate includes one or more parameters that form a coefficient of friction between the rail and interactive digital chart by way of the interactive board, which allows for various haptic and/or visual interactions between the user and the digital reality scene.

Block 1354. Referring to block 1354, in some embodiments, the rail and plate can have any suitable regular or irregular, symmetric, or asymmetric shape. For instance, the rail can have circular, oval, oblong, or polygonal shapes. The rail can also be straight or arched. As a non-limiting example, FIGS. 7L and 7M illustrate the rail having a substantially ring shape, and the plate having a substantially circular shape when viewed from top of the interactive board or from bottom of the interactive board. In some embodiments, the plate is surrounded circumferentially by the rail and connected to the rail. In some other embodiments, the plate is connected to the rail but not surrounded circumferentially by the rail. For instance, in some embodiments, the rail does not form a complete loop and does not enclose circumferentially the plate.

Block 1356. Referring to block 1356, in some embodiments, when viewed from a side of the interactive board, the plate has a first side that is sloped differently than a second side. For instance, by way of example, FIGS. 7L and 7M illustrate the plate having a first side 756-1 sloped more sharply than a second side 756-2 when viewed from a side of the interactive board. In an exemplary embodiment, when viewed from the side of the interactive board, the plate has a substantially boat-bowel shape.

Block 1358. Referring to block 1358, in some embodiments, the interactive board can include other additional, optional, or alternative features. For instance, in some embodiments, a logo, such as the logo 758, is displayed at a bottom of the plate as illustrated in FIGS. 7L and 7M. In some embodiments, the logo is set by an administrator of the digital reality system, such as by a provider or host of the client application 320. In some embodiments, the logo is set by the medical practitioner associated with the subject. In some embodiments, the logo is set by the user, such as an image provided by a user of a client device that is stored in a user profile at a digital reality system 200. By including the logo, fashionable elements such as distinctive colors, textures, ornamentation (e.g., marks, logos, etc.), or a combination thereof is incorporated into the interactive board that help immerse the subject within the digital reality scene.

Block 1360. Referring to block 1360, in some embodiments, the rail and plate can be rendered in any suitable colors with any suitable surface finishing. The rail and plate can also be rendered to resemble parts made of any suitable materials. For instance, in some embodiments, the plate is rendered white on the display and the rail is rendered on the display to resemble a rail made of a metallic material such as a stainless steel, as illustrated in FIGS. 7L and 7M. As a non-limiting example, in some embodiments, the rail is rendered with a surface finishing that gives an ornamental appearance of a compass, such as a first compass indicating a northern direction or a second compassing indicating a direction towards a final node. However, the present disclosure is not limited thereto.

Block 1362. Referring to block 1362 of FIG. 13E, in some embodiments, responsive to an avatar hovering a hand over the interactive board or adjacent to the interactive board for a period of time, one or more animated loop arrows and tool tips appear at or adjacent to the interactive board, as illustrated in FIG. 7L. Generally, the period of time is less than 8 seconds, less than 7 seconds, less than 6 seconds, less than 5 seconds, less than 4 seconds, or less than 3 seconds. However, the present disclosure is not limited thereto.

Block 1364. Referring to block 1364, in some embodiments, responsive to gripping of the rail by the avatar of the subject or interaction of the avatar of the subject with the interactive board, one or more animated loop arrows and tool tips disappear from the first digital reality scene. In this way, the user interface of the display is not overly cluttered for the user.

Block 1366. Referring to block 1366, in some embodiments, an individual node and/or one or more experience graphics associated with the individual node is tilted at an angle with respect to the interactive board, for instance, so that the individual node and/or the one or more experience graphics associated with the individual node is more discernible to the subject. For instance, in some embodiments, an activated node and/or one or more experience graphics (each representing a proposed social challenge experience) associated with the activated node are tilted at an angle with respect to the interactive board. As a non-limiting example, FIG. 7K illustrates a node or an experience graphic being tilted at an angle α with respect to the interactive board. In some embodiments, the angle is between 5 degrees to 15 degrees, between 15 degrees to 30 degrees, between 30 degrees to 45 degrees, between 45 degrees to 60 degrees, between 60 degrees to 90 degrees, or a combination thereof. Referring to FIG. 14B, in some embodiments, the one or more experience graphics is displayed within the digital reality scene as text that provides a description of a corresponding experience for the subject. For instance, as a non-limiting example, in FIG. 14B, a third experience graphic 1440-3 is associated with a third experience of presenting to a bored audience for a second node associated with a general performance category, whereas a fourth experience graphic 1440-4 is associated with a fourth experience of making a toast to a group of people with all eyes on you for the second node associated with the general performance category. Accordingly, by displaying the corresponding experience graphic that represents a proposed experience, the subject is allowed to internalize and select the proposed experience before entering the corresponding digital reality scene associated with the proposed experience.

Furthermore, in some embodiments, a position of the interactive board is limited by way of the rail to at least one rotational degree of freedom, such as a user controlling a roll, a yaw, or a pitch of the interactive board. In some embodiments, the position of the interactive board is limited by way of the rail to at least two rotational degrees of freedom, such as the user controlling the roll and the yaw of the interactive board. In some embodiments, the position of the interactive board is limited by way of the rail to three rotational degrees of freedom such that the user controls the roll, the yaw, and the pitch of the interactive board. In some embodiments, the rail allows the user to control a translational position of the interactive board, such as dragging interactive board across a portion of the digital reality scene by way of the rail. However, the present disclosure is not limited thereto.

Block 1368. Referring to block 1368 of FIG. 13F, in some embodiments, each respective node in the enumerated plurality of nodes corresponds to a respective category in a plurality of categories. Each respective category in the plurality of categories is directed to improving an ability of the subject to manage a psychiatric or mental condition of the subject. For instance, as a non-limiting example, FIG. 7B illustrates node 730-1 corresponding to category 740-1, node 730-2 corresponding to category 740-2, and node 730-3 corresponding to category 740-3.

Each respective node in the enumerated plurality of nodes is also associated with a corresponding plurality of proposed experiences associated with the respective category. Any suitable number of proposed experiences can be associated with one category. For instance, one, two, three, four, five, more than five, more than ten, more than twenty proposed experiences can be associated with a category. As a non-limiting example, FIG. 7C illustrates node 730-1 being associated with category 740-1, which includes six proposed experiences, such as experience 742-1, experience 742-2, experience 742-3, experience 742-4, experience 742-5, and experience 742-6. Each respective proposed experience in the corresponding plurality of proposed experiences is associated with a corresponding unique digital reality scene, different than the first digital reality scene, that manifests a corresponding challenge represented by the respective category and/or the respective proposed experience. The corresponding unique digital reality scene can be a virtual reality scene, or an augmented reality scene, or a combination thereof. For instance, as a non-limiting example, FIG. 7C illustrates experience 742-1 associated with a unique digital reality scene of attending a party 1, experience 742-2 associated with a unique digital reality scene of attending a wedding 1, experience 742-3 associated with a unique digital reality scene of attending a party 2, experience 742-4 associated with a unique digital reality scene of attending a wedding 2, experience 742-5 associated with a unique digital reality scene of attending a party 3, and experience 742-6 associated with a unique digital reality scene of attending a wedding 3.

It should be noted that proposed experiences associated with one category can be completely distinctive from proposed experiences associated with another category (e.g., no proposed experience is associated with two different categories) or overlap with proposed experiences associated with another category (e.g., at least one proposed experience is shared by two or more different categories). For instance, in some embodiments, the six proposed experiences illustrated in FIG. 6C are associated only with node 730-1 and category 740-1 and are not associated with node 730-2 and category 740-2 nor node 730-3 and category 740-3. In some other embodiments, at least one of the six proposed experiences illustrated in FIG. 6C is associated with node 730-2 and category 740-2 and/or node 730-3 and category 740-3. In some embodiments, a proposed experience shared by two or more different categories is used to improve an ability of the subject to manage different psychiatric or mental conditions of the subject.

It should also be noted that the number of proposed experiences associated with one category can be the same as the number of proposed experiences associated with another category or different from the number of proposed experiences associated with another category.

Each respective node in the enumerated plurality of nodes is further associated with at least one respective gate criterion in a plurality of gate criteria. In some embodiments, the at least one respective gate criterion in the plurality of gate criterion is the same, or substantially the same, as a gate criterion of method 400 of FIG. 4. However, the present disclosure is not limited thereto.

Block 1370. Referring to block 1370, in some embodiments, the method 1300 includes obtaining, in electronic form, an assessment of the subject. The obtaining process can be performed prior to or during the presenting process disclosed herein. In some embodiments, the obtaining of the assessment is the same as or similar to those disclosed elsewhere herein. The assessment generally includes an identification of each category in the plurality of categories.

Block 1372. Referring to block 1372, in some embodiments, the assessment includes a Liebowitz Social Anxiety Scale assessment and/or the assessment is provided by the subject. However, the present disclosure is not limited thereto. For instance, in some embodiments, the assessment includes a standard assessment of a Liebowitz Social Anxiety Scale, a quality of life index (e.g., Wisconsin quality of life index), a MCID, a CGI, a PGI, a Mini-International Neuropsychiatric Interview assessment, a Subjective Unit of Distress scale assessment, or a combination thereof.

Block 1374. Referring to block 1374, in some embodiments, prior to obtaining the assessment, the method 1300 obtains, from a remote device associated with a medical practitioner of the subject, a validation of the assessment. In some embodiments, the obtaining of the validation of the assessment is the same as or similar to those disclosed elsewhere herein. For instance, in some embodiments, the validation is obtained from the medical practitioner and/or the model of the digital reality system, such as obtaining an initial validation of the assessment from the model and a final validation of the assessment from the medical practitioner, or obtaining the initial validation of the assessment from the medical practitioner and the final validation of the assessment from the model. In some embodiments, the validation of the assessment includes a first selection by the subject of a set of categories and a second selection by the medical practitioner of a subset of the set of categories. The plurality of categories consists of the subset of categories. However, the present disclosure is not limited thereto. For instance, in some embodiments, the validation of the assessment includes determining if the subject satisfies a threshold change in diagnosis status for the psychiatric or mental condition exhibited by the subject. In some such embodiments, the threshold change in diagnosis status for the psychiatric or mental condition exhibited by the subject is determined when the assessment includes the CGI assessment, such as a first CGI improvement scale assessment and/or a second CGI severity scale assessment. Additionally, in some embodiments, the validation of the assessment includes determining if the subject satisfies a threshold change in subjective distress of the subject caused by the corresponding challenge. In some such embodiments, the threshold change in subjective distress of the subject caused by the corresponding challenge is determined when the assessment includes the structured clinical interview for DSM-5 (SCID-5) assessment and/or the LSAS assessment. Moreover, in some embodiments, the validation of the assessment includes determining a threshold change in cognitive symptoms of the subject. In some such embodiments, the threshold change in cognitive symptoms of the subject is determined when the assessment includes a Fear or Negative evaluation assessment, a Pennsylvania State Worry Questionnaire (PSWQ), some or all of an Emotion Regulation Questionnaire (ERQ), or a combination thereof. In some embodiments, the validation of the assessment includes determining a threshold change in mindfulness state of the subject. In some embodiments, the threshold change in mindfulness state is determined when the assessment includes a five facet mindfulness questionnaire (FFMQ-15). However, the present disclosure is not limited thereto.

Blocks 1376-1382. Referring to block 1376 through block 1782 of FIG. 13G, in some embodiments, the at least one respective gate criteria includes a ranking gate criterion associated with a hierarchical ranking of each of the nodes, a medical practitioner gate criterion associated with an approval, from the medical practitioner associated with the subject, of the selection of the first node, a user gate criterion associated with an approval, from the subject, of the first selection, an arrangement gate criterion associated with an order of one or more nodes in the enumerated plurality of nodes, or any combination thereof.

Block 1384. Referring to block 1384, in some embodiments, the enumerated plurality of nodes includes 1 node, 2 nodes, 3 nodes, 4 nodes, 5 nodes, 6 nodes, 7 nodes, 8 nodes, 9 nodes, 10 nodes, 15 nodes, 20 nodes, 30 nodes, 40 nodes, 50 nodes, or a combination thereof. In some embodiments, the enumerated plurality of nodes includes no more than 3 nodes, no more than 5 nodes, no more than 7 nodes, no more than 10 nodes, no more than 12 nodes, no more than 15 nodes, no more than 20 nodes, or a combination thereof. In some embodiments, the enumerated plurality of nodes includes no less than 3 nodes, no less than 5 nodes, no less than 7 nodes, no less than 10 nodes, no less than 12 nodes, no less than 15 nodes, no less than 20 nodes, or a combination thereof.

Blocks 1386-1388. Referring to block 1386 and block 1388, in some embodiments, the corresponding unique digital reality scene is a virtual reality scene. In some embodiments, the corresponding unique digital reality scene is an augmented reality scene. In some embodiments, the corresponding unique digital reality scene is a mixed reality scene. In some embodiments, the corresponding unique digital reality scene is dependent on a type of display of a respective client device 300, such as first client device 300-1 having processing capabilities to display a virtual reality scene such that the corresponding unique digital reality scene is a virtual reality scene or a second client device 300-1 having processing capabilities to display an augment reality scene such that the corresponding unique digital reality scene is an augmented reality scene.

Block 1390. Referring to block 1390, the method 1300 includes detecting a selection of a node, such as node 730-1, node 730-2 or node 730-3 illustrated in FIG. 7B, in the enumerated plurality of nodes. The detection can be made, for instance, by sensing input provided by a user of the client device through an input 310, such as a keyboard, a mouse, a joystick, a microphone, a camera (e.g., two-dimensional pixelated detector), and the like.

Block 1392. Referring to block 1392 of FIG. 13H, the method 1300 includes placing the selected node on, or substantially on, the interactive digital chart, thereby providing access to the corresponding plurality of proposed experiences associated with the selected node and/or respective category and thus improving the ability of the subject to manage the psychiatric or mental condition using the respective interactive digital chart.

Block 1394. Referring to block 1394, for instance, in some embodiments, responsive to detection of the selection of the node, the method moves the selected node from an initial location in the second affordance region 720-2 to a location in the first affordance region 720-1 as exemplified by at least block 1394. As a non-limiting example, FIGS. 7B and 7D illustrate selecting node 730-1 as the first node and placing node 730-1 at a first location 724-1 of the first area 722-1 in the first affordance region 720-1. In some embodiments, the method indicates, for instance, by glaring, flashing, coloring or the like, a location in the first affordance region and instructs the subject to place the selected node in the indicated location.

Block 1396. Referring to block 1396, in some embodiments, prior to the placing of the selected node (e.g., the first node), the method determines if the selection of the selected node satisfies each gate criterion in the at least one respective gate criteria associated with the selected node as exemplified by at least block 1396. In some embodiments, this determining if the selection of the node satisfies each gate criterion in the at least one respective gate criteria is performed by the model. As such, the present disclosure allows for this determining if the selection of the node satisfies each gate criterion in the at least one respective gate criteria that requires a computer system (e.g., digital reality system 200 and/or client device 300) to be used because such determining cannot be performed mentally.

Block 1398. Referring to block 1398, in some embodiments, the at least one respective gate criterion indicates an order of the selected node in the plurality of nodes. In some embodiments, each proposed experience associated with the selected node has a gate criterion, including but not limited to an eye contact, utterance, decibel, pitch, sentiment analysis, medical practitioner scene-approval criterion, or any combination thereof.

In some other embodiments, the method places the selected node in the first affordance region without determining if the selection of the selected node satisfies each gate criterion in the at least one respective gate criteria associated with the selected node. For instance, in some embodiments, the method guides the subject to select the node associated with the category with proposed experiences that the subject considers least challenging as the first node and place the selected node in the first area of the first affordance region without determining if the selection of the selected node satisfies each gate criterion in the at least one respective gate criteria associated with the selected node.

Referring to block 1400, in some embodiments, the method 1300 includes repeating the detecting and placing processes for successive nodes in the plurality of nodes, thereby selecting successive nodes for inclusion in a graph within the interactive digital chart. For instance, as a non-limiting example, FIG. 7E illustrates indication of a location in the second area 722-2 in the first affordance region 720-1, after the placement of node 730-1, i.e., the first node selected by the subject. FIG. 7F illustrates selection of node 730-3 as the second node, and FIG. 7G illustrates placement of node 730-3, e.g., the second node selected by the subject, in the indicated location in the second area 722-2. FIG. 7G also illustrates indication of a location in the third area 722-3 in the first affordance region 720-1, after the placement of node 730-3, i.e., the second node selected by the subject. FIG. 7H illustrates placement of node 730-2, i.e., the third node selected by the subject, in the indicated location in the third area 722-3.

In some embodiments, each node in the plurality of nodes is hieratically placed in the plurality of areas on the interactive digital chart based on the social challenge level of the respective category. For instance, in the embodiment illustrated in FIG. 7H, the respective category corresponding to node 730-1 (the selected first node placed in the first area on the interactive digital chart) is considered least challenging for the subject. The respective category corresponding to node 730-3 (the selected second node placed in the second area on the interactive digital chart) is considered more challenging for the subject than node 730-1. The respective category corresponding to node 730-2 (the selected third node placed in the third area on the interactive digital chart) is considered more challenging for the subject than both of node 730-1 and node 730-3, that is, the respective category corresponding to node 730-2 is considered most challenging for the subject among the three nodes. In some embodiments, the plurality of nodes hieratically placed in the plurality of areas on the interactive digital chart is referred to as a category progression. In some embodiments, the category progression that determines if a respective challenge corresponding to a node 730 is considered more or less challenging for the subject is generated by the subject, by the medical practitioner, by a respective model of the digital reality system 200, or a combination thereof. For instance, in some embodiments, the category progression that determines if a respective challenge corresponding to a node 730 is considered more or less challenging for the subject is generated from the assessment that is obtained from the subject, such that the subject defines a the hierarchy of the category progression by way of one or more responses of the assessment. As another non-limiting example, in some embodiments, the category progression that determines if a respective challenge corresponding to a node 730 is considered more or less challenging for the subject is generated by the medical practitioner associated with the subject, such as by having the medical practitioner evaluate some or all of the assessment obtained by the subject in order to generate the category progression.

As yet another non-limiting example, in some embodiments, the category progression is generated at least in part by a model. For instance, in some embodiments, the model obtains at least the assessment from the subject and, optionally, other data as input (e.g., user profile data of FIG. 2A) in order to generate the category progression. In some embodiments, the medical practitioner and the model generate the category progression, such as by having the medical practitioner provide input and/or supervision for the model. As such, the present disclosure allows for generating the category progression that determines if the respective challenge corresponding to the node 730 is considered more or less challenging for the subject that requires a computer system (e.g., digital reality system 200 and/or client device 300) to be used because such generating or determining cannot be performed mentally.

Block 1402. Referring to block 1402, in some embodiments, each node in the graph is connected by an edge in a plurality of edges to at least one other node in the graph. For instance, as a non-limiting example, FIG. 7H illustrates that node 730-1 (the selected first node placed in the first area) is connected to node 730-3 (the selected second node placed in the second area) by edge 744-1 and edge 744-2. Node 730-3 (the selected second node placed in the second area) is connected to node 730-2 (the selected third node placed in the third area) by edge 744-3.

Each edge represents a progression within the graph between an initial node and a subsequent node upon successful completion by the subject of the corresponding challenges associated with the respective initial node. For instance, in the embodiment illustrated in FIG. 7H, edge 744-1 and edge 744-2 collectively represent a progression within the graph between node 730-1 (the selected first node) and node 730-3 (the selected second node) upon successful completion by the subject of the corresponding challenges associated with node 730-1 (the selected first node). Edge 744-3 represents a progression within the graph between node 730-3 (the selected second node) and node 730-2 (the selected third node) upon successful completion by the subject of the corresponding challenges associated with node 730-3 (the selected second node).

Referring to block 1406, in some embodiments, the method 1300 includes activating the first node to allow the subject to access the respective category corresponding to the first node and locking the remaining node(s) to prevent the subject from accessing them. The activating of the first node can be performed prior to the repeating process (e.g., after the first node has been placed on the interactive digital chart), during the repeating process (e.g., after the first or second node has been placed on the interactive digital chart), or subsequent to the repeating process (e.g., after all of the plurality of nodes have been placed on the interactive digital chart). As a non-limiting example, FIG. 7I illustrates activating node 730-1, the first node selected and placed in the first area of the interactive digital chart, after all three nodes have been placed on the interactive digital chart. The activation of node 730-1 allows the subject to access category 740-1 that corresponds to node 730-1, and the six proposed experiences (e.g., proposed experience 742-1 and proposed experience 742-3) that are associated with node 730-1 and/or category 740-1. FIG. 7I also illustrates locking node 730-2 and node 730-3, thereby preventing the subject from accessing these nodes and from accessing the corresponding categories and proposed experiences associated with these nodes.

Block 1408. Referring to block 1408, in some embodiments, the activating of the first node allows the subject to access at least one unique mindfulness session customized for the respective category of the first node, at least one unique cognitive reframing session customized for the respective category of the first node, at least one universal mindfulness session, at least one universal cognitive reframing session, or any combination thereof. For instance, as a non-limiting example, FIG. 7I illustrates the activating of node 730-1 allows the subject to access session 760 and session 770.

In some embodiments, the method provides other options to the subject. For instance, as a non-limiting example, FIG. 7J illustrates the method that allows the subject to select, for instance, with a pointer, and choose whether to learn more about a proposed experience, such as proposed experience 742-3, or to proceed with the proposed experience.

In some embodiments, if the subject has satisfactorily completed a proposed experience, the method changes the status of the proposed experience from a not-completed status to a completed status. Additionally, if the subject has satisfactorily completed a required number of proposed experiences associated with a category, the method changes the status of the category from a not-completed status to a completed status. For instance, as a non-limiting example, FIG. 7K illustrates the change of the status of a proposed experience, such as proposed experience 742-1, from a not-completed status to a completed status.

Block 1410-1414. Referring to block 1410 through block 1414, in some embodiments, the method 1300 includes activating a second node to allow the subject to access the respective category corresponding to the second node. The activating of the second node is performed if the at least one respective gate criterion for progressing from the first node to the second node is satisfied. For instance, the method activates node 730-3 in FIG. 7I (the second node selected and placed in the second area on the interactive digital chart) if the at least one respective gate criterion for progressing from node 730-1 (the first node selected and placed in the first area on the interactive digital chart) to node 730-3 is satisfied. The activating of node 730-3 allows the subject to access category 740-3 corresponding to node 730-3 and the proposed experiences associated with node 730-3 and/or category 740-3. In some embodiments, the activating of the second node, such as node 730-3, also allows the subject to access at least one unique mindfulness session customized for the respective category of the second node, at least one unique cognitive reframing session customized for the respective category of the second node, at least one universal mindfulness session, at least one universal cognitive reframing session, or any combination thereof.

The at least one respective gate criterion for progressing from the first node to the second node can be associated with the first node, the second node, or both of the first and second nodes. For instance, in some embodiments, the at least one respective gate criterion for progressing from the first node to the second node is associated only with the first node, e.g., the at least one respective gate criterion is determined upon completion of the first node and/or directs the progression to the successive node. In some other embodiments, the at least one respective gate criterion for progressing from the first node to the second node is associated only with the second node, e.g., the at least one respective gate criterion is determined when the progression arrives at the second node. In still some other embodiments, the at least one respective gate criterion for progressing from the first node to the second node is associated with both of the first and second nodes. For instance, in an exemplary embodiment, the at least one respective gate criterion for progressing from the first node to the second node includes one or more criteria associated with the first node and one or more criteria associated with the second node.

In some embodiments, the at least one respective gate criterion indicates an order of the first node, the second node, or both of the first and second nodes in the plurality of nodes. In some embodiments, each proposed experience associated with the first or second node has a gate criterion. The gate criterion includes, but is not limited to, an eye contact, utterance, decibel, pitch, sentiment analysis, medical practitioner scene-approval criterion, or any combination thereof.

Block 1416. Referring to block 1416, in some exemplary embodiments, for a respective node, the method 1300 includes displaying the corresponding plurality of proposed experiences adjacent to the respective node as exemplified by at least block 1414. Each proposed experience is generally represented by a corresponding experience graphic in a plurality of experience graphics. In some embodiments, each experience graphic in the plurality of experience graphics is connected to the respective node in the enumerated plurality of nodes by a branch in a plurality of branches. For instance, as a non-limiting example, FIG. 7H illustrates that the six proposed experiences associated with node 730-1 (the first selected node) are displayed adjacent to node 730-1. Each of the six proposed experiences, represented by an experience graphic, is connected to node 730-1 by a branch. For instance, the experience graphic representing proposed experience 742-1 is connected to node 730-1 by branch 746-1, and the experience graphic representing proposed experience 742-3 is connected to node 730-1 by branch 746-3.

Block 1418. Referring to block 1418, in some embodiments, the method includes displaying each respective gate criterion associated with each respective node in a subset of nodes. For instance, in an exemplary embodiment, the method displays each respective gate criterion associated with the first node (e.g., node 730-1). In another exemplary embodiment, the method displays each respective gate criterion associated with the first node (e.g., node 730-1), and each respective gate criterion associated with the second node (e.g., node 730-3).

Block 1420. Referring to block 1420, in some exemplary embodiments, the method includes displaying each respective gate criterion associated with each respective node in the graph. For instance, in some embodiments with three nodes, the method displays each respective gate criterion associated with the first node (e.g., node 730-1), each respective gate criterion associated with the second node (e.g., node 730-3), and each respective gate criterion associated with the third node (e.g., node 730-2). In some embodiments, a gate criterion associated with one node in the graph specifies a condition that is to be satisfied by the subject prior to advancement to another node in the graph. For instance, in the embodiment illustrated in FIG. 7K, a gate criterion associated with node 730-1 in the graph specifies a condition that is to be satisfied by the subject prior to advancement to node 730-3 in the graph. A gate criterion associated with node 730-3 in the graph specifies a condition that is to be satisfied by the subject prior to advancement to node 730-2 in the graph. In some embodiments, the method displays a completion status of each respective gate criterion associated with each respective node in the graph.

Block 1422. Referring to block 1422, in some embodiments, the method 1300 includes using the one or more processors to poll for satisfaction of a respective gate criterion and update a completion status of a respective gate criterion associated with a respective node in the graph when it is determined that the respective gate criterion is satisfied. For instance, in some embodiments, the using of the one or more processors occurs by the one or more processors or via the one or more processors. As such, the present disclosure allows for determining that the respective gate criterion is satisfied that require a computer system (e.g., digital reality system 200 and/or client device 300) to be used because such determinations cannot be performed mentally.

Block 1424. Referring to block 1424, in some embodiments, the method 1300 includes populating the graph with one or more landmarks/landscapes. The one or more landmarks/landscapes include but are not limited to a house, a tree, a creek, a pond, a bridge, a hill, a park, or any combination thereof. By using one or more landmarks/landscapes, the interactive digital chart allows for great flexibility for fashionable elements and objects. By way of example, referring briefly to FIG. 6A, in some embodiments, the one or more landscapes/landmarks provide a collective theme, such as a cosmic theme. As another non-limiting example, referring briefly to FIG. 6G, in some embodiments, the one or more landscapes/landmarks provide the collective theme of a desert theme and/or a lush theme. In some embodiments, the collective theme includes one or more biomes, such as a forest biome, an artic biome, a desert biome, a demonic biome, a jungle biome, a dungeon biome, an oceanic biome, a cavernous biome, an urban biome, a rural biome, or a combination thereof. In this way, the one or more landscapes/landmarks includes fashionable elements such as distinctive colors, textures, ornamentation (e.g., marks, logos, etc.), or a combination thereof that help immerse the subject within the digital reality scene and the interactive journey map.

Additionally, or optionally, in some embodiments, the method 1300 includes animating the graph. For instance, in some embodiments, the one or more landmarks/landscapes of the interactive digital chart are animated. However, the present disclosure is not limited thereto. In some embodiments, the graph is referred to as a journey map.

Block 1426. Referring to block 1426 of FIG. 13K, in some embodiments, the at least one respective gate criterion of each node in the graph is used to determine a placement of each edge. By way of example, in some embodiments, a first gate criteria requires that a corresponding node is placed at an initial tessellated shape, an intermediate tessellated shape, a final tessellated shape, or a combination thereof in the graph. In this way, in some embodiments, the placement of each edge collectively defines a path within the interactive journey map.

Blocks 1428-1430. Referring to block 1428 and block 1430, in some embodiments, as described supra, a gate criterion associated with one node specifies a condition to be satisfied prior to node advancement. In this way, in some embodiments, the gate criterion is associated with an aspect of a challenge to be completed within the digital reality scene that must be deemed complete for the subject for the subject can advance to another node.

In some embodiments, a respective gate criterion of a node is set by a system administrator, the subject, a medical practitioner associated with the subject, or a combination thereof. In some embodiments, a respective gate criteria of a first node in the graph is set by a system administrator or a medical practitioner associated with the subject, and a respective gate criterion of a second node in the graph is set by the subject. In some embodiments, the respective gate criterion of a node is set by the model. For instance, referring briefly to FIG. 9D, in some embodiments, the medical practitioner associated with the subject sets the respective gate criteria through a client application (e.g., client application 320 of FIG. 3)).

Block 1432. Referring to block 1432, in some embodiments, a respective gate criterion of a node includes a length of eye contact. For instance, in some embodiments, the length of eye contact is with a portion of the corresponding unique digital reality scene associated with a corresponding challenge of a proposed experience in the corresponding plurality of proposed experiences of another node. By way of example, referring briefly to FIG. 10B, in some embodiments, the portion of the corresponding unique digital reality scene is associated with deeming the corresponding challenge of the proposed experience complete, such as a first portion 1050 that is associated with the eyes of a subject engaged with the user in the corresponding unique digital reality scene. Moreover, in some embodiments, the portion of the corresponding unique digital reality scene is associated with deeming the corresponding challenge of the proposed experience failed, or deeming incomplete, such as a second portion 1052 that is associated with the one or more subjects that is disengaged with the user in the corresponding unique digital reality scene.

Block 1434. Referring to block 1434, in some embodiments, a respective gate criterion of a node includes an assertiveness, a decibel level, and/or a pitch of one or more utterances by the subject during a corresponding challenge of a proposed experience of another node. For instance, in some embodiments, the one or more utterances by the subject is capture by a microphone in electronic communication with an input output subsystem 3300 of a client device 300. In some embodiments, a model (e.g., model of application model store 50 of FIG. 2B) receives a data construct obtained, or derived, from the microphone and performs an evaluation in order to determine the assertiveness, the decibel level, the pitch of one or more utterances by the subject, or a combination thereof. As such, the present disclosure allows for evaluating the assertiveness, the decibel level, and/or the pitch of one or more utterances by the subject for determining if the respective gate criterion is satisfied that requires a computer system (e.g., digital reality system 200 and/or client device 300) to be used because such evaluations and/or determinations cannot be performed mentally.

Block 1436-1438. Referring to block 1436 and block 1438, in some embodiments, a respective gate criterion of a node includes a number of utterances by the subject during a corresponding challenge of a proposed experience of another node. In some embodiments, the number of utterances is determined by a model of the digital reality system 200. In some embodiments, a respective gate criterion of a node includes a number of words spoken by the subject during a corresponding challenge of a proposed experience of another node. For instance, in some embodiments, the number of words spoken by the subject is determined based on a number of phoneme determined in the one or more utterances by the model. Each phoneme is a unit of sound that is used by the model to distinguish a first word from a second word, such as a vowel sound and/or a consonant sound. Additional details and information regarding using a model to evaluate one or more utterances by a subject can be found at White, D, 2020, "the Efficacy of Speech-to-Text Synthesis in Diagnosing Phoneme-Level Pronunciation Deficiencies," danteacher.com, print, which is hereby incorporated by reference in its entirety.

Block 1440. Referring to block 1440 of FIG. 13L, in some embodiments, a respective gate criterion of a node includes a satisfaction and/or a failure to satisfy a sentiment analysis criterion by the subject during a corresponding challenge of a proposed experience in the corresponding plurality of proposed experiences of another node in the graph. For instance, in some embodiments, a first gate criterion of a first node includes a first sentiment analysis criterion that requires satisfaction of an excited sentiment threshold and a second sentiment analysis criterion that requires failure of an overexcited sentiment threshold.

Furthermore, in some embodiments, a respective gate criterion of a node includes any combination of block 1430 through block 1440. Block 1442. Referring to block 1442, in some embodiments, the method includes determining whether the sentiment analysis criterion is satisfied or not satisfied. In some embodiments, as disclosed elsewhere herein, whether the sentiment analysis criterion is satisfied or not satisfied is determined by taking a cosine similarity measure or dot product of one or more utterances of the subject, made during the corresponding challenge, against each statement in a list of statements that are deemed to be characteristic of a predetermined sentiment. In some embodiments, the determining whether the sentiment analysis criterion is satisfied or not satisfied is performed by the model and/or the medical practitioner associated with the subject.

Block 1444. Referring to block 1444, in some exemplary embodiments, the predetermined sentiment is amusement, anger, anxiety, awkwardness, boredom, calmness, confusion, craving, disgust, empathetic pain, entrancement, excitement, fear, horror, interest, joy, annoyance, nostalgia, relief, sadness, satisfaction, or surprise. In some embodiments, the predetermined sentiment is determined by one or more parameters set by the medical practitioner and/or one or more parameters set by the model.

Block 1446. Referring to block 1446, in some embodiments, the method includes adding a node that has not previously been selected in an instance of the detecting responsive to a selection of a node that has been selected in an instance of the detecting in order to add an availability of a category in the plurality of categories to the plurality of nodes. In some embodiments, the method includes adding the node that has not previously been selected in the instance of the detecting responsive to the selection of the node that has been selected in the instance of the detecting in order to remove an availability of the category in the plurality of categories to the plurality of nodes.

Blocks 1448-1456. Referring to block 1448 to block 1456 of FIG. 13M, in some embodiments, a node in the plurality of nodes is associated with at least one educational or therapeutic session. The at least one educational or therapeutic session includes, but is not limited to, a mindfulness session or a cognitive reframing session. For instance, in some embodiments, a respective node in the enumerated plurality of nodes is associated with at least one unique mindfulness session customized for the respective category of the respective node, or at least one unique cognitive reframing session customized for the respective category of the respective node, or a combination of the at least one unique mindfulness session and at least one unique cognitive reframing session customized for the respective category of the respective node. In some embodiments, the enumerated plurality of nodes is associated with at least one universal mindfulness session that is accessible from each node in the enumerated plurality of nodes, or at least one universal cognitive reframing session that is accessible from each node in the enumerated plurality of nodes, or a combination of the at least one universal mindfulness session and at least one universal cognitive reframing session that are accessible from each node in the enumerated plurality of nodes. As a non-limiting example, FIG. 7H illustrates node 730-1 (the first selected node) is associated with session 760, session 770 and session 780. Each of session 760, session 770 and session 780 can be educational or therapeutic or both.

In some embodiments, the present disclosure provides a use of a computer system (e.g., system 100 of FIG. 1, digital reality system 200 of FIGS. 2A and 2B, client device 300-1 of FIG. 3, or a combination thereof) for improving an ability of a subject to manage a psychiatric or mental condition exhibited by the subject.

In some embodiments, the present disclosure provides a use of a method (e.g., method 400 of FIG. 4, method 1300 of FIGS. 13A through 13M, etc.) for improving an ability of a subject to manage a psychiatric or mental condition exhibited by the subject.

For instance, in some embodiments, the use of the systems (e.g., digital reality system 200 of FIGS. 2A and 2B, client device 300-1 of FIG. 3, etc.) and/or methods (e.g., method 400 of FIG. 4, method 1300 of FIG. 13A through 13M, etc.) of the present disclosure provide a treatment of a psychiatric or mental condition exhibited by the subject. That is, in some embodiments, the present disclosure includes a method of treating a psychiatric or mental condition by using the systems and/or methods of the present disclosure. In some embodiments, the method of treating a psychiatric or mental condition includes a combination therapy and/or one or more adjunctive therapies with any psychiatric medication (e.g., a pharmaceutical composition that is administered to a subject in order to treat a psychiatric or mental condition exhibited by the subject). In some embodiments, the pharmaceutical composition includes at least one selected from the group consisting of: a selective serotonin reuptake inhibitor (SSRIs) pharmaceutical composition; a selective serotonin and norepinephrine inhibitors (SNRIs) pharmaceutical composition; a norepinephrine-dopamine reuptake inhibitor (NDRIs) pharmaceutical composition; a N-Methyl-D-aspartate receptor antagonist pharmaceutical composition; a serotonergic pharmaceutical composition; a tricyclic antidepressant pharmaceutical composition; a monoamine oxidase inhibitor (MAOIs) pharmaceutical composition; a tetracyclic antidepressant pharmaceutical composition; a L-methylfolate pharmaceutical composition; a benzodiazepine pharmaceutical composition; and a beta-blocker pharmaceutical composition. In some embodiments, the pharmaceutical composition includes at least one selected from the group consisting of: chlorpromazine, perphenazine, trifluoperazine, mesoridazine, a fluphenazine, thiothixene, molindone, thioridazine, loxapine, haloperidol, aripiprazole, clozapine, ziprasidone, risperidone, quetiapine pharmaceutical composition, an olanzapine, citalopram, escitalopram, fluvoxamine, paroxetine, fluoxetine, sertraline, clomipramine, amoxapine, amitriptyline, desipramine, nortriptyline, doxepin, trimipramine, imipramine, protriptyline, desvenlafaxine, venlafaxine, duloxetine, lorazepam, buspirone, propranolol, clonazepam, chlordiazepoxide, oxazepam, atenolol, clorazepate, diazepam, lprazolam, amphetamine, dextroamphetamine, methyphenidate, lamotrigine, ketamine, and lithium.

In some embodiments, the present disclosure includes a method of treating a psychiatric or mental condition by a computer system (e.g., e.g., digital reality system 200 of FIGS. 2A and 2B, client device 300-1 of FIG. 3, etc.) for preparing a regimen for improving an ability of a subject to manage a psychiatric or mental condition exhibited by the subject. The computer system includes one or more processors (e.g., CPU 302 of FIG. 3), a display (e.g., display 308 of FIG. 3), and a memory (e.g., memory 312 of FIG. 3) coupled to the one or more processors. In some embodiments, the display 308 is a head mounted display, such as a smart garment worn by the subject.

Figure 13A:
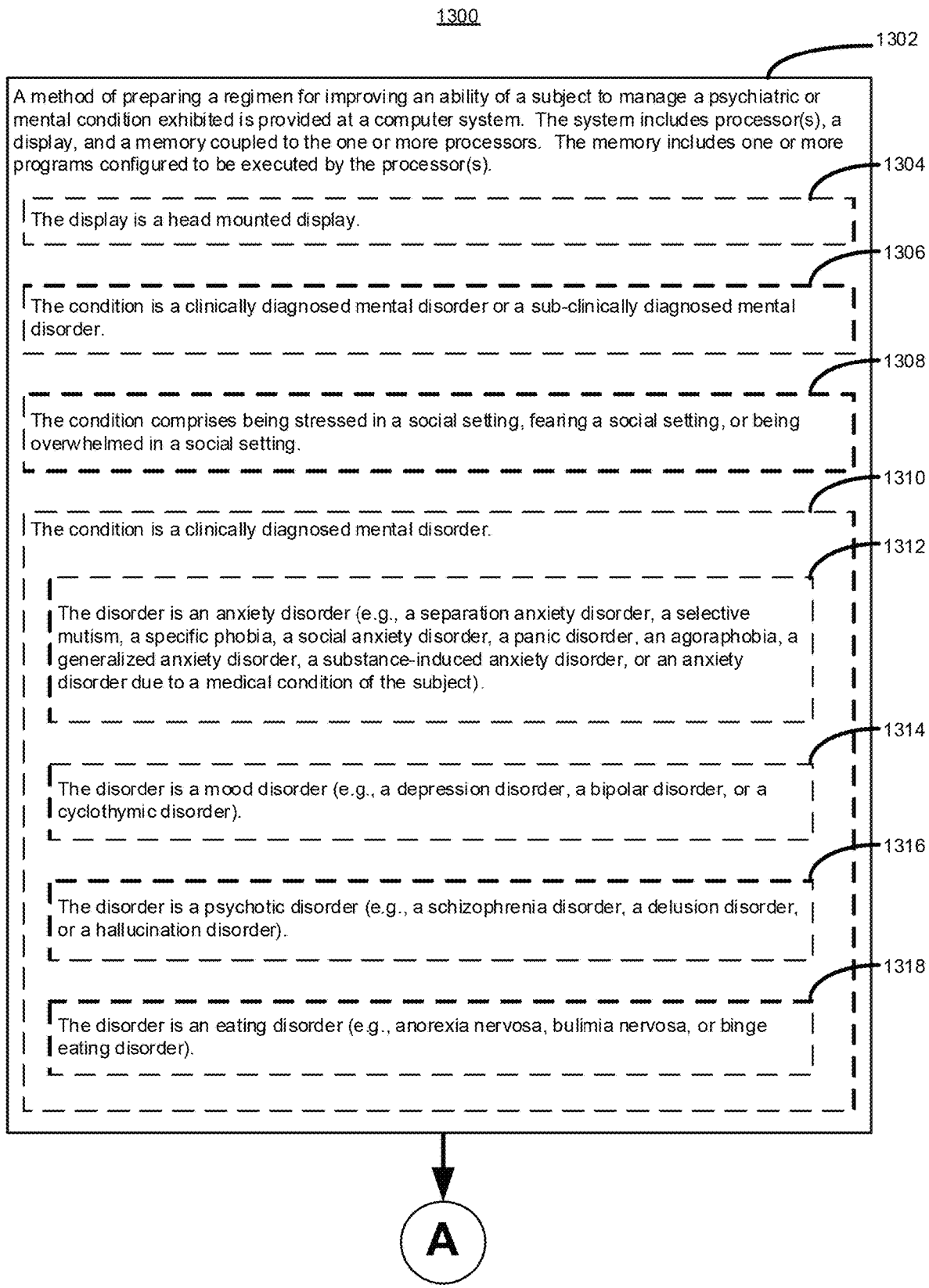
FIGS. 13A, 13B, 13C, 13D, 13E, 13F, 13G, 13H, 13I, 13J, 13K, 13L and 13M collectively illustrate a flowchart of a method in accordance with some embodiments of the present disclosure.
Figure 13B:
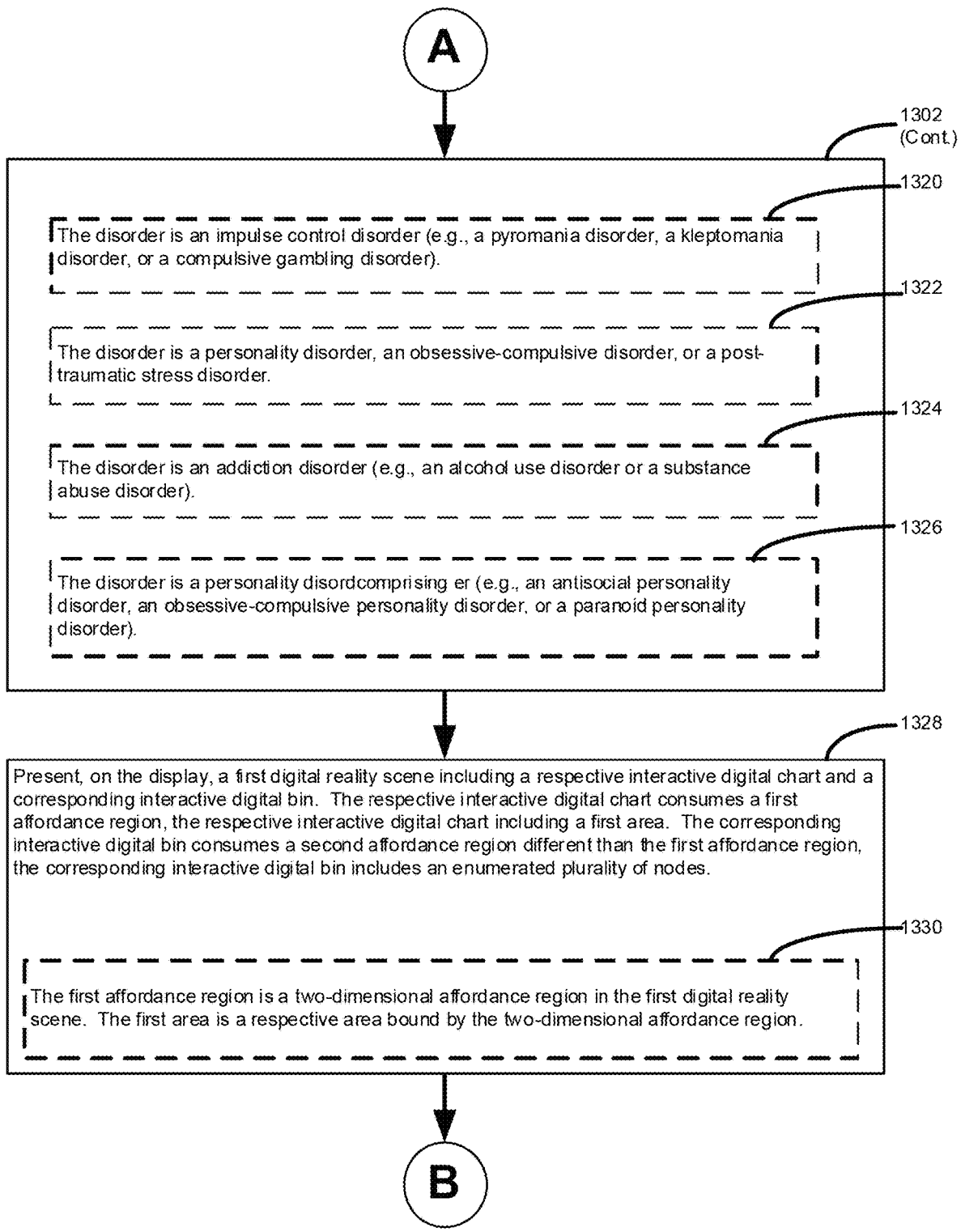
Figure 13C:
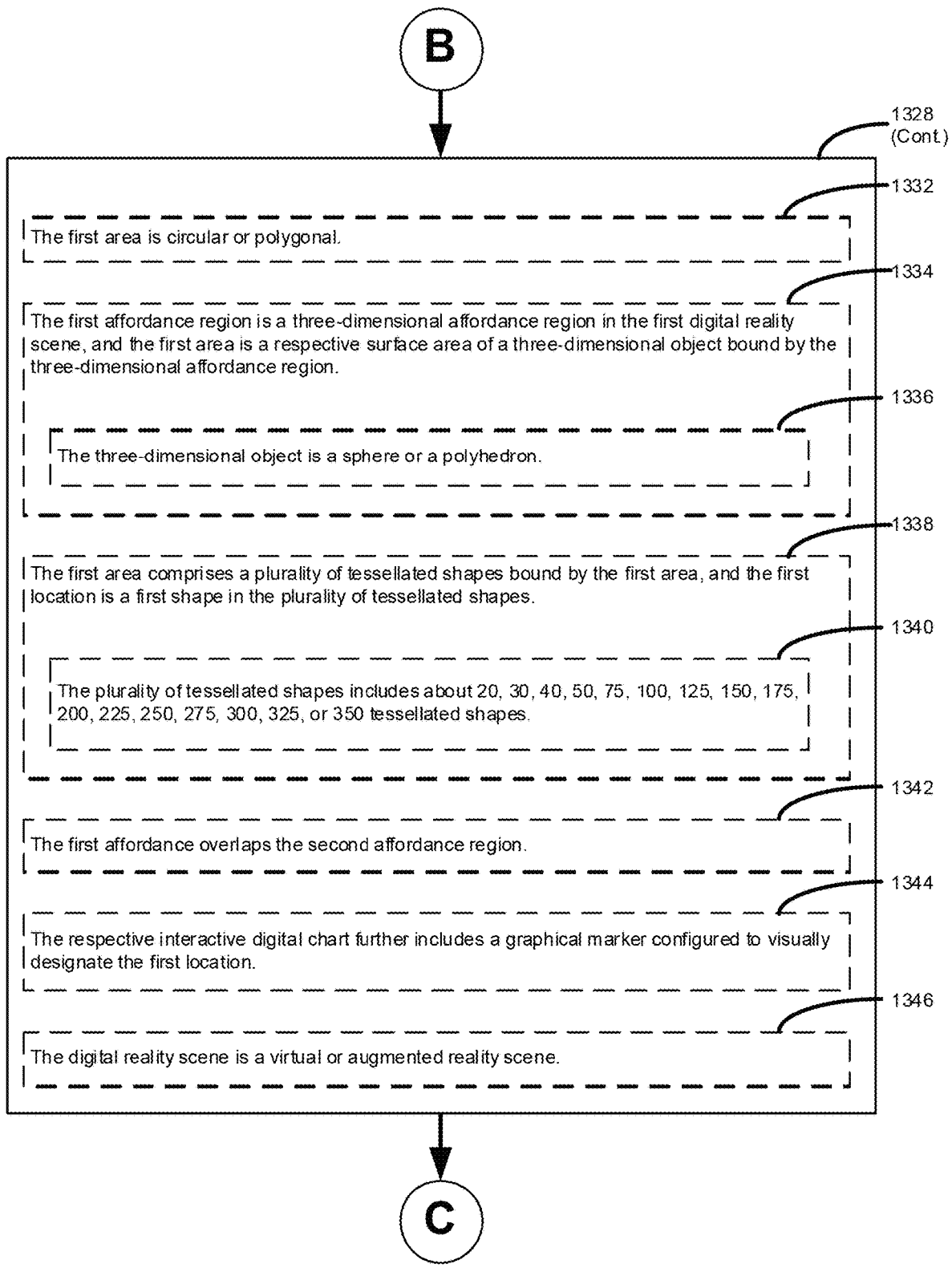
Figure 13D:
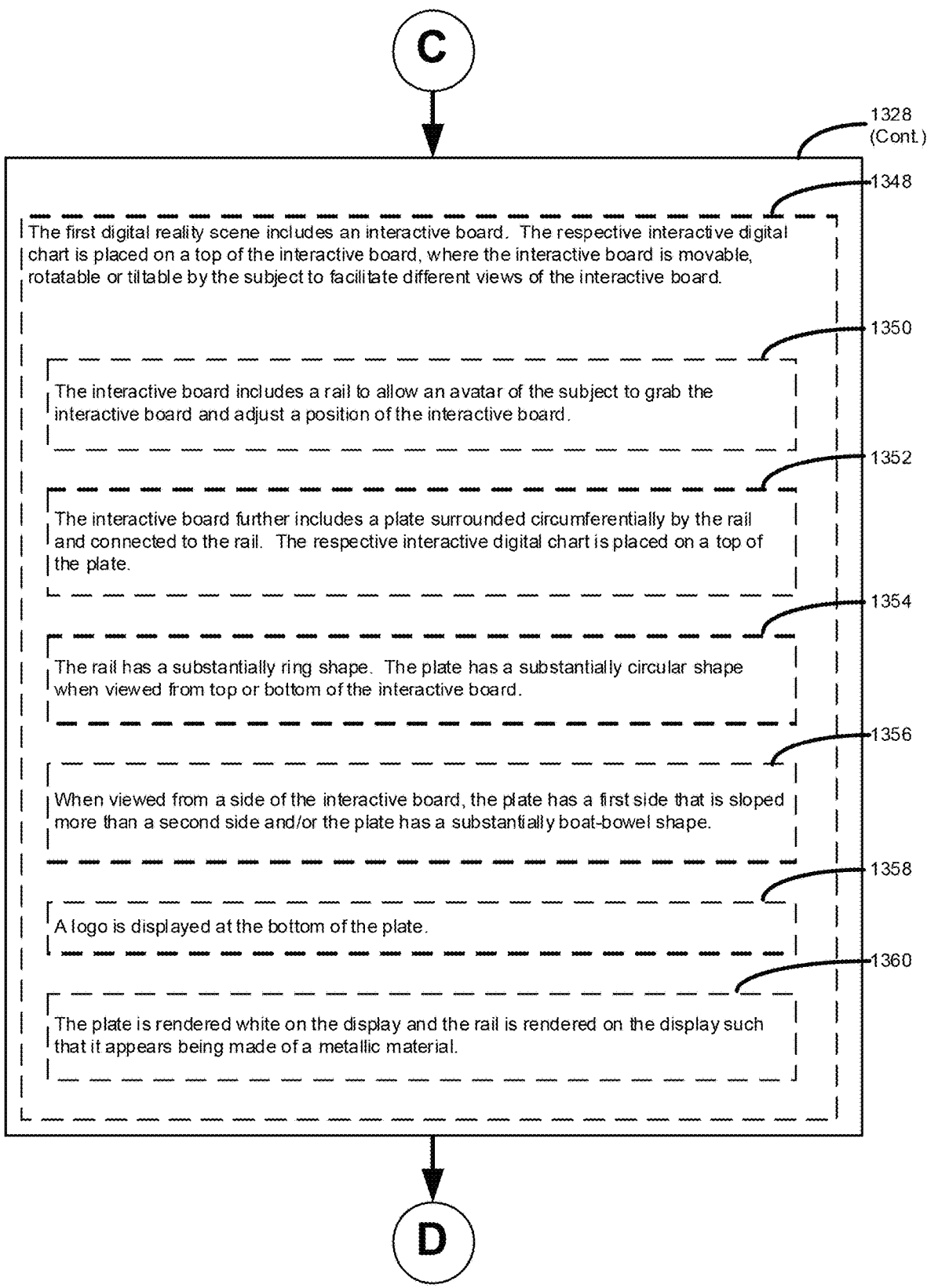
Figure 13E:
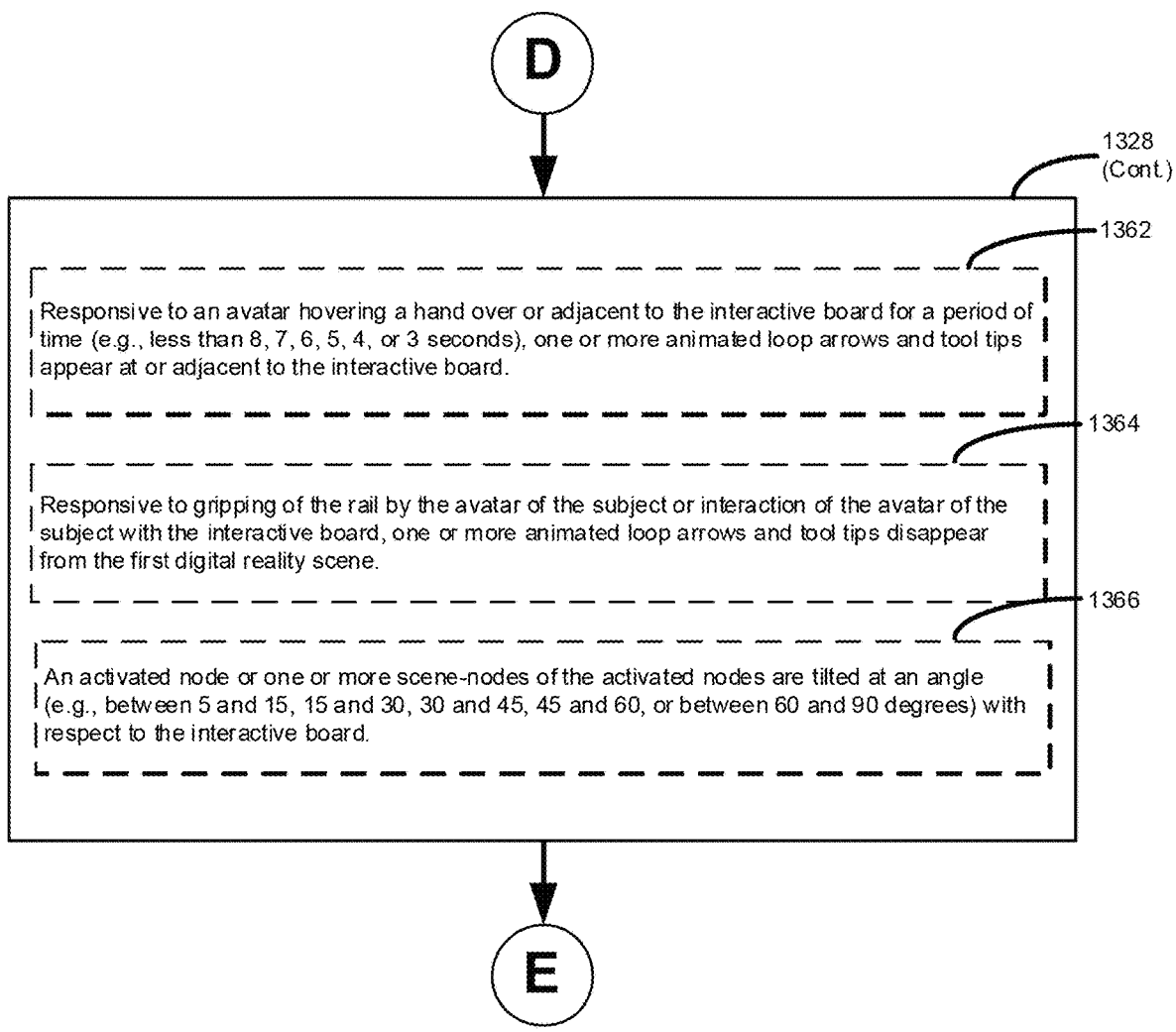
Figure 13F:
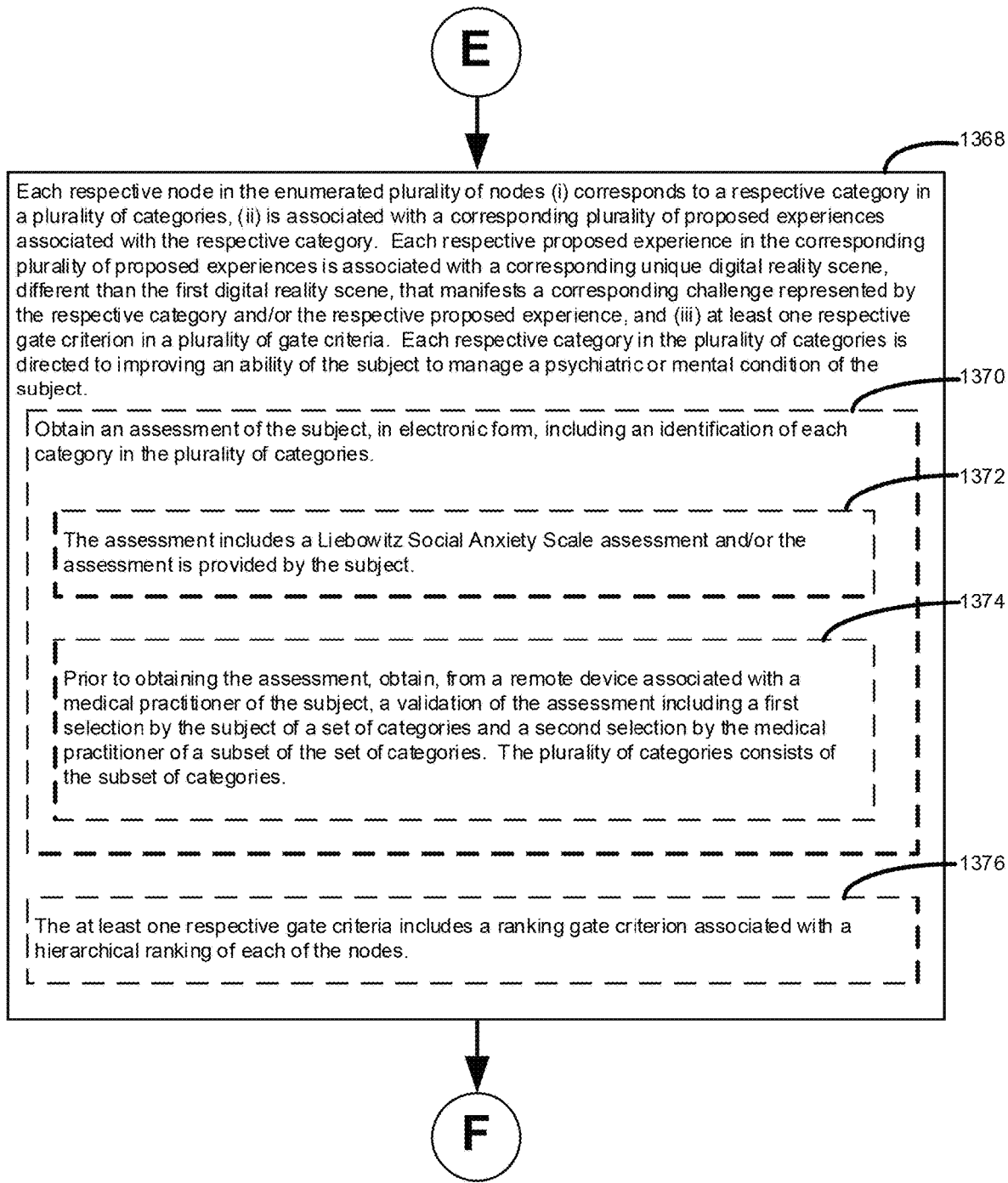
Figure 13G:
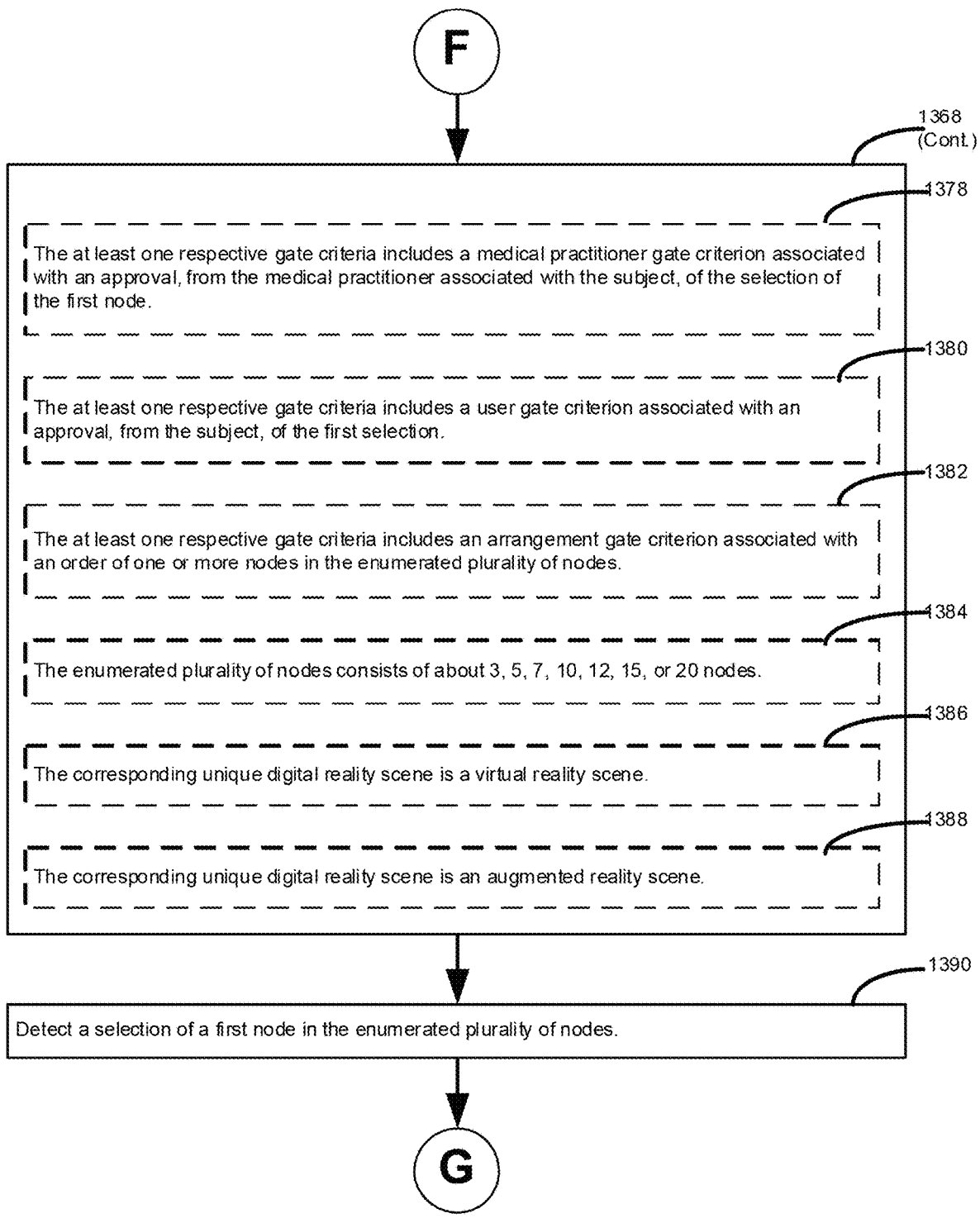
Figure 13H:
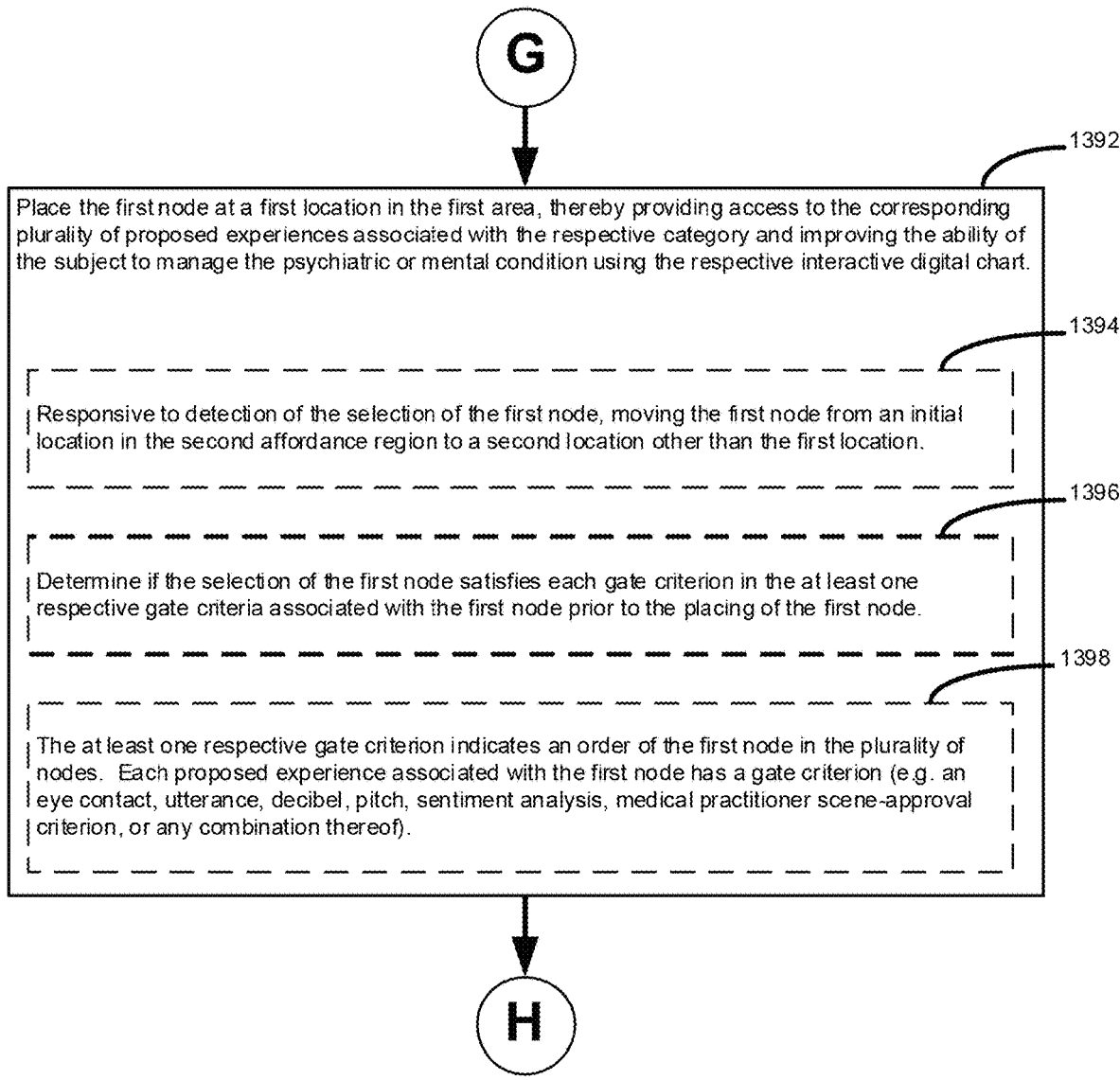
Figure 13I:
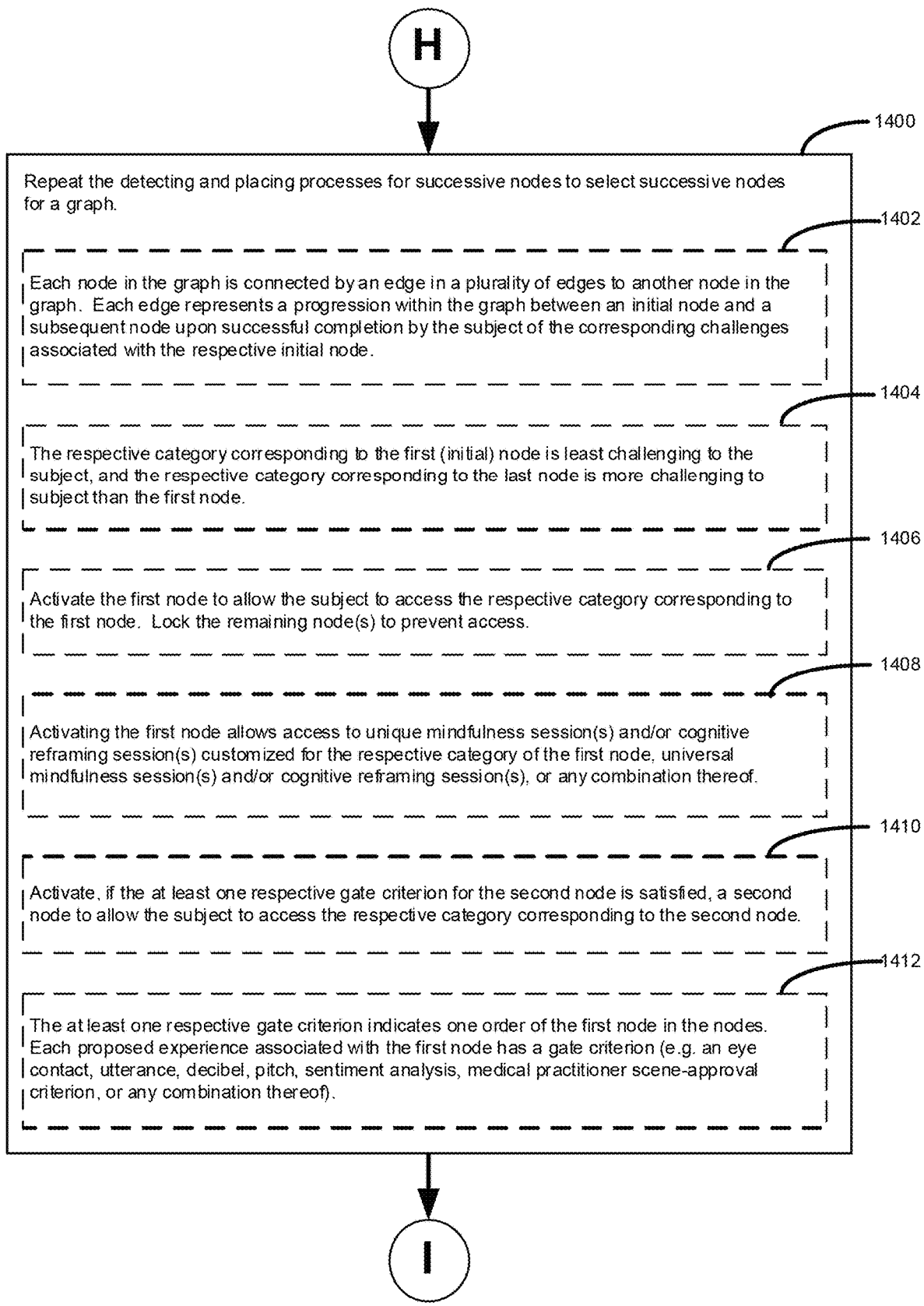
Figure 13J:
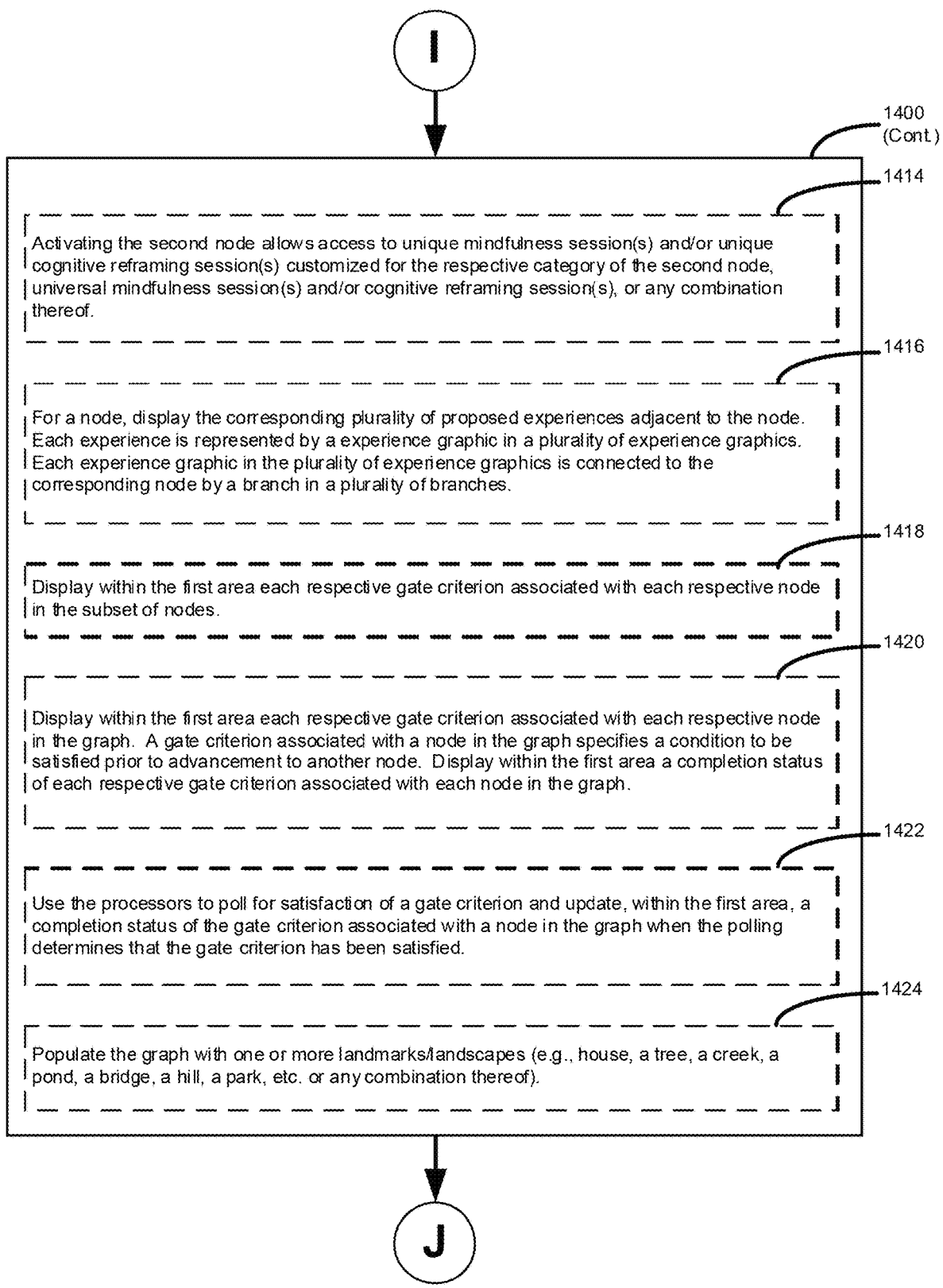
Figure 13K:
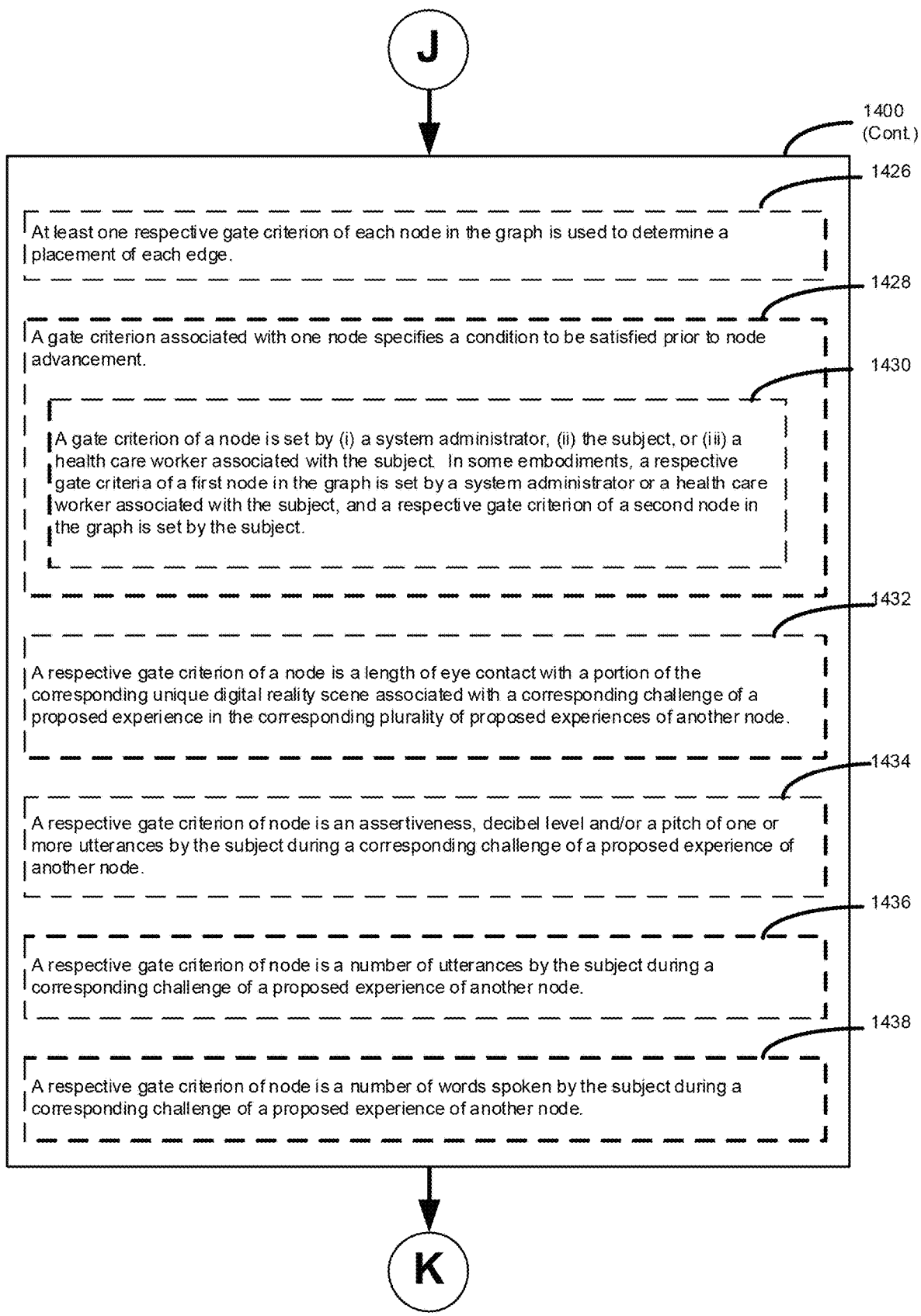
Figure 13L:
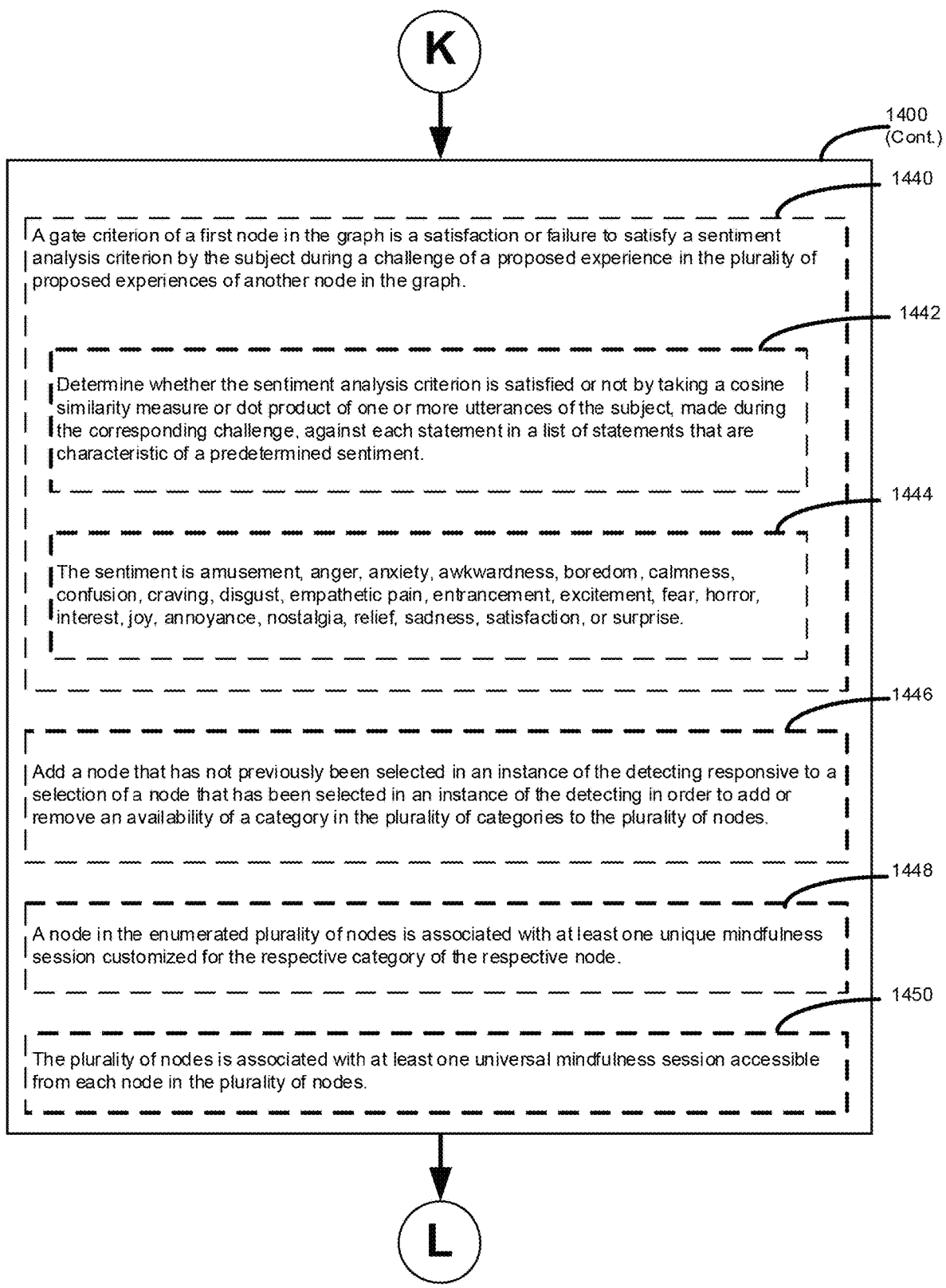
Figure 13M:
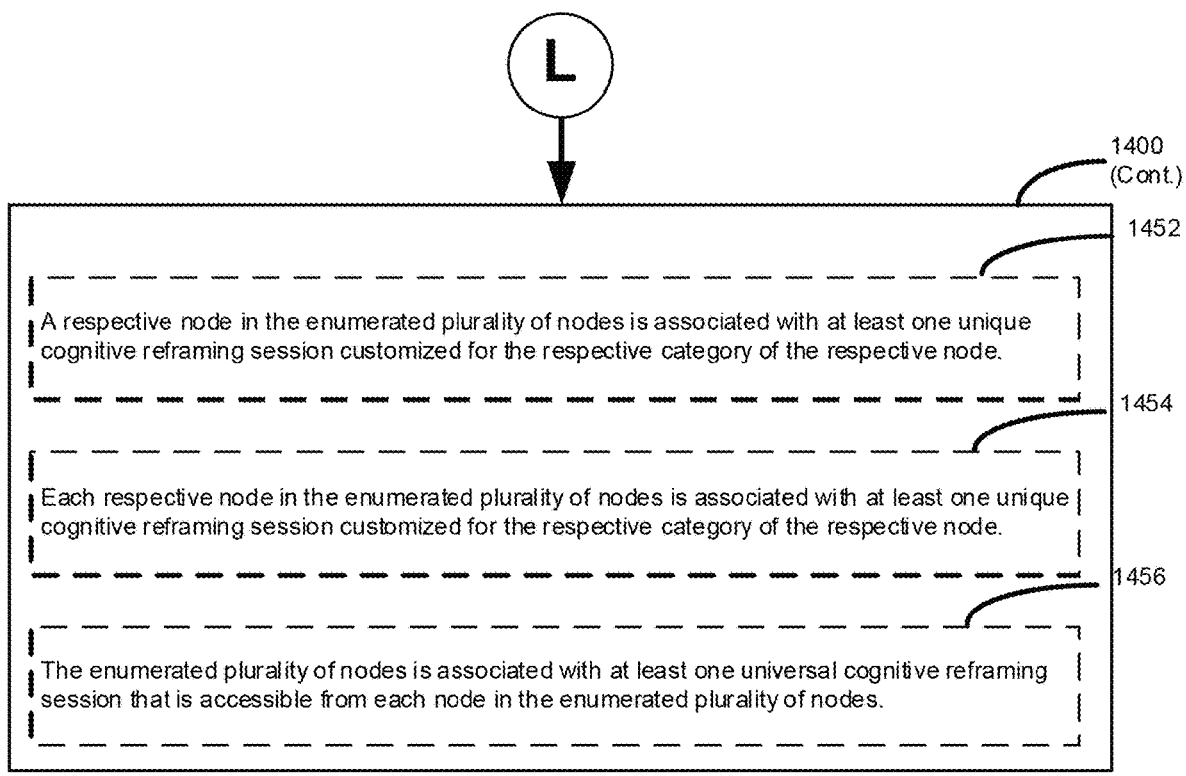

Further, the memory included one or more programs configured to be executed by the one or more processors (e.g., assessment module 12 of FIG. 2A, user profile store 14 of FIG. 2A, experience store 22 of FIG. 2B, gate store 30 of FIG. 2B, application server module 34 of FIG. 2B, application model library 50 of FIG. 2B, client application 320 of FIG. 3, engine 322 of FIG. 3, etc.) that implement a first method (e.g., method 400 of FIG. 4, method 1300 of FIGS. 13A through 13 M, etc.). The first method includes presenting, on the display, a first digital reality scene including a respective interactive digital chart and a corresponding interactive digital bin, where the respective interactive digital chart consumes a first affordance region, the respective interactive digital chart including a first area and the corresponding interactive digital bin consumes a second affordance region different than the first affordance region, the corresponding interactive digital bin including an enumerated plurality of nodes. Each respective node in the enumerated plurality of nodes (i) corresponds to a respective category in a plurality of categories, (ii) is associated with a corresponding plurality of proposed experiences associated with the respective category, in which each respective proposed experience in the corresponding plurality of proposed experiences is associated with a corresponding unique digital reality scene, different than the first digital reality scene, that manifests a corresponding challenge represented by the respective category and/or the respective proposed experience, and (iii) is associated with at least one respective gate criterion in a plurality of gate criteria. Each respective category in the plurality of categories is directed to improving an ability of the subject to manage a psychiatric or mental condition of the subject. A selection of a first node in the enumerated plurality of nodes is selected and placed at a first location in the first area, thereby providing access to the corresponding plurality of proposed experiences associated with the respective category and improving the ability of the subject to manage the psychiatric or mental condition using the respective interactive digital chart.

In some embodiments, any of the pharmaceutical compositions and/or treatments of the present disclosure is used in conjunction with a computer system (e.g., e.g., digital reality system 200 of FIGS. 2A and 2B, client device 300-1 of FIG. 3, etc.) for preparing a regimen for improving an ability of a subject to manage a psychiatric or mental condition exhibited by the subject. The computer system includes one or more processors (e.g., CPU 302 of FIG. 3), a display (e.g., display 308 of FIG. 3), and a memory (e.g., memory 312 of FIG. 3) coupled to the one or more processors. In some embodiments, the display is a head mounted display, such as a smart garment worn by the subject. Further, the memory includes one or more programs configured to be executed by the one or more processors (e.g., assessment module 12 of FIG. 2A, user profile store 14 of FIG. 2A, experience store 22 of FIG. 2B, gate store 30 of FIG. 2B, application server module 34 of FIG. 2B, application model library 50 of FIG. 2B, client application 320 of FIG. 3, engine 322 of FIG. 3, etc.) that implement a first method (e.g., method 400 of FIG. 4, method 1300 of FIGS. 13A through 13 M, etc.). The first method includes presenting, on the display, a first digital reality scene including a respective interactive digital chart and a corresponding interactive digital bin, where the respective interactive digital chart consumes a first affordance region, the respective interactive digital chart including a first area and the corresponding interactive digital bin consumes a second affordance region different than the first affordance region, the corresponding interactive digital bin including an enumerated plurality of nodes. Each respective node in the enumerated plurality of nodes (i) corresponds to a respective category in a plurality of categories, (ii) is associated with a corresponding plurality of proposed experiences associated with the respective category, in which each respective proposed experience in the corresponding plurality of proposed experiences is associated with a corresponding unique digital reality scene, different than the first digital reality scene, that manifests a corresponding challenge represented by the respective category and/or the respective proposed experience, and (iii) is associated with at least one respective gate criterion in a plurality of gate criteria. Each respective category in the plurality of categories is directed to improving an ability of the subject to manage a psychiatric or mental condition of the subject. A selection of a first node in the enumerated plurality of nodes is selected and placed at a first location in the first area, thereby providing access to the corresponding plurality of proposed experiences associated with the respective category and improving the ability of the subject to manage the psychiatric or mental condition using the respective interactive digital chart.

In some embodiments, the improving the ability of the subject to manage the psychiatric or mental condition exhibited by the subject is quantified by the model of the digital reality system and/or the medical practitioner associated with the subject by evaluating a plurality of parameters including the assessment of the subject, a respective user profile associated with the subject, a performance with respect to a corresponding gate criteria in an experience completed by the subject, or a combination thereof.

Example 1: Systems and Methods for Preparing a Regimen for Improving an Ability of a Subject to Manage a Social Anxiety Condition Exhibited by the Subject Systems, methods, and devices were provided that prepared a regimen that improved an ability of a subject to manage a social anxiety condition.

An assessment was obtained in electronic form from the subject. The assessment included a Liebowitz Social Anxiety Scale assessment that was administered, at least in part, by the subject. Additionally, the assessment was utilized by a medical practitioner associated with subject to provide a validation of the assessment, such as whether or not the subject satisfied a threshold score of 50 or more when responding to the Liebowitz Social Anxiety Scale assessment. In some embodiments, the assessment included a first selection by the subject of a set of categories. Accordingly, the medical practitioner utilized the assessment to select a second selection of a subset of the set of categories in order to provide oversight for the first selection by the subject of a set of categories. In some embodiments, the assessment was utilized by the medical practitioner to validate a condition exhibited by the subject, such as the social anxiety condition. In some such embodiments, the assessment was utilized by the medical practitioner to validate if: the subject had a marked fear or anxiety about one or more social situations in which the subject is exposed to possible scrutiny by others; the subject fears that he or she will act in a way or show anxiety symptoms that will be negatively evaluated; social situations almost always provoke fear or anxiety by the subject; social situations are avoided or endured with intense fear or anxiety by the subject; fear or anxiety is out of proportion to the actual threat posed by the social situation and to the sociocultural context; fear, anxiety, or avoidance is persistent, typically lasting for 6 months or more; fear, anxiety, or avoidance causes clinically significant distress or impairment in social, occupational, or other important areas of functioning; fear, anxiety, or avoidance is not attributable to the physiological effects of a substance (e.g., a drug of abuse, a medication) or another medical condition; fear, anxiety, or avoidance is not better explained by the symptoms of another mental disorder, such as panic disorder, body dysmorphic disorder, or autism spectrum disorder; if another medical condition (e.g., Parkinson's disease, obesity, disfigurement from burns or injury) is present, the fear, anxiety, or avoidance is clearly unrelated or is excessive; or a combination thereof.

A first virtual reality scene that included a respective interactive digital chart and a corresponding interactive digital bin was displayed on a remote device (e.g., device 300-1 of FIG. 3). Furthermore, the corresponding interactive digital bin included an enumerated plurality of nodes. Each respective node in the enumerated plurality of nodes corresponded to a respective category in a plurality of categories. Moreover, each respective node in the enumerated plurality of nodes was also associated with a corresponding plurality of proposed experiences associated with the respective category. Each respective proposed experience in the corresponding plurality of proposed experiences was associated with a corresponding unique digital reality scene, which was either a virtual reality scene, a panoramic video, a spherical video, or an omnidirectional video different than the first digital reality scene. Accordingly, this corresponding unique digital reality scene manifested a corresponding challenge represented by the respective category and/or the respective proposed experience. The corresponding challenge was challenge configured to provide exposure therapy. Further, each respective node in the enumerated plurality of nodes was further associated with at least one respective gate criterion in a plurality of gate criteria, which limited progression through the regimen by the subject in order to ensure the subject learned to manage the social anxiety condition. Accordingly, each respective category in the plurality of categories was directed to improving an ability of the subject to manage a psychiatric or mental condition of the subject. For instance, a first node in the enumerated plurality of nodes corresponded to an interactive social challenge category, and a second node in the enumerated plurality of nodes corresponded to an overall performance challenge category. A selection of a first node was detected. From this, the first node was placed at a first location in the first area to provide access to the corresponding plurality of proposed experiences associated with the respective category when the selection of the first node satisfied each gate criterion associated with the first node. Accordingly, the subject was provided the manifestation of the corresponding challenge through the corresponding unique digital reality scene associated with the first node. Upon completion of the corresponding challenge, the subject was deemed to have improved the ability to manage the social anxiety condition exhibited by the subject.

Example 2: Systems and Methods for Preparing a Regimen in a Digital Reality Scene for Improving an Ability of a Subject to Manage a Psychiatric or Mental Condition Exhibited by the Subject A method of preparing a regimen for improving an ability of a subject to manage a psychiatric or mental condition exhibited by the subject was implemented at a computer system (e.g., client device 300-1 of FIG. 3, client device 1100 of FIG. 11, etc.), which is associated with a subject (e.g., an end-user of the client device 300).

The computer system included one or more processors (e.g., CPU 302 of FIG. 3), a display (e.g., display 308 of FIG. 3), and a memory (e.g., memory 312 of FIG. 3) coupled to the one or more processors 302. In some embodiments, the display 308 was a head mounted display, such as a smart garment worn by the subject.

Further, the memory 312 included one or more programs configured to be executed by the one or more processors 302

(e.g., assessment module 12 of FIG. 2A, user profile store 14 of FIG. 2A, experience store 22 of FIG. 2B, gate store 30 of FIG. 2B, application server module 34 of FIG. 2B, application model library 50 of FIG. 2B, client application 320 of FIG. 3, engine 322 of FIG. 3, etc.).

The method presented a first digital reality scene on the display 308. The first digital reality scene included a respective interactive digital chart and a corresponding interactive digital bin. For instance, referring to FIG. 14A, a first digital reality scene having solid colored background is presented through a first user interface 1400. The first digital reality scene included a respective interactive digital chart 610 that was presented in the shape of a ladder (e.g., two or more rails coupled by a plurality of rungs). Moreover, the first digital reality scene included a corresponding interactive digital bin 625 that was presented in the shape of a tray configured to accommodate a plurality of nodes 630, such as a third node 630-3. The respective interactive digital chart 610 consumed a first affordance region (e.g., first affordance region 620-1 of FIG. 14A), which allowed for interaction by the user with the respective interactive digital chart 610. Furthermore, the respective interactive digital chart included a first area, which allowed the respective digital chart to be displayed within the first digital reality scene, such as displayed in a polygonal shape, such as a rectangle or the ladder.

Furthermore, the corresponding interactive digital bin consumed a second affordance region different than the first affordance region. Accordingly, the second affordance region is distinct from the first affordance region, which allowed for the corresponding interactive digital bin to separate positioning and/or functionality than the respective digital chart.

Moreover, the corresponding interactive digital bin included an enumerated plurality of nodes (e.g., third node 630-3 of FIG. 14A). In some embodiments, the enumerated plurality of nodes included 2 nodes, 3 nodes, or 5 nodes. Each respective node in the enumerated plurality of nodes corresponded to a respective category in a plurality of categories. For instance, in some embodiments, a first node 630-1 is associated with an assertiveness category, a second node 630-2 is associated with a general performance category, and a third node 630-3 is associated with an interaction with a stranger category.

Moreover, each respective node 630 in the enumerated plurality of nodes was associated with a corresponding plurality of proposed experiences associated with the respective category. For instance, in some embodiments, the first node 630-1 was associated with a first proposed experience 24-1 of a high pressure sales experience (e.g., "popcorn proposition with high pressure sales person" of FIG. 14A) and a second proposed experience 24-2 of reminder a person of a task experience (e.g., "remind the host to get your drink" of FIG. 14A), the second node 630-2 was associated with a third proposed experience 24-3 of presenting to a bored audience experience and a fourth proposed experience 24-4 of making a toast to an attentive group experience (e.g., "make a toast to a group of people with all eyes on you" of FIG. 14A), and the third node 630-3 was associated with a fifth proposed experience 24-5 of holding a conversation experience and a sixth proposed experience 24-6 of making small talk with another person. However, the present disclosure is not limited thereto.

Each respective proposed experience in the corresponding plurality of proposed experiences is associated with a corresponding unique digital reality scene, different than the first digital reality scene, that manifests a corresponding challenge represented by the respective category and/or the respective proposed experience. For instance, in some embodiments, the first digital reality scene was configured to display a house and the corresponding unique digital reality scene was configured to display a school cafeteria, a classroom, an office, a park, an airport, or a party.

Furthermore, each respective node 630 in the enumerated plurality of nodes was associated with at least one respective gate criterion in a plurality of gate criteria. Each respective category in the plurality of categories is directed to improving an ability of the subject to manage a psychiatric or mental condition of the subject. In some embodiments, the plurality of gate criteria required the subject to complete 20 total gate criteria over a two-month period of time.

A selection by the subject of a first node in the enumerated plurality of nodes was detected. In some embodiments, the first node was by the subject by a specific hand gesture (e.g., knocking, pulling, pushing, turning, etc.), by touching of the first node, or by clicking of the first node. However, the present disclosure is not limited thereto.

From this, the first node was at a first location in the first area. Once placed in the first area of the respective interactive digital chart, the subject is provided access to the corresponding plurality of proposed experiences associated with the respective category. For instance, in some embodiments, once the first node was placed at the first location via a first digital reality scene of FIG. 14A, the subject was provided access to the corresponding plurality of proposed experiences via a second digital reality scene of FIG. 14B.

Accordingly, in some such embodiments, by providing access to the corresponding plurality of proposed experiences by requiring the subject to interact with the interactive digital chart, through exposure to the challenges provided by the proposed experiences, the subject gradually confronts their ability to manage the psychiatric or mental condition. Overtime, through the exposure to the challenges, an anxiety level of the subject lowers that builds self-confidence for the subject, and the subject is able to expand a range of social activities.

Example 3: Onboarding a New Subject with a Medical Practitioner

In some embodiments, the systems and methods of the present disclosure were administered by a qualified medical practitioner to a first subject with a dosage of three sessions a week for eight weeks. In some embodiments, the first subject was remote from the medical practitioner (e.g., the subject was at home and the medical practitioner was in a remote laboratory), which provided the ability for the medical practitioner and/or one or more models to asynchronously monitor and/or adjust a program flow for the subject, when required.

In some embodiments, the subject was provided access to a companion client application (e.g., client application of FIG. 8A, client application of FIG. 8B, client application of FIG. 8C, client application of FIG. 8D, etc.) for registration, setup, program personalization, short-term goal setting, long term goal setting, patient/medical practitioner engagement (e.g., a communication channel to provide an audio, video, text-based, or combination thereof discussion between the subject and the medical practitioner), or a combination thereof.

In some embodiments, when medical practitioner administers the systems and methods of the present disclosure, the medical practitioner used the client application to create a new user profile for the subject, which allows for onboarding of the subject by the medical practitioner.

In some embodiments, the subject registered the new user profile by creating a username, a password, a unique identifier (e.g., a personal identifier number (PIN)), or a combination thereof.

Accordingly, the systems and methods of the present disclosure improve the ability of the subject to manage the psychiatric or mental condition using the respective interactive digital chart. More particularly, by using challenges configured to provide exposure therapy within a digital reality scene, the systems and methods of the present disclosure reduce the temporal, spatial, and financial resources needed by the subject and/or the medical practitioner in order to improve the ability of the subject to manage the psychiatric or mental condition exhibited by the subject.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer-readable storage medium. For instance, the computer program product could contain instructions for operating the user interfaces disclosed herein. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of preparing a regimen for improving an ability of a subject to manage a psychiatric or mental condition exhibited by the subject:
at a computer system associated with the subject, the computer system comprising one or more processors, a display, and a memory coupled to the one or more processors, the memory comprising one or more programs configured to be executed by the one or more processors, the method comprising:
(A) presenting, on the display, a first digital reality scene comprising a respective interactive digital chart and a corresponding interactive digital bin, wherein:
the respective interactive digital chart consumes a first affordance region, the respective interactive digital chart comprising a first area; and
the corresponding interactive digital bin consumes a second affordance region different than the first affordance region, the corresponding interactive digital bin comprising an enumerated plurality of nodes, wherein each respective node in the enumerated plurality of nodes (i) corresponds to a respective category in a plurality of categories, (ii) is associated with a corresponding plurality of proposed experiences associated with the respective category, wherein each respective proposed experience in the corresponding plurality of proposed experiences is associated with a corresponding unique digital reality scene, different than the first digital reality scene, that manifests a corresponding challenge represented by the respective category and/or the respective proposed experience, and (iii) is associated with at least one respective gate criterion in a plurality of gate criteria, wherein each respective category in the plurality of categories is directed to improving an ability of the subject to manage a psychiatric or mental condition of the subject, and wherein a gate criterion associated with one node in the enumerated plurality of nodes specifies a condition that is to be satisfied by the subject prior to advancement to another node in the enumerated plurality of nodes;
(B) detecting a selection of a first node in the enumerated plurality of nodes; and
(C) placing the first node at a first location in the first area, thereby providing access to the corresponding plurality of proposed experiences associated with the respective category and improving the ability of the subject to manage the psychiatric or mental condition using the respective interactive digital chart.

2. The method of claim 1, wherein the method further comprises determining if the selection of the first node satisfies each gate criterion in the at least one respective gate criterion associated with the first node prior to the placing (C) of the first node.

3. The method of claim 2, wherein the determining if the selection of the first node satisfies each gate criterion is performed by one or more models in a plurality of models.

4. The method of claim 1, wherein the method further comprises obtaining, in electronic form, an assessment of the subject, the assessment comprising an identification of each category in the plurality of categories.

5. The method of claim 4, wherein the assessment is provided by the subject.

6. The method of claim 5, wherein, prior to obtaining the assessment, the method further comprises obtaining, from a remote device associated with a medical practitioner of the subject, a validation of the assessment of the subject.

7. The method of claim 6, wherein the validation of the assessment comprises a first selection by the subject of a set of categories and a second selection by the medical practitioner of a subset of the set of categories, wherein the plurality of categories consists of the subset of the set of categories.

8. The method of claim 6, wherein the validation of the assessment comprises determining if the subject satisfies a threshold change in subjective distress of the subject caused by the corresponding challenge, a threshold change in cognitive symptoms of the subject, a threshold change in mindfulness state of the subject, a threshold quality of life improvement, a threshold change in diagnosis status for the psychiatric or mental condition exhibited by the subject, or a combination thereof.

9. The method of claim 4, wherein the assessment comprises a Liebowitz Social Anxiety Scale assessment, a Clinician Global Impression Severity Scale assessment, a Mini-International Neuropsychiatric Interview assessment, a Subjective Unit of Distress Scale assessment, a Minimally Clinically Important Different assessment, or a Quality-of-Life index assessment.

10. The method of claim 1, wherein the method further comprises repeating the detecting (B) and placing (C) one or more times for successive nodes in the enumerated plurality of nodes thereby selecting successive nodes in the enumerated plurality of nodes for inclusion in a graph within the respective interactive digital chart.

11. The method of claim 10, wherein:
each respective node in the graph is connected by an edge in a plurality of edges to at least one other node in the graph,
each respective edge in the plurality of edges represents a progression within the graph between a respective initial node and a respective subsequent node in the, and
the graph includes a final node other than the first node.

12. The method of claim 10, wherein a respective gate criterion of a first node in the graph is a threshold number of instances by the subject in the corresponding unique digital reality scene.

13. The method of claim 1, wherein the display is a head mounted display.

14. The method of claim 1, wherein:
the first affordance region is a two-dimensional affordance region in the first digital reality scene, and
the first area is a respective area bound by the two-dimensional affordance region.

15. The method of claim 1, wherein the method further comprises, responsive to detection of the selection of the first node, moving the first node from an initial location in the second affordance region to a second location other than the initial location.

16. The method of claim 1, wherein the at least one respective gate criterion comprises a ranking gate criterion associated with a hierarchical ranking of each node in the enumerated plurality of nodes.

17. The method of claim 1, wherein the at least one respective gate criterion comprises a medical practitioner gate criterion associated with an approval, from a medical practitioner associated with the subject, of the selection of the first node.

18. The method of claim 1, wherein the at least one respective gate criterion comprises an arrangement gate criterion associated with an order of one or more nodes in the enumerated plurality of nodes.

19. The method of claim 1, wherein the psychiatric or mental condition is a clinically diagnosed mental disorder or a sub-clinically diagnosed mental disorder.

20. The method of claim 19, wherein the psychiatric or mental condition comprises being stressed in a social setting, fearing a social setting, or being overwhelmed in a social setting.

21. The method of claim 19, wherein the psychiatric or mental condition is a clinically diagnosed mental disorder, and wherein the clinically diagnosed mental disorder is an anxiety disorder, and wherein the anxiety disorder comprises a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject.

22. The method of claim 1, wherein the method further comprises adding a node that has not previously been selected in an instance of the detecting (B) responsive to a selection of a node that has been selected in an instance of the detecting (B) in order to add or remove an availability of a category in the plurality of categories to the enumerated plurality of nodes.

23. The method of claim 1, wherein a respective gate criteria of a respective node in the enumerated plurality of nodes is set by (i) a system administrator, (ii) the subject, or (iii) a medical practitioner associated with the subject.

24. The method of claim 1, wherein the first digital reality scene is a virtual reality scene and the corresponding unique digital reality scene is a panoramic video, a spherical video, or an omnidirectional video.

25. The method of claim 1, wherein method further comprises repeating the detecting (B) and placing (C) one or more times for successive nodes in the enumerated plurality of nodes thereby selecting successive nodes in the enumerated plurality of nodes for inclusion in a graph within the respective interactive digital chart.

26. The method of claim 25, wherein the respective category corresponding to the first node in the enumerated plurality of nodes is considered least challenging for the subject, and the respective category corresponding to the last node in the enumerated plurality of nodes is considered more challenging for the subject than the first node.

27. The method of claim 1, wherein the placing (C) provides access to the corresponding plurality of proposed experiences through a second digital reality scene different than the first digital reality scene and the corresponding unique digital reality scene.

28. A computer system for preparing a regimen for improving an ability of a subject to manage a psychiatric or mental condition exhibited by the subject, the computer system comprising one or more processors, a display, and a memory coupled to the one or more processors, the memory comprising one or more programs configured to be executed by the one or more processors, the one or more programs singularly or collectively comprising instructions for:

(A) presenting, on the display, a first digital reality scene comprising a respective interactive digital chart and a corresponding interactive digital bin, wherein:
the respective interactive digital chart consumes a first affordance region, the respective interactive digital chart comprising a first area; and
the corresponding interactive digital bin consumes a second affordance region different than the first affordance region, the corresponding interactive digital bin comprising an enumerated plurality of nodes, wherein each respective node in the enumerated plurality of nodes (i) corresponds to a respective category in a plurality of categories, (ii) is associated with a corresponding plurality of proposed experiences associated with the respective category, wherein each respective proposed experience in the corresponding plurality of proposed experiences is associated with a corresponding unique digital reality scene, different than the first digital reality scene, that manifests a corresponding challenge represented by the respective category and/or the respective proposed experience, and (iii) is associated with at least one respective gate criterion in a plurality of gate criteria, wherein each respective category in the plurality of categories is directed to improving an ability of the subject to manage a psychiatric or mental condition of the subject, and wherein a gate criterion associated with one node in the enumerated plurality of nodes specifies a condition that is to be satisfied by the subject prior to advancement to another node in the enumerated plurality of nodes;

(B) detecting a selection of a first node in the enumerated plurality of nodes; and (C) placing the first node at a first location in the first area, thereby providing access to the corresponding plurality of proposed experiences associated with the respective category and improving the ability of the subject to manage the psychiatric or mental condition using the respective interactive digital chart.

29. The computer system of claim 28, wherein the one or more programs further comprises instructions for determining if the selection of the first node satisfies each gate criterion in the at least one respective gate criterion associated with the first node prior to the placing (C) of the first node.

30. The computer system of claim 29, wherein the determining if the selection of the first node satisfies each gate criterion is performed by one or more models in a plurality of models.

31. The computer system of claim 28, wherein the one or more programs further comprises instructions for obtaining, in electronic form, an assessment of the subject, the assessment comprising an identification of each category in the plurality of categories.

32. The computer system of claim 31, wherein the assessment comprises a Liebowitz Social Anxiety Scale assessment, a Clinician Global Impression Severity Scale assessment, a Mini-International Neuropsychiatric Interview assessment, a Subjective Unit of Distress Scale assessment, a Minimally Clinically Important Different assessment, or a Quality-of-Life index assessment.

33. The computer system of claim 31, wherein the assessment is provided by the subject.

34. The computer system of claim 33, wherein, prior to obtaining the assessment, the one or more programs further comprises instructions for obtaining, from a remote device associated with a medical practitioner of the subject, a validation of the assessment of the subject.

35. The computer system of claim 34, wherein the validation of the assessment comprises a first selection by the subject of a set of categories and a second selection by the medical practitioner of a subset of the set of categories, wherein the plurality of categories consists of the subset of the set of categories.

36. The computer system of claim 34, wherein the validation of the assessment comprises determining if the subject satisfies a threshold change in subjective distress of the subject caused by the corresponding challenge, a threshold change in cognitive symptoms of the subject, a threshold change in mindfulness state of the subject, a threshold quality of life improvement, a threshold change in diagnosis status for the psychiatric or mental condition exhibited by the subject, or a combination thereof.

37. The computer system of claim 28, wherein the one or more programs further comprises instructions for repeating the detecting (B) and placing (C) one or more times for successive nodes in the enumerated plurality of nodes thereby selecting successive nodes in the enumerated plurality of nodes for inclusion in a graph within the respective interactive digital chart.

38. The computer system of claim 37, wherein:
each respective node in the graph is connected by an edge in a plurality of edges to at least one other node in the graph,
each respective edge in the plurality of edges represents a progression within the graph between a respective initial node and a respective subsequent node in the, and
the graph includes a final node other than the first node.

39. The computer system of claim 37, wherein a respective gate criterion of a first node in the graph is a threshold number of instances by the subject in the corresponding unique digital reality scene.

40. The computer system of claim 28, wherein the display is a head mounted display.

41. The computer system of claim 28, wherein:
the first affordance region is a two-dimensional affordance region in the first digital reality scene, and
the first area is a respective area bound by the two-dimensional affordance region.

42. The computer system of claim 28, wherein the one or more programs further comprises instructions for, responsive to detection of the selection of the first node, moving the first node from an initial location in the second affordance region to a second location other than the initial location.

43. The computer system of claim 28, wherein the at least one respective gate criterion comprises a ranking gate criterion associated with a hierarchical ranking of each node in the enumerated plurality of nodes.

44. The computer system of claim 28, wherein the at least one respective gate criterion comprises a medical practitioner gate criterion associated with an approval, from a medical practitioner associated with the subject, of the selection of the first node.

45. The computer system of claim 28, wherein the at least one respective gate criterion comprises an arrangement gate criterion associated with an order of one or more nodes in the enumerated plurality of nodes.

46. The computer system of claim 28, wherein the psychiatric or mental condition is a clinically diagnosed mental disorder or a sub-clinically diagnosed mental disorder.

47. The computer system of claim 46, wherein the psychiatric or mental condition comprises being stressed in a social setting, fearing a social setting, or being overwhelmed in a social setting.

48. The computer system of claim 46, wherein the psychiatric or mental condition is a clinically diagnosed mental disorder, and wherein the clinically diagnosed mental disorder is an anxiety disorder, and wherein the anxiety disorder comprises a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject.

49. The computer system of claim 28, wherein the one or more programs method further comprises instructions for adding a node that has not previously been selected in an instance of the detecting (B) responsive to a selection of a node that has been selected in an instance of the detecting (B) in order to add or remove an availability of a category in the plurality of categories to the enumerated plurality of nodes.

50. The computer system of claim 28, wherein a respective gate criteria of a respective node in the enumerated plurality of nodes is set by (i) a system administrator, (ii) the subject, or (iii) a medical practitioner associated with the subject.

51. The computer system of claim 28, wherein the first digital reality scene is a virtual reality scene and the corresponding unique digital reality scene is a panoramic video, a spherical video, or an omnidirectional video.

52. The computer system of claim 28, wherein the one or more programs further comprises instructions for repeating the detecting (B) and placing (C) one or more times for successive nodes in the enumerated plurality of nodes thereby selecting successive nodes in the enumerated plurality of nodes for inclusion in a graph within the respective interactive digital chart.

53. The computer system of claim 52, wherein the respective category corresponding to the first node in the enumerated plurality of nodes is considered least challenging for the subject, and the respective category corresponding to the last node in the enumerated plurality of nodes is considered more challenging for the subject than the first node.

54. The computer system of claim 28, wherein the placing (C) provides access to the corresponding plurality of proposed experiences through a second digital reality scene different than the first digital reality scene and the corresponding unique digital reality scene.

55. A non-transitory computer readable storage medium storing one or more programs, the one or more programs comprising instructions, which when executed by a computer system cause the computer system to perform a method comprising:
  (A) presenting, on a display associated with the computer system, a first digital reality scene comprising a respective interactive digital chart and a corresponding interactive digital bin, wherein:
    the respective interactive digital chart consumes a first affordance region, the respective interactive digital chart comprising a first area; and
    the corresponding interactive digital bin consumes a second affordance region different than the first affordance region, the corresponding interactive digital bin comprising an enumerated plurality of nodes, wherein each respective node in the enumerated plurality of nodes (i) corresponds to a respective category in a plurality of categories, (ii) is associated with a corresponding plurality of proposed experiences associated with the respective category, wherein each respective proposed experience in the corresponding plurality of proposed experiences is associated with a corresponding unique digital reality scene, different than the first digital reality scene, that manifests a corresponding challenge represented by the respective category and/or the respective proposed experience, and (iii) is associated with at least one respective gate criterion in a plurality of gate criteria, wherein each respective category in the plurality of categories is directed to improving an ability of a subject to manage a psychiatric or mental condition of the subject, and wherein a gate criterion associated with one node in the enumerated plurality of nodes specifies a condition that is to be satisfied by the subject prior to advancement to another node in the enumerated plurality of nodes;
  (B) detecting a selection of a first node in the enumerated plurality of nodes; and
  (C) placing the first node at a first location in the first area, thereby providing access to the corresponding plurality of proposed experiences associated with the respective category and improving the ability of the subject to manage the psychiatric or mental condition using the respective interactive digital chart.

56. The non-transitory computer readable storage medium of claim 55, wherein the method further comprises determining if the selection of the first node satisfies each gate criterion in the at least one respective gate criterion associated with the first node prior to the placing (C) of the first node.

57. The non-transitory computer readable storage medium of claim 56, wherein the determining if the selection of the first node satisfies each gate criterion is performed by one or more models in a plurality of models.

58. The non-transitory computer readable storage medium of claim 55, wherein the method further comprises obtaining, in electronic form, an assessment of the subject, the assessment comprising an identification of each category in the plurality of categories.

59. The non-transitory computer readable storage medium of claim 58, wherein the assessment comprises a Liebowitz Social Anxiety Scale assessment, a Clinician Global Impression Severity Scale assessment, a Mini-International Neuropsychiatric Interview assessment, a Subjective Unit of Distress Scale assessment, a Minimally Clinically Important Different assessment, or a Quality-of-Life index assessment.

60. The non-transitory computer readable storage medium of claim 55, wherein the method further comprises repeating the detecting (B) and placing (C) one or more times for successive nodes in the enumerated plurality of nodes thereby selecting successive nodes in the enumerated plurality of nodes for inclusion in a graph within the respective interactive digital chart.

61. The non-transitory computer readable storage medium of claim 60, wherein a respective gate criterion of a first node in the graph is a threshold number of instances by the subject in the corresponding unique digital reality scene.

62. The non-transitory computer readable storage medium of claim 60, wherein the assessment is provided by the subject.

63. The non-transitory computer readable storage medium of claim 62, wherein, prior to obtaining the assessment, the method further comprises obtaining, from a remote device associated with a medical practitioner of the subject, a validation of the assessment of the subject.

64. The non-transitory computer readable storage medium of claim 63, wherein the validation of the assessment comprises a first selection by the subject of a set of categories and a second selection by the medical practitioner of a subset of the set of categories, wherein the plurality of categories consists of the subset of the set of categories.

65. The non-transitory computer readable storage medium of claim 63, wherein the validation of the assessment comprises determining if the subject satisfies a threshold change in subjective distress of the subject caused by the corresponding challenge, a threshold change in cognitive symptoms of the subject, a threshold change in mindfulness state of the subject, a threshold quality of life improvement, a threshold change in diagnosis status for the psychiatric or mental condition exhibited by the subject, or a combination thereof.

66. The non-transitory computer readable storage medium of claim 60, wherein:
  each respective node in the graph is connected by an edge in a plurality of edges to at least one other node in the graph,
  each respective edge in the plurality of edges represents a progression within the graph between a respective initial node and a respective subsequent node in the, and
  the graph includes a final node other than the first node.

67. The non-transitory computer readable storage medium of claim 55, wherein the display is a head mounted display.

68. The non-transitory computer readable storage medium of claim 55, wherein:
  the first affordance region is a two-dimensional affordance region in the first digital reality scene, and
  the first area is a respective area bound by the two-dimensional affordance region.

69. The non-transitory computer readable storage medium of claim 55, wherein the method further comprises, responsive to detection of the selection of the first node, moving the first node from an initial location in the second affordance region to a second location other than the initial location.

70. The non-transitory computer readable storage medium of claim 55, wherein the at least one respective gate criterion comprises a ranking gate criterion associated with a hierarchical ranking of each node in the enumerated plurality of nodes.

71. The non-transitory computer readable storage medium of claim 55, wherein the at least one respective gate criterion comprises a medical practitioner gate criterion associated with an approval, from a medical practitioner associated with the subject, of the selection of the first node.

72. The non-transitory computer readable storage medium of claim 55, wherein the at least one respective gate criterion comprises an arrangement gate criterion associated with an order of one or more nodes in the enumerated plurality of nodes.

73. The non-transitory computer readable storage medium of claim 55, wherein the psychiatric or mental condition is a clinically diagnosed mental disorder or a sub-clinically diagnosed mental disorder.

74. The non-transitory computer readable storage medium of claim 73, wherein the psychiatric or mental condition comprises being stressed in a social setting, fearing a social setting, or being overwhelmed in a social setting.

75. The non-transitory computer readable storage medium of claim 73, wherein the psychiatric or mental condition is a clinically diagnosed mental disorder, and wherein the clinically diagnosed mental disorder is an anxiety disorder, and wherein the anxiety disorder comprises a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject.

76. The non-transitory computer readable storage medium of claim 55, wherein the method further comprises adding a node that has not previously been selected in an instance of the detecting (B) responsive to a selection of a node that has been selected in an instance of the detecting (B) in order to add or remove an availability of a category in the plurality of categories to the enumerated plurality of nodes.

77. The non-transitory computer readable storage medium of claim 55, wherein a respective gate criteria of a respective node in the enumerated plurality of nodes is set by (i) a system administrator, (ii) the subject, or (iii) a medical practitioner associated with the subject.

78. The non-transitory computer readable storage medium of claim 55, wherein the first digital reality scene is a virtual reality scene and the corresponding unique digital reality scene is a panoramic video, a spherical video, or an omnidirectional video.

79. The non-transitory computer readable storage medium of claim 55, wherein method further comprises repeating the detecting (B) and placing (C) one or more times for successive nodes in the enumerated plurality of nodes thereby selecting successive nodes in the enumerated plurality of nodes for inclusion in a graph within the respective interactive digital chart.

80. The non-transitory computer readable storage medium of claim 79, wherein the respective category corresponding to the first node in the enumerated plurality of nodes is considered least challenging for the subject, and the respective category corresponding to the last node in the enumerated plurality of nodes is considered more challenging for the subject than the first node.

81. The non-transitory computer readable storage medium of claim 55, wherein the placing (C) provides access to the corresponding plurality of proposed experiences through a second digital reality scene different than the first digital reality scene and the corresponding unique digital reality scene.

* * * * *